(12) United States Patent
Foster et al.

(10) Patent No.: US 9,012,195 B2
(45) Date of Patent: *Apr. 21, 2015

(54) NON-CYTOTOXIC PROTEIN CONJUGATES

(71) Applicants: Syntaxin Ltd., Abingdon, Oxon (GB); Allergan Inc., Irvine, CA (US)

(72) Inventors: Keith Foster, Abingdon (GB); John Chaddock, Abingdon (GB); Charles Penn, Abingdon (GB); Kei Roger Aoki, Irvine, CA (US); Joseph Francis, Irvine, CA (US); Lance Steward, Irvine, CA (US)

(73) Assignees: Syntaxin, Ltd., Abingdon (GB); Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/944,427

(22) Filed: Jul. 17, 2013

(65) Prior Publication Data
US 2013/0295643 A1 Nov. 7, 2013

Related U.S. Application Data

(60) Division of application No. 13/212,868, filed on Aug. 18, 2011, now Pat. No. 8,512,984, which is a continuation-in-part of application No. 11/791,979, filed as application No. PCT/GB2005/004598 on Dec. 1, 2005, now Pat. No. 8,187,834.

(30) Foreign Application Priority Data

Dec. 1, 2004 (GB) .................................. 0426394.3
Mar. 10, 2005 (GB) .................................. 0504964.8
Mar. 10, 2005 (GB) .................................. 0504966.3

(51) Int. Cl.
C07K 14/665 (2006.01)
C12N 9/96 (2006.01)
A61K 47/48 (2006.01)
A61K 38/48 (2006.01)

(52) U.S. Cl.
CPC ............ *C12N 9/96* (2013.01); *A61K 47/48246* (2013.01); *C07K 14/665* (2013.01); *A61K 38/482* (2013.01); *A61K 38/4893* (2013.01); *C07K 2319/00* (2013.01)

(58) Field of Classification Search
CPC ....................................................... C12N 9/96
See application file for complete search history.

(56) References Cited

U.S. PATENT DOCUMENTS

| 5,668,255 | A  | 9/1997  | Murphy |
| 5,989,545 | A  | 11/1999 | Foster |
| 5,998,375 | A  | 12/1999 | Thogersen et al. |
| 6,136,564 | A  | 10/2000 | Kopetzki |
| 6,395,513 | B1 | 5/2002  | Foster |
| 6,461,617 | B1 | 10/2002 | Shone |
| 6,632,440 | B1 | 10/2003 | Quinn |
| 6,776,990 | B2 | 8/2004  | Sachs |
| 6,843,998 | B1 | 1/2005  | Steward |
| 6,962,703 | B2 | 11/2005 | Foster |
| 7,052,702 | B1 | 5/2006  | Duggan |
| 7,056,729 | B2 | 6/2006  | Donovan |
| 7,132,259 | B1 | 11/2006 | Dolly |
| 7,192,596 | B2 | 3/2007  | Shone |
| 7,208,466 | B1 | 4/2007  | Foster |
| 7,244,436 | B2 | 7/2007  | Donovan |
| 7,244,437 | B2 | 7/2007  | Donovan |
| 7,262,291 | B2 | 8/2007  | Donovan |
| 7,276,473 | B2 | 10/2007 | Sachs |
| 7,413,742 | B2 | 8/2008  | Donovan |
| 7,419,676 | B2 | 9/2008  | Dolly |
| 7,422,877 | B2 | 9/2008  | Dolly |
| 7,452,543 | B2 | 11/2008 | Chaddock |

(Continued)

FOREIGN PATENT DOCUMENTS

| EP | 1 422 240 | 5/2004 |
| EP | 1422240   | 5/2004 |

(Continued)

OTHER PUBLICATIONS

Canadian Office Action issued Apr. 26, 2013, from the Canadian Patent Office in related Canadian Patent Application No. 2,588,292.

(Continued)

*Primary Examiner* — Suzanne M Noakes
*Assistant Examiner* — Gerard Lacourciere
(74) *Attorney, Agent, or Firm* — Roylance, Abrams, Berdo & Goodman, L.L.P.

(57) ABSTRACT

The present invention is directed to non-cytotoxic protein conjugates for inhibition or reduction of exocytic fusion in a nociceptive sensory afferent cell. The protein conjugates comprise: (i) a dynorphin Targeting Moiety (TM), wherein the TM is an agonist of a receptor present on a nociceptive sensory afferent cell, and wherein the receptor undergoes endocytosis to be incorporated into an endosome within the nociceptive sensory afferent cell; (ii) a non-cytotoxic protease or a fragment thereof, wherein the protease or protease fragment is capable of cleaving a protein of the exocytic fusion apparatus of the nociceptive sensory afferent cell; and (iii) a Translocation Domain, wherein the Translocation Domain translocates the protease or protease fragment from within the endosome, across the endosomal membrane, and into the cytosol of the nociceptive sensory afferent cell. Nucleic acid sequences encoding the protein conjugates, methods of preparing same and uses thereof are also described.

21 Claims, 31 Drawing Sheets

(56) References Cited

U.S. PATENT DOCUMENTS

| | | |
|---|---|---|
| 7,494,661 B2 | 2/2009 | Sanders |
| 7,514,088 B2 | 4/2009 | Steward |
| 7,658,933 B2 | 2/2010 | Foster et al. |
| 7,659,092 B2 | 2/2010 | Foster |
| 7,709,228 B2 | 5/2010 | Dolly |
| 7,736,659 B2 | 6/2010 | Donovan |
| 7,740,868 B2 | 6/2010 | Steward |
| 7,749,514 B2 | 7/2010 | Steward |
| 7,780,968 B2 | 8/2010 | Donovan |
| 7,785,606 B2 | 8/2010 | Ichtchenko |
| 7,811,584 B2 | 10/2010 | Steward |
| 7,833,535 B2 | 11/2010 | Donovan |
| 7,887,810 B2 | 2/2011 | Foster |
| 7,892,560 B2 | 2/2011 | Foster |
| 7,897,157 B2 | 3/2011 | Steward |
| 8,067,200 B2 | 11/2011 | Foster |
| 2003/0049264 A1 | 3/2003 | Foster |
| 2003/0180289 A1 | 9/2003 | Foster |
| 2004/0071736 A1 | 4/2004 | Quinn |
| 2004/0115727 A1 | 6/2004 | Steward |
| 2005/0095251 A1 | 5/2005 | Steward |
| 2005/0244435 A1 | 11/2005 | Shone |
| 2006/0051356 A1 | 3/2006 | Foster |
| 2006/0110410 A1 | 5/2006 | Shone |
| 2006/0216283 A1 | 9/2006 | Foster |
| 2007/0010447 A1 | 1/2007 | Quinn |
| 2007/0010475 A1 | 1/2007 | Richardson |
| 2007/0066559 A1 | 3/2007 | Richardson |
| 2007/0184048 A1 | 8/2007 | Foster |
| 2007/0184070 A1 | 8/2007 | Shone |
| 2007/0248626 A1 | 10/2007 | Shone |
| 2008/0025994 A1 | 1/2008 | Steward |
| 2008/0032928 A1 | 2/2008 | Quinn |
| 2008/0032931 A1 | 2/2008 | Steward |
| 2008/0038274 A1 | 2/2008 | Foster |
| 2008/0070278 A1 | 3/2008 | North |
| 2008/0182294 A1 | 7/2008 | Dolly |
| 2008/0311622 A1 | 12/2008 | Dolly |
| 2009/0004224 A1 | 1/2009 | Steward |
| 2009/0005313 A1 | 1/2009 | Steward |
| 2009/0018081 A1 | 1/2009 | Steward |
| 2009/0030182 A1 | 1/2009 | Dolly |
| 2009/0030188 A1 | 1/2009 | Dolly |
| 2009/0042270 A1 | 2/2009 | Dolly |
| 2009/0069238 A1 | 3/2009 | Steward |
| 2009/0081730 A1 | 3/2009 | Dolly |
| 2009/0087458 A1 | 4/2009 | Dolly |
| 2009/0104234 A1 | 4/2009 | Francis |
| 2009/0117157 A1 | 5/2009 | Brin |
| 2009/0131645 A1 | 5/2009 | Foster |
| 2009/0162341 A1 | 6/2009 | Foster |
| 2009/0280066 A1 | 11/2009 | Quinn |
| 2010/0034802 A1 | 2/2010 | Foster |
| 2010/0055761 A1 | 3/2010 | Seed |
| 2010/0196421 A1 | 8/2010 | Ichtchenko |
| 2010/0209955 A1 | 8/2010 | Oyler |
| 2010/0303757 A1 | 12/2010 | Francis |
| 2010/0303789 A1 | 12/2010 | Francis |
| 2010/0303791 A1 | 12/2010 | Francis |
| 2011/0091437 A1 | 4/2011 | Foster |

FOREIGN PATENT DOCUMENTS

| | | |
|---|---|---|
| WO | 96/33273 | 10/1996 |
| WO | 97/07208 | 2/1997 |
| WO | 98/07864 | 2/1998 |
| WO | 99/17806 | 4/1999 |
| WO | 00/57897 | 10/2000 |
| WO | 01/14570 | 3/2001 |
| WO | 01/58936 | 8/2001 |
| WO | 02/07759 | 1/2002 |
| WO | 2004/024909 | 3/2004 |
| WO | 2005/023309 | 3/2005 |
| WO | 2006/026780 | 3/2006 |
| WO | 2006/059093 | 6/2006 |
| WO | 2006/059105 | 6/2006 |
| WO | 2006/059113 | 6/2006 |
| WO | 2007/138339 | 12/2007 |
| WO | 2012/156743 | 11/2012 |

OTHER PUBLICATIONS

Crasto, C. et al., LINKER: a program to generate linker sequences for fusion proteins, Protein Engineering, 2000, vol. 13, No. 5, pp. 309-312.

Smith, D. et al., Improved amino acid flexibility parameters, Protein Science, 2003, vol. 12, No. 5, pp. 1060-1072.

International Search Report and Written Opinion dated Dec. 20, 2013 in related PCT Application No. PCT/GB2013/052243.

Office Action dated Jul. 29, 2013, from the Mexican Patent Office in related Mexican Patent Application No. Application No. MX/a/2008/015227, and English summary thereof.

Office Action dated Nov. 7, 2013, from the Australian Patent Office in related Australian Patent Application No. 2012203056.

Office Action dated Nov. 7, 2013, from the Australian Patent Office in related Australian Patent Application No. 2012203055.

Office Action dated Oct. 29, 2013, from the Japanese Patent Office in related Japanese Patent Application No. 2011-258137, and English translation.

Blanc, Jacky P. et al., Examination of the Requirement for an Amphiphilic Helical Structure in B-Endorphin through the Design, Synthesis, and Study of Model Peptides, The Journal of Biological Chemistry, vol. 258, No. 13, 1983, pp. 8277-8284.

Shone, Clifford C. et al., A 50-kDa fragment from the NH2-terminus of the heavy subunit of Clostridium botulinum type A neurotoxin forms channels in lipid vesicles, Eur. J. Biochem. 167, 175-180, 1987.

Wagner, Ernst et al., Influenza virus hemagglutinin HA-2 N-terminal fusogenic peptides augment gene transfer by transferrin-polylysine-DNA complexes: Toward a synthetic virus-like gene-transfer vehicle, Proc. Natl. Acad. Sci, USA, vol. 89, pp. 7934-7938, 1992.

Plank, Christian et al., The Influence of Endosome-disruptive Peptides on Gene Transfer Using Synthetic Virus-like Gene Transfer Systems, The Journal of Biological Chemistry, vol. 269, No. 17, 1994, pp. 12918-12924.

Dooley, Colette T., et al., Binding and In Vitro Activities of Peptides with High Affinity for the Nociceptin/Orphanin FQ Receptor, ORL1, The Journal of Pharmacology and Experimental Therapeutics, 1997, vol. 283, No. 2, pp. 735-741.

Vergnollie, N. et al., Proteinase-activated receptor-2 and hyperalgesia: A novel pain pathway, Nature Medicine, vol. 7, No. 7, 2001, pp. 821-826.

Rizzi, Daniela et al., [Arg14, LYS15]Nociceptin, a Highly Potent Agonist of the Nociceptin/Orphanin FQ Receptor: in Vitro and in Vivo Studies, The Journal of Pharmacology and Experimental Therapeutics, 2002, vol. 300, No. 1 pp. 57-63.

Turton, Kathryn et al., Botulinum and tetanus neurotoxins: structure, function and therapeutic utility, Trends in Biochemical Sciences, vol. 27, No. 11, 2002, pp. 552-558.

Maile, Rebecca et al., Effects of nociceptin and analogues of nociceptin upon spontaneous dorsal root activity recorded from an in vitro preparation of rat spinal cord, Neuroscience Letters 350 (2003) 190-192.

Chaddock, John A. et al., Manipulation of Signal Transduction by Botulinum Neurotoxins and their Derivatives, Current Signal Transduction Therapy, 2007, 2, 221-225.

Guerrini, Remo et al., Address and Message Sequences for the Nociceptin Receptor: A Structure-Activity Study of Nociceptin-(1-13)-peptide amide, J. Med. Chem., 1997, 40, 1789-1793.

Schiavo, Giampietro et al., Neurotoxins Affecting Neuroexocytosis, Physiological Reviews, vol. 80, No. 2, 2000, pp. 717-766.

Xu, X.J. et al., Galanin and spinal nociceptive mechanisms: recent advances and therapeutic implications, Neuropeptides, 2000, 34(3 &4), 137-147.

Okada, Kazushi et al., Highly Potent Nociceptin Analog Containing the Arg-Lys Triple Repeat, Biochemical and Biophysical Research Communications, 278, 493-498, 2000.

(56) References Cited

OTHER PUBLICATIONS

Mogil, Jeffrey S. et al., The Molecular and Behavioral Pharmacology of the Orphanin FQ/Nociceptin Peptide and Receptor Family, Pharmacological Reviews, 2001, vol. 53, No. 3, pp. 381-415.
Chaddock, J.A., et al., A Conjugate Composed of Nerve Growth Factor Coupled to a Non-Toxic Derivative of *Clostridium botulinum* Neurotoxin Type A Can Inhibit Neurotransmitter Release In Vitro, Growth Factors 18(2):147-155, 2000.
Chaddock, J.A., et al., Expression and Purification of Catalytically Active, Non-Toxic Endopeptidase Derivatives of *Clostridium botulinum* Toxin Type A, Protein Expression and Purification 25(2):219-228, 2002.
Chaddock, J.A., et al., Inhibition of Vesicular Secretion in Both Neuronal and Nonneuronal Cells by Retargeted Endopeptidase Derivative of *Clostridium botulinum* Neurotoxin Type A, Infection and Immunity 68(5):2587-2593, 2000.
Cui, M., et al., Retargeted Clostridial Endopeptidase: Antinociceptive Activity in Preclinical Models of Pain, Naunyn-Schmiedeberg's Archives of Pharmacology:R16, 2002.
Duggan, M.J., et al., Inhibition of Release of Neurotransmitters from Rat Dorsal Root Ganglia by a Novel Conjugate of a *Clostridium Botulinum* Toxin a Endopeptidase Fragment and *Erythrina cristagalli* Lectin, Journal of Biological Chemistry 277(38):34846-34852, 2002.
Foster, K.A., et al., Re-Engineering the Target Specificity of Clostridial Neurotoxins: A Route to Novel Therapeutics, Neurotoxicity Research 9(2,3):101-107, 2006.
Inoue, M., et al., Nociceptin/Orphannin FQ-Induced Nociceptive Responses Through Substance P Release From Peripheral Nerve Endings in Mice, PNAS (Proceedings of the National Academy of Sciences USA), 95 (18):10949-10953, 1998.
Sutton, J.M., et al., Preparation of Specifically Activatable Endopeptidase Derivatives of *Clostridium botulinum* Toxins Type A, B, and C and Their Applications, Protein Expression and Purification 40(1):31-41, 2005.
Sagane et al., Dichain structure of botulinum neurotoxin : Identification of cleavage sites in Types C, D, and F neurotoxin molecules. J. Protein Chemistry 18(8) :855-892 (1999).
Chaddock, J.A., et al., Retargeted Clostridial Endopeptidases: Inhibition of Nociceptive Neurotransmitter Release In Vitro, and Antinociceptive Activity in In Vivo Models of Pain. Movement Disorders, vol. 19, pp. S42-S47; Sep. 8, 2004.
Translation of Japanese Office Action dated Jun. 28, 2011 in JP 2007-543906.
Translation of Japanese Office Action dated Jun. 28, 2011 in JP 2007-543908.
English Translation of Office Action issued Jun. 26, 2012 in JP 2007-543906.
English Translation of Office Action issued Jun. 26, 2012 in JP 2007-543908.
English Translation of Office Action issued Jun. 29, 2012 in CN 200780028089.0.
Office Action issued Sep. 10, 2012 in EP 10 166 556.0.
Office Action issued Sep. 10, 2012 in EP 10 184 150.0.
Office Action issued Sep. 10, 2012 in EP 10 184 114.6.
Office Action issued Sep. 10, 2012 in EP 05 810 711.1.
Office Action issued Aug. 22, 2012 in CA 2,595,115.
English Translation of Japanese Office Action issued Feb. 19, 2013, from the Japanese Patent Office in related Japanese Patent Application No. JP 2011-258137.
Chinese Office Action issued Mar. 25, 2013, from the Chinese Patent Office in related Chinese Patent Application No. 200780028089.0, and English translation.
Office Action dated Aug. 20, 2014, from the European Patent Office in related European Patent Application No. 10184114.6.
Office Action dated Aug. 20, 2014, from the European Patent Office in related European Patent Application No. 10184150.0.
Office Action dated Jul. 31, 2014, from the Canadian Patent Office in related Canadian Patent Application No. 2,588,292.
Office Action dated Oct. 2, 2014, from the Australian Patent Office in related Australian Patent Application No. 2012201491.
Office Action dated May 20, 2014, from the Japanese Patent Office in related Japanese Patent Application No. 2012-236094, and English translation thereof.
Office Action dated Apr. 9, 2014, from the Australian Patent Office in related Australian Patent Application No. 2011202219.
Office Action dated Apr. 9, 2014, from the Australian Patent Office in related Australian Patent Application No. 2012200046.
Office Action dated Apr. 9, 2014, from the Australian Patent Office in related Australian Patent Application No. 2012201491.
Office Action dated Mar. 10, 2014, from the Mexican Patent Office in related Mexican Patent Application No. Application No. MX/a/2008/015227, and English summary thereof.
Office Action dated Nov. 20, 2014, from the Mexican Patent Office in related Mexican Patent Application No. MX/a/20081015227, and English translation.

Figure 11

Competition Assay: CPN fusions vs 1nM [3H] - Nociceptin
on eDRGs for 1 hour at 4°C

- ●— Tocris
- ●-- CPN-LH$_N$/A
- ●-- CPNv-LH$_N$/A
- ○  Controls

CPN-A on eDRG for 1 Day

Duration of action following eDRG exposure for 1 Day

Figure 33

NON-CYTOTOXIC PROTEIN CONJUGATES

THE NAMES OF PARTIES TO A JOINT RESEARCH AGREEMENT

Allergan, Inc., a Delaware Corporation, and Syntaxin, Ltd., a United Kingdom corporation, are parties to a Joint Research Agreement.

FIELD OF THE INVENTION

This invention relates to a non-cytotoxic protein conjugate, and to the use of said conjugate for treating pain.

BACKGROUND OF THE INVENTION

Toxins may be generally divided into two groups according to the type of effect that they have on a target cell. In more detail, the first group of toxins kill their natural target cells, and are therefore known as cytotoxic toxin molecules. This group of toxins is exemplified inter alia by plant toxins such as ricin, and abrin, and by bacterial toxins such as diphtheria toxin, and *Pseudomonas* exotoxin A. Cytotoxic toxins typically kill their target cells by inhibiting the cellular process of protein synthesis.

In contrast, the second group of toxins, which are known as non-cytotoxic toxins, do not (as their name confirms) kill their natural target cells. Non-cytotoxic toxins have attracted much less commercial interest than have their cytotoxic counterparts, and exert their effects on a target cell by inhibiting cellular processes other than protein synthesis. As with their cytotoxic counterparts, non-cytotoxic toxins are produced from a variety of sources such as plants, and bacteria. Bacterial non-cytotoxic toxins are now described in more detail.

Clostridial neurotoxins are proteins that typically have a molecular mass of the order of 150 kDa. They are produced by various species of bacteria, especially of the genus *Clostridium*, most importantly *C. tetani* and several strains of *C. botulinum*, *C. butyricum* and *C. argentinense*. There are at present eight different classes of the clostridial neurotoxin, namely: tetanus toxin, and botulinum neurotoxin in its serotypes A, B, $C_1$, D, E, F and G, and they all share similar structures and modes of action.

Clostridial neurotoxins represent a major group of non-cytotoxic toxin molecules, and are synthesised by the host bacterium as single polypeptides that are modified post-translationally by a proteolytic cleavage event to form two polypeptide chains joined together by a disulphide bond. The two chains are termed the heavy chain (H-chain), which has a molecular mass of approximately 100 kDa, and the light chain (L-chain), which has a molecular mass of approximately 50 kDa.

L-chains possess a protease function (zinc-dependent endopeptidase activity) and exhibit high substrate specificity for vesicle and/or plasma membrane associated proteins involved in the exocytic process. L-chains from different clostridial species or serotypes may hydrolyse different but specific peptide bonds in one of three substrate proteins, namely synaptobrevin, syntaxin or SNAP-25. These substrates are important components of the neurosecretory machinery.

Non-cytotoxic toxins are also produced by other bacteria, such as from the genus *Neisseria*, most importantly from the species *N. gonorrhoeae*. For example, *Neisseria* sp. produces the non-cytotoxic toxin IgA protease (see WO99/58571).

It has been well documented in the art that toxin molecules may be re-targeted to a cell that is not the toxin's natural target cell. When so re-targeted, the modified toxin is capable of binding to a desired target cell and, following subsequent translocation into the cytosol, is capable of exerting its effect on the target cell. Said re-targeting is achieved by replacing the natural Targeting Moiety (TM) of the toxin with a different TM. In this regard, the TM is selected so that it will bind to a desired target cell, and allow subsequent passage of the modified toxin into an endosome within the target cell. The modified toxin also comprises a translocation domain to enable entry of the non-cytotoxic protease into the cell cytosol. The translocation domain can be the natural translocation domain of the toxin or it can be a different translocation domain obtained from a microbial protein with translocation activity.

For example, in the context of non-cytotoxic toxin molecules, it has been well documented that a clostridial neurotoxin may be re-targeted by incorporation of a Targeting Moiety (TM), which is not the natural TM of a clostridial neurotoxin. The described chemical conjugation and recombinant methodologies are now regarded as conventional, and reference is made to Hermanson, G. T. (1996), Bioconjugate techniques, Academic Press, and to Wong, S. S. (1991), Chemistry of protein conjugation and cross-linking, CRC Press.

For example, WO94/21300 describes modified clostridial neurotoxin molecules that are capable of regulating Integral Membrane Protein (IMP) density present at the cell surface of the target cell. The modified neurotoxin molecules are thus capable of controlling cell activity (e.g. glucose uptake) of the target cell. WO96/33273 and WO99/17806 describe modified clostridial neurotoxin molecules that target peripheral sensory afferents. The modified neurotoxin molecules are thus capable of demonstrating an analgesic effect. WO00/10598 describes the preparation of modified clostridial neurotoxin molecules that target mucus hypersecreting cells (or neuronal cells controlling said mucus hypersecreting cells), which modified neurotoxins are capable of inhibiting hypersecretion from said cells. WO01/21213 describes modified clostridial neurotoxin molecules that target a wide range of different types of non-neuronal target cells. The modified molecules are thus capable of preventing secretion from the target cells. Additional publications in the technical field of re-targeted toxin molecules include: WO00/62814; WO00/04926; U.S. Pat. No. 5,773,586; WO93/15766; WO00/61192; and WO99/58571.

Thus, from the above-described publications, it will be appreciated that the basic concept of re-targeting a non-cytotoxic protease to a desired target cell, by selecting a TM that has a corresponding receptor present on the target cell, has been well documented.

However, different receptors present on a target cell of interest demonstrate different binding affinities for different TMs. This may be a particular problem with pain-sensing cells, which possess a wide range of receptor types having different binding affinities for different TMs. Thus, a re-targeted conjugate comprising a particular TM (that binds to a receptor on a pain-sensing cell) may demonstrate a low binding affinity for a pain-sensing target cell, which is undesirable.

There is therefore a need to develop modified non-cytotoxic conjugates that address one or more of the above problems. Of particular interest is the development of an improved conjugate for use in treating pain.

SUMMARY OF THE INVENTION

The present invention seeks to address one or more of the above problems by using as the conjugate's Targeting Moiety (TM) an "agonist" of a receptor that is present on the pain-sensing target cell of interest. In preferred embodiments, the pain-sensing target cell is a nociceptive sensory afferent, more preferably a primary nociceptive sensory afferent. In particularly preferred embodiments, the TM is an agonist of the opioid-like receptor-1 ($ORL_1$) receptor. Accordingly, in a first aspect, the present invention provides a non-cytotoxic conjugate for inhibition or reduction of exocytic fusion in a nociceptive sensory afferent cell, comprising:

(i) a Targeting Moiety (TM),
wherein said TM is an agonist of a receptor present on said nociceptive sensory afferent cell, and wherein said receptor undergoes endocytosis to be incorporated into an endosome within the nociceptive sensory afferent cell;

(ii) a non-cytotoxic protease or a fragment thereof,
wherein the protease or protease fragment is capable of cleaving a protein of the exocytic fusion apparatus of said nociceptive sensory afferent cell; and (iii) a Translocation Domain,
wherein the Translocation Domain translocates the protease or protease fragment from within the endosome, across the endosomal membrane, and into the cytosol of the nociceptive sensory afferent cell.

BRIEF DESCRIPTION OF THE DRAWINGS

SDS-PAGE analysis of expression and purification of $recLH_N/B$ from *E. coli*. In FIG. 1, $recLH_N/B$ is purified from cell paste using a three column strategy as described in Example 3. Protein samples are separated by SDS-PAGE and visualised by staining with simplyblue safestain coomassie reagent. Crude, soluble $MBP-LH_N/B$ fusion protein contained within the clarified extract (lane 2) is loaded onto Q-Sepharose FF anion-exchange resin. Lane 3 represents recombinant $MBP-LH_N/B$ fusion eluted from column at 150-200 mM salt. This sample is treated with factor Xa protease to remove MBP affinity tag (lane 4), and cleaved mixture diluted to lower salt concentration prior to loading onto a Q-Sepharose FF anion-exchange column. Material eluted between 120-170 mM salt was rich in $LH_N/B$ (lane 5). Protein in lanes 6 and 8 represents $LH_N/B$ harvested after treatment with enterokinase and final purification using Benzamidine Sepharose, under non-reducing and reducing conditions respectively. Lanes 1 and 7 represent molecular mass markers [Mark 12 (Invitrogen)].

SDS-PAGE analysis of expression and purification of $LH_N/C$ from *E. coli*. In FIG. 2, $recLH_N/C$ is purified from *E. coli* cell paste using a two-step strategy described in Example 4. Protein samples are separated by SDS-PAGE and visualised by staining with coomassie blue. Clarified Crude cell lysate (lane 2) is loaded onto Q-Sepharose FF anion-exchange resin. Fusion protein, $MBP-LH_N/C$ is eluted with 0.1 M NaCl (lane 3). Eluted material incubated at 22° C. for 16 h with factor Xa protease (New England Biolabs) to cleave fusion tag MBP and nick $recLH_N/C$ at the linker site. The protein of interest is further purified from cleaved fusion products (lane 4) using Q-Sepharose FF. Lanes 5 and 7 show purified $recLH_N/C$ under non-reducing conditions and reduced with 10 mM DTT respectively, to illustrate disulphide bonding at the linker region between LC and $H_N$ domains after nicking with factor Xa. Lanes 1 and 6 represent molecular mass markers (shown in KDa); Mark 12 (Invitrogen).

SDS-PAGE analysis of expression and purification of $N[1-17]-LH_N/A$ from *E. coli*. In FIG. 3, $N[1-17]-LH_N/A$ is purified from *E. coli* BL21 cell paste using the methodology outlined in Example 9. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

Using the methodology outlined in Example 26, a $LC/A-nociceptin-H_N/A$ fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

Figure 5:
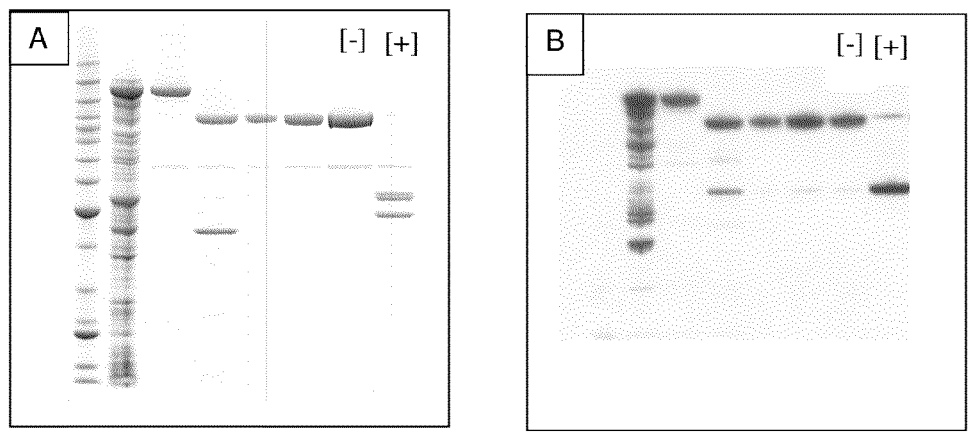

FIG. 5—Purification of a $nociceptin-LC/A-H_N/A$ fusion protein

Using the methodology outlined in Example 26, a $nociceptin-LC/A-H_N/A$ fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

Figure 6:
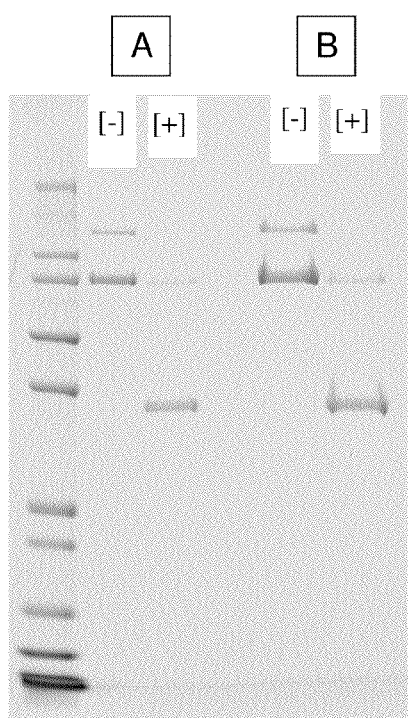

FIG. 6—Purification of a $LC/C-nociceptin-H_N/C$ fusion protein

Using the methodology outlined in Example 26, an $LC/C-nociceptin-H_N/C$ fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

Figure 7:
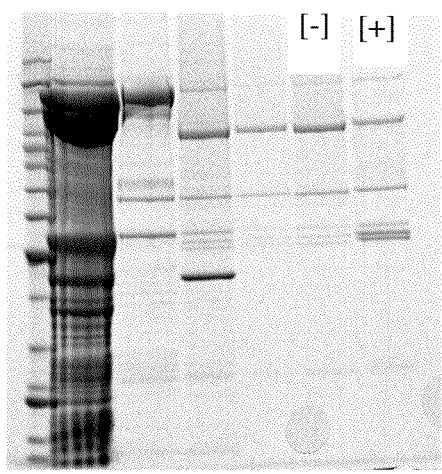

FIG. 7—Purification of a LC/A-met enkephalin-$H_N$/A fusion protein

Using the methodology outlined in Example 26, an LC/A-met enkephalin-$H_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

Figure 8:
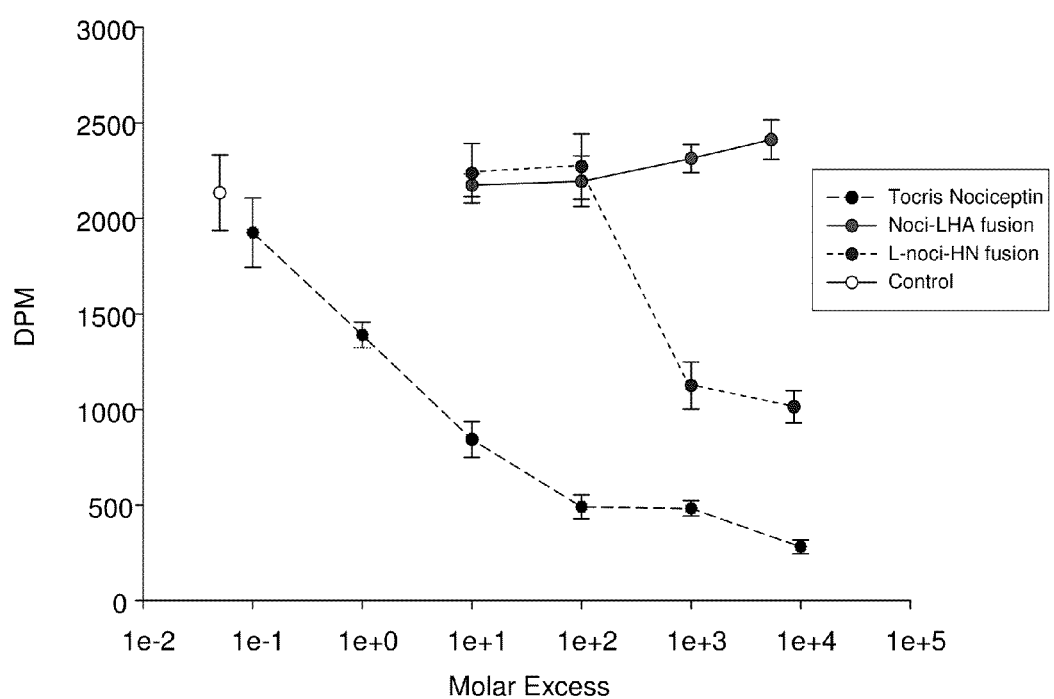

FIG. 8—Comparison of binding efficacy of a LC/A-nociceptin-$H_N$/A fusion protein and a nociceptin-LC/A-$H_N$/A fusion protein The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin-$H_N$/A fusion is far superior to the nociceptin-LC/A-$H_N$/A fusion at interacting with the $ORL_1$ receptor.

Figure 9:
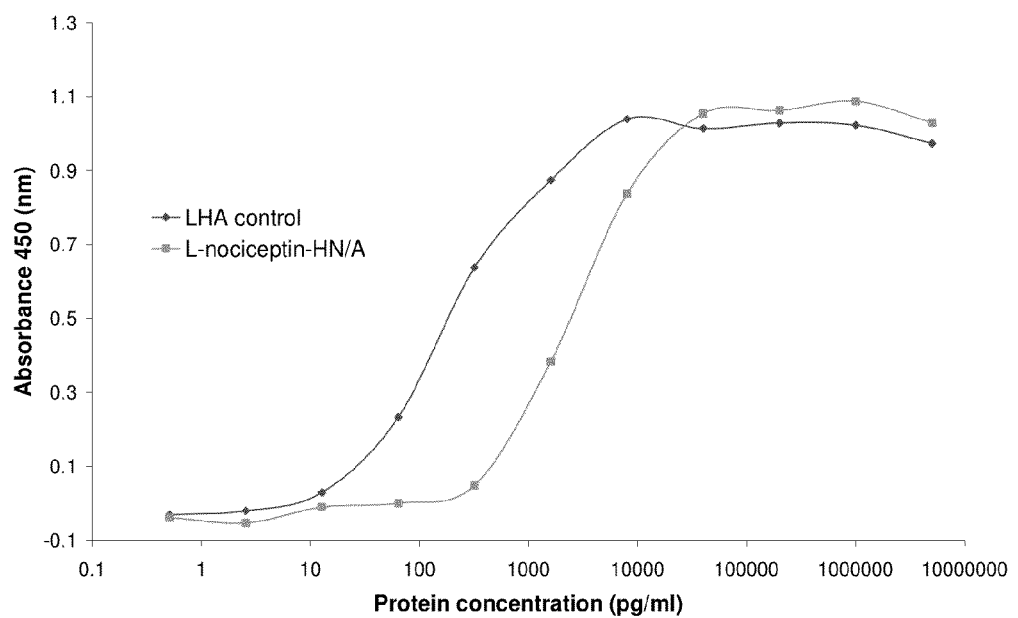

FIG. 9—In vitro catalytic activity of a LC/A-nociceptin-$H_N$/A fusion protein

The in vitro endopeptidase activity of the purified LC/A-nociceptin-$H_N$/A fusion protein was determined essentially as described in Chaddock et al 2002, Prot. Express Purif. 25, 219-228. Briefly, SNAP-25 peptide immobilised to an ELISA plate was exposed to varying concentrations of fusion protein for 1 hour at 37° C. Following a series of washes, the amount of cleaved SNAP-25 peptide was quantified by reactivity with a specific antisera.

Figure 10:
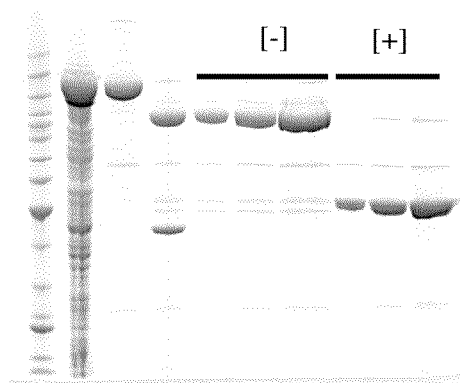

FIG. 10—Purification of a LC/A-nociceptin variant-$H_N$/A fusion protein

Using the methodology outlined in Example 26, an LC/A-nociceptin variant-$H_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

FIG. 11—comparison of binding efficacy of a LC/A-nociceptin-$H_N$/A fusion protein and a LC/A-nociceptin variant-$H_N$/A fusion protein The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin variant-$H_N$/A fusion (CPNv-LHA) is superior to the LC/A-nociceptin variant-$H_N$/A fusion (CPN-LHA) at interacting with the $ORL_1$ receptor.

Figure 12:
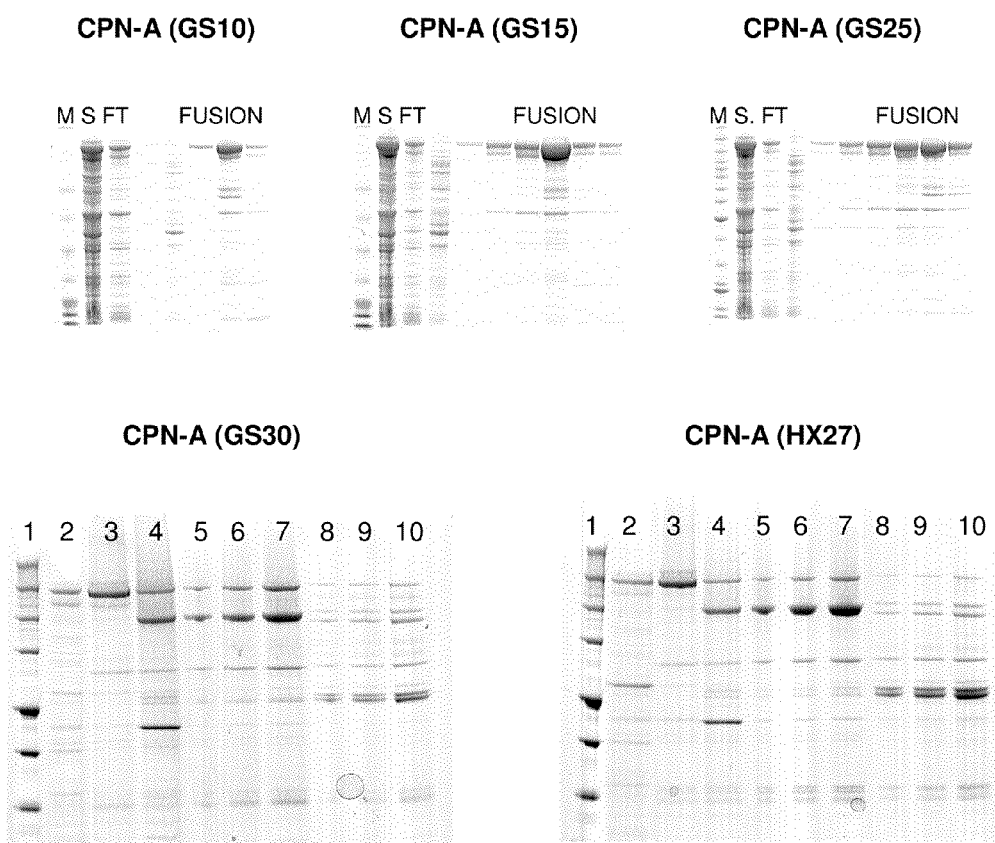

FIG. 12—Expressed/purified LC/A-nociceptin-$H_N$/A fusion protein family with variable spacer length product(s)

Using the methodology outlined in Example 26, variants of the LC/A-CPN-$H_N$/A fusion consisting of GS10, GS30 and HX27 are purified from *E. coli* cell paste. Samples from the purification of LC/A-CPN(GS10)-$H_N$/A, LC/A-CPN(GS15)-$H_N$/A, LC/A-CPN(GS25)-$H_N$/A, LC/A-CPN(GS30)-$H_N$/A and LC/A-CPN(HX27)-$H_N$/A were assessed by SDS-PAGE prior to staining with Coomassie Blue. The electrophoresis profile indicates purification of a disulphide-bonded di-chain species of the expected molecular mass of CPBE-A. Top panel: M=benchmark molecular mass markers; S=total *E. coli* protein soluble fraction; FT=proteins that did not bind to the $Ni^{2+}$-charged Sepharose column; FUSION=fusion protein eluted by the addition of imidazole. Bottom panel: Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified final material post activation with Factor Xa (5 µl); Lane 6=purified final material post activation with Factor Xa (10 µl); Lane 7=purified final material post activation with Factor Xa (20 µl); Lane 8=purified final material post activation with Factor Xa+DTT (5 µl); Lane 9=purified final material post activation with Factor Xa+DTT (10 µl); Lane 10=purified final material post activation with Factor Xa+DTT (20 µl).

Figure 13:
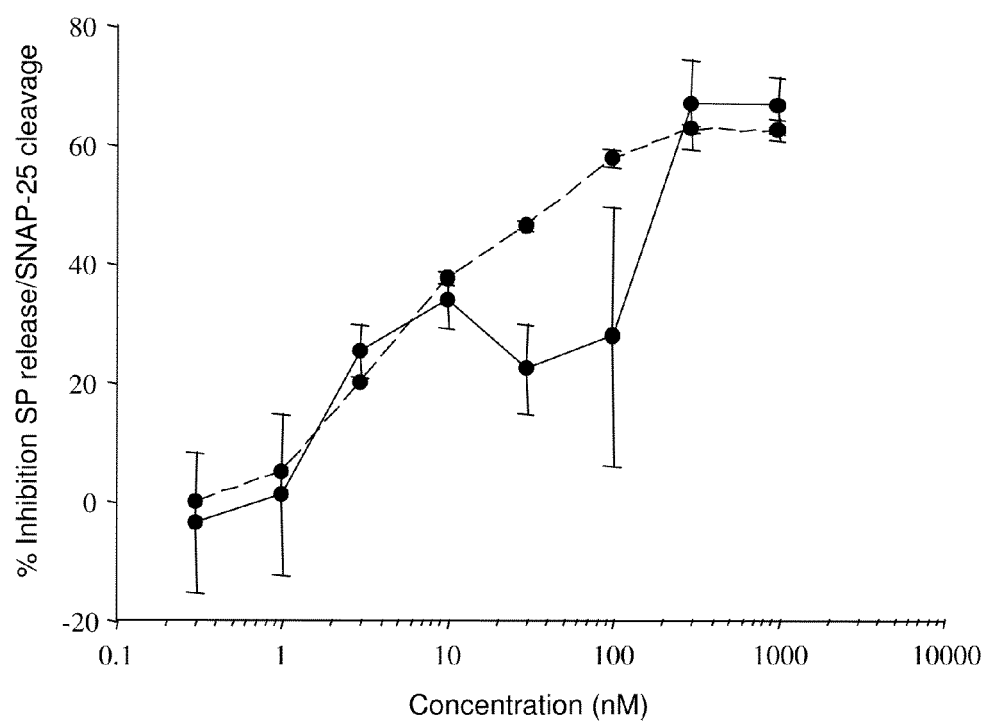

FIG. 13—Inhibition of SP release and cleavage of SNAP-25 by CPN-A

Briefly, primary cultures of dorsal root ganglia (DRG) were exposed to varying concentrations of CPN-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis and plotted against fusion concentration (dashed line). Material was also recovered for an analysis of substance P content using a specific EIA kit. Inhibition of substance P release is illustrated by the solid line. The fusion concentration required to achieve 50% maximal SNAP-25 cleavage is estimated to be 6.30±2.48 nM.

Figure 14:
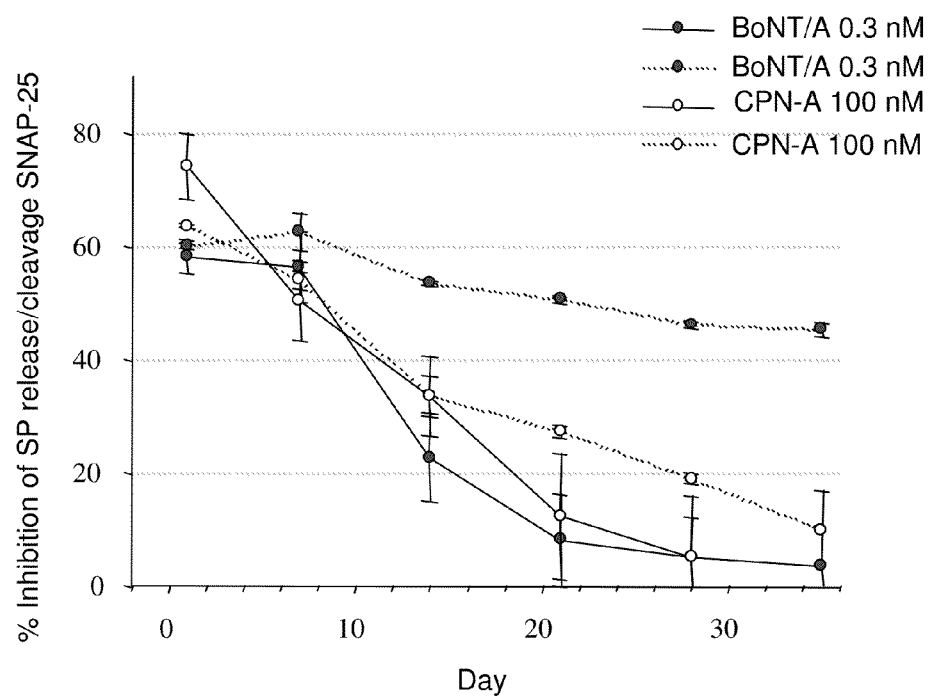

FIG. 14—Inhibition of SP release and cleavage of SNAP-25 over extended time periods after exposure of DRG to CPN-A Primary cultures of dorsal root ganglia (DRG) were exposed to varying concentrations of CPN-A for 24 hours. Botulinum neurotoxin (BoNT/A) was used as a control. After this initial exposure, extracellular material was removed by washing, and the cells incubated at 37° C. for varying periods of time. At specific time points, cellular proteins were separated by SDS-PAGE, Western blotted, and probed with anti-SNAP-25 to facilitate an assessment of SNAP-25 cleavage. The percentage of cleaved SNAP-25 was calculated by densitometric analysis and illustrated by the dotted lines. Material was also recovered for an analysis of substance P content using a specific EIA kit. Inhibition of substance P release is illustrated by the solid lines.

Figure 15:
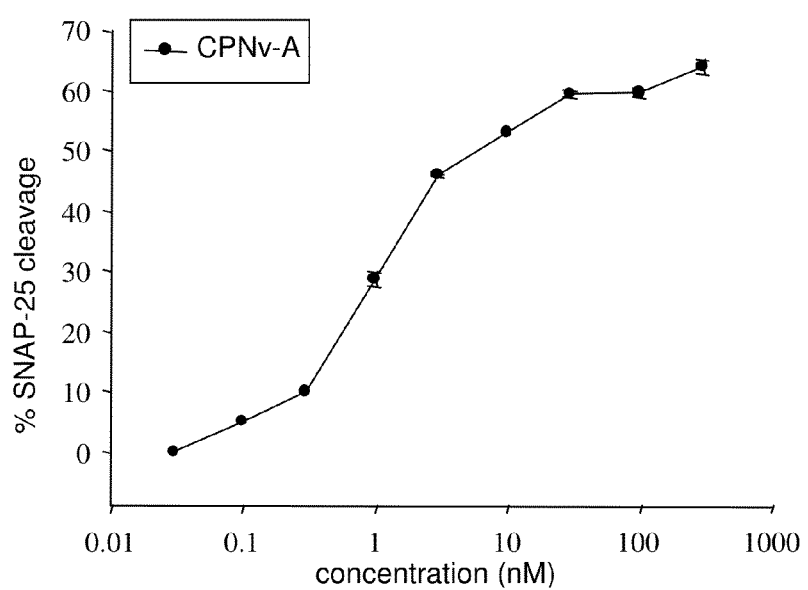

FIG. 15—Cleavage of SNAP-25 by CPNv-A

Primary cultures of dorsal root ganglia (DRG) were exposed to varying concentrations of CPNv-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The fusion concentration required to achieve 50% maximal SNAP-25 cleavage is estimated to be 1.38±0.36 nM.

Figure 16:
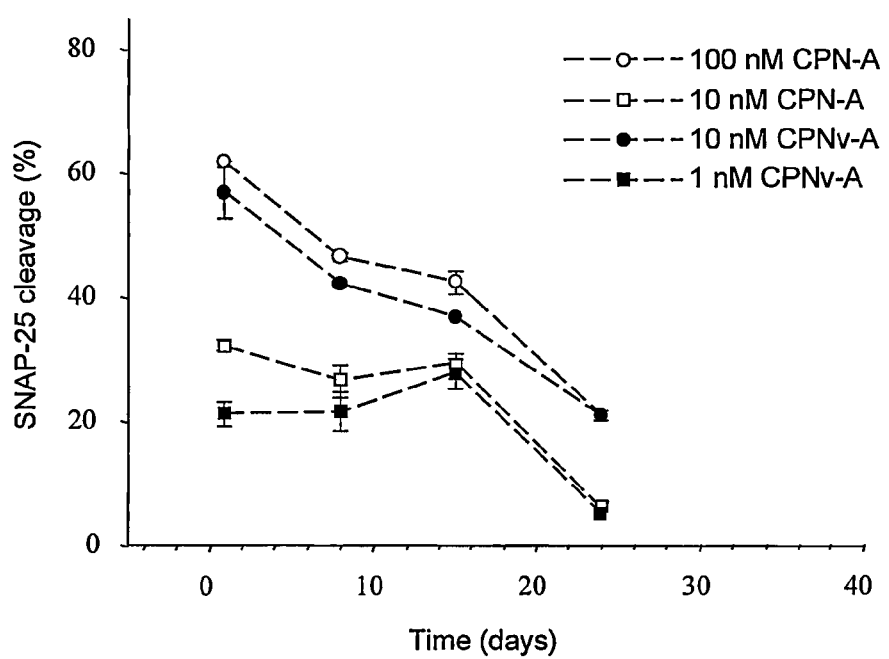

FIG. 16—Cleavage of SNAP-25 over extended time periods after exposure of DRG to CPNv-A Primary cultures of dorsal root ganglia (DRG) were exposed to varying concentrations of CPNv-A for 24 hours. CPN-A was used as a control. After this initial exposure, extracellular material was removed by washing, and the cells incubated at 37° C. for varying periods of time. At specific time points, cellular proteins were separated by SDS-PAGE, Western blotted, and probed with anti-SNAP-25 to facilitate an assessment of SNAP-25 cleavage. The percentage of cleaved SNAP-25 was calculated by densitometric analysis.

Figure 17:
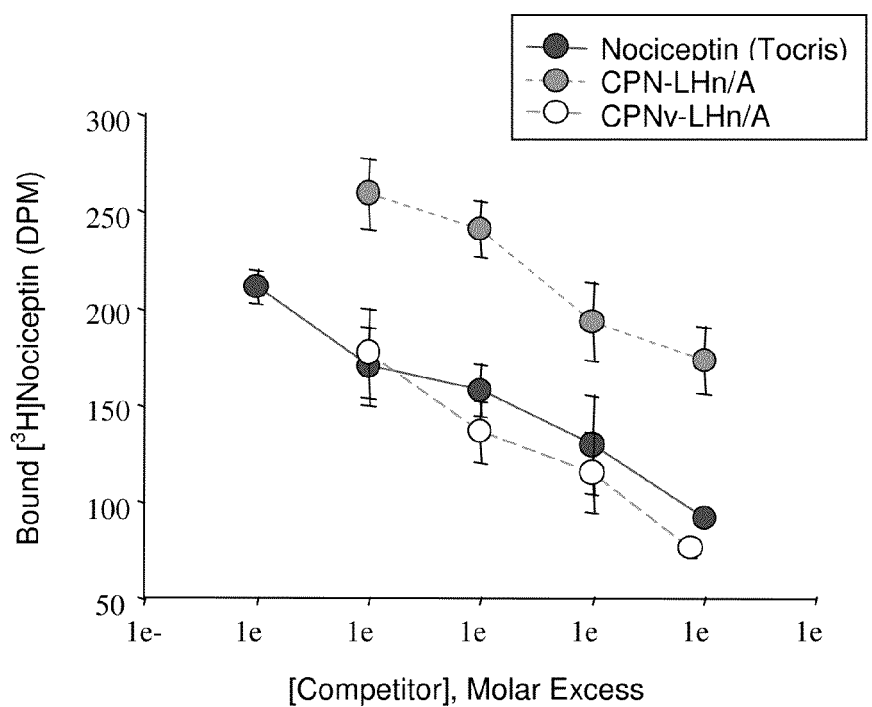

FIG. 17—CPNv-A fusion-mediated displacement of [3H]-nociceptin binding

The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin variant-$H_N$/A fusion (labelled as CPNv-LHnA) is superior to the LC/A-nociceptin-$H_N$/A fusion (labelled as CPN-LHnA) at interacting with the $ORL_1$ receptor.

Figure 18:
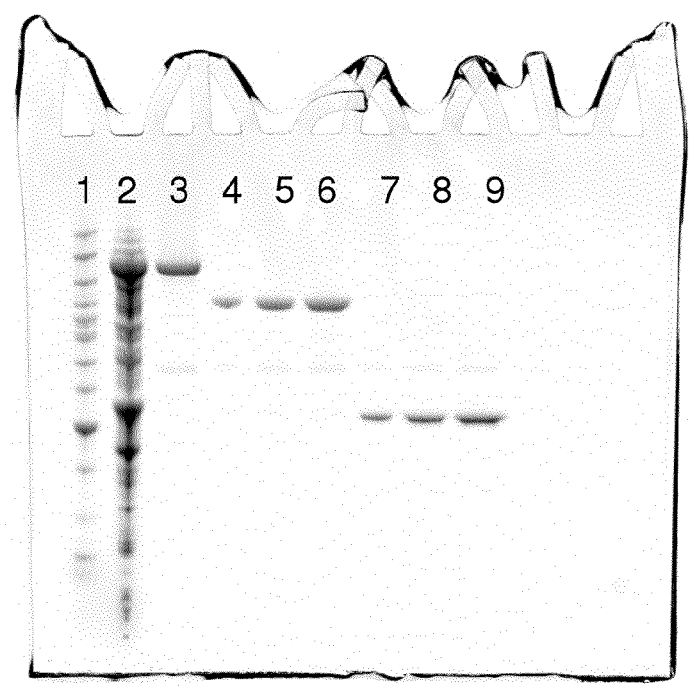

FIG. 18—Expressed/purified CPNv(Ek)-A product

Proteins were subjected to SDS-PAGE prior to staining with Coomassie Blue. The electrophoresis profile indicates purification of a disulphide-bonded di-chain species of the expected molecular mass of CPNv(Ek)-A. Lane 1=benchmark molecular mass markers; Lane 2=total *E. coli* protein soluble fraction; Lane 3=purified material following initial capture on $Ni^{2+}$-charged Sepharose; Lane 4=purified final material post activation with enterokinase (5 µl); Lane 5=purified final material post activation with enterokinase (10 µl); Lane 6=purified final material post activation with enterokinase (20 µl); Lane 7=purified final material post activation with enterokinase+DTT (5 µl); Lane 8=purified final material post activation with enterokinase+DTT (10 µl); Lane 9=purified final material post activation with enterokinase+DTT (20 µl).

Figure 19:
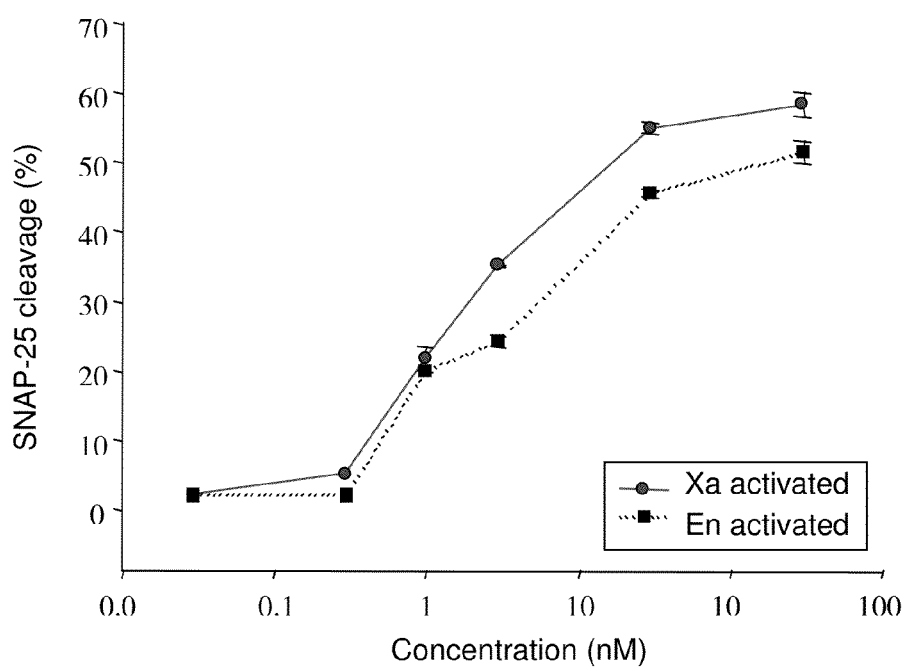

FIG. 19—Cleavage of SNAP-25 by CPNv(Ek)-A

Primary cultures of dorsal root ganglia (DRG) were exposed to varying concentrations of CPNv(Ek)-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. CPNv-A as prepared in Example 26 was used for comparison purposes. The percentage cleavage of SNAP-25 by CPNv(Ek)-A (labelled as En activated) and CPNv-A (labelled as Xa activated) are illustrated.

Figure 20:
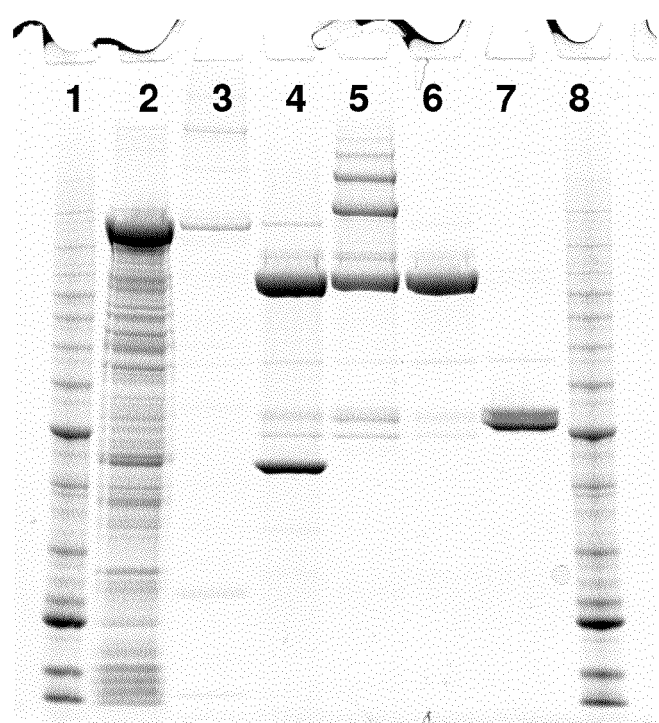

FIG. 20—Expressed/purified CPNv-C product

Proteins were subjected to SDS-PAGE prior to staining with Coomassie Blue. The electrophoresis profile indicates purification of a disulphide-bonded di-chain species of the expected molecular mass of CPNv-C. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified material following second capture on $Ni^{2+}$-charged Sepharose; Lane 6=final purified material; Lane 7=final purified material+DTT; Lane 8=benchmark molecular mass markers.

Figure 21:
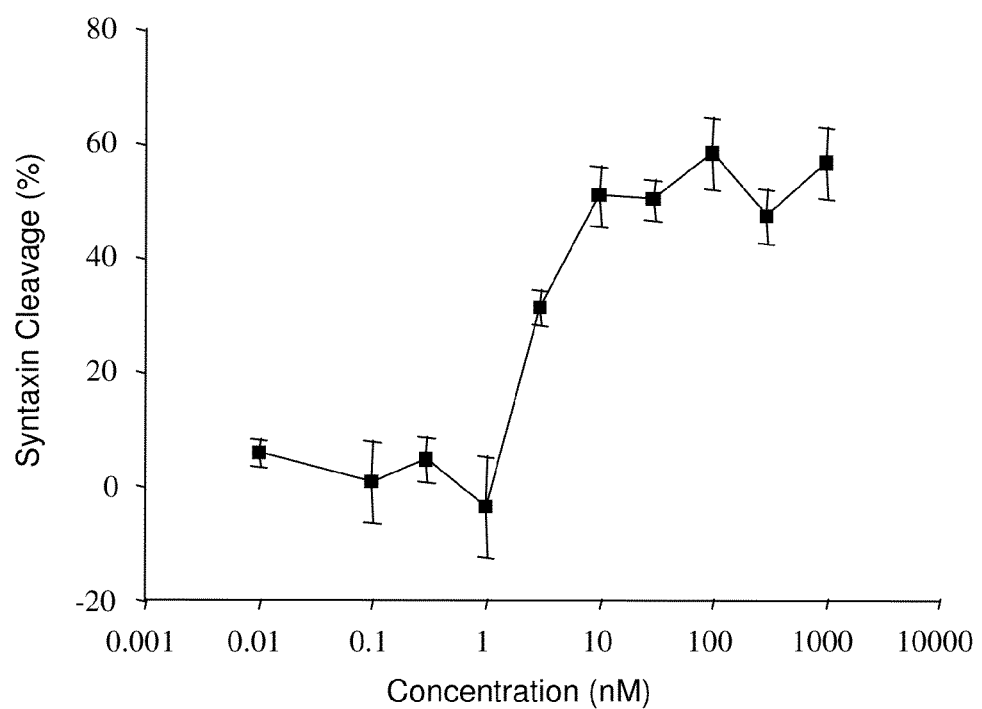

FIG. 21—Cleavage of syntaxin by CPNv-C

Primary cultures of dorsal root ganglia (DRG) were exposed to varying concentrations of CPNv-C for 24 hours. Cellular proteins were separated by SDS-PAGE, Western blotted, and probed with anti-syntaxin to facilitate an assessment of syntaxin cleavage. The percentage of cleaved syntaxin was calculated by densitometric analysis. The fusion concentration required to achieve 50% maximal syntaxin cleavage is estimated to be 3.13±1.96 nM.

Figure 22:
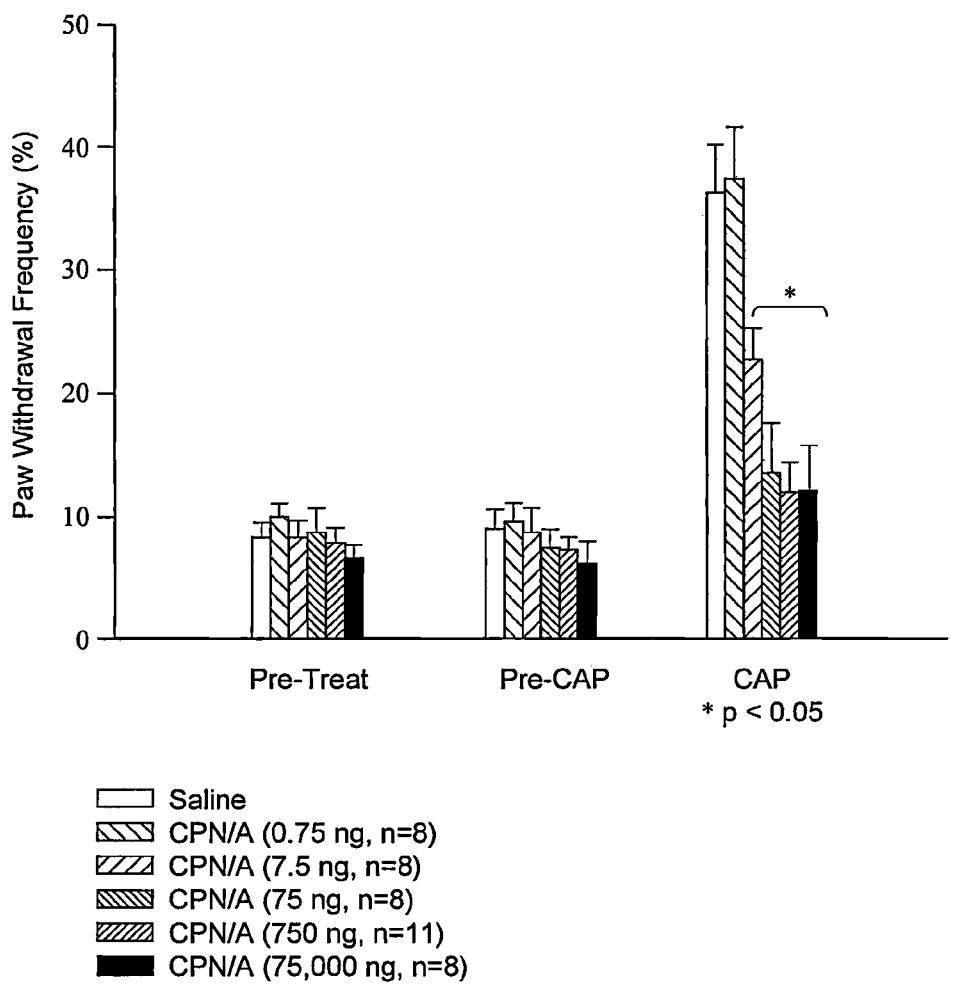

FIG. 22—CPN-A efficacy in the acute capsaicin-induced Mechanical Allodynia model The ability of an LC/A-nociceptin-$H_N$/A fusion (CPN/A) to inhibit capsaicin-induced mechanical allodynia was evaluated following subcutaneous intraplantar injection in the rat hind paw. Test animals were evaluated for paw withdrawal frequency (PWF %) in response to a 10 g Von Frey filament stimulus series (10 stimuli×3 trials) prior to recruitment into the study (Pre-Treat); after subcutaneous intraplantar treatment with CPN/A but before capsaicin (Pre-CAP); and following capsaicin challenge post-injection of CPN/A (average of responses at 15' and 30'; CAP). Capsaicin challenge was achieved by injection of 10 µL of a 0.3% solution. Sample dilutions were prepared in 0.5% BSA/saline.

Figure 23:
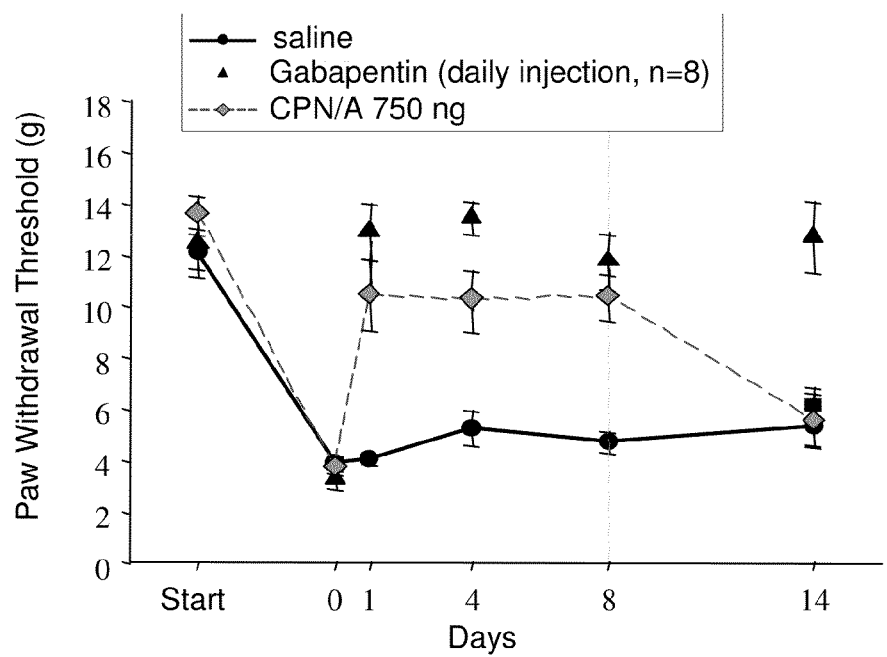

FIG. 23—CPN-A efficacy in the Streptozotocin (STZ)-Induced Peripheral Diabetic Neuropathy (Neuropathic Pain) model Male Sprague-Dawley rats (250-300 g) are treated with 65 mg/kg STZ in citrate buffer (I.V.) and blood glucose and lipid are measured weekly to define the readiness of the model. Paw Withdrawal Threshold (PWT) is measured in response to a Von Frey filament stimulus series over a period of time. Allodynia is said to be established when the PWT on two consecutive test dates (separated by 1 week) measures below 6 g on the scale. At this point, rats are randomized to either a saline group (negative efficacy control), gabapentin group (positive efficacy control) or a test group (CPN/A). Test materials (20-25 µl) are injected subcutaneously as a single injection (except gabapentin) and the PWT is measured at 1 day post-treatment and periodically thereafter over a 2 week period. Gabapentin (30 mg/kg i.p. @ 3 ml/kg injection volume) is injected daily, 2 hours prior to the start of PWT testing.

Figure 24:
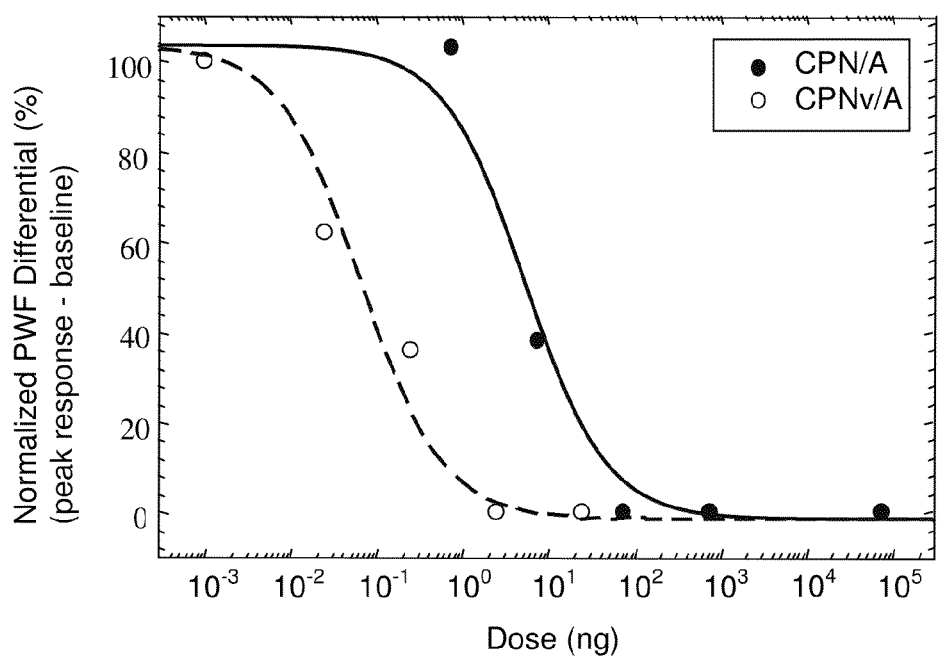

FIG. 24—CPNv-A efficacy in the Acute Capsaicin-Induced Mechanical Allodynia model The ability of an LC/A-nociceptin variant-$H_N$/A fusion (CPNv/A) to inhibit capsaicin-induced mechanical allodynia was evaluated following subcutaneous intraplantar injection in the rat hind paw. Test animals were evaluated for paw withdrawal frequency (PWF %) in response to a 10 g Von Frey filament stimulus series (10 stimuli×3 trials) prior to recruitment into the study (Pre-Treat), after subcutaneous intraplantar treatment with CPNv/A but before capsaicin (Pre-CAP), and following capsaicin challenge post-injection of CPNv/A (average of responses at 15' and 30'; CAP). Capsaicin challenge was achieved by injection of 10 µL of a 0.3% solution. Sample dilutions were prepared in 0.5% BSA/saline. These data are expressed as a normalized paw withdrawal frequency differential, in which the difference between the peak response (post-capsaicin) and the baseline response (pre-capsaicin) is expressed as a percentage. With this analysis, it can be seen that CPNv/A is more potent than CPN/A since a lower dose of CPNv/A is required to achieve similar analgesic effect to that seen with CPN/A.

Figure 25:
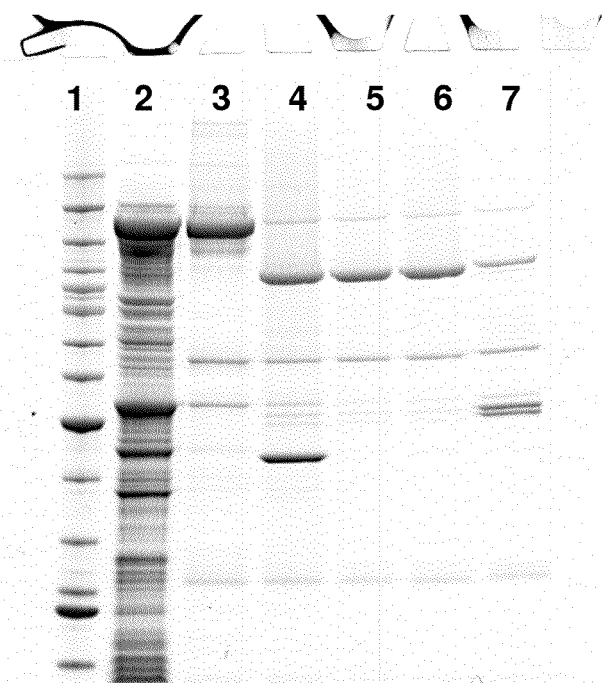

FIG. 25—Expressed/purified LC/A-CPLE-$H_N$/A product

Proteins were subjected to SDS-PAGE prior to staining with Coomassie Blue. The electrophoresis profile indicates purification of a disulphide-bonded di-chain species of the expected molecular mass of CPLE-A. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified material following second capture on $Ni^{2+}$-charged Sepharose; Lane 6=final purified material; Lane 7=final purified material+DTT.

Figure 26:
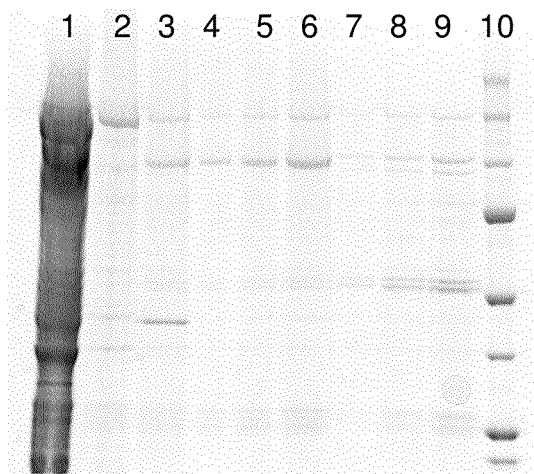

FIG. 26—Expressed/purified LC/A-CPBE-$H_N$/A product

Proteins were subjected to SDS-PAGE prior to staining with Coomassie Blue. The electrophoresis profile indicates purification of a disulphide-bonded di-chain species of the expected molecular mass of CPBE-A. Lane 1=total E. coli protein soluble fraction; Lane 2=purified material following initial capture on $Ni^{2+}$-charged Sepharose; Lane 3=Factor Xa treated material prior to final capture on $Ni^{2+}$-charged Sepharose; Lane 4=purified final material post activation with Factor Xa (5 μl); Lane 5=purified final material post activation with Factor Xa (10 μl); Lane 6=purified final material post activation with Factor Xa (20 μl); Lane 7=purified final material post activation with Factor Xa+DTT (5 μl); Lane 8=purified final material post activation with Factor Xa+DTT (10 μl); Lane 9=purified final material post activation with Factor Xa+DTT (20 μl); Lane 10=benchmark molecular mass markers.

Figure 27:
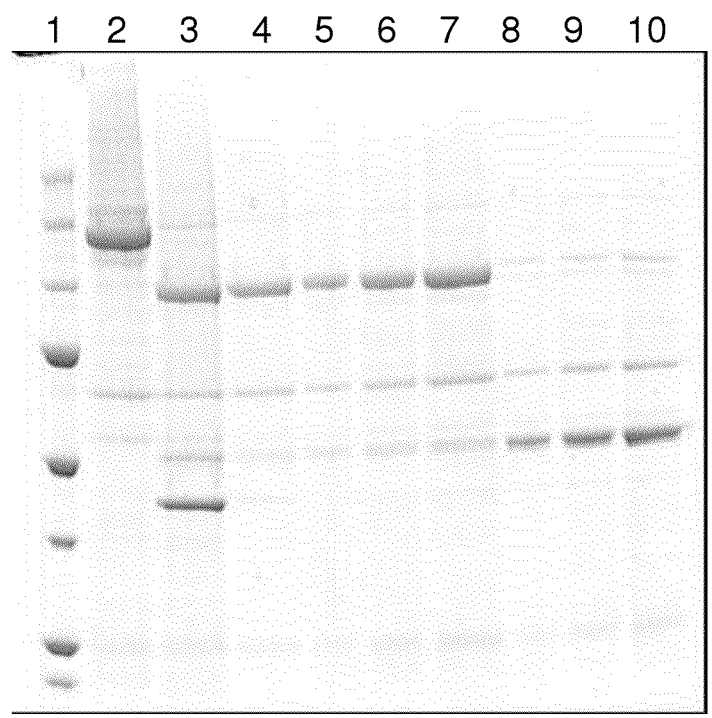

FIG. 27—Expressed/purified CPOP-A product

Proteins were subjected to SDS-PAGE prior to staining with Coomassie Blue. The electrophoresis profile indicates purification of a disulphide-bonded di-chain species of the expected molecular mass of CPOP-A. Lane 1=benchmark molecular mass markers; Lane 2=purified material following initial capture on $Ni^{2+}$-charged Sepharose; Lane 3=Factor Xa treated material prior to final capture on $Ni^{2+}$-charged Sepharose; Lane 4=purified material following second capture on $Ni^{2+}$-charged Sepharose; Lane 5=purified final material post activation with Factor Xa (5 μl); Lane 6=purified final material post activation with Factor Xa (10 μl); Lane 7=purified final material post activation with Factor Xa (20 μl); Lane 8=purified final material post activation with Factor Xa+DTT (5 μl); Lane 9=purified final material post activation with Factor Xa+DTT (10 μl); Lane 10=purified final material post activation with Factor Xa+DTT (20 μl).

Figure 28:

FIG. 28—Expressed/purified CPOPv-A product

Proteins were subjected to SDS-PAGE prior to staining with Coomassie Blue. The electrophoresis profile indicates purification of a disulphide-bonded di-chain species of the expected molecular mass of CPOPv-A. Lane 1=benchmark molecular mass markers; Lane 2=total E. coli protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified final material post activation with Factor Xa (5 μl); Lane 6=purified final material post activation with Factor Xa (10 μl); Lane 7=purified final material post activation with Factor Xa (20 μl); Lane 8=purified final material post activation with Factor Xa+DTT (5 μl); Lane 9=purified final material post activation with Factor Xa+DTT (10 μl); Lane 10=purified final material post activation with Factor Xa+DTT (20 μl).

Figure 29:
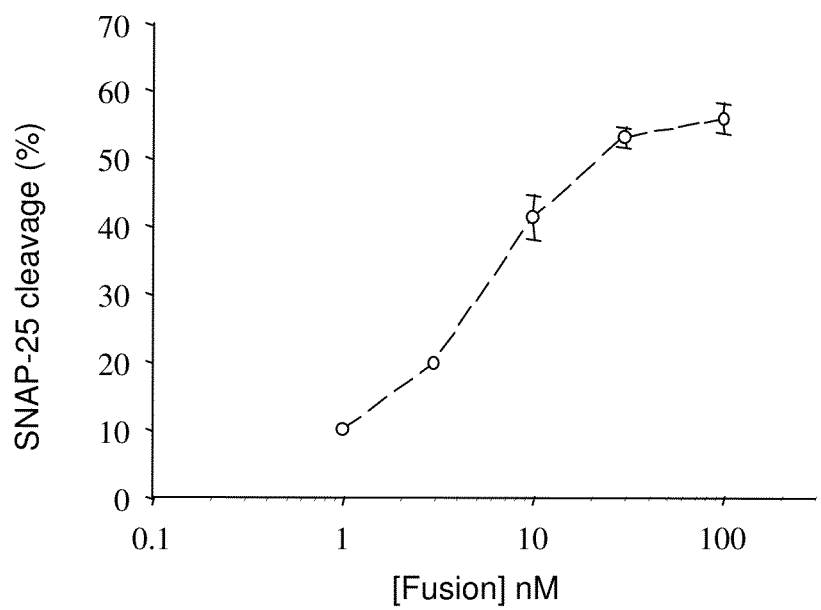

FIG. 29—In vitro SNAP-25 cleavage in a DRG cell model

Primary cultures of dorsal root ganglia (DRG) were exposed to varying concentrations of CPOPv-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis.

Figure 30:
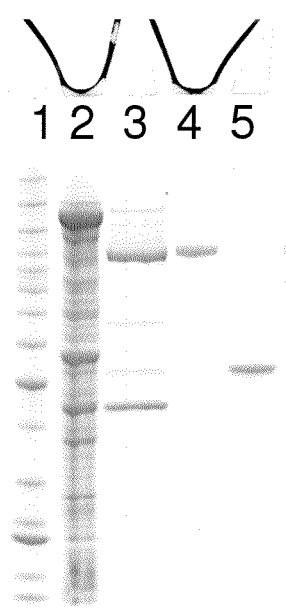

FIG. 30—Expressed/purified CPNv-A-FXa-HT (removable his-Tag)

Proteins were subjected to SDS-PAGE prior to staining with Coomassie Blue. The electrophoresis profile indicates purification of a disulphide-bonded di-chain species of the expected molecular mass of CPNv-A-FXa-HT. Lane 1=benchmark molecular mass markers; Lane 2=total E. coli protein soluble fraction; Lane 3=Factor Xa treated material prior to final capture on $Ni^{2+}$-charged Sepharose; Lane 4=purified final material post activation with Factor Xa; Lane 5=purified final material post activation with Factor Xa+DTT.

Figure 31:
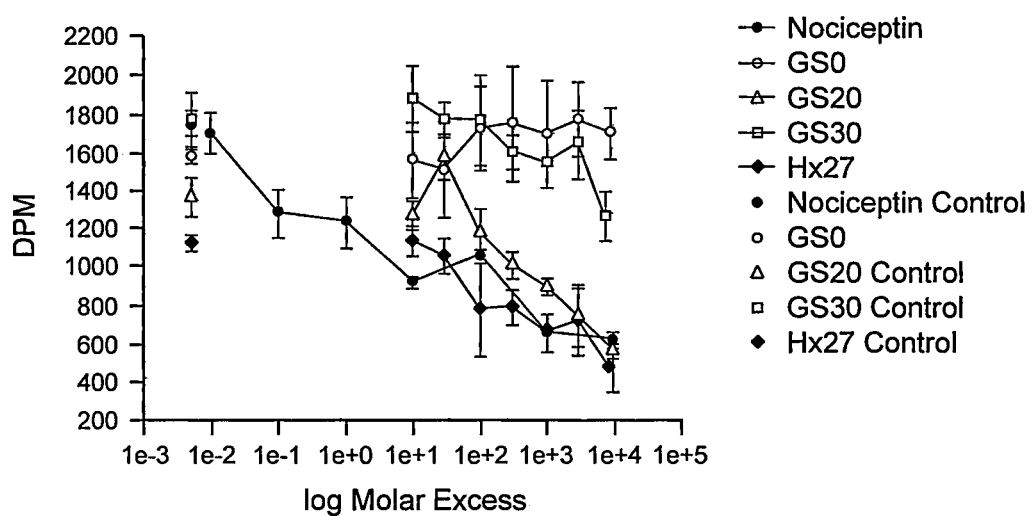
Figure 31:
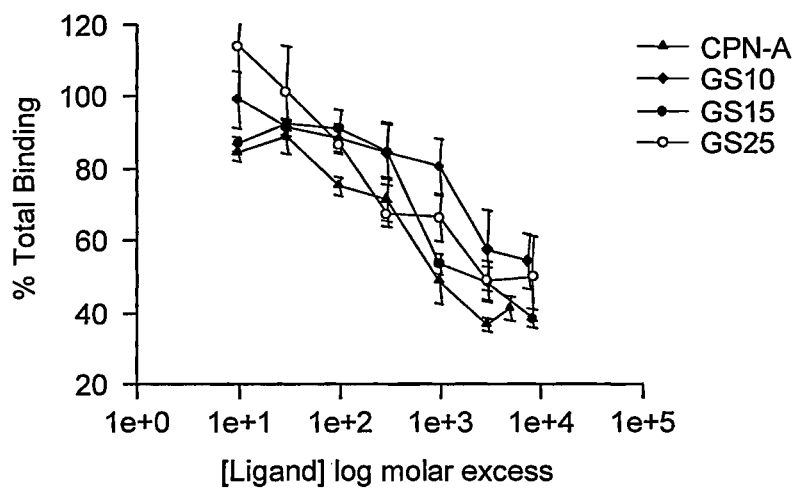

FIG. 31—In vitro efficacy of LC/A-nociceptin-$H_N$/A fusion proteins with variable spacer length, as assessed by ligand competition assay The ability of LC/A-nociceptin-$H_N$/A fusions of variable spacer length to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). The upper panel illustrates the displacement characteristics of the GS0, GS20, GS30 and Hx27 spacers, whilst the lower panel illustrates the displacement achieved by the GS10, GS15 and GS25 spaced fusion proteins. It is concluded that the GS0 and GS30 spacers are ineffective, and the GS10 is poorly effective, at displacing nociceptin from the ORL1 receptor.

Figure 32:
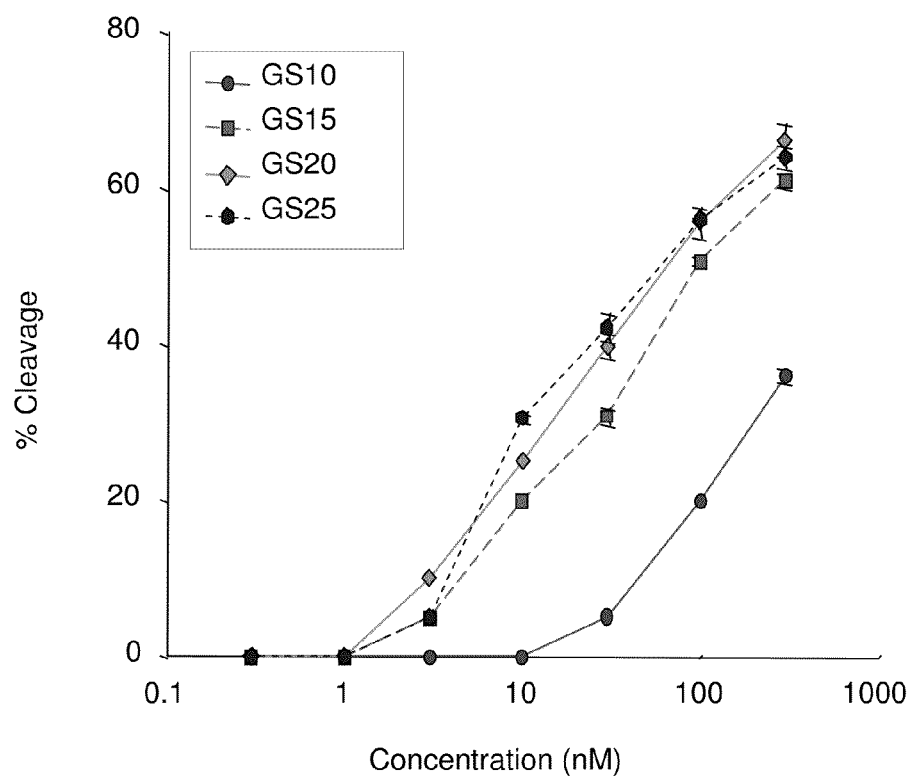

FIG. 32—In vitro efficacy of LC/A-nociceptin-$H_N$/A fusion proteins with variable spacer length, as assessed by in vitro SNAP-25 cleavage Primary cultures of dorsal root ganglia (DRG) were exposed to varying concentrations of CPN-A (of variable spacer length) for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The poorly effective binding characteristics of the GS10 spaced fusion protein (see FIG. 28) are reflected in the higher concentrations of fusion required to achieve cleavage of intracellular SNAP-25. G50 and GS30 spaced fusion proteins were completely ineffective (date not shown). GS15, 20 and 25 spaced fusion proteins were similarly effective.

Figure 33:
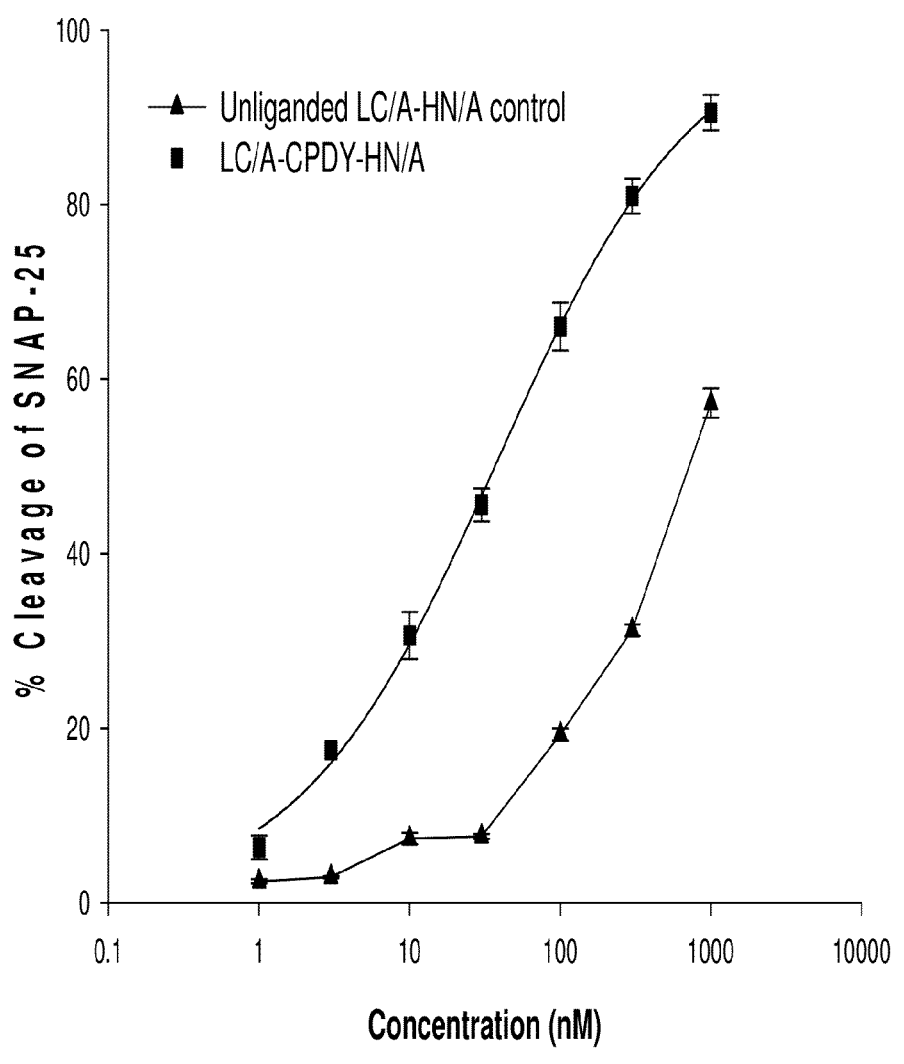

FIG. 33—Cleavage of SNARE protein by dynorphin conjugates in embryonic spinal cord neurons (eSCNs)

Embryonic spinal cord neurons were exposed to varying concentrations of dynorphin conjugates of the present invention for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. It is clear that LC/A-dynorphin-$H_N$/A fusion is more potent than an unliganded LC/A-$H_N$/A control molecule. The concentration of LC/A-dynorphin-$H_N$/A fusion required to achieve 50% maximal SNAP-25 cleavage is estimated to be 35.3 nM and the concentration for the LC/A-$H_N$/A control required to achieve 50% maximal SNAP-25 cleavage could not be determined due to it's low potency.

Figure 34:
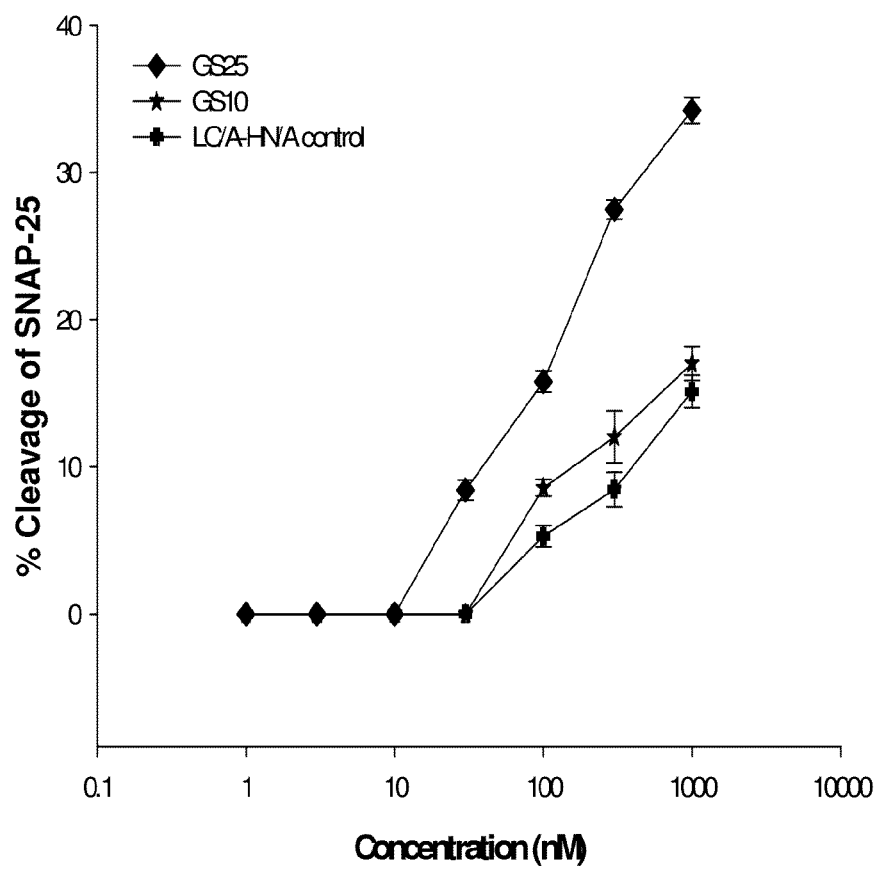
Figure 35:
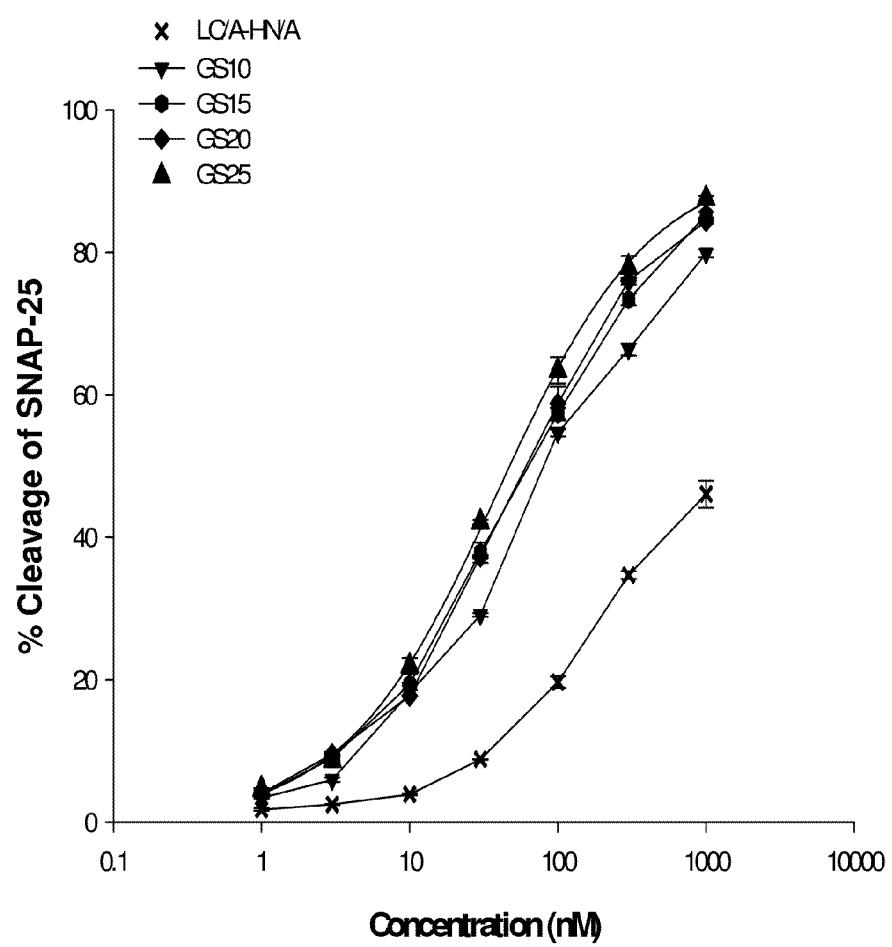
Figure 36:
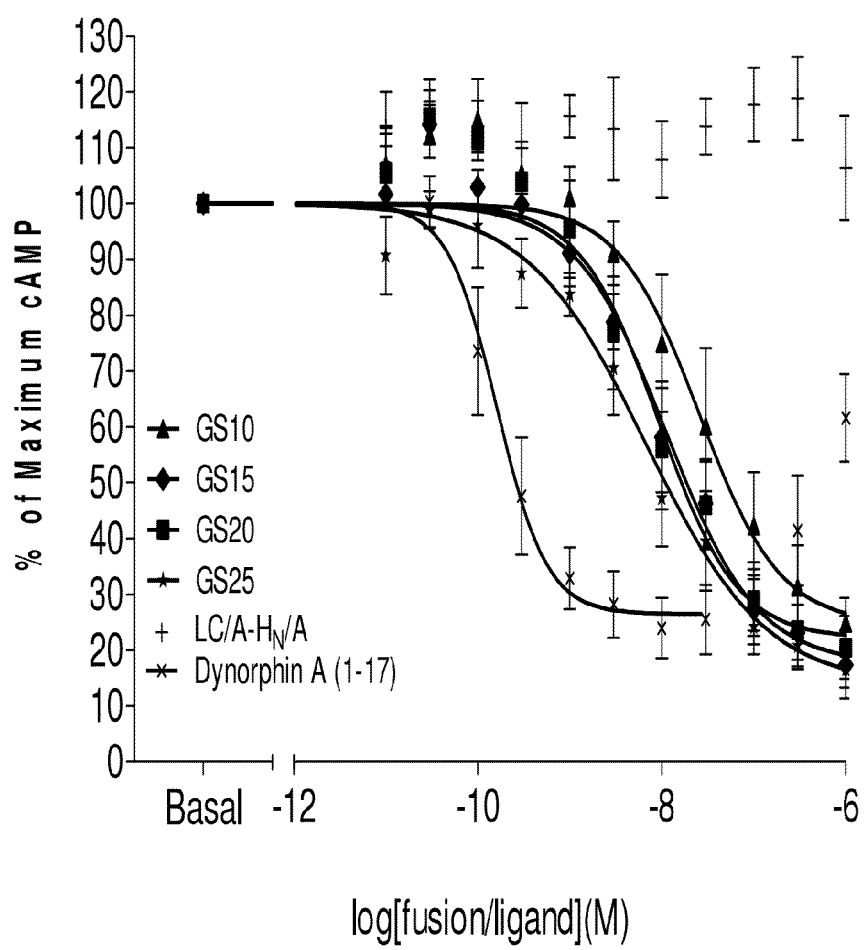
Figure 37:
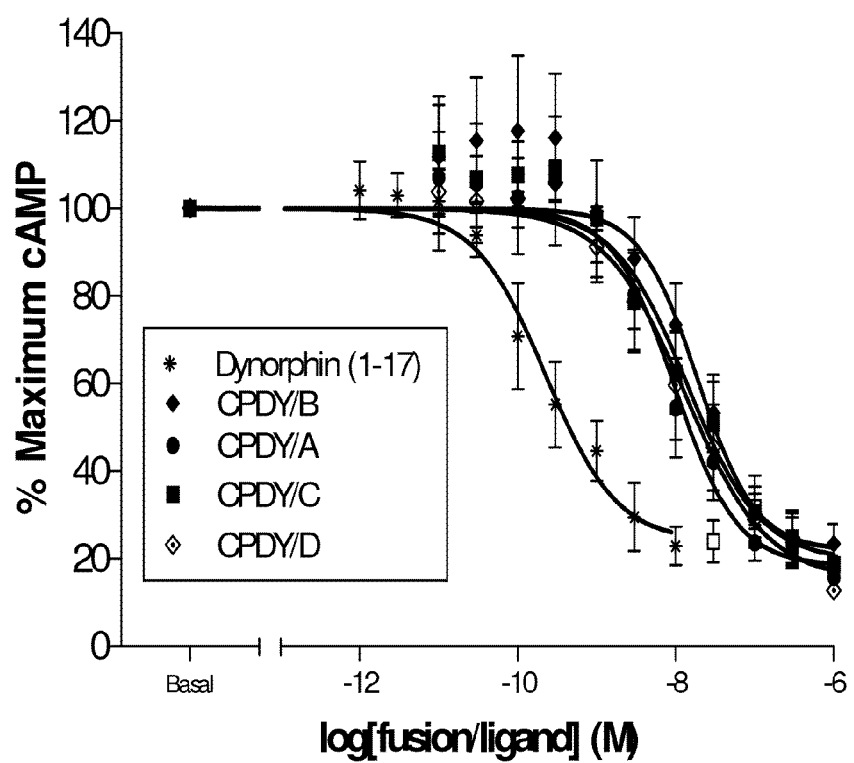

FIG. 34—Cleavage of SNARE protein by dynorphin conjugates in Chinese hamster ovary cells (CHO-K1 cells) transfected with OP2 receptor and SNAP-25

Chinese hamster ovary (CHO) cells were transfected so that they express the OP2 receptor. Said cells were further transfected to express a SNARE protein (SNAP-25). The transfected cells were exposed to varying concentrations of different dynorphin conjugates for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. It is clear that LC/A-CPDY-$H_N$/A conjugates are more potent than the unliganded LC/A-$H_N$/A control molecule (labelled as LC/A-$H_N$/A).

FIG. 35—Cleavage of SNARE protein by dynorphin conjugates in embryonic spinal cord neurons (eSCNs)

Embryonic spinal cord neurons were exposed to varying concentrations of dynorphin conjugates of the present invention for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. It is clear that LC/A-CPDY-$H_N$/A conjugates are more potent than the unliganded LC/A-$H_N$/A control molecule (labelled as LC/A-$H_N$/A).

FIG. 36—Kappa receptor activation studies with a range of dynorphin conjugates Chinese hamster ovary (CHO) cells were transfected so that they express the OP2 receptor and SNAP-25. Said cells were used to measure cAMP deletion that occurs when the receptor is activated with a dynorphin ligand, using a FRET-based cAMP kit (LANCE kit from Perkin Elmer). The transfected cells were exposed to varying concentrations of dynorphin conjugates of the present invention for 2 hours. cAMP levels were then detected by addition of a detection mix containing a fluorescently labelled cAMP tracer (Europium-streptavadi/biotin-cAMP) and fluorescently (Alexa) labelled anti-cAMP antibody and incubating at room temperature for 24 hours. Then samples are excited at 320 nM and emitted light measured at 665 nM to determine cAMP levels. It is clear that LC/A-CPDY-$H_N$/A conjugates are more potent than the unliganded LC/A-$H_N$/A control molecule (labelled as LC/A-$H_N$/A).

FIG. 37—Kappa receptor activation studies with a range of dynorphin conjugates Chinese hamster ovary (CHO) cells were transfected so that they express the OP2 receptor (purchased from Perkin Elmer). Said cells were transfected so they express SNAP-25 and used to measure cAMP deletion that occurs when the receptor is activated with a dynorphin ligand, using a FRET-based cAMP kit (LANCE kit from Perkin Elmer). The transfected cells were exposed to varying concentrations of dynorphin conjugates of the present invention for 2 hours. cAMP levels were then detected by addition of a detection mix containing a fluorescently labelled cAMP tracer (Europium-streptavadi/biotin-cAMP) and fluorescently (Alexa) labelled anti-cAMP antibody and incubating at room temperature for 24 hours. Then samples are excited at 320 nM and emitted light measured at 665 nM to determine cAMP levels. It is clear from the figure by the reduction in maximum cAMP that the OP2 receptor is activated by LC/A-CPDY-$H_N$/A (labelled as CPDY/A), LC/B-CPDY-$H_N$/B (labelled as CPDY/B), LC/C-CPDY-$H_N$/C (labelled as CPDY/C), and LC/D-CPDY-$H_N$/D (labelled as CPDY/D). The concentration required to achieve 50% reduction in cAMP with LC/A-CPDY-$H_N$/A, LC/B-CPDY-$H_N$/B, LC/C-CPDY-$H_N$/C (labelled as CPDY/, and LC/D-CPDY-$H_N$/D is 10.47 nM, 14.79 nM, 14.79 nM and 23.99 nM, respectively. Dynorphin peptide containing amino acids 1-17 of dynorphin A (labelled as dynorphin (1-17) was more potent than the fusions; 0.15 nm concentration required to achieve 50% reduction of cAMP.

DETAILED DESCRIPTION OF THE INVENTION

The use of an "agonist", which would normally stimulate a biological process, particularly exocytosis (for example, an increase in cellular secretion, or an up-regulation in membrane protein expression), is an exciting development in the technical field of re-targeted toxins. Furthermore, it is particularly surprising that an agonist may be employed in a therapeutic composition to achieve a reduction or inhibition of a biological process that the agonist would normally stimulate.

The agonist-containing conjugates of the present invention represent a distinct sub-set of toxin conjugates. In more detail, the conjugates of the present invention comprise TMs that have been selected on the basis of specific agonist properties rather than on the simple basis that they have a corresponding receptor on a pain-sensing target cell of interest.

Conventionally, an agonist has been considered any molecule that can either increase or decrease activities within a cell, namely any molecule that simply causes an alteration of cell activity. For example, the conventional meaning of an agonist would include: a chemical substance capable of combining with a receptor on a cell and initiating a reaction or activity, or a drug that induces an active response by activating receptors, whether the response is an increase or decrease in cellular activity.

However, for the purposes of this invention, an agonist is more specifically defined as a molecule that is capable of stimulating the process of exocytic fusion in a pain-sensing target cell, which process is susceptible to inhibition by a protease (or fragment thereof) capable of cleaving a protein of the exocytic fusion apparatus in said target cell.

Accordingly, the particular agonist definition of the present invention would exclude many molecules that would be conventionally considered as agonists. For example, nerve growth factor (NGF) is an agonist in respect of its ability to promote neuronal differentiation via binding to a TrkA receptor. However, NGF is not an agonist when assessed by the above criteria because it is not a principal inducer of exocytic fusion. In addition, the process that NGF stimulates (i.e. cell differentiation) is not susceptible to inhibition by the protease activity of a non-cytotoxic toxin molecule.

In use, an agonist-containing conjugate of the present invention does not deactivate an agonist receptor on a pain-sensing target cell, but rather the protease activity of the conjugate serves to negate the agonist-mediated response.

Furthermore, once delivered to the cytosol of the pain-sensing target cell, the protease component of a conjugate of the present invention inhibits or blocks the action of all subsequent agonists capable of causing the same effect (i.e. increased exocytic fusion) in the same target cell. This is advantageous and means that the conjugates of the present invention have application in situations where multiple agonists may be responsible for causing the sensation of pain. Thus, when designing a conjugate of the present invention, the TM that is selected for delivery need not necessarily be the principal agonist involved in causing the sensation of pain.

Agonist-mediated delivery according to the present invention provides the following significant advantage over previous non-cytotoxic protease-containing therapeutics: use of an agonist may confer preferential binding and/or internalisation properties on the conjugate. This, in turn, may result in more efficient delivery of the protease component to a pain-sensing target cell.

In addition, use of an agonist as a TM is self-limiting with respect to side-effects. In more detail, binding of an agonist to a pain-sensing target cell increases exocytic fusion, which may exacerbate the sensation of pain. However, the exocytic process that is stimulated by agonist binding is subsequently reduced or inhibited by the protease component of the conjugate.

In preferred embodiments of the invention, the TM is an agonist of the $ORL_1$ receptor. The $ORL_1$ receptor is present on pain-sensing cells in the body.

The ORL$_1$ receptor is a member of the G-protein-coupled class of receptors, and has a seven transmembrane domain structure. The properties of the ORL$_1$ receptor are discussed in detail in Mogil & Pasternak (2001), *Pharmacological Reviews*, Vol. 53, No. 3, pages 381-415.

Throughout this specification, reference to the "ORL$_1$ receptor" embraces all members of the ORL$_1$ receptor family. Members of the ORL$_1$ receptor family typically have a seven transmembrane domain structure, and are coupled to G-proteins of the G$_i$ and G$_o$ families. A method for determining the G-protein-stimulating activity of ligands of the ORL$_1$ receptor is given in Example 17. A method for measuring reduction in cellular cAMP levels following ORL$_1$ activation is given in Example 16. A further characteristic of members of the ORL$_1$ receptor family is that they are typically able to bind nociceptin (the natural ligand of ORL$_1$). As an example, all alternative splice variants of the ORL$_1$ receptor, are members of the ORL$_1$ receptor family.

The conjugates of the present invention generally demonstrate a reduced binding affinity (in the region of up to 100-fold) for nociceptive sensory afferent target cells when compared with the corresponding 'free' TM. However, despite this observation, the conjugates of the present invention surprisingly demonstrate good efficacy. This can be attributed to two principal features. First, the non-cytotoxic protease component is catalytic—thus, the therapeutic effect of a few such molecules is rapidly amplified. Secondly, the receptors present on the nociceptive sensory afferents need only act as a gateway for entry of the therapeutic, and need not necessarily be stimulated to a level required in order to achieve a ligand-receptor mediated pharmacological response. Accordingly, the conjugates of the present invention may be administered at a dosage that is much lower that would be employed for other types of analgesic molecules such as NSAIDS, morphine, and gabapentin. The latter molecules are typically administered at high microgram to milligram (even up to hundreds of milligram) quantities, whereas the conjugates of the present invention may be administered at much lower dosages, typically at least 10-fold lower, and more typically at 100-fold lower.

In a particularly preferred embodiment of the invention, the TM of the conjugate is nociceptin—the natural ligand for the ORL$_1$ receptor. Nociceptin targets the ORL$_1$ receptor with high affinity.

Examples of other preferred TMs include:

| Code | Sequence | Ref. | SEQ ID NO: |
|---|---|---|---|
| Nociceptin 1-17 | FGGFTGARKSARKLANQ | [1] | 1, 2 |
| Nociceptin 1-11 | FGGFTGARKSA | [1] | 3, 4 |
| Nociceptin [Y10]1-11 | FGGFTGARKYA | [1] | 5, 6 |
| Nociceptin [Y11]1-11 | FGGFTGARKSY | [1] | 7, 8 |
| Nociceptin [Y14]1-17 | FGGFTGARKSARKYANQ | [1] | 9, 10 |
| Nociceptin 1-13 | FGGFTGARKSARK | [2] | 11, 12 |
| Nociceptin [R14K15] 1-17 (also known as "variant" nociceptin) | FGGFTGARKSARKRKNQ | [3, 4] | 13, 14 |
| Nociceptin 1-13-NH$_2$ | FGGFTGARKSARK-NH$_2$ | [5] | 12 |
| Nociceptin Phe (p-NO$_2$) 1-17 | (pNO$_2$)FGGFTGARKSARKLANQ | [5] | 2 |
| Lofentanil | Non-peptide agonists | [5] | — |
| Etorphine | Non-peptide agonists | [5] | — |
| Peptide agonist | Peptide agonists from combinatorial library approach | [6] | — |

[1] Mogil & Pasternak, 2001, Pharmacol. Rev., 53, 381-415
[2] Maile et al., 2003, Neurosci. Lett., 350, 190-192
[3] Rizzi et al., 2002, J. Pharmacol. Exp. Therap., 300, 57-63
[4] Okada et al., 2000, Biochem. Biophys. Res. Commun., 278, 493-498
[5] Zaveri, 2003, Life Sci., 73, 663-678.
[6] Dooley et al., 1997, J Pharmacol Exp Ther. 283(2), 735-41.

The TM preferably comprises a maximum of 50 amino acid residues, more preferably a maximum of 40 amino acid residues, particularly preferably a maximum of 30 amino acid residues, and most preferably a maximum of 20 amino acid residues. For example, nociceptin is a 17 amino acid residue peptide.

The above-identified "variant" TM demonstrates particularly good binding affinity (when compared with natural nociceptin) for nociceptive sensory afferents. Generally speaking, a TM-containing conjugate will demonstrate an approximate 100-fold reduction in binding ability vis-à-vis the TM per se. The above-mentioned "variant" TM per se demonstrates an approximate 3- to 10-fold increase in binding ability for a nociceptive sensory afferent vis-à-vis natural nociceptin. Thus, a "variant" TM-containing fusion might be expected to demonstrate an approximate 10-fold reduction in binding ability for a nociceptive sensory afferent vis-à-vis 'free' nociceptin. However, the present inventors have demonstrated that conjugates comprising said "variant" TM demonstrate a binding ability that (most surprisingly) closely mirrors that of 'free' nociceptin—see FIG. 17.

In the context of the present invention, the term agonist of the ORL$_1$ receptor (such as nociceptin, or any one of the peptides listed in the table above) embraces molecules having at least 70%, preferably at least 80%, more preferably at least 90%, and most preferably at least 95% homology with said agonist. The agonist homologues retain the agonist properties of nociceptin at the $ORL_1$ receptor, which may be tested using the methods provided in Examples 16 and 17.

The invention also encompasses fragments, variants, and derivatives of any one of the TMs described above. These fragments, variants, and derivatives will substantially retain the properties that are ascribed to said TMs.

In addition to the above-mentioned opioid and non-opioid classes of TMs, a variety of other polypeptides are suitable for targeting the conjugates of the present invention to nociceptive sensory afferents (e.g. to nociceptors). In this regard, particular reference is made to galanin and derivatives of galanin. Galanin receptors are found pre- and post-synaptically in DRGs (Liu & Hokfelt, (2002), Trends Pharm. Sci., 23(10), 468-74), and are enhanced in expression during neuropathic pain states. Proteinase-activated receptors (PARs) are also a preferred group of TMs of the present invention, most particularly PAR-2. It is known that agonists of PAR-2 induce/elicit acute inflammation, in part via a neurogenic mechanism. PAR2 is expressed by primary spinal afferent neurons, and PAR2 agonists stimulate release of substance P (SP) and calcitonin gene-related peptide (CGRP) in peripheral tissues.

A particularly preferred set of TMs of the present invention includes:

| Ligand | Reference |
| --- | --- |
| Nociceptin | Guerrini, et al., (1997) J. Med. Chem., 40, pp. 1789-1793 |
| β-endorphin | Blanc, et al., (1983) J. Biol. Chem., 258(13), pp. 8277-8284 |
| Endomorphin-1; Endomorphin-2 | Zadina, et al., (1997). Nature, 386, pp. 499-502 |
| Dynorphin | Fields & Basbaum (2002) Chapter 11, In The Textbook of Pain, Wall & Melzack eds. |
| Met-enkephalin | Fields & Basbaum (2002) Chapter 11, In The Textbook of Pain, Wall & Melzack eds. |
| Leu-enkephalin | Fields & Basbaum (2002) Chapter 11, In The Textbook of Pain, Wall & Melzack eds. |
| Galanin | Xu et al., (2000) Neuropeptides, 34 (3&4), 137-147 |
| PAR-2 peptide | Vergnolle et al., (2001) Nat. Med., 7(7), 821-826 |

The agonist properties of a TM can be confirmed using the methods described in Example 1. These methods are based on previous experiments (see Inoue et al. (1998) Proc. Natl. Acad. Sci., 95, 10949-10953), which confirm that the natural agonist of the $ORL_1$ receptor, nociceptin, causes the induction of substance P release from nociceptive primary afferent neurons. This is supported by the facts that:
the nociceptin-induced responses are abolished by specific NK1 receptor (the substance P receptor) antagonists; and
pre-treatment of the cells with capsaicin (which depletes substance P from small diameter primary afferent neurons) attenuates the nociceptin-induced responses.

Similarly, Inoue et al. confirm that an intraplantar injection of botulinum neurotoxin type A abolishes the nociceptin-induced responses. Since it is known that BoNT inhibits the release of substance P from primary afferent neurons (Welch et al., (2000), Toxicon, 38, 245-258), this confirms the link between nociceptin-$ORL_1$ interaction and subsequent release of substance P.

Thus, a TM can be said to have agonist activity at the $ORL_1$ receptor if the TM causes an induction in the release of substance P from a nociceptive sensory afferent neuron (see Example 1).

In another embodiment, opioids represent a preferred group of TMs of the present invention. Within this family of peptides is included enkephalins (met and leu), endomorphins 1 and 2, β-endorphin and dynorphin. Opioid peptides are frequently used in the clinic to modify the activity to nociceptors, and other cells involved in the pain response. As exemplified by the three-step World Health Organisation Analgesic Ladder, opioids have entry points into the pharmacological treatment of chronic cancer and non-cancer pain at all three stages, underlining their importance to the treatment of pain. Reference to opioids embraces fragments, variants and derivatives thereof, which retain the ability to bind to nociceptive sensory afferents.

The protease of the present invention embraces all naturally-occurring non-cytotoxic proteases that are capable of cleaving one or more proteins of the exocytic fusion apparatus in eukaryotic cells.

The protease of the present invention is preferably a bacterial protease.

More preferably, the bacterial protease is selected from the genera *Clostridium* or *Neisseria* (e.g. a clostridial L-chain, or a neisserial IgA protease preferably from *N. gonorrhoeae*).

The present invention also embraces modified non-cytotoxic proteases, which include amino acid sequences that do not occur in nature and/or synthetic amino acid residues, so long as the modified proteases still demonstrate the above-mentioned protease activity.

The protease of the present invention preferably demonstrates a serine or metalloprotease activity (e.g. endopeptidase activity). The protease is preferably specific for a SNARE protein (e.g. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

A Translocation Domain is a molecule that enables translocation of a protease (or fragment thereof) into a pain-sensing target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored (see Shone C. (1987) Eur. J. Biochem; vol. 167(1): pp. 175-180).

A further example is provided by Blaustein R. (1987), which describes a simple in vitro assay employing planar phospholipid bilayer membranes. The membranes are challenged with a test molecule and the requisite translocation function is confirmed by an increase in conductance across said membranes (see Blaustein (1987) FEBS Letts; vol. 226, no. 1: pp. 115-120).

Additional methodology to enable assessment of membrane fusion and thus identification of Translocation Domains suitable for use in the present invention are provided by *Methods in Enzymology*, Vols. 220 and 221, Membrane Fusion Techniques, Parts A and B, Academic Press 1993.

The Translocation Domain is preferably capable of formation of ion-permeable pores in lipid membranes under conditions of low pH. Preferably, it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, namely the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. Examples of suitable clostridial Translocation Domains include:

| | |
|---|---|
| Botulinum type A neurotoxin | amino acid residues (449-871) |
| Botulinum type B neurotoxin | amino acid residues (441-858) |
| Botulinum type C neurotoxin | amino acid residues (442-866) |
| Botulinum type D neurotoxin | amino acid residues (446-862) |
| Botulinum type E neurotoxin | amino acid residues (423-845) |
| Botulinum type F neurotoxin | amino acid residues (440-864) |
| Botulinum type G neurotoxin | amino acid residues (442-863) |
| Tetanus neurotoxin | amino acid residues (458-879) |

For further details on the genetic basis of toxin production in *Clostridium botulinum* and *C. tetani*, we refer to Henderson et al. (1997) in *The Clostridia: Molecular Biology and Pathogenesis*, Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin (see table below). Examples of non-clostridial Translocation Domain origins include, but are not restricted to, the translocation domain of diphtheria toxin [O'Keefe et al., Proc. Natl. Acad. Sci. USA (1992) 89, 6202-6206; Silverman et al., J. Biol. Chem. (1993) 269, 22524-22532; and London, E. (1992) Biochem. Biophys. Acta., 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS*, 89, pp. 7934-79381, and amphiphilic peptides [Murata et al (1992) *Biochem.*, 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded "spike proteins" have particular application in the context of the present invention, for example, the E1 protein of SFV and the G protein of VSV.

Use of the Translocation Domains (listed below) includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

| Translocation Domain source | Amino acid residues | References |
|---|---|---|
| Diphtheria toxin | 194-380 | Silverman et al., 1994, J. Biol. Chem. 269, 22524-22532<br>London E., 1992, Biochem. Biophys. Acta., 1113, 25-51 |
| Domain II of pseudomonas exotoxin | 405-613 | Prior et al., 1992, Biochemistry 31, 3555-3559<br>Kihara & Pastan, 1994, Bioconj Chem. 5, 532-538 |
| Influenza virus haemagglutinin | GLFGAIAGFIENGWE GMIDGWYG (SEQ ID NO: 110), and Variants thereof | Plank et al., 1994, J. Biol. Chem. 269, 12918-12924<br>Wagner et al., 1992, PNAS, 89, 7934-7938<br>Murata et al., 1992, Biochemistry 31, 1986-1992 |
| Semliki Forest virus fusogenic protein | Translocation domain | Kielian et al., 1996, J Cell Biol. 134(4), 863-872 |

-continued

| Translocation Domain source | Amino acid residues | References |
|---|---|---|
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

Once a potential receptor agonist (e.g. an ORL1 agonist) has been identified, one or more of the following optional steps may be carried out:

(A) confirming that the putative agonist molecule or agonist is capable of being combined with a non-cytotoxic protease (or a fragment thereof) and optionally a Translocation Domain to form a conjugate of the present invention; and/or (B) confirming that said putative agonist molecule or agonist binds to the receptor on the pain-sensing target cell, which receptor is susceptible to receptor-mediated endocytosis; and/or (C) confirming that said putative agonist molecule or agonist is able to deliver a non-cytotoxic protease (or fragment thereof) into the cytosol of a pain-sensing target cell.

The above steps (A)-(C) may be confirmed by routine tests that would be readily available to a skilled person.

For example, step (A) may be performed by a simple chemical conjugation experiment using conventional conjugation reagents and/or linker molecules, followed by native polyacrylamide gel electrophoresis to confirm that a conjugate of the present invention is formed that has the anticipated molecular weight. The conjugate components are typically linked together (optionally via linker molecules) by covalent bonds.

For example, step (B) may be performed by any one of a range of methodologies for assessment of binding of a ligand. Standard text, for example "Receptor-Ligand Interactions. A Practical Approach. Ed. E. C. Hulme, IRL Press, 1992" are available that describe such approaches in detail. In brief, the agonist or putative agonist molecule is labelled (for example, with 125-iodine) and applied to a cell preparation in vitro in the presence of an excess of unlabelled agonist. The purpose of the unlabelled material is to saturate any non-specific binding sites. The agonist is incubated with the cell preparation for sufficient time to achieve equilibrium, and the amount of label bound to the cells assessed by measuring cell associated radioactivity, for example by scintillation or gamma counting.

A further example involves gold-labelling of the agonist (or putative agonist), followed by the use of electron microscopy to monitor the cellular transport progress of the labelled agonist [see the basic methodology described by Rabinowitz S. (1992); J. Cell. Biol. 116(1): pp. 95-112; and that described by van Deurs (1986); J. Cell. Biol. 102: pp. 37-47].

For example, step (C) may be performed by contacting the conjugate prepared in step (A) with a suitable target cell and assessing cleavage of the substrate. This is performed by extraction of the SNARE proteins, followed by Western blotting of SDS-PAGE-separated samples. Cleavage of substrate is indicative of delivery of the protease into the target cell. In this regard, cleavage may be monitored by disappearance of substrate and/or appearance of cleavage product. A particularly useful antibody that selectively binds to the cleaved substrate product is described in WO95/33850.

Preparation of a conjugate according to the present invention is now discussed.

It is known in the art that the $H_C$ portion of a neurotoxin molecule can be removed from the other portion of the H-chain, known as $H_N$, such that the $H_N$ fragment remains disulphide linked to the L-chain of the neurotoxin providing a fragment known as $LH_N$. Thus, in one embodiment of the present invention the $LH_N$ fragment of a neurotoxin is covalently linked, using linkages which may include one or more spacer regions, to a TM.

In another embodiment of the invention, the $H_C$ domain of a neurotoxin is mutated, blocked or modified, e.g. by chemical modification, to reduce or preferably incapacitate its ability to bind the neurotoxin to receptors at the neuromuscular junction. This modified neurotoxin is then covalently linked, using linkages which may include one or more spacer regions, to a TM.

In another embodiment of the invention, the H-chain of a neurotoxin, in which the $H_C$ domain is mutated, blocked or modified, e.g. by chemical modification, to reduce or preferably incapacitate its native binding ability, is combined with the L-chain of a different neurotoxin, or another protease capable of cleaving a protein of the exocytic fusion apparatus (e.g. IgA protease of N. gonorrhoeae). This hybrid, modified neurotoxin is then covalently linked, using linkages which may include one or more spacer regions, to a TM.

In another embodiment of the invention, the $H_N$ domain of a neurotoxin is combined with the L-chain of a different neurotoxin, or another protease capable of cleaving a protein of the exocytic fusion apparatus (e.g. IgA protease of N. gonorrhoeae). This hybrid is then covalently linked, using linkages which may include one or more spacer regions, to a TM.

In another embodiment of the invention, the protease (for example the L-chain component of a neurotoxin) is covalently linked, using linkages that may include one or more spacer regions, to a TM that can also effect the internalisation of the protease into the cytoplasm of the relevant target cell(s).

In another embodiment of the invention, the protease (for example the L-chain component of a neurotoxin) is covalently linked, using linkages which may include one or more spacer regions, to a translocation domain to effect transport of the protease fragment into the cytosol.

In use, the domains of a conjugate according to the present invention are associated with each other. In one embodiment, two or more of the domains may be joined together either directly (e.g. by a covalent linkage), or via a linker molecule.

A variety of different linker/spacer molecules may be employed in any of the fusion proteins of the present invention. Examples of such spacer molecules include those illustrated in FIGS. 31 and 32. Particular mention here is made to GS15, GS20, GS25, and Hx27—see FIGS. 31 and 32.

The present inventors have unexpectedly found that non-cytotoxic protease-TM conjugates (eg. CPNv/A) may demonstrate an improved binding activity for nociceptive sensory afferents when the size of the spacer is selected so that (in use) the TM (preferably the C-terminus thereof) and the translocation domain (preferably the N-terminus thereof) are separated from one another by 40-105 angstroms, preferably by 50-100 angstroms, and more preferably by 50-90 angstroms. In another embodiment, the preferred spacers have an amino acid sequence of 11-29 amino acid residues, preferably 15-27 amino acid residues, and more preferably 20-27 amino acid residues. Suitable spacers may be routinely identified and obtained according to Crasto, C. J. and Feng, J. A. (2000) May, 13(5), pp. 309-312—see also the website having a URL ending in: fccc./edu/research/labs/feng/limker.html.

Conjugation techniques suitable for use in the present invention have been well documented and are routine for a person skilled in the art.

The methodology involved in coupling two protein molecules (A and B) together is simple, and is achieved through the use of a cross-linking agent (also known as a chemical coupling agent). For example, molecules A and B are separately contacted with a cross-linking agent, which chemically modifies a specific surface group on each of molecules A and B thereby forming derivatised molecules A' and B'. The modified surface group on molecule A' is capable of covalently bonding with the modified surface group on molecule B'. Thus, the coupling reaction is completed by mixing together the two protein molecules A' and B'.

Chemical conjugation is illustrated by reference to the following embodiments, where P=non-cytotoxic protease component, T=translocation component, and TM=targeting moiety.

In one embodiment, a single chain P-T is prepared, which is then conjugated to a TM. In another embodiment, a single chain TM-T (or T-TM) is prepared, which is then conjugated to a P. In a further embodiment, a single chain P-TM (or TM-P) is prepared, which is then conjugated to a T. Another particularly preferred conjugate has the structure P-TM-T (with an optional protease cleavage site between P and TM).

Where the T and P components are prepared as a single chain polypeptide, a protease cleavage site is typically included between said components. Any protease cleavage site may be employed in this regard.

In an alternative embodiment, the three components may be simultaneously or sequentially conjugated together. Thus, the conjugation may be a one- or two-step process, and may include one or more different coupling agents.

Chemical coupling agents and cross-linking agents have been commercially available for many years.

Example 5 of the present invention describes in detail the use of one such coupling agent, namely SPDP, to chemically couple two protein molecules (nociceptin, and the $LH_N$ of botulinum neurotoxin). The two molecules are separately contacted with SPDP, and then mixed together to allow covalent conjugation.

The conjugate described in Example 6 confirms that another coupling agent, PDPH/EDAC, or Traut's reagent, may be employed as an alternative coupling agent to SPDP.

SPDP and Traut's reagent are popular and well-documented coupling agents in the technical field of protein conjugation chemistry and are presented here simply as two examples of a well known class of compounds that may be employed to covalently link together the Targeting Moiety component and the clostridial neurotoxin component of the conjugate of the present invention. Other suitable agents include SMPB, SMCC (succinimidyl 4-(N-maleimidomethyl)cyclohexan-1-carboxylate), and LC-SPDP.

In more detail, commercially available members of the well-known coupling agents may be used for conjugation purposes to produce a conjugate of the invention. Details of such agents can be found in the following publications:

Hermanson, G. T. (1996), Bioconjugate techniques, Academic Press;

Wong, S. S. (1991), Chemistry of protein conjugation and cross-linking, CRC Press;

Thorpe et al (1987), Cancer Res, 1987, 47, 5924-31. This paper describes the use of SMBT (sodium S-4-succinimidyloxycarbonyl-alpha-methyl benzyl thiosulfate) and SMPT (4-succinimidyloxycarbonyl-alpha-methyl-alpha (2-pyridyldithio)toluene); and Peeters et al (1989), J Immunol Methods. 1989, 120, 133-43. This paper describes the use of 4 coupling reagents, MHS (succinimidyl 6-(N-maleimido)-n-hexanoate), SMCC (succinimidyl 4-(N-maleimidomethyl)-cyclohexane-1-carboxylate), MBS (succinimidyl m-maleimidobenzoate), and SPDP.

The conjugates according to the present invention may also be prepared recombinantly, as detailed in Examples 9 to 12.

In one embodiment, the preparation of a recombinant conjugate involves arrangement of the coding sequences of a selected TM, a selected non-cytotoxic protease component, and a translocation component (in any order) in a single genetic construct. These coding sequences may be arranged in-frame so that subsequent transcription and translation is continuous through both coding sequences and results in a fusion protein. All constructs would have a 5' ATG codon to encode an N-terminal methionine, and a C-terminal translational stop codon.

Thus, the recombinant preparation method results in the generation of a single chain polypeptide. In order to activate this polypeptide, a protease cleavage site is present between the non-cytotoxic protease component and the translocation component. Cleavage of this site generates a di-chain polypeptide in which the protease and translocation domains are linked together by way of a covalent bond, preferably a disulphide bond. In this regard, any protease cleavage site may be employed.

In the single polypeptide aspect of the present invention, the TM is preferably either N- or C-terminally located with respect to the fusion protein. In other words, it is preferred that the TM is not located between the P and T components of the single polypeptide fusion protein. In a particularly preferred embodiment, the TM is N-terminally located with respect to the fusion protein.

In one embodiment, an L-chain of a clostridial neurotoxin or another protease capable of cleaving a protein of the exocytic fusion apparatus (e.g. an IgA protease), or a fragment/variant thereof, may be expressed recombinantly as a fusion protein with a TM, which TM can also effect the internalisation of the L-chain component into the cytoplasm of the relevant target cell(s) responsible for secretion. Alternatively, the fusion protein may further comprise a Translocation Domain. The expressed fusion protein may include one or more spacer regions.

By way of example, the following information is required to produce, recombinantly, an agent of the present invention:

(I) DNA sequence data relating to a selected TM;
(II) DNA sequence data relating to the protease component;
(III) DNA sequence data relating to the translocation domain; and (IV) a protocol to permit construction and expression of the construct comprising (I), (II) and (III).

All of the above basic information (I)-(IV) are either readily available, or are readily determinable by conventional methods. For example, both WO98/07864 and WO99/17806 exemplify recombinant technology suitable for use in the present application.

In addition, methods for the construction and expression of the constructs of the present invention may employ information from the following references and others:

Lorberboum-Galski, H., FitzGerald, D., Chaudhary, V., Adhya, S., Pastan, I. (1988), Cytotoxic activity of an interleukin 2-Pseudomonas exotoxin chimeric protein produced in *Escherichia coli*. Proc. Natl. Acad. Sci. USA, 85(6):1922-6;

Murphy, J. R. (1988), Diphtheria-related peptide hormone gene fusions: a molecular genetic approach to chimeric toxin development. Cancer Treat. Res.; 37:123-40;

Williams, D. P., Parker, K., Bacha, P., Bishai, W., Borowski, M., Genbauffe, F., Strom, T. B., Murphy, J. R. (1987), Diphtheria toxin receptor binding domain substitution with interleukin-2: genetic construction and properties of a diphtheria toxin-related interleukin-2 fusion protein. Protein Eng; 1(6):493-8;

Arora, N., Williamson, L. C., Leppla, S. H., Halpern, J. L. (1994), Cytotoxic effects of a chimeric protein consisting of tetanus toxin light chain and anthrax toxin lethal factor in non-neuronal cells J. Biol. Chem., 269(42):26165-71;

Brinkmann, U., Reiter, Y., Jung, S. H., Lee, B., Pastan, I. (1993), A recombinant immunotoxin containing a disulphide-stabilized Fv fragment. Proc. Natl. Acad. Sci. USA, 90(16):7538-42; and O'Hare, M., Brown, A. N., Hussain, K., Gebhardt, A., Watson, G., Roberts, L. M., Vitetta, E. S., Thorpe, P. E., Lord, J. M. (1990), Cytotoxicity of a recombinant ricin-A-chain fusion protein containing a proteolytically-cleavable spacer sequence. FEBS Lett October 29; 273(1-2):200-4.

Suitable clostridial neurotoxin sequence information relating to L- and LH$_N$-chains may be obtained from, for example, Kurazono, H. (1992) *J. Biol. Chem.*, vol. 267, No. 21, pp. 14721-14729; and Popoff, M. R., and Marvaud, J.-C. (1999) *The Comprehensive Sourcebook of Bacterial Protein Toxins*, 2nd edition (ed. Alouf, J. E., and Freer, J. H.), Academic Press, pp. 174-201.

All of the aforementioned publications are hereby incorporated into the present specification by reference thereto.

Similarly, suitable TM sequence data are widely available in the art. Alternatively, any necessary sequence data may be obtained by techniques which are well-known to the skilled person.

For example, DNA encoding the TM component may be cloned from a source organism by screening a cDNA library for the correct coding region (for example by using specific oligonucleotides based on the known sequence information to probe the library), isolating the TM DNA, sequencing this DNA for confirmation purposes, and then placing the isolated DNA in an appropriate expression vector for expression in the chosen host.

As an alternative to isolation of the sequence from a library, the available sequence information may be employed to prepare specific primers for use in PCR, whereby the coding sequence is then amplified directly from the source material and, by suitable use of primers, may be cloned directly into an expression vector.

Another alternative method for isolation of the coding sequence is to use the existing sequence information and synthesise a copy, possibly incorporating alterations, using DNA synthesis technology. For example, DNA sequence data may be generated from existing protein and/or RNA sequence information. Using DNA synthesis technology to do this (and the alternative described above) enables the codon bias of the coding sequence to be modified to be optimal for the chosen expression host. This may give rise to superior expression levels of the fusion protein.

Optimisation of the codon bias for the expression host may be applied to the DNA sequences encoding the TM and clostridial components of the construct. Optimisation of the codon bias is possible by application of the protein sequence into freely available DNA/protein database software, e.g. programs available from Genetics Computer Group, Inc.

Having prepared a conjugate of the invention, it is a matter of routine to confirm that the various domains have retained their specified function.

Protease function after conjugation may be tested by using, for example, any one of the following routine tests:

SNAP-25 (or synaptobrevin, or syntaxin) may be challenged with a conjugate to be tested, and then analysed by SDS-PAGE peptide separation techniques. Subsequent detection of peptides (e.g. by silver staining) having molecular weights corresponding to the cleaved products of SNAP-25 (or other component of the neurosecretory machinery) would confirm the presence of a functional L-chain.

As a further alternative, the conjugate may be tested by assaying for SNAP-25 (or synaptobrevin, or syntaxin) cleavage products via antibody-specific binding (see WO95/33850). In more detail, a specific antibody is employed for detecting cleavage of SNAP-25. Since the antibody recognises cleaved SNAP-25, but not uncleaved SNAP-25, identification of the cleaved product by the antibody confirms the presence of L-chain proteolytic function. By way of exemplification, such a method is described in Examples 2 and 3 of WO96/33273.

Translocation component function after conjugation may be tested using, for example, any one of the following routine tests:

Suitable methods are, for example, described by Shone et al. (1987) Eur. J. Biochem. 167, pp. 175-180; and by Blaustein et al. (1987) FEBS 226 (1), pp. 115-120.

The Shone et al. method employs artificial liposomes loaded with potassium phosphate buffer (pH 7.2) and radio-labelled NAD. Release of K+ and NAD from the liposomes correlates with a positive result for channel forming activity and hence translocation activity. In this regard, K+ release from liposomes may be measured using an electrode and NAD release calculated by measuring the radioactivity in the supernatant (see page 176, column 1, line 33—column 2, line 17).

The Blaustein et al. method employs planar phospholipid bilayer membranes, which are used to test for channel forming activity. In more detail, salt solutions on either side of the membrane are buffered at a different pH—on the cis side, pH 4.7 or 5.5 and on the trans side, pH 7.4. The "conjugate" to be tested is added to the cis side of the membrane and electrical measurements are made under voltage clamp conditions, in order to monitor the flow of current across the membrane (see paragraph 2.2, pages 116-118). The presence of an active translocation function is confirmed by a steady rate of channel turn-on (i.e. a positive result for channel formation)-see paragraph 3, page 118.

Targeting Moiety (TM) function after conjugation may be tested by assaying for the agonist function inherent to the TM. Suitable methods include those described in Example 1.

The ability of the conjugate of the invention to inhibit substance P release from nociceptive afferent cells can be assessed using the methods described in Example 15.

In Example 15, a nociceptin-LHN/A conjugate according to the first aspect of the invention is assessed for its ability to inhibit the release of substance P from primary nociceptive sensory afferent neurons. As can be seen from Table 1, incubation of the conjugate with cultures of nociceptive afferent neurons results in a significant inhibition of release of substance P (when compared to incubation of the cells with LHN/A alone). The experiment therefore confirms that the conjugate is inhibiting substance P release from these cells.

In use of the present invention, a pain-sensing target cell is selected in which it is desired to reduce or inhibit the process of exocytic fusion, which exocytic process contributes to the symptoms associated with the sensation of pain. For example, the target cell in question may demonstrate an undesirable phenotype (e.g. an undesirable secretion, or the expression of an undesirable concentration of membrane receptor, transporter or membrane channel), which contributes to the symptoms associated with pain. Alternatively, a target cell may be selected in which the process of exocytic fusion contributes to the sensation of pain.

In preferred embodiments of the invention, the target cell is a nociceptive sensory afferent cell, preferably a primary nociceptive afferent cell (e.g. an A-fibre such as an Aδ-fibre or a C-fibre). Thus, the conjugates of the present invention are capable of inhibiting neurotransmitter or neuromodulator (e.g. glutamate, substance P, calcitonin-gene related peptide (CGRP), and/or neuropeptide Y) release from discrete populations of nociceptive sensory afferent neurons. In use, the conjugates reduce or prevent the transmission of sensory afferent signals (e.g. neurotransmitters or neuromodulators) from peripheral to central pain fibres, and therefore have application as therapeutic molecules for the treatment of pain, in particular chronic pain.

It is routine to confirm that a TM binds to a nociceptive sensory afferent. For example, a simple radioactive displacement experiment may be employed in which tissue or cells representative of the nociceptive sensory afferent (for example DRGs) are exposed to labelled (e.g. tritiated) ligand in the presence of an excess of unlabelled ligand. In such an experiment, the relative proportions of non-specific and specific binding may be assessed, thereby allowing confirmation that the ligand binds to the nociceptive sensory afferent target cell. Optionally, the assay may include one or more binding antagonists, and the assay may further comprise observing a loss of ligand binding. Examples of this type of experiment can be found in Hulme, E. C. (1990), Receptor-binding studies, a brief outline, pp 303-311, in Receptor biochemistry, A Practical Approach, Ed. E. C. Hulme, Oxford University Press.

According to a second aspect, the present invention provides a non-cytotoxic conjugate for inhibition or reduction of exocytotic fusion in a nociceptive sensory afferent cell, comprising:
  (i) a Targeting Moiety (TM),
    wherein said TM is an agonist of a receptor that is present on said nociceptive sensory afferent cell, and wherein said receptor undergoes endocytosis to be incorporated into an endosome within the nociceptive sensory afferent cell;
  (ii) a DNA sequence encoding a non-cytotoxic protease or a fragment thereof,
    wherein the DNA sequence is expressible in the nociceptive sensory afferent cell and when so expressed provides a protease or protease fragment capable of cleaving a protein of the exocytic fusion apparatus of said nociceptive sensory afferent cell; and
  (iii) a Translocation Domain,
    wherein the Translocation Domain translocates the DNA sequence encoding the protease or protease fragment from within the endosome, across the endosomal membrane, and into the nociceptive sensory afferent cell.

In a preferred embodiment, the receptor is an $ORL_1$ receptor.

DNA encoding a protein of interest can be transfected into eukaryotic cells through receptor-mediated endocytosis of a protein-DNA conjugate, as confirmed by Cotton et al. (Cotton, M., Wagner, E. and Birnstiel, L. (1993) Receptor-mediated transport of DNA into eukaryotic cells. Methods in Enzymol. 217, 619-645). Several methods exist for condensing DNA to a suitable size using polycationic ligands. These include: polylysine, various cationic peptides and cationic liposomes. Of these, polylysine was used in the present study because of its successfully reported use in receptor-mediated transfection studies (Cotton et al., 1993).

The DNA sequence encoding the non-cytotoxic protease component may be expressed under the control of an operably linked promoter present as part of the agent (e.g. as part of the protease DNA sequence upstream of the coding region). Alternatively, expression of the protease component in the target cell may rely on a promoter present in the target cell.

The DNA sequence encoding the protease component may integrate into a DNA sequence of the target cell. One or more integration site(s) may be provided as part of the conjugate (e.g. as part of the protease DNA sequence).

The TM, Translocation Domain and protease components of this second aspect of the invention are as defined for the first aspect of the invention. Examples 13 and 14 describe the preparation of conjugates according to the second aspect of the invention.

According to a third aspect, the present invention provides a pharmaceutical composition comprising a conjugate according to the first and/or second aspect of the present invention.

The pharmaceutical composition may further comprise a pharmaceutically-acceptable carrier, and/or a suitable diluent and/or excipient, although the exact form of the composition may be tailored to the mode of administration. Administration is preferably to a mammal, more preferably to a human.

The components of the composition may, for example, be employed in the form of an aerosol or nebulisable solution for inhalation or a sterile solution for parenteral administration, intra-articular administration or intra-cranial administration.

The composition may also be administered by i.v. injection, which includes the use of pump systems. Spinal injection (e.g. epidural or intrathecal) or indwelling pumps may also be used.

The dosage ranges for administration of the components of the present invention are those to produce the desired therapeutic effect. It will be appreciated that the dosage range required depends on the precise nature of the components, the route of administration, the nature of the formulation, the age of the patient, the nature, extent or severity of the patient's condition, contraindications, if any, and the judgement of the attending physician.

Suitable daily dosages (for each component) are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or preferably less frequently, such as weekly or six monthly.

A particularly preferred dosing regimen is based on 2.5 ng of fusion protein (e.g. CPNv/A) as the 1× dose. In this regard, preferred dosages are in the range 1×-100× (i.e. 2.5-250 ng). This dosage range is significantly lower (i.e. at least 10-fold, typically 100-fold lower) than would be employed with other types of analgesic molecules such as NSAIDS, morphine, and gabapentin. Moreover, the above-mentioned difference is considerably magnified when the same comparison is made on a molar basis—this is because the fusion proteins of the present invention have a considerably greater Mw than do conventional 'small' molecule therapeutics.

Wide variations in the required dosage, however, are to be expected depending on the precise nature of the components, and the differing efficiencies of various routes of administration. For example, oral administration would be expected to require higher dosages than administration by intravenous injection.

Variations in these dosage levels can be adjusted using standard empirical routines for optimisation, as is well understood in the art.

Compositions suitable for injection may be in the form of solutions, suspensions or emulsions, or dry powders which are dissolved or suspended in a suitable vehicle prior to use.

Fluid unit dosage forms are typically prepared utilising a pyrogen-free sterile vehicle.

The active ingredients, depending on the vehicle and concentration used, can be either dissolved or suspended in the vehicle.

Solutions may be used for all forms of parenteral administration, and are particularly used for intravenous injection. In preparing solutions the components can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving.

Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area.

Alternatively the components of the composition may be dissolved in an aqueous vehicle, the solution is sterilized by filtration and distributed into suitable containers using aseptic technique in a sterile area. The product is then freeze-dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition(s) to facilitate uniform distribution of the components.

Compositions suitable for administration via the respiratory tract include aerosols, nebulisable solutions or microfine powders for insufflation. In the latter case, particle size of less than 50 microns, especially less than 10 microns, is preferred. Such compositions may be made up in a conventional manner and employed in conjunction with conventional administration devices.

The compositions described in this invention can be used in vivo, either directly or as a pharmaceutically acceptable salt, for the treatment of conditions involving exocytosis (for example secretion, or the delivery of proteins such as receptors, transporters, and membrane channels to the plasma membrane of a cell).

According to a fourth aspect, the present invention provides a DNA construct that encodes a conjugate according to the first or second aspects of the invention.

By expressing the construct in a host cell, conjugates of the invention may be prepared.

According to a fifth aspect, the present invention provides a method of treatment of pain by administration to a patient of a conjugate, composition, or construct according to the first to fourth aspects of the invention, or any combination thereof.

In a preferred embodiment, the invention provides a method of treating chronic pain.

According to a sixth aspect, the present invention provides for the use of a conjugate, composition or construct according to the first to fourth aspects of the invention, for the manufacture of a medicament for treating pain, preferably chronic pain.

According to a further aspect of the present invention, there is provided use of a conjugate of the invention, for the manufacture of a medicament for treating, preventing or ameliorating pain.

According to a related aspect, there is provided a method of treating, preventing or ameliorating pain in a subject, comprising administering to said patient a therapeutically effective amount of a conjugate or composition of the invention.

The conjugates and compositions described here may be used to treat a patient suffering from one or more types of chronic pain including neuropathic pain, inflammatory pain, headache pain, somatic pain, visceral pain, and referred pain.

To "treat," as used here, means to deal with medically. It includes, for example, administering a compound of the invention to prevent pain or to lessen its severity.

The term "pain," as used here, means any unpleasant sensory experience, usually associated with a physical disorder. The physical disorder may or may not be apparent to a clinician. Pain is of two types: chronic and acute. An "acute pain" is a pain of short duration having a sudden onset. One type of acute pain, for example, is cutaneous pain felt on injury to the skin or other superficial tissues, such as caused by a cut or a burn. Cutaneous nociceptors terminate just below the skin, and due to the high concentration of nerve endings, produce a well-defined, localized pain of short duration. "Chronic pain" is a pain other than an acute pain. Chronic pain includes neuropathic pain, inflammatory pain, headache pain, somatic pain visceral pain and referred pain.

I. Neuropathic Pain

The compounds of the invention may be used to treat pain caused by or otherwise associated with any of the following neuropathic pain conditions. "Neuropathic pain" means abnormal sensory input, resulting in discomfort, from the peripheral nervous system, central nervous systems, or both.

A. Symptoms of Neuropathic Pain

Symptoms of neuropathic pain can involve persistent, spontaneous pain, as well as allodynia (a painful response to a stimulus that normally is not painful), hyperalgesia (an accentuated response to a painful stimulus that usually causes only a mild discomfort, such as a pin prick), or hyperpathia (where a short discomfort becomes a prolonged severe pain).

B. Causes of Neuropathic Pain

Neuropathic pain may be caused by any of the following.

1. A traumatic insult, such as, for example, a nerve compression injury (e.g., a nerve crush, a nerve stretch, a nerve entrapment or an incomplete nerve transsection); a spinal cord injury (e.g., a hemisection of the spinal cord); a limb amputation; a contusion; an inflammation (e.g., an inflammation of the spinal cord); or a surgical procedure.

2. An ischemic event, including, for example, a stroke and heart attack.

3. An infectious agent

4. Exposure to a toxic agent, including, for example, a drug, an alcohol, a heavy metal (e.g., lead, arsenic, mercury), an industrial agent (e.g., a solvent, fumes from a glue) or nitrous oxide.

5. A disease, including, for example, an inflammatory disorder, a neoplastic tumor, an acquired immune deficiency syndrome (AIDS), Lymes disease, a leprosy, a metabolic disease, a peripheral nerve disorder, like neuroma, a mononeuropathy or a polyneuropathy.

C. Types of Neuropathic Pain

1. Neuralgia.

A neuralgia is a pain that radiates along the course of one or more specific nerves usually without any demonstrable pathological change in the nerve structure. The causes of neuralgia are varied. Chemical irritation, inflammation, trauma (including surgery), compression by nearby structures (for instance, tumors), and infections may all lead to neuralgia. In many cases, however, the cause is unknown or unidentifiable. Neuralgia is most common in elderly persons, but it may occur at any age. A neuralgia, includes, without limitation, a trigeminal neuralgia, a post-herpetic neuralgia, a postherpetic neuralgia, a glossopharyngeal neuralgia, a sciatica and an atypical facial pain.

Neuralgia is pain in the distribution of a nerve or nerves. Examples are trigeminal neuralgia, atypical facial pain, and postherpetic neuralgia (caused by shingles or herpes). The affected nerves are responsible for sensing touch, temperature and pressure in the facial area from the jaw to the forehead. The disorder generally causes short episodes of excruciating pain, usually for less than two minutes and on only one side of the face. The pain can be described in a variety of ways such as "stabbing," "sharp," "like lightning," "burning," and even "itchy". In the atypical form of TN, the pain can also present as severe or merely aching and last for extended periods. The pain associated with TN is recognized as one the most excruciating pains that can be experienced.

Simple stimuli such as eating, talking, washing the face, or any light touch or sensation can trigger an attack (even the sensation of a gentle breeze). The attacks can occur in clusters or as an isolated attack.

Symptoms include sharp, stabbing pain or constant, burning pain located anywhere, usually on or near the surface of the body, in the same location for each episode; pain along the path of a specific nerve; impaired function of affected body part due to pain, or muscle weakness due to concomitant motor nerve damage; increased sensitivity of the skin or numbness of the affected skin area (feeling similar to a local anesthetic such as a Novacaine shot); and any touch or pressure is interpreted as pain. Movement may also be painful.

Trigeminal neuralgia is the most common form of neuralgia. It affects the main sensory nerve of the face, the trigeminal nerve ("trigeminal" literally means "three origins", referring to the division of the nerve into 3 branches). This condition involves sudden and short attacks of severe pain on the side of the face, along the area supplied by the trigeminal nerve on that side. The pain attacks may be severe enough to cause a facial grimace, which is classically referred to as a painful tic (tic douloureux). Sometimes, the cause of trigeminal neuralgia is a blood vessel or small tumor pressing on the nerve. Disorders such as multiple sclerosis (an inflammatory disease affecting the brain and spinal cord), certain forms of arthritis, and diabetes (high blood sugar) may also cause trigeminal neuralgia, but a cause is not always identified. In this condition, certain movements such as chewing, talking, swallowing, or touching an area of the face may trigger a spasm of excruciating pain.

A related but rather uncommon neuralgia affects the glosso-pharyngeal nerve, which provides sensation to the throat. Symptoms of this neuralgia are short, shock-like episodes of pain located in the throat.

Neuralgia may occur after infections such as shingles, which is caused by the varicella-zoster virus, a type of herpesvirus. This neuralgia produces a constant burning pain after the shingles rash has healed. The pain is worsened by movement of or contact with the affected area. Not all of those diagnosed with shingles go on to experience postherpetic neuralgia, which can be more painful than shingles. The pain and sensitivity can last for months or even years. The pain is usually in the form of an intolerable sensitivity to any touch but especially light touch. Postherpetic neuralgia is not restricted to the face; it can occur anywhere on the body but usually occurs at the location of the shingles rash. Depression is not uncommon due to the pain and social isolation during the illness.

Postherpetic neuralgia may be debilitating long after signs of the original herpes infection have disappeared. Other infectious diseases that may cause neuralgia are syphilis and Lyme disease.

Diabetes is another common cause of neuralgia. This very common medical problem affects almost 1 out of every 20 Americans during adulthood. Diabetes damages the tiny arteries that supply circulation to the nerves, resulting in nerve fiber malfunction and sometimes nerve loss. Diabetes can produce almost any neuralgia, including trigeminal neuralgia, carpal tunnel syndrome (pain and numbness of the hand and wrist), and meralgia paresthetica (numbness and pain in the thigh due to damage to the lateral femoral cutaneous nerve). Strict control of blood sugar may prevent diabetic nerve damage and may accelerate recovery in patients who do develop neuralgia.

Other medical conditions that may be associated with neuralgias are chronic renal insufficiency and porphyria—a hereditary disease in which the body cannot rid itself of certain substances produced after the normal breakdown of blood in the body. Certain drugs may also cause this problem.

2. Deafferentation.

Deafferentation indicates a loss of the sensory input from a portion of the body, and can be caused by interruption of either peripheral sensory fibres or nerves from the central nervous system. A deafferentation pain syndrome, includes, without limitation, an injury to the brain or spinal cord, a post-stroke pain, a phantom pain, a paraplegia, a brachial plexus avulsion injuries, lumbar radiculopathies.

3. Complex Regional Pain Syndromes (CRPSs)

CRPS is a chronic pain syndrome resulting from sympathetically-maintained pain, and presents in two forms. CRPS 1 currently replaces the term "reflex sympathetic dystrophy syndrome". It is a chronic nerve disorder that occurs most often in the arms or legs after a minor or major injury. CRPS 1 is associated with severe pain; changes in the nails, bone, and skin; and an increased sensitivity to touch in the affected limb. CRPS 2 replaces the term causalgia, and results from an identified injury to the nerve. A CRPS, includes, without limitation, a CRPS Type I (reflex sympathetic dystrophy) and a CRPS Type II (causalgia).

4. Neuropathy.

A neuropathy is a functional or pathological change in a nerve and is characterized clinically by sensory or motor neuron abnormalities.

Central neuropathy is a functional or pathological change in the central nervous system.

Peripheral neuropathy is a functional or pathological change in one or more peripheral nerves. The peripheral nerves relay information from your central nervous system (brain and spinal cord) to muscles and other organs and from your skin, joints, and other organs back to your brain. Peripheral neuropathy occurs when these nerves fail to carry information to and from the brain and spinal cord, resulting in pain, loss of sensation, or inability to control muscles. In some cases, the failure of nerves that control blood vessels, intestines, and other organs results in abnormal blood pressure, digestion problems, and loss of other basic body processes. Risk factors for neuropathy include diabetes, heavy alcohol use, and exposure to certain chemicals and drugs. Some people have a hereditary predisposition for neuropathy. Prolonged pressure on a nerve is another risk for developing a nerve injury. Pressure injury may be caused by prolonged immobility (such as a long surgical procedure or lengthy illness) or compression of a nerve by casts, splints, braces, crutches, or other devices. Polyneuropathy implies a widespread process that usually affects both sides of the body equally. The symptoms depend on which type of nerve is affected. The three main types of nerves are sensory, motor, and autonomic. Neuropathy can affect any one or a combination of all three types of nerves. Symptoms also depend on whether the condition affects the whole body or just one nerve (as from an injury). The cause of chronic inflammatory polyneuropathy is an abnormal immune response. The specific antigens, immune processes, and triggering factors are variable and in many cases are unknown. It may occur in association with other conditions such as HIV, inflammatory bowel disease, lupus erythematosis, chronic active hepatitis, and blood cell abnormalities.

Peripheral neuropathy may involve a function or pathological change to a single nerve or nerve group (monneuropathy) or a function or pathological change affecting multiple nerves (polyneuropathy).

Peripheral Neuropathies
Hereditary Disorders
   Charcot-Marie-Tooth disease
   Friedreich's ataxia
Systemic or Metabolic Disorders
   Diabetes (diabetic neuropathy)
   Dietary deficiencies (especially vitamin B-12)
   Excessive alcohol use (alcoholic neuropathy)
   Uremia (from kidney failure)
   Cancer
Infectious or Inflammatory Conditions
   AIDS
   Hepatitis
   Colorado tick fever
   diphtheria
   Guillain-Barre syndrome
   HIV infection without development of AIDS
   leprosy
   Lyme
   polyarteritis nodosa
   rheumatoid arthritis
   sarcoidosis
   Sjogren syndrome
   syphilis
   systemic lupus erythematosus
   amyloid
Exposure to Toxic Compounds
   sniffing glue or other toxic compounds
   nitrous oxide
   industrial agents—especially solvents
   heavy metals (lead, arsenic, mercury, etc.)
   Neuropathy secondary to drugs like analgesic nephropathy
Miscellaneous Causes
   ischemia (decreased oxygen/decreased blood flow)
   prolonged exposure to cold temperature a. Polyneuropathy Polyneuropathy is a peripheral neuropathy involving the loss of movement or sensation to an area caused by damage or destruction to multiple peripheral nerves. Polyneuropathic pain, includes, without limitation, post-polio syndrome, post-mastectomy syndrome, diabetic neuropathy, alcohol neuropathy, amyloid, toxins, AIDS, hypothyroidism, uremia, vitamin deficiencies, chemotherapy-induced pain, 2',3'-s didexoycytidine (ddC) treatment, Guillain-Barré syndrome or Fabry's disease.

b. Mononeuropathy

Mononeuropathy is a peripheral neuropathy involving loss of movement or sensation to an area caused by damage or destruction to a single peripheral nerve or nerve group. Mononeuropathy is most often caused by damage to a local area resulting from injury or trauma, although occasionally systemic disorders may cause isolated nerve damage (as with mononeuritis multiplex). The usual causes are direct trauma, prolonged pressure on the nerve, and compression of the nerve by swelling or injury to nearby body structures. The damage includes destruction of the myelin sheath (covering) of the nerve or of part of the nerve cell (the axon). This damage slows or prevents conduction of impulses through the nerve. Mononeuropathy may involve any part of the body. Mononeuropathic pain, includes, without limitation, a sciatic nerve dysfunction, a common peroneal nerve dysfunction, a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome and a sixth (abducent) nerve palsy c. Generalized Peripheral Neuropathies Generalized peripheral neuropathis are symmetrical, and usually due to various systematic illnesses and disease processes that affect the peripheral nervous system in its entirety. They are further subdivided into several categories:

i. Distal axonopathies are the result of some metabolic or toxic derangement of neurons. They may be caused by metabolic diseases such as diabetes, renal failure, deficiency syndromes such as malnutrition and alcoholism, or the effects of toxins or drugs. Distal axonopathy (aka dying back neuropathy) is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. The most common cause of distal axonopathy is diabetes, and the most common distal axonopathy is diabetic neuropathy.

ii. Myelinopathies are due to a primary attack on myelin causing an acute failure of impulse conduction. The most common cause is acute inflammatory demyelinating polyneuropathy (AIDP; aka Guillain-Barré syndrome), though other causes include chronic inflammatory demyelinating syndrome (CIDP), genetic metabolic disorders (e.g., leukodystrophy), or toxins. Myelinopathy is due to primary destruction of myelin or the myelinating Schwann cells, which leaves the axon intact, but causes an acute failure of impulse conduction. This demyelination slows down or completely blocks the conduction of electical impulses through the nerve. The most common cause is acute inflammatory demyelinating polyneuropathy (AIDP, better known as Guillain-Barré syndrome), though other causes include chronic inflammatory demyelinating polyneuropathy (CIDP), genetic metabolic disorders (e.g., leukodystrophy or Charcot-Marie-Tooth disease), or toxins.

iii. Neuronopathies are the result of destruction of peripheral nervous system (PNS) neurons. They may be caused by motor neurone diseases, sensory neuronopathies (e.g., Herpes zoster), toxins or autonomic dysfunction. Neurotoxins may cause neuronopathies, such as the chemotherapy agent vincristine. Neuronopathy is dysfunction due to damage to neurons of the peripheral nervous system (PNS), resulting in a peripheral neuropathy. It may be caused by motor neurone diseases, sensory neuronopathies (e.g., Herpes zoster), toxic substances or autonomic dysfunction. A person with neuronopathy may present in different ways, depending on the cause, the way it affects the nerve cells, and the type of nerve cell that is most affected.

iv. Focal entrapment neuropathies (e.g., carpal tunnel syndrome).

II. Inflammatory Pain

The compounds of the invention may be used to treat pain caused by or otherwise associated with any of the following inflammatory conditions A. Arthritic Disorder Arthritic disorders include, for example, a rheumatoid arthritis; a juvenile rheumatoid arthritis; a systemic lupus erythematosus (SLE); a gouty arthritis; a scleroderma; an osteoarthritis; a psoriatic arthritis; an ankylosing spondylitis; a Reiter's syndrome (reactive arthritis); an adult Still's disease; an arthritis from a viral infection; an arthritis from a bacterial infection, such as, e.g., a gonococcal arthritis and a non-gonococcal bacterial arthritis (septic arthritis); a Tertiary Lyme disease; a tuberculous arthritis; and an arthritis from a fungal infection, such as, e,g. a blastomycosis.

B. Autoimmune Diseases

Autoimmune diseases include, for example, a Guillain-Barré syndrome, a Hashimoto's thyroiditis, a pernicious anemia, an Addison's disease, a type I diabetes, a systemic lupus erythematosus, a dermatomyositis, a Sjogren's syndrome, a lupus erythematosus, a multiple sclerosis, a myasthenia gravis, a Reiter's syndrome and a Grave's disease.

C. Connective Tissue Disorder

Connective tissue disorders include, for example, a spondyloarthritis a dermatomyositis, and a fibromyalgia.

D. Injury

Inflammation caused by injury, including, for example, a crush, puncture, stretch of a tissue or joint, may cause chronic inflammatory pain.

E. Infection

Inflammation caused by infection, including, for example, a tuberculosis or an interstitial keratitis may cause chronic inflammatory pain.

F. Neuritis

Neuritis is an inflammatory process affecting a nerve or group of nerves. Symptoms depend on the nerves involved, but may include pain, paresthesias, paresis, or hypesthesia (numbness).

Examples include:

a. Brachial neuritis b. Retrobulbar neuropathy, an inflammatory process affecting the part of the optic nerve lying immediately behind the eyeball.

c. Optic neuropathy, an inflammatory process affecting the optic nerve causing sudden, reduced vision in the affected eye. The cause of optic neuritis is unknown. The sudden inflammation of the optic nerve (the nerve connecting the eye and the brain) leads to swelling and destruction of the myelin sheath. The inflammation may occasionally be the result of a viral infection, or it may be caused by autoimmune diseases such as multiple sclerosis. Risk factors are related to the possible causes.

d. Vestibular neuritis, a viral infection causing an inflammatory process affecting the vestibular nerve.

G. Joint Inflammation

Inflammation of the joint, such as that caused by bursitis or tendonitis, for example, may cause chronic inflammatory pain.

III. Headache Pain

The compounds of the invention may be used to treat pain caused by or otherwise associated with any of the following headache conditions. A headache (medically known as cephalgia) is a condition of mild to severe pain in the head; sometimes neck or upper back pain may also be interpreted as a headache. It may indicate an underlying local or systemic disease or be a disorder in itself.

A. Muscular/Myogenic Headache

Muscular/myogenic headaches appear to involve the tightening or tensing of facial and neck muscles; they may radiate to the forehead. Tension headache is the most common form of myogenic headache.

A tension headache is a condition involving pain or discomfort in the head, scalp, or neck, usually associated with muscle tightness in these areas. Tension headaches result from the contraction of neck and scalp muscles. One cause of this muscle contraction is a response to stress, depression or anxiety. Any activity that causes the head to be held in one position for a long time without moving can cause a headache. Such activities include typing or use of computers, fine work with the hands, and use of a microscope. Sleeping in a cold room or sleeping with the neck in an abnormal position may also trigger this type of headache. A tension-type headache, includes, without limitation, an episodic tension headache and a chronic tension headache.

B. Vascular Headache

The most common type of vascular headache is migraine. Other kinds of vascular headaches include cluster headaches, which cause repeated episodes of intense pain, and headaches resulting from high blood pressure 1. Migraine A migraine is a heterogeneous disorder that generally involves recurring headaches. Migraines are different from other headaches because they occur with other symptoms, such as, e.g., nausea, vomiting, or sensitivity to light. In most people, a throbbing pain is felt only on one side of the head. Clinical features such as type of aura symptoms, presence of prodromes, or associated symptoms such as vertigo, may be seen in subgroups of patients with different underlying pathophysiological and genetic mechanisms. A migraine headache, includes, without limitation, a migraine without aura (common migraine), a migraine with aura (classic migraine), a menstrual migraine, a migraine equivalent (acephalic headache), a complicated migraine, an abdominal migraine and a mixed tension migraine.

2. Cluster Headache

Cluster headaches affect one side of the head (unilateral) and may be associated with tearing of the eyes and nasal congestion. They occurs in clusters, happening repeatedly every day at the same time for several weeks and then remitting.

C. High Blood Pressure Headache

D. Traction and Inflammatory Headache

Traction and inflammatory headaches are usually symptoms of other disorders, ranging from stroke to sinus infection.

E. Hormone Headache

F. Rebound Headache

Rebound headaches, also known as medication overuse headaches, occur when medication is taken too frequently to relieve headache. Rebound headaches frequently occur daily and can be very painful.

G. Chronic Sinusitis Headache

Sinusitis is inflammation, either bacterial, fungal, viral, allergic or autoimmune, of the paranasal sinuses. Chronic sinusitis is one of the most common complications of the common cold. Symptoms include: Nasal congestion; facial pain; headache; fever; general malaise; thick green or yellow discharge; feeling of facial 'fullness' worsening on bending over. In a small number of cases, chronic maxillary sinusitis can also be brought on by the spreading of bacteria from a dental infection. Chronic hyperplastic eosinophilic sinusitis is a noninfective form of chronic sinusitis.

H. An Organic Headache

I. Ictal Headaches

Ital headaches are headaches associated with seizure activity.

IV. Somatic Pain

The compounds of the invention may be used to treat pain caused by or otherwise associated with any of the following somatic pain conditions. Somatic pain originates from ligaments, tendons, bones, blood vessels, and even nerves themselves. It is detected with somatic nociceptors. The scarcity of pain receptors in these areas produces a dull, poorly-localized pain of longer duration than cutaneous pain; examples include sprains and broken bones. Additional examples include the following.

A. Excessive Muscle Tension

Excessive muclse tension can be caused, for example, by a sprain or a strain.

B. Repetitive Motion Disorders

Repetitive motion disorders can result from overuse of the hands, wrists, elbows, shoulders, neck, back, hips, knees, feet, legs, or ankles.

C. Muscle Disorders

Muscle disorders causing somatic pain include, for example, a polymyositis, a dermatomyositis, a lupus, a fibromyalgia, a polymyalgia rheumatica, and a rhabdomyolysis.

D. Myalgia

Myalgia is muscle pain and is a symptom of many diseases and disorders. The most common cause for myalgia is either overuse or over-stretching of a muscle or group of muscles. Myalgia without a traumatic history is often due to viral infections. Longer-term myalgias may be indicative of a metabolic myopathy, some nutritional deficiencies or chronic fatigue syndrome.

E. Infection

Infection can cause somatic pain. Examples of such infection include, for example, an abscess in the muscle, a trichinosis, an influenza, a Lyme disease, a malaria, a Rocky Mountain spotted fever, Avian influenza, the common cold, community-acquired pneumonia, meningitis, monkeypox, Severe Acute Respiratory Syndrome, toxic shock syndrome, trichinosis, typhoid fever, and upper respiratory tract infection.

F. Drugs

Drugs can cause somatic pain. Such drugs include, for example, cocaine, a statin for lowering cholesterol (such as atorvastatin, simvastatin, and lovastatin), and an ACE inhibitor for lowering blood pressure (such as enalapril and captopril)

V. Visceral Pain

The compounds of the invention may be used to treat pain caused by or otherwise associated with any of the following visceral pain conditions. Visceral pain originates from body's viscera, or organs. Visceral nociceptors are located within body organs and internal cavities. The even greater scarcity of nociceptors in these areas produces pain that is usually more aching and of a longer duration than somatic pain. Visceral pain is extremely difficult to localise, and several injuries to visceral tissue exhibit "referred" pain, where the sensation is localised to an area completely unrelated to the site of injury. Examples of visceral pain include the following.

A. Functional Visceral Pain

Functional visceral pain includes, for example, an irritable bowel syndrome and a chronic functional abdominal pain (CFAP), a functional constipation and a functional dyspepsia, a non-cardiac chest pain (NCCP) and a chronic abdominal pain.

B. Chronic Gastrointestinal Inflammation

Chronic gastrointestinal inflammation includes, for example, a gastritis, an inflammatory bowel disease, like, e.g., a Crohn's disease, an ulcerative colitis, a microscopic colitis, a diverticulitis and a gastroenteritis; an interstitial cystitis; an intestinal ischemia; a cholecystitis; an appendicitis; a gastroesophageal reflux; an ulcer, a nephrolithiasis, an urinary tract infection, a pancreatitis and a hernia.

C. Autoimmune Pain

Autoimmune pain includes, for example, a sarcoidosis and a vasculitis.

D. Orangic Visceral Pain

Organic visceral pain includes, for example, pain resulting from a traumatic, inflammatory or degenerative lesion of the gut or produced by a tumor impinging on sensory innervation.

E. Treatment-Induced Visceral Pain

Treatment-induced visceral pain includes, for example, a pain attendant to chemotherapy therapy or a pain attendant to radiation therapy.

VI. Referred Pain

The compounds of the invention may be used to treat pain caused by or otherwise associated with any of the following referred pain conditions.

Referred pain arises from pain localized to an area separate from the site of pain stimulation. Often, referred pain arises when a nerve is compressed or damaged at or near its origin. In this circumstance, the sensation of pain will generally be felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain will also be felt in the region served by the compressed nerve (for example, the thigh, knee, or foot). Relieving the pressure on the nerve root may ameliorate the referred pain, provided that permanent nerve damage has not occurred. Myocardial ischaemia (the loss of blood flow to a part of the heart muscle tissue) is possibly the best known example of referred pain; the sensation can occur in the upper chest as a restricted feeling, or as an ache in the left shoulder, arm or even hand.

DEFINITIONS SECTION

Exocytic fusion is a process by which intracellular molecules are transported from the cytosol of a pain-sensing target cell to the plasma (i.e. cell) membrane thereof. Thereafter, the intracellular molecules may become displayed on the outer surface of the plasma membrane, or may be secreted into the extracellular environment.

In a healthy individual, the rate of exocytic fusion is carefully regulated and allows control of the transport of molecules between the cytosol and the plasma membrane of a pain-sensing cell. For example, regulation of the exocytic cycle allows control of the density of receptors, transporters, or membrane channels present at the cell's surface, and/or allows control of the secretion rate of intracellular components (e.g. neurotransmitters) from the cytosol of the cell.

However, in an unhealthy individual, the regulation of exocytic fusion may be modified. For example, exocytic fusion may cause affected pain-sensing cells to enter a state of hyper-secretion. Alternatively, exocytic fusion may result in the display of an increased concentration of receptors, transporters, or membrane channels present on the surface of the pain-sensing, which may expose the cell to undesirable external stimuli. Thus, the process of exocytic fusion may contribute to the progression and/or severity of pain, and therefore provides a target for therapeutic intervention.

It should also be appreciated that otherwise normal rates of cellular exocytic fusion may contribute to the progression and severity of pain in compromised patients. Thus, by targeting exocytic fusion in accordance with the present invention, it is also possible to provide therapy in such patients Targeting Moiety (TM) means any chemical structure associated with a conjugate that functionally interacts with a receptor, e.g. an ORL$_1$ receptor, to cause a physical association between the conjugate and the surface of a pain-sensing target cell. The term TM embraces any molecule (i.e. a naturally occurring molecule, or a chemically/physically modified variant thereof) that is capable of binding to a receptor on the target cell, which receptor is capable of internalisation (e.g. endosome formation)—also referred to as receptor-mediated endocytosis. The TM may possess an endosomal membrane translocation domain, in which case separate TM and Translocation Domain components need not be present in an agent of the present invention.

The term "fragment" means a peptide having at least thirty-five, preferably at least twenty-five, more preferably at least fifteen, and most preferably at least ten amino acid residues of the TM in question. In one embodiment, the first amino acid residue of the fragment is the N-terminal amino acid residue of the TM from which the fragment has been derived.

An example of a "variant" is a peptide or peptide fragment of a TM that contains one or more analogues of an amino acid (e.g. an unnatural amino acid), or a substituted linkage.

A "derivative" comprises the TM in question, and a further peptide sequence. The further peptide sequence should preferably not interfere with the basic folding and thus conformational structure of the TM. Two or more peptides (or fragments, or variants) may be joined together to form a derivative. Alternatively, a peptide (or fragment, or variant) may be joined to an unrelated molecule (e.g. a second, unrelated peptide). Derivatives may be chemically synthesized, but will be typically prepared by recombinant nucleic acid methods. Additional components such as lipid, and/or polysaccharide, and/or polyketide components may be included.

The term non-cytotoxic means that the protease molecule in question does not kill the pain-sensing target cell to which it has been re-targeted.

The "protease cleavage site" of the present invention allows cleavage (preferably controlled cleavage) of the conjugate at a position between the non-cytotoxic protease component and the TM component. In one embodiment, the conjugate may include more than one proteolytic cleavage site. However, where two or more such sites exist, they are different, thereby substantially preventing the occurrence of multiple cleavage events in the presence of a single protease. In another embodiment, it is preferred that the conjugate has a single protease cleavage site. The protease cleavage sequence (s) may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.).

Whilst any protease cleavage site may be employed, the following are preferred:

| | |
|---|---|
| Enterokinase | SEQ ID NO: 111<br>(DDDDK↓) |
| Factor Xa | SEQ ID NO: 112<br>(IEGR↓/IDGR↓) |
| TEV (Tobacco Etch virus) | SEQ ID NO: 113<br>(ENLYFQ↓G) |
| Thrombin | SEQ ID NO: 114<br>(LVPR↓GS) |
| PreScission | SEQ ID NO: 115<br>(LEVLFQ↓GP). |

Also embraced by the term protease cleavage site is an intein, which is a self-cleaving sequence. The self-splicing reaction is controllable, for example by varying the concentration of reducing agent present.

The present invention is now described by reference to the following Examples and Figures, without intended limitation thereto.

SEQ ID NOs

Where an initial Met amino acid residue or a corresponding initial codon is indicated in any of the following SEQ ID NOs, said residue/codon is optional.

SEQ ID NO:1 DNA sequence of N[1-17]
SEQ ID NO:2 Protein Sequence of N[1-17]
SEQ ID NO:3 DNA sequence of N[1-11]
SEQ ID NO:4 Protein sequence of N[1-11]
SEQ ID NO:5 DNA sequence of N[[Y10]1-11]
SEQ ID NO:6 Protein sequence of N[[Y10]1-11]
SEQ ID NO:7 DNA sequence of N[[Y11]1-11]
SEQ ID NO:8 Protein sequence of N[[Y11]1-11]
SEQ ID NO:9 DNA sequence of N[[Y141]-17]
SEQ ID NO:10 Protein sequence of N[[Y14]1-17]
SEQ ID NO:11 DNA sequence of N[1-13]
SEQ ID NO:12 Protein sequence of N[1-13]
SEQ ID NO:13 DNA sequence of Nv (also known as N[[R14K15]1-17])

SEQ ID NO:14 Protein sequence of Nv (also known as N[[R14K15]1-17])
SEQ ID NO:15 DNA sequence of N[1-17]-LH$_N$/A fusion protein
SEQ ID NO:16 Protein sequence of N[1-17]-LH$_N$/A fusion protein
SEQ ID NO:17 DNA sequence of N[[Y11]1-11]-LHN/A fusion protein
SEQ ID NO:18 Protein sequence of N[[Y11]1-11]-LHN/A fusion protein
SEQ ID NO:19 DNA sequence of N[1-13]-LHN/A fusion protein
SEQ ID NO:20 Protein sequence of N[1-13]-LHN/A fusion protein
SEQ ID NO:21 DNA sequence of LHN/A-N[1-17] fusion protein
SEQ ID NO:22 Protein sequence of LHN/A-N[1-17] fusion protein
SEQ ID NO:23 DNA sequence of LHN/C-N[1-11] fusion protein
SEQ ID NO:24 Protein sequence of LHN/C-N[1-11] fusion protein
SEQ ID NO:25 DNA sequence of N[[Y14]1-17]-LHN/C fusion protein
SEQ ID NO:26 Protein sequence of N[[Y14]1-17]-LHN/C fusion protein
SEQ ID NO:27 DNA sequence of the LC/A
SEQ ID NO:28 DNA sequence of the H$_N$/A
SEQ ID NO:29 DNA sequence of the LC/B
SEQ ID NO:30 DNA sequence of the H$_N$/B
SEQ ID NO:31 DNA sequence of the LC/C
SEQ ID NO:32 DNA sequence of the H$_N$/C
SEQ ID NO:33 DNA sequence of the CPN-A linker
SEQ ID NO:34 DNA sequence of the A linker SEQ ID NO:35 DNA sequence of the N-terminal presentation nociceptin insert SEQ ID NO:36 DNA sequence of the CPN-C linker SEQ ID NO:37 DNA sequence of the CPBE-A linker SEQ ID NO:38 DNA sequence of the CPNvar-A linker SEQ ID NO:39 DNA sequence of the LC/A-CPN-H$_N$/A fusion SEQ ID NO:40 Protein sequence of the LC/A-CPN-H$_N$/A fusion SEQ ID NO:41 DNA sequence of the N-LC/A-H$_N$/A fusion SEQ ID NO:42 Protein sequence of the N-LC/A-H$_N$/A fusion SEQ ID NO:43 DNA sequence of the LC/C-CPN-H$_N$/C fusion SEQ ID NO:44 Protein sequence of the LC/C-CPN-H$_N$/C fusion SEQ ID NO:45 DNA sequence of the LC/C-CPN-H$_N$/C (A-linker) fusion SEQ ID NO:46 Protein sequence of the LC/C-CPN-H$_N$/C (A-linker) fusion SEQ ID NO:47 DNA sequence of the LC/A-CPME-H$_N$/A fusion SEQ ID NO:48 Protein sequence of the LC/A-CPME-H$_N$/A fusion SEQ ID NO:49 DNA sequence of the LC/A-CPBE-H$_N$/A fusion SEQ ID NO:50 Protein sequence of the LC/A-CPBE-H$_N$/A fusion SEQ ID NO:51 DNA sequence of the LC/A-CPNv-H$_N$/A fusion SEQ ID NO:52 Protein sequence of the LC/A-CPNv-H$_N$/A fusion SEQ ID NO:53 DNA sequence of the LC/A-CPN[1-11]-HN/A fusion SEQ ID NO:54 Protein sequence of the LC/A-CPN[1-11]-HN/A fusion SEQ ID NO:55 DNA sequence of the LC/A-CPN[[Y10]1-11]-HN/A fusion SEQ ID NO:56 Protein sequence of the LC/A-CPN[[Y10]1-11]-HN/A fusion SEQ ID NO:57 DNA sequence of the LC/A-CPN[[Y11]1-11]-HN/A fusion SEQ ID NO:58 Protein sequence of the LC/A-CPN[[Y11]1-11]-HN/A fusion SEQ ID NO:59 DNA sequence of the LC/A-CPN[[Y14]1-17]-HN/A fusion SEQ ID NO:60 Protein sequence of the LC/A-CPN[[Y14]1-17]-HN/A fusion SEQ ID NO:61 DNA sequence of the LC/A-CPN[1-13]-HN/A fusion SEQ ID NO:62 Protein sequence of the LC/A-CPN[1-13]-HN/A fusion SEQ ID NO:63 DNA sequence of the nociceptin-spacer-LC/A-H$_N$/A fusion SEQ ID NO:64 Protein sequence of the nociceptin-spacer-LC/A-H$_N$/A fusion SEQ ID NO:65 DNA sequence of the CPN-A GS10 linker SEQ ID NO:66 DNA sequence of the CPN-A GS15 linker SEQ ID NO:67 DNA sequence of the CPN-A GS25 linker SEQ ID NO:68 DNA sequence of the CPN-A GS30 linker SEQ ID NO:69 DNA sequence of the CPN-A HX27 linker SEQ ID NO:70 DNA sequence of the LC/A-CPN(GS15)-H$_N$/A fusion SEQ ID NO:71 Protein sequence of the LC/A-CPN(GS15)-H$_N$/A fusion SEQ ID NO:72 DNA sequence of the LC/A-CPN(GS25)-H$_N$/A fusion SEQ ID NO:73 Protein sequence of the LC/A-CPN(GS25)-H$_N$/A fusion SEQ ID NO:74 DNA sequence of the CPNvar-A Enterokinase activatable linker SEQ ID NO:75 DNA sequence of the LC/A-CPNv(Ek)-H$_N$/A fusion SEQ ID NO:76 Protein sequence of the LC/A-CPNv(Ek)-H$_N$/A fusion SEQ ID NO:77 DNA sequence of the CPNvar-A linker SEQ ID NO:78 DNA sequence of the LC/C-CPNv-H$_N$/C fusion (act. A)

SEQ ID NO:79 Protein sequence of the LC/C-CPNv-H$_N$/C fusion (act. A)

SEQ ID NO:80 DNA sequence of the LC/A-CPLE-H$_N$/A fusion

SEQ ID NO:81 Protein sequence of the LC/A-CPLE-H$_N$/A fusion

SEQ ID NO:82 DNA sequence of the LC/A-CPOP-H$_N$/A fusion

SEQ ID NO:83 Protein sequence of the LC/A-CPOP-H$_N$/A fusion

SEQ ID NO:84 DNA sequence of the LC/A-CPOPv-H$_N$/A fusion

SEQ ID NO:85 Protein sequence of the LC/A-CPOPv-H$_N$/A fusion

SEQ ID NO:86 DNA sequence of the IgA protease

SEQ ID NO:87 DNA sequence of the IgA-CPNv-H$_N$/A fusion

SEQ ID NO:88 Protein sequence of the IgA-CPNv-H$_N$/A fusion

SEQ ID NO:89 DNA sequence of the FXa-HT

SEQ ID NO:90 DNA sequence of the CPNv-A-FXa-HT

SEQ ID NO:91 Protein sequence of the CPNv-A-FXa-HT fusion

SEQ ID NO:92 DNA sequence of the DT translocation domain
SEQ ID NO:93 DNA sequence of the CPLE-DT-A
SEQ ID NO:94 Protein sequence of the CPLE-DT-A fusion
SEQ ID NO:95 DNA sequence of the TeNT LC
SEQ ID NO:96 DNA sequence of the CPNv-TENT LC
SEQ ID NO:97 Protein sequence of the CPNV-TeNT LC fusion
SEQ ID NO:98 DNA sequence of the CPNvar-C linker
SEQ ID NO:99 DNA sequence of the LC/C-CPNv-$H_N$/C fusion (act. C)
SEQ ID NO:100 Protein sequence of the LC/C-CPNv-$H_N$/C fusion (act. C)
SEQ ID NO:101 Protein sequence of dynorphin
SEQ ID NO:102 DNA sequence of LC/A-CPDY-HN/A fusion
SEQ ID NO:103 Protein sequence of LC/A-CPDY-HN/A fusion
SEQ ID NO:104 Protein sequence of LC/A-CPDY(GS10)-$H_N$/A fusion
SEQ ID NO:105 Protein sequence of LC/A-CPDY(GS15)-$H_N$/A fusion
SEQ ID NO:106 Protein sequence of LC/A-CPDY(GS25)-$H_N$/A fusion
SEQ ID NO:107 Protein sequence of LC/C-CPDY-HN/C fusion
SEQ ID NO:108 Protein sequence of IgA-CPDY-HN/A fusion
SEQ ID NO:109 Protein sequence of CPDY-TeNT LC fusion

EXAMPLES

Example 1

Confirmation of TM Agonist Activity by Measuring Release of Substance P from Neuronal Cell Cultures Materials
Substance P EIA is obtained from R&D Systems, UK.
Methods
Primary neuronal cultures of eDRG are established as described previously (Duggan et al., 2002). Substance P release from the cultures is assessed by EIA, essentially as described previously (Duggan et al., 2002). The TM of interest is added to the neuronal cultures (established for at least 2 weeks prior to treatment); control cultures are performed in parallel by addition of vehicle in place of TM. Stimulated (100 mM KCl) and basal release, together with total cell lysate content, of substance P are obtained for both control and TM treated cultures. Substance P immunoreactivity is measured using Substance P Enzyme Immunoassay Kits (Cayman Chemical Company, USA or R&D Systems, UK) according to manufacturers' instructions.

The amount of Substance P released by the neuronal cells in the presence of the TM of interest is compared to the release obtained in the presence and absence of 100 mM KCl. Stimulation of Substance P release by the TM of interest above the basal release, establishes that the TM of interest is an "agonist ligand" as defined in this specification. If desired the stimulation of Substance P release by the TM of interest can be compared to a standard Substance P release-curve produced using the natural ORL-1 receptor ligand, nociceptin (Tocris).

Example 2

Expression and Purification of Catalytically Active $LH_N$/A

Materials
Synthetic DNA obtained from Sigma Genosys. Restriction enzymes obtained from New England Biolabs.
Methods
The expression and purification of catalytically active $LH_N$/A was carried out essentially as described in Sutton et al., (2005), Prot. Express. Purif., 40, pp 31-41.

Briefly, DNA encoding the light chain plus 423 amino acids from the N-terminal of the heavy chain of BoNT/A was synthesised by Sigma-Genosys to produce a synthetic $LH_N$/A gene with an *E. coli* codon bias. The linker region between the light chain and $H_N$ domain was engineered to contain a Factor Xa cleavage site by splice-overlap extension PCR. Two PCR products were generated using primer pairs consisting of a long, mutagenic primer and a shorter, non-mutagenic primer:

```
(5'-tccaaaactaaatctctgATAGAAGGTAGAaacaaagcgctga
acgac; SEQ ID NO: 116) with (5'-CTTGATGTACTCTGTGAACGTGCTC; SEQ ID NO: 117);
and (5'-gtcgttcagcgctttgttTCTACCTTCTATcagagatttagtt
ttgga; SEQ ID NO: 118) with (5'-ATGGAGTTCGTTAACAAACAGTTC; SEQ ID NO: 119).
```

The products from these two reactions were used as templates for the splice-overlap extension PCR. A further PCR reaction was set up to add BamHI and SalI sites at either end of the activatable recLH$_N$/A gene and these sites were used for insertion into an Invitrogen gateway entry vector. The entry vector was then used, along with a gateway recombination site adapted pMAL c2x, in a LR clonase reaction to form pMAL c2x recLH$_N$/A. The pMAL c2x recLH$_N$/A was modified to incorporate a 6'HIS tag at the N-terminus of the MBP. This was achieved by the insertion of annealed oligonucleotides encoding the HIS tag into the NdeI site of pMAL.

The expression vector expressing LH$_N$/A was transformed into *E. coli* HMS174 or AD494(DE3) (Novagen). Cultures were grown in Terrific broth complex medium supplemented with ZnCl$_2$ (1 μM), ampicillin (100 μg/ml), 0.2% (w/v) glucose. Parameters for expression of all the constructs were initially determined in shake flask cultures before transferring into 8 L fermentor systems. Starter cultures were grown for 16 hours at 37° C., 220 rpm and used to inoculate 1 L in which growth was continued at 37° C., 250 rpm. At an OD600 nm of 0.6 the temperature was reduced to 25° C. for 30 minutes before induction with 1 mM IPTG. Induction was continued for 4 hours before the cells were harvested and stored at −70° C.

Typically 16 g of cell paste was suspended in 160 ml PBS and lysed by sonication (MSE Soniprep 150). The resulting lysate was clarified by centrifugation prior loading onto a 25 ml amylose column and eluted with 10 mM maltose in PBS. The eluant contained approx. 50% pure fusion protein and was treated with Factor Xa (1 unit Factor Xa/100 μg fusion protein; 20 hours; 26° C.) to remove the HISMBP and cleave the LC-H$_N$ junction to activate the protein. After incubation the sample was filtered (0.45 mm) and diluted two fold with water to give a 0.5×PBS buffer composition. The cleaved, filtered and diluted recLH$_N$/A was processed through a Q Sepharose FF column (10 ml) and eluted with a step gradient of 80 mM NaCl containing HISMBP and 120 mM NaCl containing approx. 75% pure recLH$_N$/A. The addition of His tag to MBP overcame previous co-elution problems with LH$_N$/A and MBP. As a final polishing step to ensure complete removal of the HISMBP, the 120 mM NaCl elution from the Q Sepharose column was passed through a Nickel charged 5 ml HisTrap column (Amersham). The flow through from the HisTrap column contained approx. 95% pure recLH$_N$/A (see the Figures in Sutton et al., (2005), Prot. Express. Purif., 40, pp 31-41 for an illustration of the purification scheme for LHN/A).

Example 3

Expression and Purification of Catalytically Active Recombinant LH$_N$/B

The methodology described below will purify catalytically active LH$_N$/B protease from *E. coli* transformed with the appropriate plasmid encoding the LH$_N$/B polypeptide. It should be noted that various sequences of suitable LH$_N$/B polypeptides have been described in PCT/GB97/02273, granted U.S. Pat. No. 6,461,617 and U.S. patent application Ser. No. 10/241,596, incorporated herein by reference.

Methods

The coding region for LH$_N$/B is inserted in-frame to the 3' of the gene encoding maltose binding protein (MBP) in the expression vector pMAL (New England Biolabs) to create pMAL-c2x-LH$_N$/B. In this construct, the expressed MBP and LH$_N$/B polypeptides are separated by a Factor Xa cleavage site, and the LC and H$_N$ domains are separated by a peptide that is susceptible to cleavage with enterokinase. The expression clone is termed pMAL-c2X-synLH$_N$/B.

pMAL-c2X-synLH$_N$/B is transformed into *E. coli* HMS174 and cultured in Terrific broth complex medium in 8 L fermentor systems. Pre-induction bacterial growth is maintained at 37° C. to an OD600 nm of 5.0, at which stage expression of recMBP-LH$_N$/B is induced by addition of IPTG to 0.5 mM and a reduction in temperature to 30° C. After four hours at 30° C. the bacteria are harvested by centrifugation and the resulting paste stored at −70° C.

The cell paste is resuspended in 20 mM Hepes pH 7.2, 125 mM NaCl, 1 μM $ZnCl_2$ and cell disruption achieved using an APV-Gaulin lab model 1000 homogeniser or a MSE Soniprep 150 sonicator. The resulting suspension is clarified by centrifugation prior to purification.

Following cell disruption, the MBP-fusion protein is captured either on an amylose affinity resin in 20 mM Hepes pH 7.2, 125 mM NaCl, 1 μM $ZnCl_2$, or on a Q-Sepharose FF anion-exchange resin in 50 mM Hepes pH 7.2, 1 μM $ZnCl_2$ with no salt. A single peak is eluted from the amylose resin in the same buffer plus 10 mM maltose and from the Q-Sepharose in 150-200 mM salt. Cleavage of the MBP-LH$_N$/B junction is completed in an 18 hours incubation step at 22° C. with Factor Xa (NEB) at 1 U/50 μg fusion protein. A substrate (MBP-LH$_N$/B) concentration of at least 4 mg/ml is desirable for efficient cleavage to take place.

The cleaved protein is diluted with 20 mM Hepes to a buffer composition of 20 mM Hepes, 25 mM NaCl, 1 μM $ZnCl_2$, pH 7.2 and processed through a Q Sepharose column to separate the MBP from LH$_N$/B. The LH$_N$/B is eluted from the Q-Sepharose column with 120-170 mM salt. The linker between the light chain and H$_N$ domain is then nicked by incubation with enterokinase at 1 U/100 μg of LH$_N$/B at 22° C. for 16 hours. Finally, the enterokinase is separated from the nicked LH$_N$/B and other contaminating proteins on a Benzamidine Sepharose column, the enzyme preferentially binding to the resin over an incubation of 30 minutes at 4° C. Purified LH$_N$/B is stored at −20° C. until required. See FIG. 1 for an illustration of the purification scheme for recLH$_N$/B.

Example 4

Expression and Purification of Catalytically Active Recombinant LH$_N$/C

The coding region for LH$_N$/C is inserted in-frame to the 3' of the gene encoding maltose binding protein (MBP) in the expression vector pMAL (New England Biolabs) to create pMAL-c2x-LH$_N$/C. In this construct the expressed MBP and LH$_N$/C polypeptides are separated by a Factor Xa cleavage site.

pMAL-c2x-LH$_N$/C is transformed into *E. coli* AD494 (DE3, IRL) and cultured in Terrific broth complex medium in 8 L fermentor systems. Pre-induction bacterial growth are maintained at 30° C. to an OD600 nm of 8.0, at which stage expression of recMBP-c2x-LH$_N$/C is induced by addition of IPTG to 0.5 mM and a reduction in temperature of culture to 25° C. After 4 hours at 25° C. the bacteria are harvested by centrifugation and the resulting paste stored at −70° C.

The cell paste is resuspended in 50 mM Hepes pH 7.2, 1 μM $ZnCl_2$ at 1:6 (w/v) and cell disruption is achieved using an APV-Gaulin lab model 1000 homogeniser or a MSE Soniprep 150 sonicator. The resulting suspension is clarified by centrifugation prior to purification.

Following cell disruption and clarification, the MBP-fusion protein is separated on a Q-Sepharose Fast Flow anion-exchange resin in 50 mM Hepes pH 7.2, 1 μM $ZnCl_2$ and eluted with the same buffer plus 100 mM NaCl. A double point cleavage is performed at the MBP-LH$_N$/C junction and the H$_N$-LC linker in a single incubation step with Factor Xa. The reaction is completed in a 16-hour incubation step at 22° C. with Factor Xa (NEB) at 1 U/100 ìg fusion protein. The cleaved protein is diluted with 20 mM Hepes to a buffer composition of 20 mM Hepes, 25 mM NaCl, pH 7.2 and processed through a second Q-Sepharose column to separate the MBP from LH$_N$/C. Activated (disulphide-bonded cleaved linker) LH$_N$/C is eluted from the Q-Sepharose column by a salt gradient (20 mM Hepes, 500 mM NaCl, 1 μM $ZnCl_2$, pH 7.2) in 120-170 mM salt. See FIG. 2 for an illustration of the purification of LH$_N$/C.

Example 5

Production of a Chemical Conjugate of Nociceptin and LH$_N$/A

Materials

C-terminally extended nociceptin peptide obtained from Sigma Genosys. Conjugation chemicals obtained from Pierce.

Methods

In order to couple the nociceptin peptide via a C-terminal Cys, the peptide was first synthesised (by standard procedures, commercially obtainable) to include a Cys as the final C-terminal amino acid.

This peptide was then used as the second component in a sulphydryl based coupling reaction as described below (see also previous publications WO 99/17806 and WO 96/33273 and Duggan et al., (2002), J. Biol. Chem. 277, 24846-34852 and Chaddock et al., (2000), Infect Immun., 68, 2587-2593).

Sulphydryl Based Coupling Reaction

Briefly, approximately two reactive leaving groups were introduced into LH$_N$/A (5 mg/ml in phosphate-buffered saline) by reaction with N-succinimidyl-3-(2-pyridyldithio) propionate (SPDP).

Derivatised material was isolated from excess SPDP by size exclusion chromatography. Reconstituted cysteine-tagged nociceptin ligand was mixed with the derivatised LH$_N$/A in a 4:1 molar ratio, and incubated at room temperature for 1 hour with gentle agitation in order to create a chemical conjugate through a reducible covalent disulphide bond. Initial fractionation of the conjugate mixture to remove unconjugated peptide was performed by size exclusion chromatography (Superose-12, or Superdex G-200 depending on scale of conjugation).

Example 6

Production of a Chemical Conjugate of Nociceptin and LH$_N$/B

Materials

C-terminally extended nociceptin peptide obtained from Sigma Genosys. Conjugation chemicals obtained from Pierce.

Methods

Lyophilised nociceptin was dissolved by the addition of water and dialysed into MES buffer (0.1 M MES, 0.1 M NaCl, pH 5.0). To this solution (at a concentration of about 0.3 mg/ml) was added PDPH (100 mg/ml in DMF) to a final concentration of 1 mg/ml. After mixing, solid EDAC was added to produce a final concentration of about 0.2 mg/ml. The reaction was allowed to proceed for at least 30 minutes at room temperature. Excess PDPH was then removed by desalting over a PD-10 column (Pharmacia) previously equilibrated with MES buffer.

An amount of LH$_N$/B equivalent to half the weight of nociceptin used dissolved in triethanolamine buffer (0.02 M triethanolamine/HCl, 0.1 M sodium chloride, pH 7.8) at a concentration of about 1 mg/ml, was reacted with Traut's reagent (100 mM stock solution in 1 M triethanolamine/HCl, pH 8.0) at a final concentration of 2 mM. After 1 hour, the LH$_N$/B was desalted into PBSE (phosphate buffered saline with 1 mM EDTA) using a PD-10 column (Pharmacia). The protein peak from the column eluate was concentrated using a Microcon 50 (Amicon) to a concentration of about 2 mg/ml.

The derivatised nociceptin was subjected to a final concentration step resulting in a reduction in volume to less than 10% of the starting volume and then mixed with the derivatised LH$_N$/B overnight at room temperature. The products of the reaction were analysed by polyacrylamide gel electrophoresis in the presence of sodium dodecyl-sulphate (SDS-PAGE).

The conjugate resulting from the above reaction was partially purified by size exclusion chromatography over Bio-Gel P-100 (BioRad). The elution profile was followed by measuring the optical density at 280 nm and SDS-PAGE analysis of the fractions. This allowed the separation of conjugate from free nociceptin and by-products of the reaction.

Example 7

Production of a Chemical Conjugate of Nociceptin 1-11 and LH$_N$/B

Materials

C-terminally extended nociceptin 1-11 peptide obtained from Sigma Genosys. Conjugation chemicals obtained from Pierce.

Methods

In order to couple the nociceptin 1-11 peptide via a C-terminal Cys, the peptide was first synthesised (by standard procedures, commercially obtainable) to include a Cys as the final C-terminal amino acid.

This peptide was then used as the second component in a sulphydryl based coupling reaction as described in Example 5.

Example 8

Production of a Chemical Conjugate of Nociceptin N[[Y14]1-17] and LH$_N$/C

Materials

C-terminally extended nociceptin N[[Y14]1-17] peptide obtained from Sigma Genosys. Conjugation chemicals obtained from Pierce.

Methods

In order to couple the peptide via a C-terminal Cys, the peptide was first synthesised (by standard procedures, commercially obtainable) to include a Cys as the final C-terminal amino acid.

This peptide was then used as the second component in a sulphydryl based coupling reaction as described in Example 5.

Example 9

Recombinant Production of a Single Polypeptide Fusion of Nociceptin-LH$_N$/A (SEQ ID NO:15 and SEQ ID NO:16)

The DNA sequence for the nociceptin-LH$_N$/A was designed by back translation of the LC/A, H$_N$/A, and nociceptin amino acid sequences. The complete ORF containing the nociceptin-LC/A-activation loop-H$_N$/A sequence was assembled within standard DNA sequence manipulation software (EditSeq). The activation loop between the LC/A cysteine and the H$_N$/A cysteine (CVRGIITSKTKSLDKGY-NKALNDLC; SEQ ID NO:120) was modified to incorporate a Factor Xa protease recognition site.

Restriction sites appropriate to facilitate cloning into the required expression vector (for example BamHI/SalI) were incorporated at the 5' and 3' ends respectively of the sequence maintaining the correct reading frame. The DNA sequence was screened (using software such as MapDraw, DNASTAR Inc.) for restriction enzyme cleavage sequences incorporated during the back translation. Any cleavage sequences that were found to be common to those required by the cloning system were removed manually from the proposed coding sequence ensuring common E. coli codon usage was maintained. E. coli codon usage was assessed by reference to software programs such as Graphical Codon Usage Analyser (Geneart), and the % GC content and codon usage ratio assessed by reference to published codon usage tables (for example GenBank Release 143, 13 Sep. 2004).

This optimised DNA sequence containing the nociceptin-LC/A-activation loop-H$_N$/A open reading frame (ORF) was then commercially synthesized and provided in the pCR 4 vector.

The DNA encoding the nociceptin-LH$_N$/A fusion was isolated from pCR 4 and transferred into pMAL vector backbone to facilitate protein expression. The resultant pMAL NO-LHN/A vector was transformed into competent E. coli BL21 and correct transformants selected. A single colony of pMAL NO-LH$_N$/A was grown in Terrific broth complex medium supplemented with ZnCl$_2$ (1 mM), ampicillin (100 µg/ml), 0.2% (w/v) glucose. Expression of the insert was induced by the addition of IPTG (0.1 mM) and the culture maintained at 16° C. for 16 hours. After this period of expression the bacteria were isolated by centrifugation and the cell pellet stored at −20° C. until use.

10 g of *E. coli* BL21 cell paste was defrosted in a falcon tube containing 25 ml 50 mM HEPES, pH 7.2, 200 mM NaCl. The thawed cell paste was made up to 80 ml with 50 mM HEPES, pH 7.2, 200 mM NaCl and sonicated on ice 30 seconds on, 30 seconds off for 10 cycles at a power of 22 microns ensuring the sample remained cool. The lysed cells were centrifuged at 18 000 rpm, 4° C. for 30 minutes. The supernatant was loaded onto a 0.1 M NiSO$_4$ charged chelating column (20-30 ml column is sufficient) and equilibrated with 50 mM HEPES, pH 7.2, 200 mM NaCl.

Using a step gradient of 10 and 40 mM imidazol, the non-specific bound protein was washed away and the fusion protein eluted with 100 mM imidazol. The eluted fusion protein was dialysed against 5 L of 50 mM HEPES, pH 7.2, 200 mM NaCl at 4° C. overnight and the OD of the dialysed fusion protein measured. 1 unit of Factor Xa was added per 100 µg fusion protein and incubated at 25° C. static overnight. The cleavage mixture was loaded onto a 0.1 M NiSO$_4$ charged Chelating column (20-30 ml column is sufficient) and equilibrated with 50 mM HEPES, pH 7.2, 200 mM NaCl.

Using a step gradient of 10 and 40 mM imidazol, the non-specific bound protein was washed away and the fusion protein eluted with 100 mM imidazol. The eluted fusion protein was dialysed against 5 L of 50 mM HEPES, pH 7.2, 200 mM NaCl at 4° C. overnight and the fusion concentrated to about 2 mg/ml, aliquoted and stored at −20° C.

Figure 1:
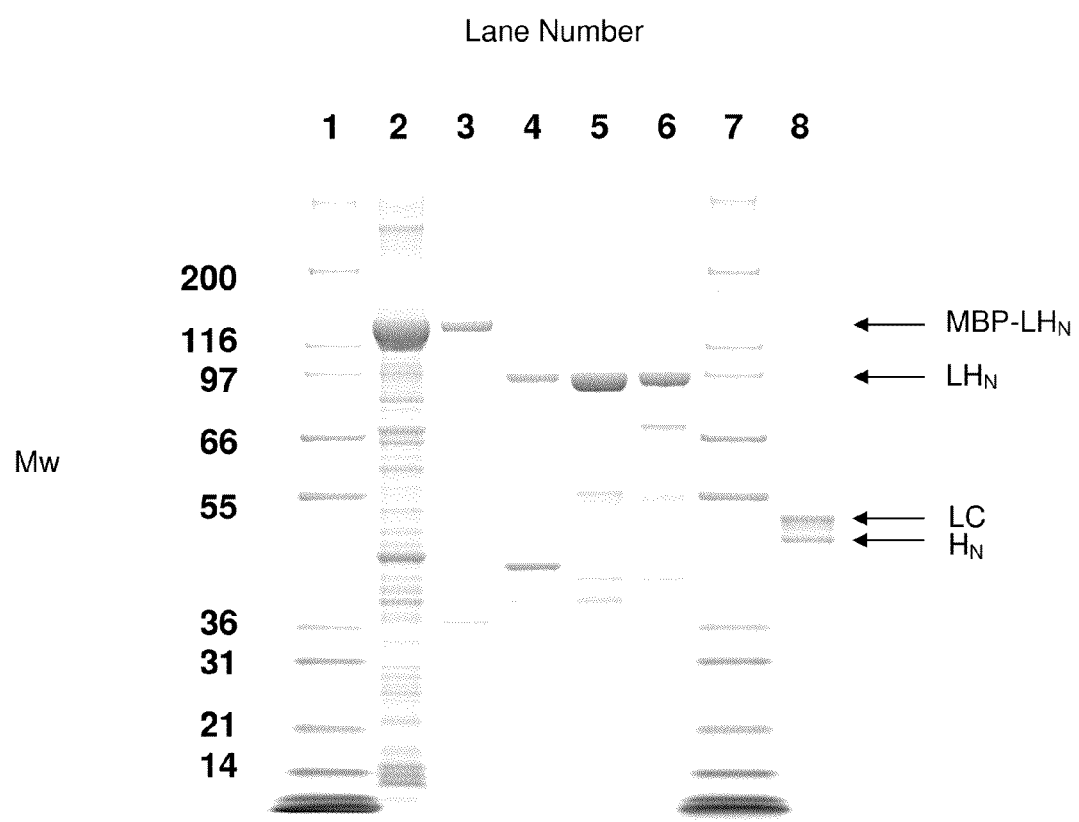
FIG. 1—Expression and purification of $recLH_N/B$ fusion protein
Figure 2:
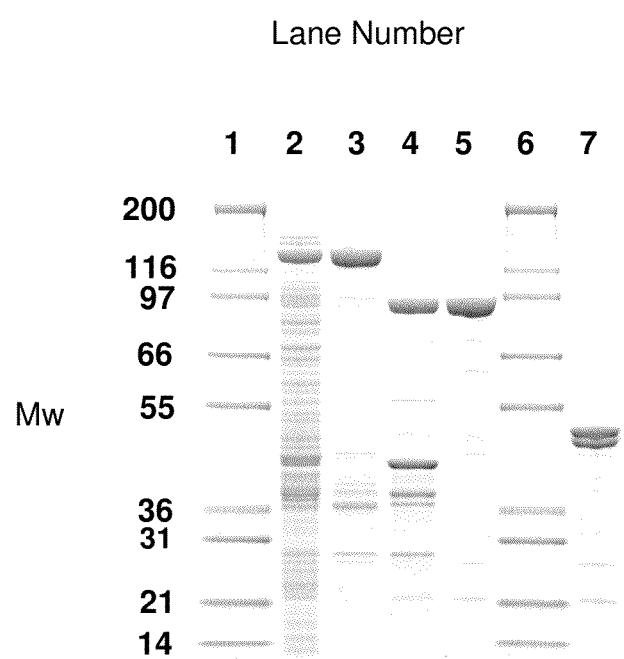
FIG. 2—Expression and purification of $LH_N/C$ fusion protein
Figure 3:
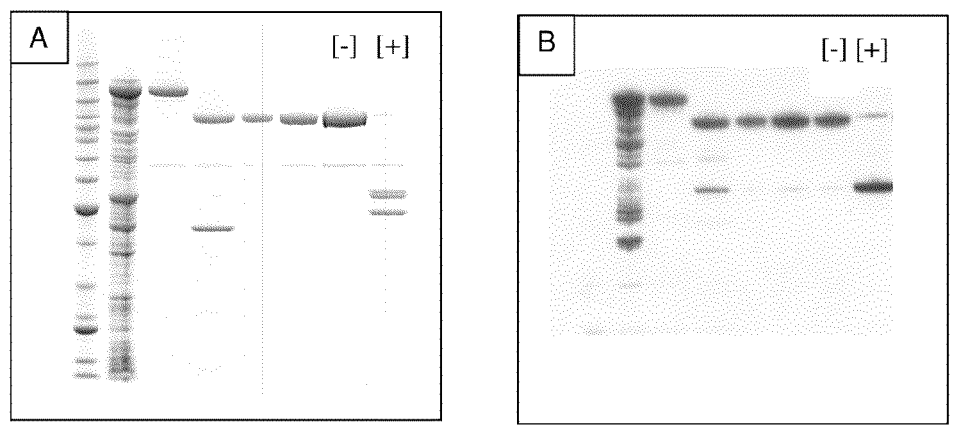
FIG. 3—Expression and purification of $N[1-17]-LH_N/A$ fusion protein
Figure 4:
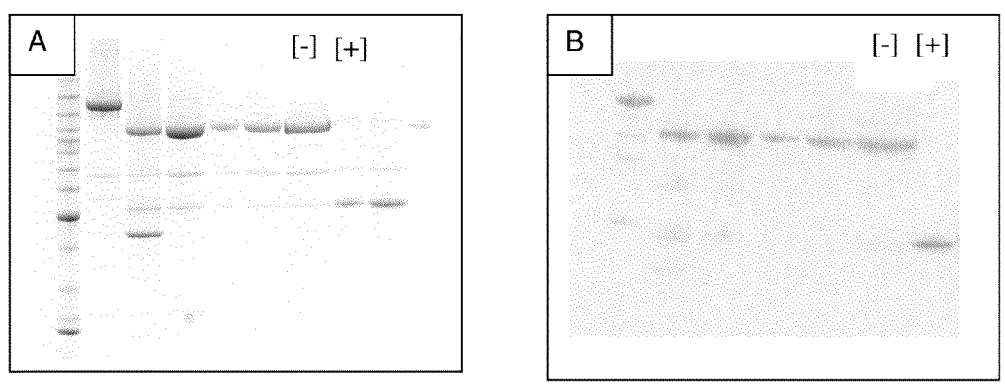
FIG. 4—Purification of a $LC/A-Nociceptin-H_N/A$ fusion protein

FIG. 3 shows the SDS-PAGE analysis of expression and purification of N[1-17]-LH$_N$/A.

Example 10

Recombinant Production of a Single Polypeptide Fusion of (nociceptin 1-11)-LH$_N$/B The DNA sequence for the (nociceptin 1-11)-LH$_N$/B was designed by back translation of the LC/B, H$_N$/B, and nociceptin 1-11 amino acid sequences. The complete ORF containing the (nociceptin1-11)-LC/B-activation loop-H$_N$/B sequence was assembled within standard DNA sequence manipulation software (EditSeq). The activation loop between the LC/B cysteine and the H$_N$/B cysteine was modified to incorporate a Factor Xa protease recognition site.

The recombinant fusion protein was then produced essentially as described in Example 9.

Example 11

Recombinant Production of a Single Polypeptide Fusion of (Nociceptin N[[Y14]1-17])-LH$_N$/C (SEQ ID NO:25 and SEQ ID NO:26)

The DNA sequence for the nociceptin N[[Y14]1-17] was designed by back translation of the LC/C, H$_N$/C, and nociceptin N[[Y14]1-17] amino acid sequences. The complete ORF containing the (nociceptin N[[Y14]1-17])-LC/C-activation loop-H$_N$/C sequence was assembled within standard DNA sequence manipulation software (EditSeq). The activation loop between the LC/C cysteine and the H$_N$/C cysteine was modified to incorporate a Factor Xa protease recognition site.

The recombinant fusion protein was then produced essentially as described in Example 9.

Example 12

Recombinant Production of a Single Polypeptide Fusion of LH$_N$/C-(Nociceptin 1-11) (SEQ ID NO:23 and SEQ ID NO:24)

The DNA sequence for the LH$_N$/C-(nociceptin 1-11) was designed by back translation of the LC/C, H$_N$/C and nociceptin 1-11 amino acid sequences. The complete ORF (SEQ ID NO:23) containing the LC/C-activation loop-H$_N$/C-flexible spacer-(nociceptin 1-11) was assembled within standard DNA sequence manipulation software (EditSeq).

The recombinant fusion protein (SEQ ID NO:24) was then produced essentially as described in Example 9.

Example 13

Production of a Conjugate for Delivery of DNA Encoding LC/C into a Cell

The construction of a nociceptin-H$_N$-[LC/C] conjugate is described below, where [LC/C] represents the polylysine condensed DNA encoding the light chain of botulinum neurotoxin type C.

Materials

SPDP is from Pierce Chemical Co. Additional reagents are obtained from Sigma Ltd.

Methods

Using a plasmid containing the gene encoding LC/C under the control of a CMV (immediate early) promoter, condensation of DNA was achieved using SPDP-derivatised polylysine to a ratio of 2 DNA to 1 polylysine. Conjugates were then prepared by mixing condensed DNA (0.4 mg/ml) with H$_N$-nociceptin (100 µg/ml) for 16 h at 25° C. The SPDP-derivatised polylysine and the free —SH group present on the H$_N$ domain combine to facilitate covalent attachment of the DNA and protein.

Example 14

Production of a Conjugate for Delivery of DNA Encoding LC/B into a Cell

The construction of a (nociceptin 1-11)-H$_N$-[LC/B] conjugate is described below, where [LC/B] represents the polylysine condensed DNA encoding the light chain of botulinum neurotoxin type B.

Materials

SPDP is from Pierce Chemical Co. Additional reagents are obtained from Sigma Ltd.

Methods

Using a plasmid containing the gene encoding LC/B under the control of a CMV (immediate early) promoter, condensation of DNA was achieved using SPDP-derivatised polylysine to a ratio of 2 DNA to 1 polylysine. Conjugates were then prepared by mixing condensed DNA (0.4 mg/ml) with H$_N$-(nociceptin 1-11) (100 µg/ml) for 16 h at 25° C. The SPDP-derivatised polylysine and the free —SH group present on the H$_N$ domain combine to facilitate covalent attachment of the DNA and protein.

Example 15

Assessment of the Activity of Nociceptin-LH$_N$/A in Substance P Releasing Neuronal Cells Using methodology described in Duggan et al., (2002, J. Biol. Chem., 277, 34846-34852), the activity of nociceptin-LH$_N$/A in substance P releasing neuronal cells was assessed.

Nociceptin-LH$_N$/A fusion protein was applied to 2-week old dorsal root ganglia neuronal cultures, and incubated at 37° C. for 16 hours. Following the incubation, the media was removed and the ability of the cells to undergo stimulated release of substance P (SP) was assessed.

The release of SP from the neuronal cells incubated with the nociceptin-LH$_N$/A fusion protein was assayed in comparison to (i) LH$_N$/A-only treated cells and (ii) cells treated with media alone. This allowed the % inhibition of substance P from the eDRG to be calculated. The ability of the nociceptin-LH$_N$/A fusion protein to inhibit SP release (relative to cells treated with media alone) was reported in Table 1. The data represent the mean of 3 determinations:

TABLE 1

| Test Material (µM) | nociceptin-LH$_N$/A fusion protein % Inhibition | LH$_N$/A-only % Inhibition |
|---|---|---|
| 1.0 | 47.3 | 25.6 |
| 0.1 | 13.8 | −11.5 |

Example 16

Confirmation of ORL$_1$ Receptor Activation by Measuring Forskolin-Stimulated cAMP Production Confirmation that a given TM is acting via the ORL$_1$ receptor is provided by the following test, in which the TMs ability to inhibit forskolin-stimulated cAMP production is assessed.

Materials

[$^3$H]adenine and [$^{14}$C]cAMP are obtained from GE Healthcare

Methods

The test is conducted essentially as described previously by Meunier et al. [Isolation and structure of the endogenous agonist of opioid receptor-like ORL$_1$ receptor. Nature 377: 532-535, 1995] in intact transfected-CHO cells plated on 24-well plastic plates.

To the cells is added [3H]adenine (1.0 µCi) in 0.4 ml of culture medium. The cells remain at 37° C. for 2 h to allow the adenine to incorporate into the intracellular ATP pool. After 2 h, the cells are washed once with incubation buffer containing: 130 mM NaCl, 4.8 mM KCl, 1.2 mM KH$_2$PO$_4$, 1.3 mM CaCl$_2$, 1.2 mM MgSO$_4$, 10 mM glucose, 1 mg/ml bovine serum albumin and 25 mM HEPES, pH 7.4, and replaced with buffer containing forskolin (10 µM) and isobutylmethylxanthine (50 µM) with or without the TM of interest. After 10 min., the medium is aspirated and replaced with 0.5 ml, 0.2 M HCl. Approximately 1000 cpm of [$^{14}$C]cAMP is added to each well and used as an internal standard. The contents of the wells are then transferred to columns of 0.65 g dry alumina powder. The columns are eluted with 4 ml of 5 mM HCl, 0.5 ml of 0.1 M ammonium acetate, then two additional milliliters of ammonium acetate. The final eluate is collected into scintillation vials and counted for $^{14}$C and tritium. Amounts collected are corrected for recovery of [$^{14}$C]cAMP. TMs that are agonists at the ORL$_1$ receptor cause a reduction in the level of cAMP produced in response to forskolin.

Example 17

Confirmation of ORL$_1$ Receptor Activation Using a GTPγS Binding Functional Assay Confirmation that a given TM is acting via the ORL$_1$ receptor is also provided by the following test, a GTPγS binding functional assay.

Materials

[$^{35}$S]GTPγS is obtained from GE Healthcare. Wheatgerm agglutinin-coated (SPA) beads are obtained from GE Healthcare Methods This assay is carried out essentially as described by Traynor and Nahorski [Modulation by µ-opioid agonists of guanosine-5-O-(3-[$^{35}$S]thio)triphosphate binding to membranes from human neuroblastoma SH-SY5Y cells. Mol. Pharmacol. 47: 848-854, 1995].

Cells are scraped from tissue culture dishes into 20 mM HEPES, 1 mM ethylenediaminetetraacetic acid, then centrifuged at 500×g for 10 min. Cells are resuspended in this buffer and homogenized with a Polytron Homogenizer.

The homogenate is centrifuged at 27,000×g for 15 min., and the pellet resuspended in buffer A, containing: 20 mM HEPES, 10 mM MgCl$_2$, 100 mM NaCl, pH 7.4. The suspension is recentrifuged at 20,000×g and suspended once more in buffer A. For the binding assay, membranes (8-15 µg protein) are incubated with [$^{35}$S]GTP S (50 pM), GDP (10 µM), with and without the TM of interest, in a total volume of 1.0 ml, for 60 min. at 25° C. Samples are filtered over glass fibre filters and counted as described for the binding assays.

Example 18

Preparation of a LC/A and H$_N$/A Backbone Clones

The following procedure creates the LC and H$_N$ fragments for use as the component backbone for multidomain fusion expression. This example is based on preparation of a serotype A based clone (SEQ ID NO:27 and SEQ ID NO:28), though the procedures and methods are equally applicable to the other serotypes [illustrated by the sequence listing for serotype B (SEQ ID NO:29 and SEQ ID NO:30) and serotype C (SEQ ID NO:31 and SEQ ID NO:32)].

Preparation of Cloning and Expression Vectors pCR 4 (Invitrogen) is the chosen standard cloning vector, selected due to the lack of restriction sequences within the vector and adjacent sequencing primer sites for easy construct confirmation. The expression vector is based on the pMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (e.g. LC/A) Insert

The LC/A (SEQ ID NO:27) is created by one of two ways:

The DNA sequence is designed by back translation of the LC/A amino acid sequence [obtained from freely available database sources such as GenBank (accession number P10845) or Swissprot (accession locus BXA1_CLOBO) using one of a variety of reverse translation software tools (for example EditSeq best E. coli reverse translation (DNASTAR Inc.), or Backtranslation tool v2.0 (Entelechon)]. BamHI/SalI recognition sequences are incorporated at the 5' and 3' ends respectively of the sequence, maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the LC/A open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a supplier (for example MWG or Sigma-Genosys), so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for $Mg^{2+}$ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis [for example, using Quickchange (Stratagene Inc.)].

Preparation of Translocation (e.g. $H_N$) Insert

The $H_N$/A (SEQ ID NO:28) is created by one of two ways:

The DNA sequence is designed by back translation of the $H_N$/A amino acid sequence [obtained from freely available database sources such as GenBank (accession number P10845) or Swissprot (accession locus BXA1_CLOBO)] using one of a variety of reverse translation software tools [for example EditSeq best *E. coli* reverse translation (DNASTAR Inc.), or Backtranslation tool v2.0 (Entelechon)]. A PstI restriction sequence added to the N-terminus and XbaI-stop codon-HindIII to the C-terminus ensuring the correct reading frame is maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis [for example using Quickchange (Stratagene Inc.)].

Example 19

Preparation of a LC/A-Nociceptin-$H_N$/A Fusion Protein (Nociceptin is N-Terminal of the $H_N$-Chain)

Preparation of Linker-Nociceptin-Spacer Insert

The LC-$H_N$ linker can be designed from first principle, using the existing sequence information for the linker as the template. For example, the serotype A linker (in this case defined as the inter-domain polypeptide region that exists between the cysteines of the disulphide bridge between LC and $H_N$) is 23 amino acids long and has the sequence VRGIITSKTKSLDKGYNKALNDL (amino acids 2-24 of SEQ ID NO:120). Within this sequence, it is understood that proteolytic activation in nature leads to an $H_N$ domain that has an N-terminus of the sequence ALNDL. This sequence information is freely available from available database sources such as GenBank (accession number P10845) or Swissprot (accession locus BXA1_CLOBO). Into this linker a Factor Xa site, nociceptin and spacer are incorporated; and using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-nociceptin-NheI-spacer-SpeI-PstI-XbaI-stop codon-HindIII (SEQ ID NO:33). It is important to ensure the correct reading frame is maintained for the spacer, nociceptin and restriction sequences and that the XbaI sequence is not preceded by the bases, TC, which would result on DAM methylation. The DNA sequence is screened for restriction sequence incorporation, and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example, GenBank Release 143, 13 Sep. 2004). This optimised DNA sequence is then commercially synthesized (for example by Entelechon, Geneart or Sigma-Genosys) and is provided in the pCR 4 vector.

Preparation of the LC/A-Nociceptin-$H_N$/A Fusion

In order to create the LC-linker-nociceptin-spacer-$H_N$ construct (SEQ ID NO:39), the pCR 4 vector encoding the linker (SEQ ID NO:33) is cleaved with BamHI+SalI restriction enzymes. This cleaved vector then serves as the recipient vector for insertion and ligation of the LC/A DNA (SEQ ID NO:27) cleaved with BamHI+San. The resulting plasmid DNA is then cleaved with PstI+XbaI restriction enzymes and serves as the recipient vector for the insertion and ligation of the $H_N$/A DNA (SEQ ID NO:28) cleaved with PstI+XbaI. The final construct contains the LC-linker-nociceptin-spacer-H$_N$ ORF (SEQ ID NO:39) for transfer into expression vectors for expression to result in a fusion protein of the sequence illustrated in SEQ ID NO:40.

Example 20

Preparation of a Nociceptin-LC/A-H$_N$/A Fusion Protein (Nociceptin is N-Terminal of the LC-Chain)

The LC/A-H$_N$/A backbone is constructed as described in Example 19 using the synthesised A serotype linker with the addition of a Factor Xa site for activation, arranged as BamHI-SalI-linker-protease site-linker-PstI-XbaI-stop codon-HindIII (SEQ ID NO:34). The LC/A-H$_N$/A backbone and the synthesised N-terminal presentation nociceptin insert (SEQ ID NO:35) are cleaved with BamHI+HindIII restriction enzymes, gel purified and ligated together to create a nociceptin-spacer-LC-linker-H$_N$. The ORF (SEQ ID NO:41) is then cut out using restriction enzymes AvaI+XbaI for transfer into expression vectors for expression to result in a fusion protein of the sequence illustrated in SEQ ID NO:42.

Example 21

Preparation of a LC/C-Nociceptin-H$_N$/C Fusion Protein

Following the methods used in Examples 1 and 2, the LC/C (SEQ ID NO:31) and H$_N$/C (SEQ ID NO:32) are created and inserted into the C serotype linker arranged as BamHI-SalI-linker-protease site-nociceptin-NheI-spacer-SpeI-PstI-XbaI-stop codon-HindIII (SEQ ID NO:36). The final construct contains the LC-linker-nociceptin-spacer-H$_N$ ORF (SEQ ID NO:43) for expression as a protein of the sequence illustrated in SEQ ID NO:44.

Example 22

Preparation of a LC/C-Nociceptin-H$_N$/C Fusion Protein with a Serotype A Activation Sequence Following the methods used in Examples 1 and 2, the LC/C (SEQ ID NO:31) and H$_N$/C (SEQ ID NO:32) are created and inserted into the A serotype linker arranged as BamHI-SalI-linker-protease site-nociceptin-NheI-spacer-SpeI-PstI-XbaI-stop codon-HindIII (SEQ ID NO:33). The final construct contains the LC-linker-nociceptin-spacer-H$_N$ ORF (SEQ ID NO:45) for expression as a protein of the sequence illustrated in SEQ ID NO:46.

Example 23

Preparation of a LC/A-Met Enkephalin-H$_N$/A Fusion Protein

Due to the small, five-amino acid, size of the met-enkephalin ligand the LC/A-met enkephalin-H$_N$/A fusion is created by site directed mutagenesis [for example using Quickchange (Stratagene Inc.)] using the LC/A-nociceptin-H$_N$/A fusion (SEQ ID NO:39) as a template. Oligonucleotides are designed encoding the YGGFM met-enkephalin peptide (SEQ ID NO:121), ensuring standard E. coli codon usage is maintained and no additional restriction sites are incorporated, flanked by sequences complimentary to the linker region of the LC/A-nociceptin-H$_N$/A fusion (SEQ ID NO:39) either side on the nociceptin section. The SDM product is checked by sequencing and the final construct containing the LC-linker-met enkephalin-spacer-H$_N$ ORF (SEQ ID NO:47) for expression as a protein of the sequence illustrated in SEQ ID NO:48.

Example 24

Preparation of a LC/A-β Endorphin-H$_N$/A Fusion Protein

Following the methods used in Examples 1 and 2, the LC/A (SEQ ID NO:27) and H$_N$/A (SEQ ID NO:28) are created and inserted into the A serotype β endorphin linker arranged as BamHI-SalI-linker-protease site-β endorphin-NheI-spacer-SpeI-PstI-XbaI-stop codon-HindIII (SEQ ID NO:37). The final construct contains the LC-linker-β endorphin-spacer-H$_N$ ORF (SEQ ID NO:49) for expression as a protein of the sequence illustrated in SEQ ID NO:50.

Example 25

Preparation of a LC/A-Nociceptin Variant-H$_N$/A Fusion Protein

Following the methods used in Examples 1 and 2, the LC/A (SEQ ID NO:27) and H$_N$/A (SEQ ID NO:28) are created and inserted into the A serotype nociceptin variant linker arranged as BamHI-SalI-linker-protease site-nociceptin variant-NheI-spacer-SpeI-PstI-XbaI-stop codon-HindIII (SEQ ID NO:38). The final construct contains the LC-linker-nociceptin variant-spacer-H$_N$ ORF (SEQ ID NO:51) for expression as a protein of the sequence illustrated in SEQ ID NO:52.

Example 26

Purification Method for LC/A-Nociceptin-H$_N$/A Fusion Protein

Defrost falcon tube containing 25 ml 50 mM HEPES pH 7.2, 200 mM NaCl and approximately 10 g of E. coli BL21 cell paste. Make the thawed cell paste up to 80 ml with 50 mM HEPES pH 7.2, 200 mM NaCl and sonicate on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M NiSO$_4$ charged Chelating column (20-30 ml column is sufficient) equilibrated with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and measure the OD of the dialysed fusion protein. Add 1 unit of factor Xa per 100 µg fusion protein and Incubate at 25° C. static overnight. Load onto a 0.1 M NiSO$_4$ charged Chelating column (20-30 ml column is sufficient) equilibrated with 50 mM HEPES pH 7.2, 200 mM NaCl. Wash column to baseline with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and concentrate the fusion to about 2 mg/ml, aliquot sample and freeze at −20° C. Test purified protein using OD, BCA, purity analysis and SNAP-25 assessments.

Example 27

Preparation of a LC/A-Nociceptin-H$_N$/A Fusion Protein (Nociceptin is N-Terminal of the H$_N$-Chain)

The linker-nociceptin-spacer insert is prepared as described in Example 19.
Preparation of the LC/A-Nociceptin-H$_N$/A Fusion In order to create the LC-linker-nociceptin-spacer-H$_N$ construct (SEQ ID NO:39), the pCR 4 vector encoding the linker (SEQ ID NO:33) is cleaved with BamHI+SalI restriction enzymes. This cleaved vector then serves as the recipient for insertion and ligation of the LC/A DNA (SEQ ID NO:27) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The H$_N$/A DNA (SEQ ID NO:28) is then cleaved with PstI+HindIII restriction enzymes and inserted into the similarly cleaved pMAL-LC/A-linker construct. The final construct contains the LC-linker-nociceptin-spacer-H$_N$ ORF (SEQ ID NO:39) for expression as a protein of the sequence illustrated in SEQ ID NO:40.

Example 28

Preparation of a Nociceptin-LC/A-H$_N$/A Fusion Protein (Nociceptin is N-Terminal of the LC-Chain)

In order to create the nociceptin-spacer-LC/A-H$_N$/A construct, an A serotype linker with the addition of a Factor Xa site for activation, arranged as BamHI-SalI-linker-protease site-linker-PstI-XbaI-stop codon-HindIII (SEQ ID NO:34) is synthesised as described in Example 27. The pCR 4 vector encoding the linker is cleaved with BamHI+SalI restriction enzymes. This cleaved vector then serves as the recipient for insertion and ligation of the LC/A DNA (SEQ ID NO:27) also cleaved with BamHI+SalI. The resulting plasmid DNA is then cleaved with BamHI+HindIII restriction enzymes and the LC/A-linker fragment inserted into a similarly cleaved vector containing the synthesised N-terminal presentation nociceptin insert (SEQ ID NO:35). This construct is then cleaved with AvaI+HindIII and inserted into an expression vector such as the pMAL plasmid (NEB). The H$_N$/A DNA (SEQ ID NO:28) is then cleaved with PstI+HindIII restriction enzymes and inserted into the similarly cleaved pMAL-nociceptin-LC/A-linker construct. The final construct contains the nociceptin-spacer-LC/A-H$_N$/A ORF (SEQ ID NO:63) for expression as a protein of the sequence illustrated in SEQ ID NO:64.

Example 29

Preparation and Purification of an LC/A-Nociceptin-H$_N$/A Fusion Protein Family with Variable Spacer Length Using the same strategy as employed in Example 19, a range of DNA linkers were prepared that encoded nociceptin and variable spacer content. Using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-nociceptin-NheI-spacer-SpeI-PstI-XbaI-stop codon-HindIII (SEQ ID NO:65 to SEQ ID NO:69). It is important to ensure the correct reading frame is maintained for the spacer, nociceptin and restriction sequences and that the XbaI sequence is not preceded by the bases, TC which would result on DAM methylation. The DNA sequence is screened for restriction sequence incorporation and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The spacers that were created included:

TABLE 2

| Code | Protein sequence of the linker | SEQ ID NO: of the linker DNA |
| --- | --- | --- |
| GS10 | ALAGGGGSALVLQ | 122 |
| GS15 | ALAGGGGSGGGGSALVLQ | 123 |
| GS25 | ALAGGGGSGGGGSGGGGSGGGGSALVLQ | 124 |
| GS30 | ALAGGGGSGGGGSGGGGSGGGGSGGGGSALVLQ | 125 |
| HX27 | ALAAEAAAKEAAAKEAAAKAGGGGSALVLQ | 126 |

By way of example, in order to create the LC/A-CPN (GS15)-H$_N$/A fusion construct (SEQ ID NO:70), the pCR 4 vector encoding the linker (SEQ ID NO:66) is cleaved with BamHI+SalI restriction enzymes. This cleaved vector then serves as the recipient vector for insertion and ligation of the LC/A DNA (SEQ ID NO:27) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The H$_N$/A DNA (SEQ ID NO:28) is then cleaved with PstI+HindIII restriction enzymes and inserted into the similarly cleaved pMAL-LC/A-linker construct. The final construct contains the LC/A-CPN(GS15)-H$_N$/A ORF (SEQ ID NO:70) for expression as a protein of the sequence illustrated in SEQ ID NO:71.

As a further example, to create the LC/A-CPN(GS25)-H$_N$/A fusion construct (SEQ ID NO:72), the pCR 4 vector encoding the linker (SEQ ID NO:67) is cleaved with BamHI+SalI restriction enzymes. This cleaved vector then serves as the recipient vector for insertion and ligation of the LC/A DNA (SEQ ID NO:27) cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The H$_N$/A DNA (SEQ ID NO:28) is then cleaved with PstI+HindIII restriction enzymes and inserted into the similarly cleaved pMAL-LC/A-linker construct. The final construct contains the LC/A-CPN(GS25)-H$_N$/A ORF (SEQ ID NO:72) for expression as a protein of the sequence illustrated in SEQ ID NO:73.

Variants of the LC/A-CPN-H$_N$/A fusion consisting of GS10, GS30 and HX27 are similarly created. Using the purification methodology described in Example 26, fusion protein is purified from *E. coli* cell paste. FIG. 12 illustrates the purified product obtained in the case of LC/A-CPN(GS10)-$H_N$/A, LC/A-CPN(GS15)-$H_N$/A, LC/A-CPN(GS25)-$H_N$/A, LC/A-CPN(GS30)-$H_N$/A and LC/A-CPN(HX27)-$H_N$/A.

Example 30

Assessment of In Vitro Efficacy of an LC/A-Nociceptin-$H_N$/A Fusion

Fusion protein prepared according to Examples 2 and 9 was assessed in the eDRG neuronal cell model.

Assays for the inhibition of substance P release and cleavage of SNAP-25 have been previously reported (Duggan et al., 2002, J. Biol. Chem., 277, 34846-34852). Briefly, dorsal root ganglia neurons are harvested from 15-day-old fetal Sprague-Dawley rats and dissociated cells plated onto 24-well plates coated with Matrigel at a density of $1 \times 10^6$ cells/well. One day post-plating the cells are treated with 10 μM cytosine β-D-arabinofuranoside for 48 h. Cells are maintained in Dulbecco's minimal essential medium supplemented with 5% heat-inactivated fetal bovine serum, 5 mM L-glutamine, 0.6% D-glucose, 2% B27 supplement, and 100 ng/ml 2.5S mouse nerve growth factor. Cultures are maintained for 2 weeks at 37° C. in 95% air/5% $CO_2$ before addition of test materials.

Release of substance P from eDRG is assessed by enzyme-linked immunosorbent assay. Briefly, eDRG cells are washed twice with low potassium-balanced salt solution (BSS: 5 mM KCl, 137 mM NaCl, 1.2 mM $MgCl_2$, 5 mM glucose, 0.44 mM $KH_2PO_4$, 20 mM HEPES, pH 7.4, 2 mM $CaCl_2$). Basal samples are obtained by incubating each well for 5 min. with 1 ml of low potassium BSS. After removal of this buffer, the cells are stimulated to release by incubation with 1 ml of high potassium buffer (BSS as above with modification to include 100 mM KCl isotonically balanced with NaCl) for 5 min. All samples are removed to tubes on ice prior to assay of substance P. Total cell lysates are prepared by addition of 250 μl of 2 M acetic acid/0.1% trifluoroacetic acid to lyse the cells, centrifugal evaporation, and resuspension in 500 μl of assay buffer. Diluted samples are assessed for substance P content. Substance P immunoreactivity is measured using Substance P Enzyme Immunoassay Kits (Cayman Chemical Company or R&D Systems) according to manufacturers' instructions. Substance P is expressed in pg/ml relative to a standard substance P curve run in parallel.

SDS-PAGE and Western blot analysis were performed using standard protocols (Novex). SNAP-25 proteins were resolved on a 12% Tris/glycine polyacrylamide gel (Novex) and subsequently transferred to nitrocellulose membrane. The membranes were probed with a monoclonal antibody (SMI-81) that recognises cleaved and intact SNAP-25. Specific binding was visualised using peroxidase-conjugated secondary antibodies and a chemiluminescent detection system. Cleavage of SNAP-25 was quantified by scanning densitometry (Molecular Dynamics Personal SI, ImageQuant data analysis software). Percent SNAP-25 cleavage was calculated according to the formula: (Cleaved SNAP-25/(Cleaved+Intact SNAP-25))×100.

Following exposure of eDRG neurons to an LC/A-nociceptin-$H_N$/A fusion (termed CPN-A), both inhibition of substance P release and cleavage of SNAP-25 are observed (FIG. 13). After 24 h exposure to the fusion, 50% of maximal SNAP-25 cleavage is achieved by a fusion concentration of 6.3±2.5 nM.

The effect of the fusion is also assessed at defined time points following a 16 h exposure of eDRG to CPN-A. FIG. 14 illustrates the prolonged duration of action of the CPN-A fusion protein, with measurable activity still being observed at 28 days post exposure.

Example 31

Assessment of In Vitro Efficacy of an LC/A-Nociceptin Variant-$H_N$/A Fusion

Fusion protein prepared according to Examples 8 and 9 was assessed in the eDRG neuronal cell mode using the method described in Example 30.

Following exposure of eDRG neurons to an LC/A-nociceptin variant-$H_N$/A fusion (termed CPNv-A), both inhibition of substance P release and cleavage of SNAP-25 are observed. After 24 h exposure to the fusion, 50% of maximal SNAP-25 cleavage is achieved by a fusion concentration of 1.4±0.4 nM (FIG. 15).

The effect of the fusion is also assessed at defined time points following a 16 h exposure of eDRG to CPN-A. FIG. 16 illustrates the prolonged duration of action of the CPN-A fusion protein, with measurable activity still being observed at 24 days post exposure.

The binding capability of the CPNv-A fusion protein is also assessed in comparison to the CPN-A fusion. FIG. 17 illustrates the results of a competition experiment to determine binding efficacy at the ORL-1 receptor. CPNv-A is demonstrated to displace [3H]-nociceptin, thereby confirming that access to the receptor is possible with the ligand in the central presentation format.

Example 32

Preparation of an LC/A-Nociceptin Variant-$H_N$/A Fusion Protein that is Activated by Treatment with Enterokinase Following the methods used in Examples 1 and 2, the LC/A (SEQ ID NO:27) and $H_N$/A (SEQ ID NO:28) are created and inserted into the A serotype nociceptin variant linker arranged as BamHI-SalI-linker-enterokinase protease site-nociceptin variant-NheI-spacer-SpeI-PstI-XbaI-stop codon-HindIII (SEQ ID NO:74). The final construct contains the LC-linker-nociceptin variant-spacer-$H_N$ ORF sequences (SEQ ID NO:75) for expression as a protein of the sequence illustrated in SEQ ID NO:76. The fusion protein is termed CPNv(Ek)-A. FIG. 18 illustrates the purification of CPNv(Ek)-A from *E. coli* following the methods used in Example 26 but using Enterokinase for activation at 0.00064 μg per 100 μg of fusion protein.

Example 33

Assessment of In Vitro Efficacy of an LC/A-Nociceptin Variant-$H_N$/A Fusion that has been Activated by Treatment with Enterokinase The CPNv(Ek)-A prepared in Example 32 is obtained in a purified form and applied to the eDRG cell model to assess cleavage of SNAP-25 (using methodology from Example 30). FIG. 19 illustrates the cleavage of SNAP-25 following 24 h exposure of eDRG to CPNv(Ek)-A. The efficiency of cleav-

Example 34

Preparation of an LC/C-Nociceptin Variant-$H_N$/C Fusion Protein with a Factor Xa Activation Linker Derived from Serotype A Following the methods used in Example 21, the LC/C (SEQ ID NO:31) and $H_N$/C (SEQ ID NO:32) are created and inserted into the A serotype nociceptin variant linker arranged as BamHI-SalI-linker-nociceptin variant-NheI-spacer-SpeI-PstI-XbaI-stop codon-HindIII (SEQ ID NO:77). The final construct contains the LC-linker-nociceptin variant-spacer-$H_N$ ORF sequences (SEQ ID NO:78) for expression as a protein of the sequence illustrated in SEQ ID NO:79. The fusion protein is termed CPNv-C (act. A). FIG. 20 illustrates the purification of CPNv-C (act. A) from *E. coli* following the methods used in Example 26.

Example 35

Assessment of In Vitro Efficacy of an LC/C-Nociceptin Variant-$H_N$/C Fusion Protein Following the methods used in Example 26, the CPNv-C (act. A) prepared in Example 34 is obtained in a purified form and applied to the eDRG cell model to assess cleavage of SNAP-25 (using methodology from Example 30). After 24 h exposure to the fusion, 50% of maximal syntaxin cleavage is achieved by a fusion concentration of 3.1±2.0 nM. FIG. 21 illustrates the cleavage of syntaxin following 24 h exposure of eDRG to CPNv-C (act. A).

Example 36

Assessment of In Vivo Efficacy of an LC/A-Nociceptin-HN/A Fusion

The ability of an LC/A-nociceptin-$H_N$/A fusion (CPN/A) to inhibit acute capsaicin-induced mechanical allodynia is evaluated following subcutaneous intraplantar injection in the rat hind paw. Test animals are evaluated for paw withdrawal frequency (PWF %) in response to a 10 g Von Frey filament stimulus series (10 stimuli×3 trials) prior to recruitment into the study, after subcutaneous treatment with CPN/A but before capsaicin, and following capsaicin challenge post-injection of CPN/A (average of responses at 15' and 30'). Capsaicin challenge is achieved by injection of 10 μL of a 0.3% solution. Sample dilutions are prepared in 0.5% BSA/saline. FIG. 22 illustrates the reversal of mechanical allodynia that is achieved by pre-treatment of the animals with a range of concentrations of LC/A-nociceptin-HN/A fusion.

The ability of an LC/A-nociceptin-HN/A fusion (CPN/A) to inhibit streptozotocin (STZ)-induced mechanical (tactile) allodynia in rats is evaluated. STZ-induced mechanical allodynia in rats is achieved by injection of streptozotocin (i.p. or i.v.) which yields destruction of pancreatic β-cells leading to loss of insulin production, with concomitant metabolic stress (hyperglycemia and hyperlipidemia). As such, STZ induces Type I diabetes. In addition, STZ treatment leads to progressive development of neuropathy, which serves as a model of chronic pain with hyperalgesia and allodynia that may reflect signs observed in diabetic humans (peripheral diabetic neuropathy).

Male Sprague-Dawley rats (250-300 g) are treated with 65 mg/kg STZ in citrate buffer (I.V.) and blood glucose and lipid are measured weekly to define the readiness of the model. Paw Withdrawal Threshold (PWT) is measured in response to a Von Frey filament stimulus series over a period of time. Allodynia is said to be established when the PWT on two consecutive test dates (separated by 1 week) measures below 6 g on the scale. At this point, rats are randomized to either a saline group (negative efficacy control), gabapentin group (positive efficacy control) or a test group (CPN/A). Test materials (20-25 μl) are injected subcutaneously as a single injection (except gabapentin) and the PWT is measured at 1 day post-treatment and periodically thereafter over a 2-week period. Gabapentin (30 mg/kg i.p. @ 3 ml/kg injection volume) is injected daily, 2 hours prior to the start of PWT testing. FIG. 23 illustrates the reversal of allodynia achieved by pre-treatment of the animals with 750 ng of CPN/A. Data were obtained over a 2-week period after a single injection of CPN/A

Example 37

Assessment of In Vivo Efficacy of an LC/A-Nociceptin Variant-$H_N$/A Fusion

The ability of an LC/A-nociceptin variant-$H_N$/A fusion (CPNv/A) to inhibit capsaicin-induced mechanical allodynia is evaluated following subcutaneous intraplantar injection in the rat hind paw. Test animals are evaluated for paw withdrawal frequency (PWF %) in response to a 10 g Von Frey filament stimulus series (10 stimuli×3 trials) prior to recruitment into the study (Pre-Treat); after subcutaneous intraplantar treatment with CPNv/A but before capsaicin (Pre-CAP); and following capsaicin challenge post-injection of CPNv/A (average of responses at 15' and 30'; CAP). Capsaicin challenge is achieved by injection of 10 μL of a 0.3% solution. Sample dilutions are prepared in 0.5% BSA/saline.

FIG. 24 illustrates the reversal of allodynia that is achieved by pre-treatment of the animals with a range of concentrations of LC/A-nociceptin variant-$H_N$/A fusion in comparison to the reversal achieved with the addition of LC/A-nociceptin-$H_N$/A fusion. These data are expressed as a normalized paw withdrawal frequency differential, in which the difference between the peak response (post-capsaicin) and the baseline response (pre-capsaicin) is expressed as a percentage. With this analysis, it can be seen that CPNv/A is more potent than CPN/A since a lower dose of CPNv/A is required to achieve similar analgesic effect to that seen with CPN/A.

Example 38

Preparation of an LC/A-Leu Enkephalin-$H_N$/A Fusion Protein

Due to the small, five-amino acid, size of the leu-enkephalin ligand the LC/A-leu enkephalin-$H_N$/A fusion is created by site directed mutagenesis [for example using Quickchange (Stratagene Inc.)] using the LC/A-nociceptin-$H_N$/A fusion (SEQ ID NO:39) as a template. Oligonucleotides are designed encoding the YGGFL leu-enkephalin peptide, ensuring standard *E. coli* codon usage is maintained and no additional restriction sites are incorporated, flanked by sequences complimentary to the linker region of the LC/A-nociceptin-$H_N$/A fusion (SEQ ID NO:39) either side on the nociceptin section. The SDM product is checked by sequencing and the final construct containing the LC-linker-leu enkephalin-spacer-$H_N$ ORF (SEQ ID NO:80) for expression as a protein of the sequence illustrated in SEQ ID NO:81. The fusion protein is termed CPLE-A. FIG. 25 illustrates the purification of CPLE-A from *E. coli* following the methods used in Example 26.

Example 39

Expression and Purification of an LC/A-Beta-Endorphin-$H_N$/A Fusion Protein

Following the methods used in Example 26, and with the LC/A-beta-endorphin-$H_N$/A fusion protein (termed CPBE-A) created in Example 24, the CPBE-A is purified from *E. coli*. FIG. 26 illustrates the purified protein as analysed by SDS-PAGE.

Example 40

Preparation of an LC/A-Nociceptin Mutant-$H_N$/A Fusion Protein

Due to the single amino acid modification necessary to mutate the nociceptin sequence at position 1 from a Phe to a Tyr, the LC/A-nociceptin mutant-$H_N$/A fusion is created by site directed mutagenesis [for example using Quickchange (Stratagene Inc.)] using the LC/A-nociceptin-$H_N$/A fusion (SEQ ID NO:39) as a template. Oligonucleotides are designed encoding tyrosine at position 1 of the nociceptin sequence, ensuring standard *E. coli* codon usage is maintained and no additional restriction sites are incorporated, flanked by sequences complimentary to the linker region of the LC/A-nociceptin-$H_N$/A fusion (SEQ ID NO:39) either side on the nociceptin section. The SDM product is checked by sequencing and the final construct containing the LC/A-nociceptin mutant-spacer-$H_N$/A fusion ORF (SEQ ID NO:82) for expression as a protein of the sequence illustrated in SEQ ID NO:83. The fusion protein is termed CPOP-A. FIG. 27 illustrates the purification of CPOP-A from *E. coli* following the methods used in Example 26.

Example 41

Preparation and Assessment of an LC/A-Nociceptin Variant Mutant-$H_N$/A Fusion Protein Due to the single amino acid modification necessary to mutate the nociceptin sequence at position 1 from a Phe to a Tyr, the LC/A-nociceptin variant mutant-$H_N$/A fusion is created by site directed mutagenesis [for example using Quickchange (Stratagene Inc.)] using the LC/A-nociceptin variant-$H_N$/A fusion (SEQ ID NO:51) as a template. Oligonucleotides are designed encoding tyrosine at position 1 of the nociceptin sequence, ensuring standard *E. coli* codon usage is maintained and no additional restriction sites are incorporated, flanked by sequences complimentary to the linker region of the LC/A-nociceptin variant-$H_N$/A fusion (SEQ ID NO:51) either side on the nociceptin section. The SDM product is checked by sequencing and the final construct containing the LC/A-nociceptin mutant-spacer-$H_N$/A fusion ORF (SEQ ID NO:84) for expression as a protein of the sequence illustrated in SEQ ID NO:85. The fusion protein is termed CPOPv-A. FIG. 28 illustrates the purification of CPOPv-A from *E. coli* following the methods used in Example 26.

Using methodology described in Example 30, CPOPv-A is assessed for its ability to cleave SNAP-25 in the eDRG cell model. FIG. 29 illustrates that CPOPv-A is able to cleave SNAP-25 in the eDRG model, achieving cleavage of 50% of the maximal SNAP-25 after exposure of the cells to approximately 5.9 nM fusion for 24 h.

Example 42

Preparation of an IgA Protease-Nociceptin Variant-$H_N$/A Fusion Protein

The IgA protease amino acid sequence was obtained from freely available database sources such as GenBank (accession number P09790). Information regarding the structure of the *N. Gonorrhoeae* IgA protease gene is available in the literature (Pohlner et al., Gene structure and extracellular secretion of *Neisseria gonorrhoeae* IgA protease, Nature, 1987, 325 (6103), 458-62). Using Backtranslation tool v2.0 (Entelechon), the DNA sequence encoding the IgA protease modified for *E. coli* expression was determined. A BamHI recognition sequence was incorporated at the 5' end and a codon encoding a cysteine amino acid and SalI recognition sequence were incorporated at the 3' end of the IgA DNA. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID NO:86) containing the IgA open reading frame (ORF) is then commercially synthesized.

The IgA (SEQ ID NO:86) is inserted into the LC-linker-nociceptin variant-spacer-$H_N$ ORF (SEQ ID NO:51) using BamHI and SalI restriction enzymes to replace the LC with the IgA protease DNA. The final construct contains the IgA-linker-nociceptin variant-spacer-$H_N$ ORF (SEQ ID NO:87) for expression as a protein of the sequence illustrated in SEQ ID NO:88.

Example 43

Preparation and Assessment of a Nociceptin Targeted Endopeptidase Fusion Protein with a Removable Histidine Purification Tag DNA was prepared that encoded a Factor Xa removable his-tag (his6), although it is clear that alternative proteases site such as Enterokinase and alternative purification tags such as longer histidine tags are also possible. Using one of a variety of reverse translation software tools [for example EditSeq best *E. coli* reverse translation (DNASTAR Inc.), or Backtranslation tool v2.0 (Entelechon)], the DNA sequence encoding the Factor Xa removable his-tag region is determined. Restriction sites are then incorporated into the DNA sequence and can be arranged as NheI-linker-SpeI-PstI-$H_N$/A-XbaI-LEIEGRSGHHHHHHStop codon-HindIII (SEQ ID NO:89). The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector. In order to create CPNv-A-FXa-HT (SEQ ID NO:90, removable his-tag construct) the pCR 4 vector encoding the removable his-tag is cleaved with NheI and HindIII. The NheI-HindIII fragment is then inserted into the LC/A-CPNv-$H_N$/A vector (SEQ ID NO:51) that has also been cleaved by NheI and HindIII. The final construct contains the LC/A-linker-nociceptin variant-spacer-$H_N$-FXa-Histag-HindIII ORF sequences (SEQ ID NO:90) for expression as a protein of the sequence illustrated in SEQ ID NO:91. FIG. 30 illustrates the purification of CPNv-A-FXa-HT from *E. coli* following the methods used in Example 26.

Example 44

Preparation of a Leu-Enkephalin Targeted Endopeptidase Fusion Protein Containing a Translocation Domain Derived from Diphtheria Toxin The DNA sequence is designed by back translation of the amino acid sequence of the translocation domain of the diphtheria toxin (obtained from freely available database sources such as GenBank (accession number 1xDTT) using one of a variety of reverse translation software tools [for example EditSeq best *E. coli* reverse translation (DNASTAR Inc.), or Backtranslation tool v2.0 (Entelechon)]. Restriction sites are then incorporated into the DNA sequence and can be arranged as NheI-Linker-SpeI-PstI-diphtheria translocation domain-XbaI-stop codon-HindIII (SEQ ID NO:92). PstI/XbaI recognition sequences are incorporated at the 5' and 3' ends of the translocation domain respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the diphtheria translocation domain is then commercially synthesized as NheI-Linker-SpeI-PstI-diphtheria translocation domain-XbaI-stop codon-HindIII (for example by Entelechon, Geneart or Sigma-Genosys) and is provided in the pCR 4 vector (Invitrogen). The pCR 4 vector encoding the diphtheria translocation domain is cleaved with NheI and XbaI. The NheI-XbaI fragment is then inserted into the LC/A-CPLE-$H_N$/A vector (SEQ ID NO:80) that has also been cleaved by NheI and XbaI. The final construct contains the LC/A-leu-enkephalin-spacer-diphtheria translocation domain ORF sequences (SEQ ID NO:93) for expression as a protein of the sequence illustrated in SEQ ID NO:94.

Example 45

Preparation of a Nociceptin Variant Targeted Endopeptidase Fusion Protein Containing a LC Domain Derived from Tetanus Toxin The DNA sequence is designed by back translation of the tetanus toxin LC amino acid sequence (obtained from freely available database sources such as GenBank (accession number X04436) using one of a variety of reverse translation software tools [for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence maintaining the correct reading frame (SEQ ID NO:95). The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the tetanus toxin LC open reading frame (ORF) is then commercially synthesized (for example by Entelechon, Geneart or Sigma-Genosys) and is provided in the pCR 4 vector (invitrogen). The pCR 4 vector encoding the TeNT LC is cleaved with BamHI and SalI. The BamHI-SalI fragment is then inserted into the LC/A-CPNv-$H_N$/A vector (SEQ ID NO:51) that has also been cleaved by BamHI and SalI. The final construct contains the TeNT LC-linker-nociceptin variant-spacer-$H_N$ ORF sequences (SEQ ID NO:96) for expression as a protein of the sequence illustrated in SEQ ID NO:97.

Example 46

Preparation of an LC/C-Nociceptin Variant-$H_N$/C Fusion Protein with a Native Serotype C Linker that is Susceptible to Factor Xa Cleavage Following the methods used in Example 21, the LC/C (SEQ ID NO:31) and $H_N$/C (SEQ ID NO:32) are created and inserted into the C serotype nociceptin variant linker arranged as BamHI-SalI-linker-nociceptin variant-NheI-spacer-SpeI-PstI-XbaI-stop codon-HindIII (SEQ ID NO:98). The final construct contains the LC-linker-nociceptin variant-spacer-$H_N$ ORF sequences (SEQ ID NO:99) for expression as a protein of the sequence illustrated in SEQ ID NO:100. The fusion protein is termed CPNv-C (act. C).

Example 47

Construction of CHO-K10P2 Receptor Activation Assay and SNAP-25 Cleavage Assay

Cell-Line Creation

CHO OP2 cell line was purchased from Perkin Elmer (ES-541-C, lot 451-719-A). Cells were transfected with SNAP-25 DNA using Lipofectamine™ 2000 and incubated for 4 hours before media replacement. After 24 hours, cells were transferred to a T175 flask. 100 ug/ml Zeocin was added after a further 24 hours to begin selection of SNAP-25 expressing cells, and 5 ug/ml Blasticidin added to maintain selective pressure for the receptor. Cells were maintained in media containing selection agents for two weeks, passaging cells every two to three days to maintain 30-70% confluence. Cells were then diluted in selective media to achieve 0.5 cell per well in a 96 well microplate. After a few days, the plates were examined under a microscope, and those containing single colonies were marked. Media in these wells was changed weekly. As cells became confluent in the wells, they were transferred to T25 flasks. When they had expanded sufficiently each clone was seeded to 24 wells of a 96 well plate, plus a frozen stock vial created. LC/A-CPDY-$H_N$A fusion and LC/A-$H_N$A were applied to the cells for 24 hours, and then western blots performed to detect SNAP-25 cleavage. Clones from which SNAP-25 bands were strong and cleavage levels were high with fusion were maintained for further investigation. Full dose curves were run on these, and the clone (D30) with the highest differential between LC/A-CPDY-$H_N$A fusion and LC/A-$H_N$A cleavage levels was selected.

OP2 Receptor Activation Assay

The OP2 receptor activation measures the potency and intrinsic efficacy of ligands at OP2 receptor in transfected CHO-K1 cells by quantifying the reduction of forskolin-stimulated intracellular cAMP using a FRET-based cAMP (Perkin Elmer LANCE cAMP kit). After stimulation, a fluorescently labelled cAMP tracer (Europium-streptavadin/biotin-cAMP) and fluorescently (Alexa) labelled anti-cAMP antibody are added to the cells in a lysis buffer. cAMP from the cells competes with the cAMP tracer for antibody binding sites. When read, a light pulse at 320 nm excites the fluorescent portion (Europium) of the cAMP tracer. The energy emitted from the europium is transferred to the Alexa fluor-labelled antibodies bound to the tracer, generating a TR-FRET signal at 665 nm (Time-resolved fluorescence resonance energy transfer is based on the proximity of the donor label, europium, and the acceptor label, Alexa fluor, which have been brought together by a specific binding reaction). Residual energy from the europium produces light at 615 nm. In agonist treated cells there will be less cAMP to compete with the tracer so a dose dependant increase in signal at 665 nm will be observed compared with samples treated with forskolin alone. The signal at 665 nm signal is converted to cAMP concentration by interpolation to a cAMP standard curve which is included in each experiment.

Culture of Cells for Receptor Activation Assay:

Cells were seeded and cultured in T175 flasks containing Ham F12 with Glutamax, 10% Foetal bovine serum, 5 μg ml-1 Blasticidin and 100 μg ml-1 Zeocin. The flasks were incubated at 37° C. in a humidified environment containing 5% $CO_2$ until 60-80% confluent. On the day of harvest the media was removed and the cells washed twice with 25 ml PBS. The cells were removed from the flask by addition of 10 ml of Tryple Express, and incubation at 37° C. for 10 min followed by gentle tapping of the flask. The dislodged cells were transferred to a 50 ml centrifuge tube and the flask washed twice with 10 ml media which was added to the cell suspension. The tube was centrifuged at 1300×g for 3 min and the supernatant removed. Cells were gently re-suspended in 10 ml media (if freezing cells) or assay buffer (if using 'fresh' cells in assay), and a sample was removed for counting using a nucleocounter (ChemoMetec). Cells for use 'fresh' in an assay were diluted further in assay buffer to the appropriate concentration. Cells harvested for freezing were re-centrifuged (1300×g; 3 min), the supernatant removed and cells re-suspended in Synth-a-freeze at 4° C. to 3×106 cells/ml. Cryovials containing 1 ml suspension each were placed in a chilled Nalgene Mr Frosty freezing container (−1° C./minute cooling rate), and left overnight in a −80° C. freezer. The following day vials were transferred to the vapour phase of a liquid nitrogen storage tank.

Dilution of Test Materials and Cell Assay

Using Gilson pipettes and Sigmacoted or lo-bind tips, test materials and standards were diluted to the appropriate concentrations in the wells of the first two columns of an eppendorf 500 μl deep-well lo-bind plate, in assay buffer containing 10 μM forskolin. The chosen concentrations in columns one and two were half a log unit apart. From these, serial 1:10 dilutions were made across the plate (using an electronic eight channel pipette with sigmacote or lo-bind tips) until eleven concentrations at half log intervals had been created. In the twelfth column, assay buffer only was added as a 'basal'. Using a 12 channel digital pipette, 10 μl of sample from the lo-bind plate was transferred to the optiplate 96 well microplate.

To wells containing the standard curve, 10 ul of assay buffer was added using a multichannel digital pipette. To wells containing the test materials, 10 ul of cells in assay buffer at the appropriate concentration were added. Plates were sealed and incubated for 120 min at room temperature, for the first hour on an IKA MTS 2/4 orbital shaker set to maximum speed.

Detection

LANCE Eu-W8044 labelled streptavidin (Eu-SA) and Biotin-cAMP (b-cAMP) were diluted in cAMP Detection Buffer (both from Perkin Elmer LANCE cAMP kit) to create sub-stocks, at dilution ratios of 1:17 and 1:5, respectively. The final detection mix was prepared by diluting from the two sub stocks into detection buffer at a ratio of 1:125. The mixture was incubated for 15-30 min at room temperature before addition of 1:200 Alexa Fluor® 647-anti cAMP Antibody (Alexa-Fluor Ab). After briefly vortex mixing, 20 μl was immediately added to each well using a digital multichannel pipette. Microplate sealers were applied and plates incubated for 24 h at room temperature (for the first hour on an IKA MTS 2/4 orbital shaker set to maximum speed). Plate sealers were removed prior to reading on the Envision.

FIGS. 36 and 37 show that dynorphin conjugates with LC/A-$H_N$/A, LC/B-$H_N$/B, LC/C—$H_N$/C and LC/D-$H_N$/D backbones active the OP2 receptor.

CHO-K1 OP2 SNAP-25 Cleavage Assay

Cultures of cells were exposed to varying concentrations of fusion protein for 24 hours. Cellular proteins were separated by SDS-PAGE and western blotted with anti-SNAP-25 antibody to facilitate assessment of SNAP-25 cleavage. SNAP-25 cleavage calculated by densitometric analysis (Syngene).

Plating Cells

Prepare cells at 2×10e5 cells/ml and seed 125 μl per well of 96 well plate. Use the following media: 500 ml Gibco Ham F12 with Glutamax (product code 31765068), 50 ml FBS, 5 ug/ml Blasticidin (250 μl aliquot from box in freezer, G13) (Calbiochem #203351, 10 ml at 10 mg/ml), 100 ug/ml Zeocin (500 μl from box in freezer, G35). (Invitrogen from Fisher, 1 g in 8×1.25 ml tubes at 100 mg/ml product code VXR25001). Allow cells to grow for 24 hrs (37° C., 5% $CO_2$, humidified atmosphere).

Cell Treatment

Prepare dilutions of test protein for a dose range of each test proteins (make up double (2×) the desired final concentrations because 125 μl will be applied directly onto 125 μl of media already in each well). Filter sterilize CHO KOR D30 feeding medium (20 ml syringe, 0.2 μm syringe filter) to make the dilutions. Add the filtered medium into 5 labelled bijoux's (7 ml tubes), 0.9 ml each using a Gilson pipette or multi-stepper. Dilute the stock test protein to 2000 nM (working stock solution 1) and 600 nM (working stock solution 2). Using a Gilson pipette prepare 10-fold serial dilutions of each working stock, by adding 100 μl to the next concentration in the series. Pipette up and down to mix thoroughly. Repeat to obtain 4 serial dilutions for solution 1, and 3 serial dilutions for solution 2. A 0 nM control (filtered feeding medium only) should also be prepared as a negative control for each plate. Repeat the above for each test protein. In each experiment a 'standard' batch of material must be included as control/reference material, this is unliganded LC/A-$H_N$/A.

Apply Diluted Sample to CHO KOR D30 Plates

Apply 125 µl of test sample (double concentration) per well. Each test sample should be applied to triplicate wells and each dose range should include a 0 nM control. Incubate for 24 hrs (37° C., 5% $CO_2$, humidified atmosphere).

Cell Lysis

Prepare fresh lysis buffer (20 mls per plate) with 25% (4×) NuPAGE LDS sample buffer, 65% $dH_2O$ and 10% 1 M DTT. Remove medium from the CHO KOR D30 plate by inverting over a waste receptacle. Drain the remaining media from each well using a fine-tipped pipette. Lyse the cells by adding 125 µl of lysis buffer per well using a multi-stepper pipette. After a minimum of 20 mins, remove the buffer from each well to a 1.5 ml microcentrifuge tube. Tubes must be numbered to allowing tracking of the CHO KOR treatments throughout the blotting procedure. A1-A3 down to H1-H3 numbered 1-24, A4-A6 down to H4-H6 numbered 25-48, A7-A9 down to H7-H93 numbered 49-72, A10-A12 down to H10-H12 numbered 73-96. Vortex each sample and heat at 90° C. for 5-10 mins in a prewarmed heat block. Store at −20° C. or use on the same day on an SDS gel.

Gel Electrophoresis

If the sample has been stored o/n or longer, put in a heat block prewarmed to 90° C. for 5-10 mins. Set up SDS page gels, use 1 gel per 12 samples, prepare running buffer (1×, Invitrogen NuPAGE MOPS SDS Running Buffer (20×) (NP0001))≈800 ml/gel tank. Add 500 µl of NuPAGE antioxidant to the upper buffer chamber. Load 15 ul samples onto gel lanes from left to right as and load 2.5 ul of Invitrogen Magic Marker XP and 5 ul Invitrogen See Blue Plus 2 pre-stained standard and 15 ul of non-treated control. It is important to maximize the resolution of separation during SDS_PAGE. This can be achieved by running 12% bis-tris gels at 200 V for 1 hour and 25 minutes (until the pink (17 kDa) marker reaches the bottom of the tank).

Western Blotting

Complete a Semi-dry transfer: using an Invitrogen iBlot (use iBlot Programme 3 for 6 minutes). Put the nitrocellulose membranes in individual small trays. Incubate the membranes with blocking buffer solution (5 g Marvel milk powder per 100 ml 0.1% PBS/Tween) at room temperature, on a rocker, for 1 hour. Apply primary antibody (Anti-SNAP-25 1:1000 dilution) and incubate the membranes with primary antibody (diluted in blocking buffer) for 1 hour on a rocker at room temperature. Wash the membranes by rinsing 3 times with PBS/Tween (0.1%). Then apply the secondary (Anti-Rabbit-HRP conjugate diluted 1:1000) and incubate the membranes with secondary antibody (diluted in blocking buffer) at room temperature, on a rocker, for 1 hour. Wash the membranes by rinsing 3 times with PBS/Tween (0.1%), leave membrane a minimum of 20 mins for the last wash. Detect the bound antibody using Syngene: Drain blots of PBS/Tween, mix WestDura reagents 1:1 and add to blots for 5 minutes. Ensure enough solution is added to the membranes to completely cover them. Place membrane in Syngene tray, set up Syngene software for 5 min expose time.

FIG. 34 clearly shows that LC/A-CPDY-$H_N$/A conjugates effectively cleave SNAP-25.

Example 48

Construction and Activation of Dynorphin Conjugates

Preparation of a LC/A and $H_N$/A Backbone Clones

The following procedure creates the LC and $H_N$ fragments for use as the component backbone for multidomain fusion expression. This example is based on preparation of a serotype A based clone (SEQ ID NO:27 and SEQ ID NO:28), though the procedures and methods are equally applicable to the other serotypes [illustrated by the sequence listing for serotype B (SEQ ID NO:29 and SEQ ID NO:30) and serotype C (SEQ ID NO:31 and SEQ ID NO:32)].

Preparation of Cloning and Expression Vectors pCR 4 (Invitrogen) is the chosen standard cloning vector, selected due to the lack of restriction sequences within the vector and adjacent sequencing primer sites for easy construct confirmation. The expression vector is based on the pMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (e.g. LC/A) Insert

The LC/A (SEQ ID NO:27) is created by one of two ways:

The DNA sequence is designed by back translation of the LC/A amino acid sequence [obtained from freely available database sources such as GenBank (accession number P10845) or Swissprot (accession locus BXA1_CLOBO) using one of a variety of reverse translation software tools (for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence, maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the LC/A open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a supplier (for example MWG or Sigma-Genosys), so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 µM) and a buffer appropriate for the enzyme optimised for $Mg^{2+}$ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis [for example, using Quickchange (Stratagene Inc.)].

Preparation of Translocation (e.g. $H_N$) Insert

The $H_N$/A (SEQ ID NO:28) is created by one of two ways:

The DNA sequence is designed by back translation of the $H_N$/A amino acid sequence [obtained from freely available database sources such as GenBank (accession number P10845) or Swissprot (accession locus BXA1_CLOBO)] using one of a variety of reverse translation software tools [for example EditSeq best *E. coli* reverse translation (DNASTAR Inc.), or Backtranslation tool v2.0 (Entelechon)]. A PstI restriction sequence added to the N-terminus and XbaI-stop codon-HindIII to the C-terminus ensuring the correct reading frame is maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis [for example using Quickchange (Stratagene Inc.)].

Preparation of Linker-Dynorphin-Spacer Insert

The LC-$H_N$ linker can be designed from first principle, using the existing sequence information for the linker as the template. For example, the serotype A linker (in this case defined as the inter-domain polypeptide region that exists between the cysteines of the disulphide bridge between LC and $H_N$) is 23 amino acids long and has the sequence VRGIITSKTKSLDKGYNKALNDL. Within this sequence, it is understood that proteolytic activation in nature leads to an $H_N$ domain that has an N-terminus of the sequence ALNDL. This sequence information is freely available from available database sources such as GenBank (accession number P10845) or Swissprot (accession locus BXA1_CLOBO). Into this linker an enterokinase site, dynorphin and spacer are incorporated; and using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-dynorphin-NheI-spacer-SpeI-PstI-XbaI-stop codon-HindIII. It is important to ensure the correct reading frame is maintained for the spacer, dynorphin and restriction sequences and that the XbaI sequence is not preceded by the bases, TC, which would result on DAM methylation. The DNA sequence is screened for restriction sequence incorporation, and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example, GenBank Release 143, 13 Sep. 2004). This optimised DNA sequence is then commercially synthesized (for example by Entelechon, Geneart or Sigma-Genosys) and is provided in the pCR 4 vector.

Preparation of the LC/A-dynorphin-$H_N$/A Fusion

In order to create the LC-linker-dynorphin-spacer-$H_N$ construct (SEQ ID NO:102), the pCR 4 vector encoding the linker is cleaved with BamHI+SalI restriction enzymes. This cleaved vector then serves as the recipient vector for insertion and ligation of the LC/A DNA (SEQ ID NO:27) cleaved with BamHI+SalI. The resulting plasmid DNA is then cleaved with PstI+XbaI restriction enzymes and serves as the recipient vector for the insertion and ligation of the $H_N$/A DNA (SEQ ID NO:28) cleaved with PstI+XbaI. The final construct contains the LC-linker-dynorphin-spacer-$H_N$ ORF (SEQ ID NO:102) for transfer into expression vectors for expression to result in a fusion protein of the sequence illustrated in SEQ ID NO:103.

Examples 49

Preparation and Purification of an LC/A-Dynorphin-$H_N$/A Fusion Protein Family with Variable Spacer Length Using the same strategy as employed in Example 48, a range of DNA linkers were prepared that encoded dynorphin and variable spacer content. Using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-dynorphin-NheI-spacer-SpeI-PstI-XbaI-stop codon-HindIII. It is important to ensure the correct reading frame is maintained for the spacer, dynorphin and restriction sequences and that the XbaI sequence is not preceded by the bases, TC which would result on DAM methylation. The DNA sequence is screened for restriction sequence incorporation and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The spacers that were created included:

(1)

| Code | Protein sequence of the linker | SEQ ID NO: of the linker DNA |
|---|---|---|
| GS10 | ALAGGGGSALVLQ | 104 |
| GS15 | ALAGGGGSGGGGSALVLQ | 105 |
| GS25 | ALAGGGGSGGGGSGGGGSGGGGSALVLQ | 106 |

By way of example, in order to create the LC/A-CPDY (GS25)-$H_N$/A fusion construct (SEQ ID NO:106), the pCR 4 vector encoding the linker is cleaved with BamHI+SalI restriction enzymes. This cleaved vector then serves as the recipient vector for insertion and ligation of the LC/A DNA (SEQ ID NO:27) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The $H_N$/A DNA (SEQ ID NO:28) is then cleaved with PstI+HindIII restriction enzymes and inserted into the similarly cleaved pMAL-LC/A-linker construct. The final construct contains the LC/A-CPDY(GS25)-$H_N$/A ORF for expression as a protein of the sequence illustrated in SEQ ID NO:106.

Example 50

Purification Method for LC/A-Dynorphin-$H_N$/A Fusion Protein

Defrost falcon tube containing 25 ml 50 mM HEPES pH 7.2, 200 mM NaCl and approximately 10 g of *E. coli* BL21 cell paste. Make the thawed cell paste up to 80 ml with 50 mM HEPES pH 7.2, 200 mM NaCl and sonicate on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M $NiSO_4$ charged Chelating column (20-30 ml column is sufficient) equilibrated with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and measure the OD of the dialysed fusion protein. Add 3.2 µl of enterokinase (2 µg/ml) per 1 mg fusion protein and Incubate at 25° C. static overnight. Load onto a 0.1 M $NiSO_4$ charged Chelating column (20-30 ml column is sufficient) equilibrated with 50 mM HEPES pH 7.2, 200 mM NaCl. Wash column to baseline with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and concentrate the fusion to about 2 mg/ml, aliquot sample and freeze at −20° C. Test purified protein using OD, BCA, purity analysis and SNAP-25 assessments.

Example 51

Preparation of a LC/C-Dynorphin-$H_N$/C Fusion Protein with a Serotype A Activation Sequence Following the methods used in Examples 18 and 19, the LC/C (SEQ ID NO:31) and $H_N$/C (SEQ ID NO:32) are created and inserted into the A serotype linker arranged as BamHI-SalI-linker-protease site-dynorphin-NheI-spacer-SpeI-PstI-XbaI-stop codon-HindIII. The final construct contains the LC-linker-dynorphin-spacer-$H_N$ ORF for expression as a protein of the sequence illustrated in SEQ ID NO:107.

Example 52

Preparation of an IgA Protease-Dynorphin Variant-$H_N$/A Fusion Protein

The IgA protease amino acid sequence was obtained from freely available database sources such as GenBank (accession number P09790). Information regarding the structure of the *N. Gonorrhoeae* IgA protease gene is available in the literature (Pohlner et al., Gene structure and extracellular secretion of *Neisseria gonorrhoeae* IgA protease, Nature, 1987, 325 (6103), 458-62). Using Backtranslation tool v2.0 (Entelechon), the DNA sequence encoding the IgA protease modified for *E. coli* expression was determined. A BamHI recognition sequence was incorporated at the 5' end and a codon encoding a cysteine amino acid and SalI recognition sequence were incorporated at the 3' end of the IgA DNA. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID NO:86) containing the IgA open reading frame (ORF) is then commercially synthesized.

The IgA (SEQ ID NO:86) is inserted into the LC-linker-dynorphin-spacer-$H_N$ ORF (SEQ ID NO:102) using BamHI and SalI restriction enzymes to replace the LC with the IgA protease DNA. The final construct contains the IgA-linker-dynorphin-spacer-$H_N$ ORF for expression as a protein of the sequence illustrated in SEQ ID NO:108.

Example 53

Preparation of a Dynorphin Targeted Endopeptidase Fusion Protein Containing a LC Domain Derived from Tetanus Toxin The DNA sequence is designed by back translation of the tetanus toxin LC amino acid sequence (obtained from freely available database sources such as GenBank (accession number X04436) using one of a variety of reverse translation software tools [for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence maintaining the correct reading frame (SEQ ID NO:95). The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the tetanus toxin LC open reading frame (ORF) is then commercially synthesized (for example by Entelechon, Geneart or Sigma-Genosys) and is provided in the pCR 4 vector (invitrogen). The pCR 4 vector encoding the TeNT LC is cleaved with BamHI and SalI. The BamHI-SalI fragment is then inserted into the LC/A-dynorphin-$H_N$/A vector (SEQ ID NO:102) that has also been cleaved by BamHI and San. The final construct contains the TeNT LC-linker-dynorphin-spacer-$H_N$ ORF sequences for expression as a protein of the sequence illustrated in SEQ ID NO:109.

Example 54

A method of treating, preventing or ameliorating pain in a subject, comprising administration to said patient a therapeutic effective amount of fusion protein, wherein said pain is selected from the group consisting of: chronic pain arising from malignant disease, chronic pain not caused by malignant disease (peripheral neuropathies).

Patient A

A 73 year old woman suffering from severe pain caused by posthepatic neuralgia is treated by a peripheral injection with fusion protein to reduce neurotransmitter release at the synapse of nerve terminals to reduce the pain. The patient experiences good analgesic effect within 2 hours of said injection.

Patient B

A 32 year old male suffering from phantom limb pain after having his left arm amputated following a car accident is treated by peripheral injection with fusion protein to reduce the pain. The patient experiences good analgesic effect within 1 hour of said injection.

Patient C

A 55 year male suffering from diabetic neuropathy is treated by a peripheral injection with fusion protein to reduce neurotransmitter release at the synapse of nerve terminals to reduce the pain. The patient experiences good analgesic effect within 4 hours of said injection.

Patient D

A 63 year old woman suffering from cancer pain is treated by a peripheral injection with fusion protein to reduce neurotransmitter release at the synapse of nerve terminals to reduce the pain. The patient experiences good analgesic effect within 4 hours of said injection.

All documents, books, manuals, papers, patents, published patent applications, guides, abstracts and other reference materials cited herein are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. An isolated polynucleotide molecule comprising a polynucleotide encoding a non-cytotoxic protein conjugate for inhibition or reduction of exocytic fusion in a nociceptive sensory afferent cell, comprising:
   (i) a dynorphin Targeting Moiety (TM), wherein said TM is an agonist of a receptor present on a nociceptive sensory afferent cell, and wherein said receptor undergoes endocytosis to be incorporated into an endosome within the nociceptive sensory afferent cell;
   (ii) a non-cytotoxic protease or a fragment thereof, wherein the protease or protease fragment cleaves a protein of the exocytic fusion apparatus of said nociceptive sensory afferent cell; and
   (iii) a Translocation Domain, wherein the Translocation Domain translocates the protease or protease fragment from within the endosome, across the endosomal membrane, and into the cytosol of the nociceptive sensory afferent cell.

2. The isolated polynucleotide molecule of claim 1, wherein the receptor is an opioid receptor-like 1 (ORL1) receptor.

3. The isolated polynucleotide molecule of claim 1, wherein the dynorphin TM has at least 70% or at least 80% sequence identity to SEQ ID NO:101 or a fragment thereof.

4. The isolated polynucleotide molecule of claim 1, wherein the dynorphin TM has at least 90% sequence identity to SEQ ID NO:101 or a fragment thereof.

5. The isolated polynucleotide molecule of claim 1, wherein the dynorphin TM has at least 95% sequence identity to SEQ ID NO:101 or a fragment thereof.

6. The isolated polynucleotide molecule of claim 1, wherein the dynorphin TM is SEQ ID NO:101 or a fragment thereof.

7. The isolated polynucleotide molecule of claim 1, wherein the non-cytotoxic protease is selected from a clostridial neurotoxin, or an IgA protease.

8. The isolated polynucleotide molecule of claim 1, wherein the Translocation Domain is a botulinum $H_N$ domain.

9. The isolated polynucleotide molecule of claim 1, wherein the nociceptive sensory afferent cell is a primary nociceptive sensory afferent cell.

10. The isolated polynucleotide molecule of claim 1, wherein the conjugate has the structure, arranged amino terminal to carboxy terminal, or vice versa: protease or fragment thereof—dynorphin TM—Translocation Domain.

11. An expression vector comprising a polynucleotide molecule of claim 1.

12. A host cell comprising an expression vector of claim 11.

13. A method of producing a polypeptide comprising (a) culturing a host cell of claim 12 under conditions promoting expression of a polypeptide encoded by the polynucleotide molecule, and (b) recovering said polypeptide from the cell culture.

14. An isolated polynucleotide molecule comprising a polynucleotide encoding the amino acid sequence of any one of SEQ ID NOs:103, 104, 105, 106, 107, 108, and 109.

15. An expression vector comprising a polynucleotide molecule of claim 14.

16. A host cell comprising an expression vector of claim 15.

17. A method of producing a polypeptide comprising (a) culturing a host cell of claim 16 under conditions promoting expression of a polypeptide encoded by the polynucleotide molecule, and (b) recovering said polypeptide from the cell culture.

18. An isolated polynucleotide molecule comprising the nucleic acid sequence set forth in SEQ ID NO:102.

19. An expression vector comprising a polynucleotide molecule of claim 18.

20. A host cell comprising an expression vector of claim 19.

21. A method of producing a polypeptide comprising (a) culturing a host cell of claim 20 under conditions promoting expression of a polypeptide encoded by the polynucleotide molecule, and (b) recovering said polypeptide from the cell culture.

\* \* \* \* \*

SEQUENCE LISTING

```
<160> NUMBER OF SEQ ID NOS: 126

<210> SEQ ID NO 1
<211> LENGTH: 51
<212> TYPE: DNA
<213> ORGANISM: Artificial Sequence
<220> FEATURE:
<223> OTHER INFORMATION: Synthetic

<400> SEQUENCE: 1
tttggcggtt tcacgggcgc acgcaaatca gcgcgtaaat tagctaacca g              51

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Phe Gly Gly Phe Thr Gly Ala Arg Lys Ser Ala Arg Lys Leu Ala Asn
1               5                   10                  15

Gln

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
tttggcggtt tcacgggcgc acgcaaatca gcg                                  33

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Phe Gly Gly Phe Thr Gly Ala Arg Lys Ser Ala
1               5                   10
```

```
<210> SEQ ID NO 5
<211> LENGTH: 33
<212> TYPE: DNA
<213> ORGANISM: Artificial Sequence
<220> FEATURE:
<223> OTHER INFORMATION: Synthetic

<400> SEQUENCE: 5
tttggcggtt tcacgggcgc acgcaaatat gcg                          33

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Phe Gly Gly Phe Thr Gly Ala Arg Lys Tyr Ala
1               5                   10

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
tttggcggtt tcacgggcgc acgcaaatca tat                          33

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Phe Gly Gly Phe Thr Gly Ala Arg Lys Ser Tyr
1               5                   10

<210> SEQ ID NO 9
<211> LENGTH: 51
<212> TYPE: DNA
<213> ORGANISM: Artificial Sequence
<220> FEATURE:
<223> OTHER INFORMATION: Synthetic

<400> SEQUENCE: 9
tttggcggtt tcacgggcgc acgcaaatca gcgcgtaaat atgctaacca g       51

<210> SEQ ID NO 10
<211> LENGTH: 17
<212> TYPE: PRT
<213> ORGANISM: Artificial Sequence
<220> FEATURE:
<223> OTHER INFORMATION: Synthetic

<400> SEQUENCE: 10

Phe Gly Gly Phe Thr Gly Ala Arg Lys Ser Ala Arg Lys Tyr Ala Asn
1               5                   10                  15

Gln

<210> SEQ ID NO 11
<211> LENGTH: 39
```

<212> TYPE: DNA
<213> ORGANISM: Artificial Sequence
<220> FEATURE:
<223> OTHER INFORMATION: Synthetic

<400> SEQUENCE: 11
tttggcggtt tcacgggcgc acgcaaatca gcgcgtaaa          39

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Phe Gly Gly Phe Thr Gly Ala Arg Lys Ser Ala Arg Lys
1               5                   10

<210> SEQ ID NO 13
<211> LENGTH: 51
<212> TYPE: DNA
<213> ORGANISM: Artificial Sequence
<220> FEATURE:
<223> OTHER INFORMATION: Synthetic

<400> SEQUENCE: 13
tttggcggtt tcacgggcgc acgcaaatca gcgcgtaaac gcaaaaacca g          51

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Phe Gly Gly Phe Thr Gly Ala Arg Lys Ser Ala Arg Lys Arg Lys Asn
1               5                   10                  15

Gln

<210> SEQ ID NO 15
<211> LENGTH: 2736
<212> TYPE: DNA
<213> ORGANISM: Artificial Sequence
<220> FEATURE:
<223> OTHER INFORMATION: Synthetic

<400> SEQUENCE: 15
ctcgggattg agggtcgttt tggcggtttc acgggcgcac gcaaatcagc gcgtaaatta      60
gctaaccaga ctagtggcgg tggggtagt ggcggtggcg gttcgggcgg gggtgggagc     120 cctagggat ccatggagtt cgttaacaaa cagttcaact ataaagaccc agttaacggt      180
gttgacattg cttacatcaa atcccgaac gctggccaga tgcagccggt aaaggcattc     240
aaaatccaca acaaaatctg ggttatcccg gaacgtgata cctttactaa cccggaagaa     300
ggtgacctga acccgccacc ggaagcgaaa caggtgccgg tatcttacta tgactccacc     360
tacctgtcta ccgataacga aaggacaac tacctgaaag tgttactaa actgttcgag     420 cgtatttact ccaccgacct gggccgtatg ctgctgacta gcatcgttcg cggtatcccg     480
ttctggggcg gttctaccat cgataccgaa ctgaaagtaa tcgacactaa ctgcatcaac     540
gttattcagc cggacggttc ctatcgttcc gaagaactga acctggtgat catcggcccg     600

```
tctgctgata tcatccagtt cgagtgtaag agctttggtc acgaagttct gaacctcacc      660
cgtaacggct acggttccac tcagtacatc cgtttctctc cggacttcac cttcggtttt      720
gaagaatccc tggaagtaga cacgaaccca ctgctgggcg ctggtaaatt cgcaactgat      780
cctgcggtta ccctggctca cgaactgatt catgcaggcc accgcctgta cggtatcgcc      840
atcaatccga accgtgtctt caaagttaac accaacgcgt attacgagat gtccggtctg      900
gaagttagct tcgaagaact gcgtactttt ggcggtcacg acgctaaatt catcgactct      960
ctgcaagaaa acgagttccg tctgtactac tataacaagt tcaaagatat cgcatccacc     1020
ctgaacaaag cgaaatccat cgtgggtacc actgcttctc tccagtacat gaagaacgtt     1080
tttaaagaaa atacctgct cagcgaagac acctccggca aattctctgt agacaagttg      1140
aaattcgata actttacaa aatgctgact gaaatttaca ccgaagacaa cttcgttaag      1200
ttctttaaag ttctgaaccg caaaacctat ctgaacttcg acaaggcagt attcaaaatc     1260
aacatcgtgc cgaaagttaa ctacactatc tacgatggtt tcaacctgcg taacaccaac     1320
ctggctgcta attttaacgg ccagaacacg gaaatcaaca catgaacttc acaaaactg     1380 aaaaacttca ctggtctgtt cgagttttac aagctgctgt gcgtcgacgg catcattacc     1440
tccaaaacta atctctgat agaaggtaga acaaagcgc tgaacgacct ctgtatcaag      1500
gttaacaact gggatttatt cttcagcccg agtgaagaca acttccacca cgacctgaac     1560
aaaggtgaag aaatcacctc agatactaac atcgaagcag ccgaagaaaa catctcgctg     1620
gacctgatcc agcagtacta cctgaccttt aatttcgaca acgagccgga aaacatttct     1680
atcgaaaacc tgagctctga tatcatcggc cagctggaac tgatgccgaa catcgaacgt     1740
ttcccaaacg gtaaaaagta cgagctggac aaatatacca tgttccacta cctgcgcgcg     1800
caggaatttg aacacggcaa atcccgtatc gcactgacta actccgttaa cgaagctctg     1860
ctcaacccgt cccgtgtata caccttcttc tctagcgact acgtgaaaaa ggtcaacaaa     1920
gcgactgaag ctgcaatgtt cttgggttgg gttaacagc ttgtttatga ttttaccgac      1980
gagacgtccg aagtatctac taccgacaaa attgcggata tcactatcat catcccgtac     2040
atcggtccgg ctctgaacat tggcaacatg ctgtacaaag acgacttcgt tggcgcactg     2100
atcttctccg gtgcggtgat cctgctggag ttcatcccgg aaatcgccat cccggtactg     2160
ggcacctttg ctctggtttc ttacattgca acaaggttc tgactgtaca aaccatcgac      2220
aacgcgctga gcaaacgtaa cgaaaaatgg gatgaagttt acaaatatat cgtgaccaac     2280
tggctggcta aggttaatac tcagatcgac ctcatccgca aaaaatgaa agaagcactg     2340 gaaaaccagg cggaagctac caaggcaatc attaactacc agtacaacca gtacaccgag     2400
gaagaaaaaa acaacatcaa cttcaacatc gacgatctgt cctctaaact gaacgaatcc     2460
atcaacaaag ctatgatcaa catcaacaag ttcctgaacc agtgctctgt aagctatctg     2520
atgaactcca tgatcccgta cggtgttaaa cgtctggagg acttcgatgc gtctctgaaa     2580
gacgccctgc tgaaatacat ttacgacaac cgtggcactc tgatcggtca ggttgatcgt     2640
ctgaaggaca aagtgaacaa taccttatcg accgacatcc ttttcagct cagtaaatat      2700 gtcgataacc aacgcctttt gtccactcta gactag                              2736
```

<210> SEQ ID NO 16
<211> LENGTH: 911
<212> TYPE: PRT
<213> ORGANISM: Artificial Sequence
<220> FEATURE:
<223> OTHER INFORMATION: Synthetic

<400> SEQUENCE: 16

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Ser Gly Gly
            20                  25                  30

Gly Gly Ser Gly Gly Gly Ser Pro Arg Gly Ser Met Glu Phe Val
        35                  40                  45

Asn Lys Gln Phe Asn Tyr Lys Asp Pro Val Asn Gly Val Asp Ile Ala
    50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Glu Ala Lys Gln Val
            100                 105                 110

Pro Val Ser Tyr Tyr Asp Ser Thr Tyr Leu Ser Thr Asp Asn Glu Lys
        115                 120                 125

Asp Asn Tyr Leu Lys Gly Val Thr Lys Leu Phe Glu Arg Ile Tyr Ser
    130                 135                 140

Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu Glu
            180                 185                 190

Leu Asn Leu Val Ile Ile Gly Pro Ser Ala Asp Ile Ile Gln Phe Glu
        195                 200                 205

Cys Lys Ser Phe Gly His Glu Val Leu Asn Leu Thr Arg Asn Gly Tyr
    210                 215                 220

Gly Ser Thr Gln Tyr Ile Arg Phe Ser Pro Asp Phe Thr Phe Gly Phe
225                 230                 235                 240

Glu Glu Ser Leu Glu Val Asp Thr Asn Pro Leu Leu Gly Ala Gly Lys
                245                 250                 255

Phe Ala Thr Asp Pro Ala Val Thr Leu Ala His Glu Leu Ile His Ala
            260                 265                 270

Gly His Arg Leu Tyr Gly Ile Ala Ile Asn Pro Asn Arg Val Phe Lys
        275                 280                 285

Val Asn Thr Asn Ala Tyr Tyr Glu Met Ser Gly Leu Glu Val Ser Phe
    290                 295                 300

Glu Glu Leu Arg Thr Phe Gly Gly His Asp Ala Lys Phe Ile Asp Ser
305                 310                 315                 320

Leu Gln Glu Asn Glu Phe Arg Leu Tyr Tyr Tyr Asn Lys Phe Lys Asp
                325                 330                 335

Ile Ala Ser Thr Leu Asn Lys Ala Lys Ser Ile Val Gly Thr Thr Ala
            340                 345                 350

Ser Leu Gln Tyr Met Lys Asn Val Phe Lys Glu Lys Tyr Leu Leu Ser
        355                 360                 365

Glu Asp Thr Ser Gly Lys Phe Ser Val Asp Lys Leu Lys Phe Asp Lys
    370                 375                 380

Leu Tyr Lys Met Leu Thr Glu Ile Tyr Thr Glu Asp Asn Phe Val Lys
385                 390                 395                 400

Phe Phe Lys Val Leu Asn Arg Lys Thr Tyr Leu Asn Phe Asp Lys Ala
```

```
            405                 410                 415
Val Phe Lys Ile Asn Ile Val Pro Lys Val Asn Tyr Thr Ile Tyr Asp
            420                 425                 430

Gly Phe Asn Leu Arg Asn Thr Asn Leu Ala Ala Asn Phe Asn Gly Gln
435                 440                 445

Asn Thr Glu Ile Asn Asn Met Asn Phe Thr Lys Leu Lys Asn Phe Thr
    450                 455                 460

Gly Leu Phe Glu Phe Tyr Lys Leu Leu Cys Val Asp Gly Ile Ile Thr
465                 470                 475                 480

Ser Lys Thr Lys Ser Leu Ile Glu Gly Arg Asn Lys Ala Leu Asn Asp
                485                 490                 495

Leu Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
            515                 520                 525

Thr Asn Ile Glu Ala Ala Glu Glu Asn Ile Ser Leu Asp Leu Ile Gln
    530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
            595                 600                 605

Arg Ile Ala Leu Thr Asn Ser Val Asn Glu Ala Leu Leu Asn Pro Ser
610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Pro Tyr Ile Gly Pro Ala Leu Asn Ile Gly
            675                 680                 685

Asn Met Leu Tyr Lys Asp Asp Phe Val Gly Ala Leu Ile Phe Ser Gly
            690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
            755                 760                 765

Ile Asp Leu Ile Arg Lys Lys Met Lys Glu Ala Leu Glu Asn Gln Ala
    770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
            820                 825                 830
```

```
Asn Gln Cys Ser Val Ser Tyr Leu Met Asn Ser Met Ile Pro Tyr Gly
            835                 840                 845

Val Lys Arg Leu Glu Asp Phe Asp Ala Ser Leu Lys Asp Ala Leu Leu
    850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
                900                 905                 910
```

<210> SEQ ID NO 17
<211> LENGTH: 2700
<212> TYPE: DNA
<213> ORGANISM: Artificial Sequence
<220> FEATURE:
<223> OTHER INFORMATION: Synthetic

<400> SEQUENCE: 17

| | | | | | |
|---|---|---|---|---|---|
| tttggcggtt | tcacgggcgc | acgcaaatca | tatactagtg | gcggtggggg | tagtggcggt | 60 |
| ggcggttcgg | gcggggtgg | gagccctagg | ggatccatgg | agttcgttaa | caaacagttc | 120 |
| aactataaag | acccagttaa | cggtgttgac | attgcttaca | tcaaaatccc | gaacgctggc | 180 |
| cagatgcagc | cggtaaaggc | attcaaaatc | acaacaaaa | tctgggttat | cccggaacgt | 240 |
| gatacctta | ctaacccgga | gaaggtgac | ctgaacccgc | accggaagc | gaaacaggtg | 300 |
| ccggtatctt | actatgactc | cacctacctg | tctaccgata | cgaaaagga | caactacctg | 360 |
| aaaggtgtta | ctaaactgtt | cgagcgtatt | tactccaccg | acctgggccg | tatgctgctg | 420 |
| actagcatcg | ttcgcggtat | cccgttctgg | ggcggttcta | ccatcgatac | cgaactgaaa | 480 |
| gtaatcgaca | ctaactgcat | caacgttatt | cagccggacg | ttcctatcg | ttccgaagaa | 540 |
| ctgaacctgg | tgatcatcgg | cccgtctgct | gatatcatcc | agttcgagtg | taagagcttt | 600 |
| ggtcacgaag | ttctgaacct | cacccgtaac | ggctacggtt | ccactcagta | catccgtttc | 660 |
| tctccggact | tcaccttcgg | ttttgaagaa | tccctggaag | tagacacgaa | cccactgctg | 720 |
| ggcgctggta | aattcgcaac | tgatcctgcg | gttaccctgg | ctcacgaact | gattcatgca | 780 |
| ggccaccgcc | tgtacggtat | cgccatcaat | ccgaaccgtg | tcttcaaagt | taacaccaac | 840 |
| gcgtattacg | agatgtccgg | tctggaagtt | agcttcgaag | aactgcgtac | ttttggcggt | 900 |
| cacgacgcta | aattcatcga | ctctctgcaa | gaaaacgagt | ccgtctgta | ctactataac | 960 |
| aagttcaaag | atatcgcatc | cacccctgaac | aaagcgaaat | ccatcgtggg | taccactgct | 1020 |
| tctctccagt | acatgaagaa | cgttttaaa | gaaaatacc | tgctcagcga | agacaccttcc | 1080 |
| ggcaaattct | ctgtagacaa | gttgaaattc | gataaacttt | acaaaatgct | gactgaaatt | 1140 |
| tacaccgaag | acaacttcgt | taagttcttt | aaagttctga | accgcaaaac | ctatctgaac | 1200 |
| ttcgacaagg | cagtattcaa | aatcaacatc | gtgccgaaag | ttaactacac | tatctacgat | 1260 |
| ggtttcaacc | tgcgtaacac | caacctggct | gctaattta | acggccagaa | cacggaaatc | 1320 |
| aacaacatga | acttcacaaa | actgaaaaac | ttcactggtc | tgttcgagtt | ttacaagctg | 1380 |
| ctgtgcgtcg | acggcatcat | tacctccaaa | actaaatctc | tgatagaagg | tagaaacaaa | 1440 |
| gcgctgaacg | acctctgtat | caaggttaac | aactgggatt | tattcttcag | cccgagtgaa | 1500 |
| gacaacttca | ccaacgacct | gaacaaaggt | gaagaaatca | cctcgatac | taacatcgaa | 1560 |
| gcagccgaag | aaaacatctc | gctggacctg | atccagcagt | actacctgac | ctttaatttc | 1620 |

-continued

```
gacaacgagc cggaaaacat tctatcgaa aacctgagct ctgatatcat cggccagctg   1680
gaactgatgc cgaacatcga acgtttccca acggtaaaa agtacgagct ggacaaatat   1740
accatgttcc actacctgcg cgcgcaggaa tttgaacacg gcaaatcccg tatcgcactg   1800
actaactccg ttaacgaagc tctgctcaac ccgtcccgtg tatacacctt cttctctagc   1860
gactacgtga aaaaggtcaa caaagcgact gaagctgcaa tgttcttggg ttgggttgaa   1920
cagcttgttt atgattttac cgacgagacg tccgaagtat ctactaccga caaaattgcg   1980
gatatcacta tcatcatccc gtacatcggt ccggctctga acattggcaa catgctgtac   2040
aaagacgact tcgttggcgc actgatcttc tccggtgcgg tgatcctgct ggagttcatc   2100
ccggaaatcg ccatcccggt actgggcacc tttgctctgg tttcttacat tgcaaacaag   2160
gttctgactg tacaaaccat cgacaacgcg ctgagcaaac gtaacgaaaa atgggatgaa   2220
gtttacaaat atatcgtgac caactggctg gctaaggtta atactcagat cgacctcatc   2280
cgcaaaaaaa tgaaagaagc actggaaaac caggcggaag ctaccaaggc aatcattaac   2340
taccagtaca accagtacac cgaggaagaa aaaaacaaca tcaacttcaa catcgacgat   2400
ctgtcctcta aactgaacga atccatcaac aaagctatga tcaacatcaa caagttcctg   2460
aaccagtgct ctgtaagcta tctgatgaac tccatgatcc cgtacggtgt taaacgtctg   2520
gaggacttcg atgcgtctct gaaagacgcc ctgctgaaat acatttacga caaccgtggc   2580
actctgatcg gtcaggttga tcgtctgaag gacaaagtga acaataccct tatcgaccgac   2640 atccctttc agctcagtaa atatgtcgat aaccaacgcc ttttgtccac tctagactag   2700
```

<210> SEQ ID NO 18
<211> LENGTH: 899
<212> TYPE: PRT
<213> ORGANISM: Artificial Sequence
<220> FEATURE:
<223> OTHER INFORMATION: Synthetic

<400> SEQUENCE: 18

```
Phe Gly Gly Phe Thr Gly Ala Arg Lys Ser Tyr Thr Ser Gly Gly Gly
1               5                   10                  15

Gly Ser Gly Gly Gly Gly Ser Gly Gly Gly Ser Pro Arg Gly Ser
            20                  25                  30

Met Glu Phe Val Asn Lys Gln Phe Asn Tyr Lys Asp Pro Val Asn Gly
        35                  40                  45

Val Asp Ile Ala Tyr Ile Lys Ile Pro Asn Ala Gly Gln Met Gln Pro
    50                  55                  60

Val Lys Ala Phe Lys Ile His Asn Lys Ile Trp Val Ile Pro Glu Arg
65                  70                  75                  80

Asp Thr Phe Thr Asn Pro Glu Glu Gly Asp Leu Asn Pro Pro Glu
                85                  90                  95

Ala Lys Gln Val Pro Val Ser Tyr Tyr Asp Ser Thr Tyr Leu Ser Thr
            100                 105                 110

Asp Asn Glu Lys Asp Asn Tyr Leu Lys Gly Val Thr Lys Leu Phe Glu
        115                 120                 125

Arg Ile Tyr Ser Thr Asp Leu Gly Arg Met Leu Leu Thr Ser Ile Val
    130                 135                 140

Arg Gly Ile Pro Phe Trp Gly Gly Ser Thr Ile Asp Thr Glu Leu Lys
145                 150                 155                 160

Val Ile Asp Thr Asn Cys Ile Asn Val Ile Gln Pro Asp Gly Ser Tyr
                165                 170                 175
```

Arg Ser Glu Glu Leu Asn Leu Val Ile Ile Gly Pro Ser Ala Asp Ile
            180                 185                 190

Ile Gln Phe Glu Cys Lys Ser Phe Gly His Glu Val Leu Asn Leu Thr
        195                 200                 205

Arg Asn Gly Tyr Gly Ser Thr Gln Tyr Ile Arg Phe Ser Pro Asp Phe
    210                 215                 220

Thr Phe Gly Phe Glu Glu Ser Leu Glu Val Asp Thr Asn Pro Leu Leu
225                 230                 235                 240

Gly Ala Gly Lys Phe Ala Thr Asp Pro Ala Val Thr Leu Ala His Glu
                245                 250                 255

Leu Ile His Ala Gly His Arg Leu Tyr Gly Ile Ala Ile Asn Pro Asn
            260                 265                 270

Arg Val Phe Lys Val Asn Thr Asn Ala Tyr Tyr Glu Met Ser Gly Leu
        275                 280                 285

Glu Val Ser Phe Glu Glu Leu Arg Thr Phe Gly Gly His Asp Ala Lys
    290                 295                 300

Phe Ile Asp Ser Leu Gln Glu Asn Glu Phe Arg Leu Tyr Tyr Tyr Asn
305                 310                 315                 320

Lys Phe Lys Asp Ile Ala Ser Thr Leu Asn Lys Ala Lys Ser Ile Val
                325                 330                 335

Gly Thr Thr Ala Ser Leu Gln Tyr Met Lys Asn Val Phe Lys Glu Lys
            340                 345                 350

Tyr Leu Leu Ser Glu Asp Thr Ser Gly Lys Phe Ser Val Asp Lys Leu
        355                 360                 365

Lys Phe Asp Lys Leu Tyr Lys Met Leu Thr Glu Ile Tyr Thr Glu Asp
    370                 375                 380

Asn Phe Val Lys Phe Phe Lys Val Leu Asn Arg Lys Thr Tyr Leu Asn
385                 390                 395                 400

Phe Asp Lys Ala Val Phe Lys Ile Asn Ile Val Pro Lys Val Asn Tyr
                405                 410                 415

Thr Ile Tyr Asp Gly Phe Asn Leu Arg Asn Thr Asn Leu Ala Ala Asn
            420                 425                 430

Phe Asn Gly Gln Asn Thr Glu Ile Asn Asn Met Asn Phe Thr Lys Leu
        435                 440                 445

Lys Asn Phe Thr Gly Leu Phe Glu Phe Tyr Lys Leu Leu Cys Val Asp
    450                 455                 460

Gly Ile Ile Thr Ser Lys Thr Lys Ser Leu Ile Glu Gly Arg Asn Lys
465                 470                 475                 480

Ala Leu Asn Asp Leu Cys Ile Lys Val Asn Asn Trp Asp Leu Phe Phe
                485                 490                 495

Ser Pro Ser Glu Asp Asn Phe Thr Asn Asp Leu Asn Lys Gly Glu Glu
            500                 505                 510

Ile Thr Ser Asp Thr Asn Ile Glu Ala Ala Glu Glu Asn Ile Ser Leu
        515                 520                 525

Asp Leu Ile Gln Gln Tyr Tyr Leu Thr Phe Asn Phe Asp Asn Glu Pro
    530                 535                 540

Glu Asn Ile Ser Ile Glu Asn Leu Ser Ser Asp Ile Ile Gly Gln Leu
545                 550                 555                 560

Glu Leu Met Pro Asn Ile Glu Arg Phe Pro Asn Gly Lys Lys Tyr Glu
                565                 570                 575

Leu Asp Lys Tyr Thr Met Phe His Tyr Leu Arg Ala Gln Glu Phe Glu
            580                 585                 590

His Gly Lys Ser Arg Ile Ala Leu Thr Asn Ser Val Asn Glu Ala Leu
            595                 600                 605

Leu Asn Pro Ser Arg Val Tyr Thr Phe Phe Ser Asp Tyr Val Lys
610                 615                 620

Lys Val Asn Lys Ala Thr Glu Ala Ala Met Phe Leu Gly Trp Val Glu
625                 630                 635                 640

Gln Leu Val Tyr Asp Phe Thr Asp Glu Thr Ser Glu Val Ser Thr Thr
                645                 650                 655

Asp Lys Ile Ala Asp Ile Thr Ile Ile Pro Tyr Ile Gly Pro Ala
                660                 665                 670

Leu Asn Ile Gly Asn Met Leu Tyr Lys Asp Asp Phe Val Gly Ala Leu
                675                 680                 685

Ile Phe Ser Gly Ala Val Ile Leu Leu Glu Phe Ile Pro Glu Ile Ala
690                 695                 700

Ile Pro Val Leu Gly Thr Phe Ala Leu Val Ser Tyr Ile Ala Asn Lys
705                 710                 715                 720

Val Leu Thr Val Gln Thr Ile Asp Asn Ala Leu Ser Lys Arg Asn Glu
                725                 730                 735

Lys Trp Asp Glu Val Tyr Lys Tyr Ile Val Thr Asn Trp Leu Ala Lys
                740                 745                 750

Val Asn Thr Gln Ile Asp Leu Ile Arg Lys Lys Met Lys Glu Ala Leu
                755                 760                 765

Glu Asn Gln Ala Glu Ala Thr Lys Ala Ile Ile Asn Tyr Gln Tyr Asn
                770                 775                 780

Gln Tyr Thr Glu Glu Lys Asn Asn Ile Asn Phe Asn Ile Asp Asp
785                 790                 795                 800

Leu Ser Ser Lys Leu Asn Glu Ser Ile Asn Lys Ala Met Ile Asn Ile
                805                 810                 815

Asn Lys Phe Leu Asn Gln Cys Ser Val Ser Tyr Leu Met Asn Ser Met
                820                 825                 830

Ile Pro Tyr Gly Val Lys Arg Leu Glu Asp Phe Asp Ala Ser Leu Lys
                835                 840                 845

Asp Ala Leu Leu Lys Tyr Ile Tyr Asp Asn Arg Gly Thr Leu Ile Gly
850                 855                 860

Gln Val Asp Arg Leu Lys Asp Lys Val Asn Asn Thr Leu Ser Thr Asp
865                 870                 875                 880

Ile Pro Phe Gln Leu Ser Lys Tyr Val Asp Asn Gln Arg Leu Leu Ser
                885                 890                 895

Thr Leu Asp

<210> SEQ ID NO 19
<211> LENGTH: 2706
<212> TYPE: DNA
<213> ORGANISM: Artificial Sequence
<220> FEATURE:
<223> OTHER INFORMATION: Synthetic

<400> SEQUENCE: 19
tttggcggtt tcacgggcgc acgcaaatca gcgcgtaaaa ctagtggcgg tgggggtagt      60
ggcggtggcg gttcggcgg gggtgggagc cctaggggat ccatggagtt cgttaacaaa     120
cagttcaact ataaagaccc agttaacggt gttgacattg cttacatcaa atcccgaac     180 gctggccaga tgcagccggt aaaggcattc aaaatccaca acaaaatctg gttatcccg     240 gaacgtgata cctttactaa cccggaagaa ggtgacctga cccgccacc ggaagcgaaa     300

```
caggtgccgg tatcttacta tgactccacc tacctgtcta ccgataacga aaaggacaac    360
tacctgaaag gtgttactaa actgttcgag cgtatttact ccaccgacct gggccgtatg    420
ctgctgacta gcatcgttcg cggtatcccg ttctggggcg ttctaccat cgataccgaa    480 ctgaaagtaa tcgacactaa ctgcatcaac gttattcagc cggacggttc ctatcgttcc    540
gaagaactga acctggtgat catcggcccg tctgctgata tcatccagtt cgagtgtaag    600
agctttggtc acgaagttct gaacctcacc cgtaacggct acggttccac tcagtacatc    660
cgtttctctc cggacttcac cttcggtttt gaagaatccc tggaagtaga cacgaaccca    720
ctgctgggcg ctggtaaatt cgcaactgat cctgcggtta ccctggctca cgaactgatt    780
catgcaggcc accgcctgta cggtatcgcc atcaatccga accgtgtctt caaagttaac    840
accaacgcgt attacgagat gtccggtctg gaagttagct cgaagaact gcgtactttt    900 ggcggtcacg acgctaaatt catcgactct ctgcaagaaa acgagttccg tctgtactac    960
tataacaagt tcaaagatat cgcatccacc ctgaacaaag cgaaatccat cgtgggtacc    1020
actgcttctc tccagtacat gaagaacgtt tttaaagaaa ataccctgct cagcgaagac    1080
acctccggca aattctctgt agacaagttg aaattcgata aactttacaa aatgctgact    1140
gaaatttaca ccgaagacaa cttcgttaag ttctttaaag ttctgaaccg caaaacctat    1200
ctgaacttcg acaaggcagt attcaaaatc aacatcgtgc cgaaagttaa ctacactatc    1260
tacgatggtt tcaacctgcg taacaccaac ctggctgcta attttaacgg ccagaacacg    1320
gaaatcaaca acatgaactt cacaaaactg aaaaacttca ctggtctgtt cgagttttac    1380
aagctgctgt gcgtcgacgg catcattacc tccaaaacta atctctgat agaaggtaga    1440 aacaaagcgc tgaacgacct ctgtatcaag gttaacaact gggattatt cttcagcccg    1500 agtgaagaca acttccaccaa cgacctgaac aaaggtgaag aaatcacctc agatactaac    1560
atcgaagcag ccgaagaaaa catctcgctg gacctgatcc agcagtacta cctgaccttt    1620
aatttcgaca acgagccgga aaacatttct atcgaaaacc tgagctctga tatcatcggc    1680
cagctggaac tgatgccgaa catcgaacgt ttcccaaacg gtaaaaagta cgagctggac    1740
aaatatacca tgttccacta cctgcgcgcg caggaatttg aacacggcaa atcccgtatc    1800
gcactgacta actccgttaa cgaagctctg ctcaacccgt cccgtgtata caccttcttc    1860
tctagcgact acgtgaaaaa ggtcaacaaa gcgactgaag ctgcaatgtt cttgggttgg    1920
gttgaacagc ttgtttatga ttttaccgac gagacgtccg aagtatctac taccgacaaa    1980
attgcggata tcactatcat catcccgtac atcggtccgg ctctgaacat ggcaacatg    2040 ctgtacaaag acgacttcgt tggcgcactg atcttctccg gtgcggtgat cctgctggag    2100
ttcatcccgg aaatcgccat cccggtactg ggcacctttg ctctggtttc ttacattgca    2160
aacaaggttc tgactgtaca aaccatcgac aacgcgctga gcaaacgtaa cgaaaaatgg    2220
gatgaagttt acaaatatat cgtgaccaac tggctggcta aggttaatac tcagatcgac    2280
ctcatccgca aaaaaatgaa agaagcactg gaaaaccagg cggaagctac caaggcaatc    2340
attaactacc agtacaacca gtacaccgag gaagaaaaaa acaacatcaa cttcaacatc    2400
gacgatctgt cctctaaact gaacgaatcc atcaacaaag ctatgatcaa catcaacaag    2460
ttcctgaacc agtgctctgt aagctatctg atgaactcca tgatcccgta cggtgttaaa    2520
cgtctggagg acttcgatgc gtctctgaaa gacgccctgc tgaaatacat ttacgacaac    2580
cgtggcactc tgatcggtca ggttgatcgt ctgaaggaca agtgaacaa taccttatcg    2640 accgacatcc ctttcagct cagtaaatat gtcgataacc aacgccttt gtccactcta    2700
``` gactag                                                                                                      2706

<210> SEQ ID NO 20
<211> LENGTH: 901
<212> TYPE: PRT
<213> ORGANISM: Artificial Sequence
<220> FEATURE:
<223> OTHER INFORMATION: Synthetic

<400> SEQUENCE: 20

Phe Gly Gly Phe Thr Gly Ala Arg Lys Ser Ala Arg Lys Thr Ser Gly
1               5                   10                  15

Gly Gly Gly Ser Gly Gly Gly Ser Gly Gly Gly Ser Pro Arg
            20                  25                  30

Gly Ser Met Glu Phe Val Asn Lys Gln Phe Asn Tyr Lys Asp Pro Val
        35                  40                  45

Asn Gly Val Asp Ile Ala Tyr Ile Lys Ile Pro Asn Ala Gly Gln Met
    50                  55                  60

Gln Pro Val Lys Ala Phe Lys Ile His Asn Lys Ile Trp Val Ile Pro
65                  70                  75                  80

Glu Arg Asp Thr Phe Thr Asn Pro Glu Glu Gly Asp Leu Asn Pro Pro
                85                  90                  95

Pro Glu Ala Lys Gln Val Pro Val Ser Tyr Tyr Asp Ser Thr Tyr Leu
            100                 105                 110

Ser Thr Asp Asn Glu Lys Asp Asn Tyr Leu Lys Gly Val Thr Lys Leu
        115                 120                 125

Phe Glu Arg Ile Tyr Ser Thr Asp Leu Gly Arg Met Leu Leu Thr Ser
    130                 135                 140

Ile Val Arg Gly Ile Pro Phe Trp Gly Gly Ser Thr Ile Asp Thr Glu
145                 150                 155                 160

Leu Lys Val Ile Asp Thr Asn Cys Ile Asn Val Ile Gln Pro Asp Gly
                165                 170                 175

Ser Tyr Arg Ser Glu Glu Leu Asn Leu Val Ile Ile Gly Pro Ser Ala
            180                 185                 190

Asp Ile Ile Gln Phe Glu Cys Lys Ser Phe Gly His Glu Val Leu Asn
        195                 200                 205

Leu Thr Arg Asn Gly Tyr Gly Ser Thr Gln Tyr Ile Arg Phe Ser Pro
    210                 215                 220

Asp Phe Thr Phe Gly Phe Glu Glu Ser Leu Glu Val Asp Thr Asn Pro
225                 230                 235                 240

Leu Leu Gly Ala Gly Lys Phe Ala Thr Asp Pro Ala Val Thr Leu Ala
                245                 250                 255

His Glu Leu Ile His Ala Gly His Arg Leu Tyr Gly Ile Ala Ile Asn
            260                 265                 270

Pro Asn Arg Val Phe Lys Val Asn Thr Asn Ala Tyr Tyr Glu Met Ser
        275                 280                 285

Gly Leu Glu Val Ser Phe Glu Glu Leu Arg Thr Phe Gly Gly His Asp
    290                 295                 300

Ala Lys Phe Ile Asp Ser Leu Gln Glu Asn Glu Phe Arg Leu Tyr Tyr
305                 310                 315                 320

Tyr Asn Lys Phe Lys Asp Ile Ala Ser Thr Leu Asn Lys Ala Lys Ser
                325                 330                 335

Ile Val Gly Thr Thr Ala Ser Leu Gln Tyr Met Lys Asn Val Phe Lys
            340                 345                 350

```
Glu Lys Tyr Leu Leu Ser Glu Asp Thr Ser Gly Lys Phe Ser Val Asp
            355                 360                 365

Lys Leu Lys Phe Asp Lys Leu Tyr Lys Met Leu Thr Glu Ile Tyr Thr
    370                 375                 380

Glu Asp Asn Phe Val Lys Phe Phe Lys Val Leu Asn Arg Lys Thr Tyr
385                 390                 395                 400

Leu Asn Phe Asp Lys Ala Val Phe Lys Ile Asn Ile Val Pro Lys Val
                405                 410                 415

Asn Tyr Thr Ile Tyr Asp Gly Phe Asn Leu Arg Asn Thr Asn Leu Ala
            420                 425                 430

Ala Asn Phe Asn Gly Gln Asn Thr Glu Ile Asn Asn Met Asn Phe Thr
        435                 440                 445

Lys Leu Lys Asn Phe Thr Gly Leu Phe Glu Phe Tyr Lys Leu Leu Cys
    450                 455                 460

Val Asp Gly Ile Ile Thr Ser Lys Thr Lys Ser Leu Ile Glu Gly Arg
465                 470                 475                 480

Asn Lys Ala Leu Asn Asp Leu Cys Ile Lys Val Asn Asn Trp Asp Leu
                485                 490                 495

Phe Phe Ser Pro Ser Glu Asp Asn Phe Thr Asn Asp Leu Asn Lys Gly
            500                 505                 510

Glu Glu Ile Thr Ser Asp Thr Asn Ile Glu Ala Ala Glu Glu Asn Ile
        515                 520                 525

Ser Leu Asp Leu Ile Gln Gln Tyr Tyr Leu Thr Phe Asn Phe Asp Asn
    530                 535                 540

Glu Pro Glu Asn Ile Ser Ile Glu Asn Leu Ser Ser Asp Ile Ile Gly
545                 550                 555                 560

Gln Leu Glu Leu Met Pro Asn Ile Glu Arg Phe Pro Asn Gly Lys Lys
                565                 570                 575

Tyr Glu Leu Asp Lys Tyr Thr Met Phe His Tyr Leu Arg Ala Gln Glu
            580                 585                 590

Phe Glu His Gly Lys Ser Arg Ile Ala Leu Thr Asn Ser Val Asn Glu
        595                 600                 605

Ala Leu Leu Asn Pro Ser Arg Val Tyr Thr Phe Phe Ser Ser Asp Tyr
    610                 615                 620

Val Lys Lys Val Asn Lys Ala Thr Glu Ala Ala Met Phe Leu Gly Trp
625                 630                 635                 640

Val Glu Gln Leu Val Tyr Asp Phe Thr Asp Glu Thr Ser Glu Val Ser
                645                 650                 655

Thr Thr Asp Lys Ile Ala Asp Ile Thr Ile Ile Pro Tyr Ile Gly
            660                 665                 670

Pro Ala Leu Asn Ile Gly Asn Met Leu Tyr Lys Asp Asp Phe Val Gly
        675                 680                 685

Ala Leu Ile Phe Ser Gly Ala Val Ile Leu Leu Glu Phe Ile Pro Glu
    690                 695                 700

Ile Ala Ile Pro Val Leu Gly Thr Phe Ala Leu Val Ser Tyr Ile Ala
705                 710                 715                 720

Asn Lys Val Leu Thr Val Gln Thr Ile Asp Asn Ala Leu Ser Lys Arg
                725                 730                 735

Asn Glu Lys Trp Asp Glu Val Tyr Lys Tyr Ile Val Thr Asn Trp Leu
            740                 745                 750

Ala Lys Val Asn Thr Gln Ile Asp Leu Ile Arg Lys Lys Met Lys Glu
        755                 760                 765

Ala Leu Glu Asn Gln Ala Glu Ala Thr Lys Ala Ile Ile Asn Tyr Gln
```

```
              770           775           780
Tyr Asn Gln Tyr Thr Glu Glu Lys Asn Asn Ile Asn Phe Asn Ile
785                 790                 795                 800

Asp Asp Leu Ser Ser Lys Leu Asn Glu Ser Ile Asn Lys Ala Met Ile
            805                 810                 815

Asn Ile Asn Lys Phe Leu Asn Gln Cys Ser Val Ser Tyr Leu Met Asn
                820                 825                 830

Ser Met Ile Pro Tyr Gly Val Lys Arg Leu Glu Asp Phe Asp Ala Ser
            835                 840                 845

Leu Lys Asp Ala Leu Leu Lys Tyr Ile Tyr Asp Asn Arg Gly Thr Leu
            850                 855                 860

Ile Gly Gln Val Asp Arg Leu Lys Asp Lys Val Asn Asn Thr Leu Ser
865                 870                 875                 880

Thr Asp Ile Pro Phe Gln Leu Ser Lys Tyr Val Asp Asn Gln Arg Leu
                885                 890                 895

Leu Ser Thr Leu Asp
                900

<210> SEQ ID NO 21
<211> LENGTH: 2691
<212> TYPE: DNA
<213> ORGANISM: Artificial Sequence
<220> FEATURE:
<223> OTHER INFORMATION: Synthetic

<400> SEQUENCE: 21
```

| | | | | | |
|---|---|---|---|---|---|
| atggagttcg | ttaacaaaca | gttcaactat | aaagacccag | ttaacggtgt | tgacattgct | 60 |
| tacatcaaaa | tcccgaacgc | tggccagatg | cagccggtaa | aggcattcaa | atccacaac | 120 |
| aaaatctggg | ttatcccgga | acgtgatacc | tttactaacc | cggaagaagg | tgacctgaac | 180 |
| ccgccaccgg | aagcgaaaca | ggtgccggta | tcttactatg | actccaccta | cctgtctacc | 240 |
| gataacgaaa | aggacaacta | cctgaaaggt | gttactaaac | tgttcgagcg | tatttactcc | 300 |
| accgacctgg | ccgtatgct | gctgactagc | atcgttcgcg | gtatcccgtt | ctgggcggt | 360 |
| tctaccatcg | ataccgaact | gaaagtaatc | gacactaact | gcatcaacgt | tattcagccg | 420 |
| gacggttcct | atcgttccga | gaactgaac | ctggtgatca | tcggcccgtc | tgctgatatc | 480 |
| atccagttcg | agtgtaagag | ctttggtcac | gaagttctga | acctcacccg | taacggctac | 540 |
| ggttccactc | agtacatccg | tttctctccg | gacttcacct | tcggttttga | agaatccctg | 600 |
| gaagtagaca | cgaacccact | gctgggcgct | ggtaaattcg | caactgatcc | tgcggttacc | 660 |
| ctggctcacg | aactgattca | tgcaggccac | cgcctgtacg | gtatcgccat | caatccgaac | 720 |
| cgtgtcttca | agttaacac | caacgcgtat | tacgagatgt | ccggtctgga | agttagcttc | 780 |
| gaagaactgc | gtacttttgg | cggtcacgac | gctaaattca | tcgactctct | gcaagaaaac | 840 |
| gagttccgtc | tgtactacta | taacaagttc | aaagatatcg | catccaccct | gaacaaagcg | 900 |
| aaatccatcg | tgggtaccac | tgcttctctc | cagtacatga | agaacgtttt | taagaaaaa | 960 |
| tacctgctca | gcgaagacac | ctccggcaaa | ttctctgtag | acaagttgaa | attcgataaa | 1020 |
| ctttacaaaa | tgctgactga | aatttacacc | gaagacaact | cgttaagtt | ctttaaagtt | 1080 |
| ctgaaccgca | aaacctatct | gaacttcgac | aaggcagtat | tcaaaatcaa | catcgtgccg | 1140 |
| aaagttaact | acactatcta | cgatggtttc | aacctgcgta | acaccaacct | ggctgctaat | 1200 |
| tttaacggcc | agaacacgga | aatcaacaac | atgaacttca | aaaactgaa | aaacttcact | 1260 |
| ggtctgttcg | agttttacaa | gctgctgtgc | gtcgacggca | tcattacctc | caaaactaaa | 1320 |

```
tctctgatag aaggtagaaa caaagcgctg aacgacctct gtatcaaggt taacaactgg    1380
gatttattct tcagcccgag tgaagacaac ttcaccaacg acctgaacaa aggtgaagaa    1440
atcacctcag atactaacat cgaagcagcc gaagaaaaca tctcgctgga cctgatccag    1500
cagtactacc tgacctttaa tttcgacaac gagccggaaa acatttctat cgaaaacctg    1560
agctctgata tcatcggcca gctggaactg atgccgaaca tcgaacgttt cccaaacggt    1620
aaaaagtacg agctggacaa atataccatg ttccactacc tgcgcgcgca ggaatttgaa    1680
cacggcaaat cccgtatcgc actgactaac tccgttaacg aagctctgct caacccgtcc    1740
cgtgtataca ccttcttctc tagcgactac gtgaaaaagg tcaacaaagc gactgaagct    1800
gcaatgttct tgggttgggt tgaacagctt gtttatgatt ttaccgacga dacgtccgaa    1860
gtatctacta ccgacaaaat tgcggatatc actatcatca tcccgtacat cggtccggct    1920
ctgaacattg caacatgct gtacaaagac gacttcgttg gcgcactgat cttctccggt    1980
gcggtgatcc tgctggagtt catcccggaa atcgccatcc cggtactggg cacctttgct    2040
ctggtttctt acattgcaaa caaggttctg actgtacaaa ccatcgacaa cgcgctgagc    2100
aaacgtaacg aaaaatggga tgaagtttac aaatatatcg tgaccaactg gctggctaag    2160
gttaatactc agatcgacct catccgcaaa aaaatgaaag aagcactgga aaaccaggcg    2220
gaagctacca aggcaatcat taactaccag tacaaccagt acaccgagga agaaaaaaac    2280
aacatcaact tcaacatcga cgatctgtcc tctaaactga cgaatccat caacaaagct    2340 atgatcaaca tcaacaagtt cctgaaccag tgctctgtaa gctatctgat gaactccatg    2400
atcccgtacg gtgttaaacg tctggaggac ttcgatgcgt ctctgaaaga cgccctgctg    2460
aaatacattt acgacaaccg tggcactctg atcggtcagg ttgatcgtct gaaggacaaa    2520
gtgaacaata ccttatcgac cgacatccct tttcagctca gtaaatatgt cgataaccaa    2580
cgccttttgt ccactggcgg tgggggtagt ggcggtggcg gttcgggcgg gggtgggagc    2640
tttggcggtt tcacgggcgc acgcaaatca gcgcgtaaat tagctaacca g             2691
```

<210> SEQ ID NO 22
<211> LENGTH: 897
<212> TYPE: PRT
<213> ORGANISM: Artificial Sequence
<220> FEATURE:
<223> OTHER INFORMATION: Synthetic

<400> SEQUENCE: 22

```
Met Glu Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
```

-continued

```
            115                 120                 125
Val Ile Asp Thr Asn Cys Ile Asn Val Ile Gln Pro Asp Gly Ser Tyr
130                 135                 140
Arg Ser Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
                180                 185                 190
Thr Phe Gly Phe Glu Glu Ser Leu Glu Val Asp Thr Asn Pro Leu Leu
                195                 200                 205
Gly Ala Gly Lys Phe Ala Thr Asp Pro Ala Val Thr Leu Ala His Glu
210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Ile Ala Ser Thr Leu Asn Lys Ala Lys Ser Ile Val
290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
                370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Asp
                420                 425                 430
Gly Ile Ile Thr Ser Lys Thr Lys Ser Leu Ile Glu Gly Arg Asn Lys
                435                 440                 445
Ala Leu Asn Asp Leu Cys Ile Lys Val Asn Asn Trp Asp Leu Phe Phe
                450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
                500                 505                 510
Glu Asn Ile Ser Ile Glu Asn Leu Ser Ser Asp Ile Ile Gly Gln Leu
                515                 520                 525
Glu Leu Met Pro Asn Ile Glu Arg Phe Pro Asn Gly Lys Lys Tyr Glu
530                 535                 540
```

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
        580                 585                 590

Lys Val Asn Lys Ala Thr Glu Ala Ala Met Phe Leu Gly Trp Val Glu
    595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
        660                 665                 670

Ile Pro Val Leu Gly Thr Phe Ala Leu Val Ser Tyr Ile Ala Asn Lys
    675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
        740                 745                 750

Gln Tyr Thr Glu Glu Lys Asn Asn Ile Asn Phe Asn Ile Asp Asp
    755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
        820                 825                 830

Gln Val Asp Arg Leu Lys Asp Lys Val Asn Asn Thr Leu Ser Thr Asp
    835                 840                 845

Ile Pro Phe Gln Leu Ser Lys Tyr Val Asp Asn Gln Arg Leu Leu Ser
850                 855                 860

Thr Gly Gly Gly Ser Gly Gly Gly Ser Gly Gly Gly Ser
865                 870                 875                 880

Phe Gly Gly Phe Thr Gly Ala Arg Lys Ser Ala Arg Lys Leu Ala Asn
            885                 890                 895

Gln

<210> SEQ ID NO 23
<211> LENGTH: 2676
<212> TYPE: DNA
<213> ORGANISM: Artificial Sequence
<220> FEATURE:
<223> OTHER INFORMATION: Synthetic

<400> SEQUENCE: 23

```
atgccaataa caattaacaa ctttaattat tcagatcctg ttgataataa aaatatttta      60
tatttagata ctcatttaaa tacactagct aatgagcctg aaaaagcctt tcgcattaca     120
ggaaatatat gggtaatacc tgatagattt tcaagaaatt ctaatccaaa tttaaataaa     180
cctcctcgag ttacaagccc taaaagtggt tattatgatc ctaattattt gagtactgat     240
tctgacaaag atacattttt aaaagaaatt ataaagttat ttaaaagaat taattctaga     300
gaaataggag aagaattaat atatagactt tcgacagata tacccttttcc tgggaataac     360
aatactccaa ttaataccct tgattttgat gtagatttta acagtgttga tgttaaaact     420
agacaaggta caactgggt taaaactggt agcataaatc ctagtgttat aataactgga     480
cctagagaaa acattataga tccagaaact tctacgttta aattaactaa caataccttt     540
gcggcacaag aaggatttgg tgctttatca ataatttcaa tatcacctag atttatgcta     600
acatatagta atgcaactaa tgatgtagga gagggtagat tttctaagtc tgaattttgc     660
atggatccaa tactaatttt aatgcatgaa cttaatcatg caatgcataa tttatatgga     720
ataggctatac caaatgatca aacaatttca tctgtaacta gtaatatttt ttattctcaa     780
tataatgtga aattagagta tgcagaaata tatgcatttg gaggtccaac tatagaccctt    840
attcctaaaa gtgcaaggaa atatttttgag gaaaaggcat tggattatta tagatctata     900
gctaaaagac ttaatagtat aactactgca aatccttcaa gctttaataa atatataggg     960
gaatataaac agaaacttat tagaaagtat agattcgtag tagaatcttc aggtgaagtt    1020
acagtaaatc gtaataagtt tgttgagtta tataatgaac ttacacaaat atttacagaa    1080
tttaactacg ctaaaatata taatgtacaa aataggaaaa tatatcttttc aaatgtatat    1140
actccggtta cggcgaatat attagacgat aatgtttatg atatacaaaa tggatttaat    1200
atacctaaaa gtaatttaaa tgtactattt atgggtcaaa atttatctcg aaatccagca    1260
ttaagaaaag tcaatcctga aaatatgctt tatttatttta caaaattttg tcataaagca    1320
atagatggta gatcattata taataaaaca ttagattgta gagagctttt agttaaaaat    1380
actgacttac cctttatagg tgatattagt gatgttaaaa ctgatatatt tttaagaaaa    1440
gatattaatg aagaaactga agttatatac tatccggaca atgtttcagt agatcaagtt    1500
attctcagta agaataccttc agaacatgga caactagatt tattatacccc tagtattgac    1560
agtgagagtg aaatattacc aggggagaat caagtcttttt atgataatag aactcaaaat    1620
gttgattatt tgaattctta ttattaccta gaatctcaaa aactaagtga taatgttgaa    1680
gattttactt ttacgagatc aattgaggag gctttggata atagtgcaaa agtatatact    1740
tactttccta cactagctaa taaagtaaat gcgggtgttc aaggtggttt atttttaatg    1800
tgggcaaatg atgtagttga agatttttact acaaatattc taagaaaaga tacattagat    1860
aaaatatcag atgtatcagc tattattccc tatataggac ccgcattaaa tataagtaat    1920
tctgtaagaa gaggaaattt tactgaagca tttgcagtta ctggtgtaac tatttttatta    1980
gaagcatttc ctgaatttac aatacctgca cttggtgcat ttgtgattta tagtaaggtt    2040
caagaaagaa acgagattat taaaactata gataattgtt tagaacaaag gattaagaga    2100
tggaaagatt catatgaatg gatgatggga acgtggttat ccaggattat tactcaatttt   2160
aataatataa gttatcaaat gtatgattct ttaaattatc aggcaggtgc aatcaaagct    2220
aaaatagatt tagaatataa aaaatattca ggaagtgata agaaaatat aaaaagtcaa    2280
gttgaaaatt taaaaatag tttagatgta aaaattcgg aagcaatgaa taatataaat    2340
aaatttatac gagaatgttc cgtaacatat ttatttaaaa atatgttacc taaagtaatt    2400
```

```
gatgaattaa atgagtttga tcgaaatact aaagcaaaat taattaatct tatagatagt    2460
cataatatta ttctagttgg tgaagtagat aaattaaaag caaaagtaaa taatagcttt    2520
caaaatacaa tacccttttaa tatttttca tatactaata attctttatt aaaagatata    2580
attaatgaat atttcaatgg cggtgggggt agtggcggtg gcggttcggg cggggggtggg    2640 agctttggcg gtttcacggg cgcacgcaaa tcagcg                              2676
```

```
<210> SEQ ID NO 24
<211> LENGTH: 892
<212> TYPE: PRT
<213> ORGANISM: Artificial Sequence
<220> FEATURE:
<223> OTHER INFORMATION: Synthetic

<400> SEQUENCE: 24
```

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly

```
                305                 310                 315                 320
Glu Tyr Lys Gln Lys Leu Ile Arg Lys Tyr Arg Phe Val Val Glu Ser
                325                 330                 335
Ser Gly Glu Val Thr Val Asn Arg Asn Lys Phe Val Glu Leu Tyr Asn
                340                 345                 350
Glu Leu Thr Gln Ile Phe Thr Glu Phe Asn Tyr Ala Lys Ile Tyr Asn
                355                 360                 365
Val Gln Asn Arg Lys Ile Tyr Leu Ser Asn Val Tyr Thr Pro Val Thr
                370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
                420                 425                 430
Phe Thr Lys Phe Cys His Lys Ala Ile Asp Gly Arg Ser Leu Tyr Asn
                435                 440                 445
Lys Thr Leu Asp Cys Arg Glu Leu Leu Val Lys Asn Thr Asp Leu Pro
450                 455                 460
Phe Ile Gly Asp Ile Ser Asp Val Lys Thr Asp Ile Phe Leu Arg Lys
465                 470                 475                 480
Asp Ile Asn Glu Glu Thr Glu Val Ile Tyr Tyr Pro Asp Asn Val Ser
                485                 490                 495
Val Asp Gln Val Ile Leu Ser Lys Asn Thr Ser Glu His Gly Gln Leu
                500                 505                 510
Asp Leu Leu Tyr Pro Ser Ile Asp Ser Glu Ser Glu Ile Leu Pro Gly
                515                 520                 525
Glu Asn Gln Val Phe Tyr Asp Asn Arg Thr Gln Asn Val Asp Tyr Leu
                530                 535                 540
Asn Ser Tyr Tyr Tyr Leu Glu Ser Gln Lys Leu Ser Asp Asn Val Glu
545                 550                 555                 560
Asp Phe Thr Phe Thr Arg Ser Ile Glu Glu Ala Leu Asp Asn Ser Ala
                565                 570                 575
Lys Val Tyr Thr Tyr Phe Pro Thr Leu Ala Asn Lys Val Asn Ala Gly
                580                 585                 590
Val Gln Gly Gly Leu Phe Leu Met Trp Ala Asn Asp Val Val Glu Asp
                595                 600                 605
Phe Thr Thr Asn Ile Leu Arg Lys Asp Thr Leu Asp Lys Ile Ser Asp
                610                 615                 620
Val Ser Ala Ile Ile Pro Tyr Ile Gly Pro Ala Leu Asn Ile Ser Asn
625                 630                 635                 640
Ser Val Arg Arg Gly Asn Phe Thr Glu Ala Phe Ala Val Thr Gly Val
                645                 650                 655
Thr Ile Leu Leu Glu Ala Phe Pro Glu Phe Thr Ile Pro Ala Leu Gly
                660                 665                 670
Ala Phe Val Ile Tyr Ser Lys Val Gln Glu Arg Asn Glu Ile Ile Lys
                675                 680                 685
Thr Ile Asp Asn Cys Leu Glu Gln Arg Ile Lys Arg Trp Lys Asp Ser
                690                 695                 700
Tyr Glu Trp Met Met Gly Thr Trp Leu Ser Arg Ile Ile Thr Gln Phe
705                 710                 715                 720
Asn Asn Ile Ser Tyr Gln Met Tyr Asp Ser Leu Asn Tyr Gln Ala Gly
                725                 730                 735
```

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Val Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
            805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
            835                 840                 845

Phe Ser Tyr Thr Asn Asn Ser Leu Leu Lys Asp Ile Ile Asn Glu Tyr
850                 855                 860

Phe Asn Gly Gly Gly Gly Ser Gly Gly Gly Gly Ser Gly Gly Gly Gly
865                 870                 875                 880

Ser Phe Gly Gly Phe Thr Gly Ala Arg Lys Ser Ala
            885                 890

<210> SEQ ID NO 25
<211> LENGTH: 2712
<212> TYPE: DNA
<213> ORGANISM: Artificial Sequence
<220> FEATURE:
<223> OTHER INFORMATION: Synthetic

<400> SEQUENCE: 25 tttgcggtt tcacgggcgc acgcaaatca gcgcgtaaat atgctaacca gactagtggc        60
ggtgggggta gtggcggtgg cggttcgggc ggggggtggga gccctagggg atccatgcca      120
ataacaatta acaactttaa ttattcagat cctgttgata taaaaatat tttatattta       180 gatactcatt taaatacact agctaatgag cctgaaaaag cctttcgcat tacaggaaat       240
atatgggtaa tacctgatag attttcaaga aattctaatc caaatttaaa taaacctcct       300
cgagttacaa gccctaaaag tggttattat gatcctaatt atttgagtac tgattctgac       360
aaagatacat ttttaaaaga aattataaag ttatttaaaa gaattaattc tagagaaata       420
ggagaagaat aatatatag actttcgaca gatataccct ttcctgggaa taacaatact       480
ccaattaata cctttgattt tgatgtagat tttaacagtg ttgatgttaa aactagacaa       540
ggtaacaact gggttaaaac tggtagcata atcctagtg ttataataac tggacctaga       600
gaaaacatta tagatccaga aacttctacg tttaaattaa ctaacaatac ctttgcggca       660
caagaaggat tggtgctttt atcaataatt tcaatatcac ctagatttat gctaacatat       720
agtaatgcaa ctaatgatgt aggagagggt agattttcta gtctgaatt ttgcatggat        780 ccaatactaa ttttaatgca tgaacttaat catgcaatgc ataatttata tggaatagct       840
ataccaaatg atcaaacaat ttcatctgta actagtaata ttttttattc tcaatataat       900
gtgaaattag agtatgcaga atatatgca tttgaggtc caactataga ccttattcct         960
aaaagtgcaa ggaaatattt tgaggaaaag gcattggatt attatagatc tatagctaaa      1020
agacttaata gtataactac tgcaaatcct tcaagcttta ataaatatat agggaatat       1080 aaacagaaac ttattagaaa gtatagattc gtagtagaat cttcaggtga agttacagta      1140

```
aatcgtaata agtttgttga gttatataat gaacttacac aaatatttac agaatttaac    1200
tacgctaaaa tatataatgt acaaaatagg aaaatatatc tttcaaatgt atatactccg    1260
gttacggcga atatattaga cgataatgtt tatgatatac aaaatggatt taatataacct   1320 aaaagtaatt taaatgtact atttatgggt caaaatttat ctcgaaatcc agcattaaga    1380
aaagtcaatc ctgaaaatat gctttattta tttacaaaat tttgtcataa agcaatagat    1440
ggtagatcat tatataataa aacattagat tgtagagagc ttttagttaa aaatactgac    1500
ttacccttta taggtgatat tagtgatgtt aaaactgata tatttttaag aaaagatatt    1560
aatgaagaaa ctgaagttat atactatccg gacaatgttt cagtagatca agttattctc    1620
agtaagaata cctcagaaca tggacaacta gatttattat accctagtat tgacagtgag    1680
agtgaaatat taccagggga gaatcaagtc ttttatgata atagaactca aaatgttgat    1740
tatttgaatt cttattatta cctagaatct caaaaactaa gtgataatgt tgaagatttt    1800
acttttacga gatcaattga ggaggctttg gataatagtg caaaagtata tacttacttt    1860
cctacactag ctaataaagt aaatgcgggt gttcaaggtg gtttatttt aatgtgggca    1920 aatgatgtag ttgaagattt tactacaaat attctaagaa aagatacatt agataaaata    1980
tcagatgtat cagctattat tccctatata ggacccgcat taaatataag taattctgta    2040
agaagaggaa attttactga agcatttgca gttactggtg taactatttt attagaagca    2100
tttcctgaat ttacaatacc tgcacttggt gcatttgtga tttatagtaa ggttcaagaa    2160
agaaacgaga ttattaaaac tatagataat tgtttagaac aaaggattaa gagatggaaa    2220
gattcatatg aatggatgat gggaacgtgg ttatccagga ttattactca atttaataat    2280
ataagttatc aaatgtatga ttctttaaat tatcaggcag gtgcaatcaa agctaaaata    2340
gatttagaat ataaaaaata ttcaggaagt gataaagaaa atataaaaag tcaagttgaa    2400
aatttaaaaa atagtttaga tgtaaaaatt tcggaagcaa tgaataatat aaataaattt    2460
atacgagaat gttccgtaac atatttattt aaaaatatgt tacctaaagt aattgatgaa    2520
ttaaatgagt ttgatcgaaa tactaaagca aaattaatta atcttataga tagtcataat    2580
attattctag ttggtgaagt agataaatta aaagcaaaag taataatag ctttcaaaat    2640 acaatacccct ttaatatttt ttcatatact aataattctt tattaaaaga tataattaat    2700
gaatatttca at                                                        2712
```

<210> SEQ ID NO 26
<211> LENGTH: 904
<212> TYPE: PRT
<213> ORGANISM: Artificial Sequence
<220> FEATURE:
<223> OTHER INFORMATION: Synthetic

<400> SEQUENCE: 26

```
Phe Gly Gly Phe Thr Gly Ala Arg Lys Ser Ala Arg Lys Tyr Ala Asn
1               5                   10                  15

Gln Thr Ser Gly Gly Gly Ser Gly Gly Gly Ser Gly Gly Gly
            20                  25                  30

Gly Ser Pro Arg Gly Ser Met Pro Ile Thr Ile Asn Asn Phe Asn Tyr
        35                  40                  45

Ser Asp Pro Val Asp Asn Lys Asn Ile Leu Tyr Leu Asp Thr His Leu
    50                  55                  60

Asn Thr Leu Ala Asn Glu Pro Glu Lys Ala Phe Arg Ile Thr Gly Asn
65                  70                  75                  80
```

-continued

```
Ile Trp Val Ile Pro Asp Arg Phe Ser Arg Asn Ser Asn Pro Asn Leu
                85                  90                  95
Asn Lys Pro Pro Arg Val Thr Ser Pro Lys Ser Gly Tyr Tyr Asp Pro
            100                 105                 110
Asn Tyr Leu Ser Thr Asp Ser Asp Lys Asp Thr Phe Leu Lys Glu Ile
        115                 120                 125
Ile Lys Leu Phe Lys Arg Ile Asn Ser Arg Glu Ile Gly Glu Glu Leu
    130                 135                 140
Ile Tyr Arg Leu Ser Thr Asp Ile Pro Phe Pro Gly Asn Asn Asn Thr
145                 150                 155                 160
Pro Ile Asn Thr Phe Asp Phe Asp Val Asp Phe Asn Ser Val Asp Val
                165                 170                 175
Lys Thr Arg Gln Gly Asn Asn Trp Val Lys Thr Gly Ser Ile Asn Pro
            180                 185                 190
Ser Val Ile Ile Thr Gly Pro Arg Glu Asn Ile Ile Asp Pro Glu Thr
        195                 200                 205
Ser Thr Phe Lys Leu Thr Asn Asn Thr Phe Ala Ala Gln Glu Gly Phe
    210                 215                 220
Gly Ala Leu Ser Ile Ile Ser Ile Ser Pro Arg Phe Met Leu Thr Tyr
225                 230                 235                 240
Ser Asn Ala Thr Asn Asp Val Gly Glu Gly Arg Phe Ser Lys Ser Glu
                245                 250                 255
Phe Cys Met Asp Pro Ile Leu Ile Leu Met His Glu Leu Asn His Ala
            260                 265                 270
Met His Asn Leu Tyr Gly Ile Ala Ile Pro Asn Asp Gln Thr Ile Ser
        275                 280                 285
Ser Val Thr Ser Asn Ile Phe Tyr Ser Gln Tyr Asn Val Lys Leu Glu
    290                 295                 300
Tyr Ala Glu Ile Tyr Ala Phe Gly Gly Pro Thr Ile Asp Leu Ile Pro
305                 310                 315                 320
Lys Ser Ala Arg Lys Tyr Phe Glu Glu Lys Ala Leu Asp Tyr Tyr Arg
                325                 330                 335
Ser Ile Ala Lys Arg Leu Asn Ser Ile Thr Thr Ala Asn Pro Ser Ser
            340                 345                 350
Phe Asn Lys Tyr Ile Gly Glu Tyr Lys Gln Lys Leu Ile Arg Lys Tyr
        355                 360                 365
Arg Phe Val Val Glu Ser Ser Gly Glu Val Thr Val Asn Arg Asn Lys
    370                 375                 380
Phe Val Glu Leu Tyr Asn Glu Leu Thr Gln Ile Phe Thr Glu Phe Asn
385                 390                 395                 400
Tyr Ala Lys Ile Tyr Asn Val Gln Asn Arg Lys Ile Tyr Leu Ser Asn
                405                 410                 415
Val Tyr Thr Pro Val Thr Ala Asn Ile Leu Asp Asp Asn Val Tyr Asp
            420                 425                 430
Ile Gln Asn Gly Phe Asn Ile Pro Lys Ser Asn Leu Asn Val Leu Phe
        435                 440                 445
Met Gly Gln Asn Leu Ser Arg Asn Pro Ala Leu Arg Lys Val Asn Pro
    450                 455                 460
Glu Asn Met Leu Tyr Leu Phe Thr Lys Phe Cys His Lys Ala Ile Asp
465                 470                 475                 480
Gly Arg Ser Leu Tyr Asn Lys Thr Leu Asp Cys Arg Glu Leu Leu Val
                485                 490                 495
Lys Asn Thr Asp Leu Pro Phe Ile Gly Asp Ile Ser Asp Val Lys Thr
```

```
            500                 505                 510
Asp Ile Phe Leu Arg Lys Asp Ile Asn Glu Glu Thr Glu Val Ile Tyr
            515                 520                 525
Tyr Pro Asp Asn Val Ser Val Asp Gln Val Ile Leu Ser Lys Asn Thr
            530                 535                 540
Ser Glu His Gly Gln Leu Asp Leu Leu Tyr Pro Ser Ile Asp Ser Glu
545                 550                 555                 560
Ser Glu Ile Leu Pro Gly Glu Asn Gln Val Phe Tyr Asp Asn Arg Thr
                565                 570                 575
Gln Asn Val Asp Tyr Leu Asn Ser Tyr Tyr Leu Glu Ser Gln Lys
                580                 585                 590
Leu Ser Asp Asn Val Glu Asp Phe Thr Phe Thr Arg Ser Ile Glu Glu
                595                 600                 605
Ala Leu Asp Asn Ser Ala Lys Val Tyr Thr Tyr Phe Pro Thr Leu Ala
                610                 615                 620
Asn Lys Val Asn Ala Gly Val Gln Gly Gly Leu Phe Leu Met Trp Ala
625                 630                 635                 640
Asn Asp Val Val Glu Asp Phe Thr Thr Asn Ile Leu Arg Lys Asp Thr
                645                 650                 655
Leu Asp Lys Ile Ser Asp Val Ser Ala Ile Ile Pro Tyr Ile Gly Pro
                660                 665                 670
Ala Leu Asn Ile Ser Asn Ser Val Arg Arg Gly Asn Phe Thr Glu Ala
                675                 680                 685
Phe Ala Val Thr Gly Val Thr Ile Leu Leu Glu Ala Phe Pro Glu Phe
                690                 695                 700
Thr Ile Pro Ala Leu Gly Ala Phe Val Ile Tyr Ser Lys Val Gln Glu
705                 710                 715                 720
Arg Asn Glu Ile Ile Lys Thr Ile Asp Asn Cys Leu Glu Gln Arg Ile
                725                 730                 735
Lys Arg Trp Lys Asp Ser Tyr Glu Trp Met Met Gly Thr Trp Leu Ser
                740                 745                 750
Arg Ile Ile Thr Gln Phe Asn Asn Ile Ser Tyr Gln Met Tyr Asp Ser
                755                 760                 765
Leu Asn Tyr Gln Ala Gly Ala Ile Lys Ala Lys Ile Asp Leu Glu Tyr
                770                 775                 780
Lys Lys Tyr Ser Gly Ser Asp Lys Glu Asn Ile Lys Ser Gln Val Glu
785                 790                 795                 800
Asn Leu Lys Asn Ser Leu Asp Val Lys Ile Ser Glu Ala Met Asn Asn
                805                 810                 815
Ile Asn Lys Phe Ile Arg Glu Cys Ser Val Thr Tyr Leu Phe Lys Asn
                820                 825                 830
Met Leu Pro Lys Val Ile Asp Glu Leu Asn Glu Phe Asp Arg Asn Thr
                835                 840                 845
Lys Ala Lys Leu Ile Asn Leu Ile Asp Ser His Asn Ile Ile Leu Val
                850                 855                 860
Gly Glu Val Asp Lys Leu Lys Ala Lys Val Asn Asn Ser Phe Gln Asn
865                 870                 875                 880
Thr Ile Pro Phe Asn Ile Phe Ser Tyr Thr Asn Asn Ser Leu Leu Lys
                885                 890                 895
Asp Ile Ile Asn Glu Tyr Phe Asn
                900

<210> SEQ ID NO 27
```

```
<211> LENGTH: 1302
<212> TYPE: DNA
<213> ORGANISM: Artificial Sequence
<220> FEATURE:
<223> OTHER INFORMATION: Synthetic

<400> SEQUENCE: 27
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccgacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta attcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc caccctgaac     900
aaagcgaaat ccatcgtggg taccactgct tctctccagt acatgaagaa cgttttaaaa     960
gaaaatacc tgctcagcga agacacctcc ggcaaattct ctgtagacaa gttgaaattc    1020
gataaactttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggcagaa cacggaaatc aacaacatga acttcacaaa actgaaaaac    1260
ttcactggtc tgttcgagtt ttacaagctg ctgtgcgtcg ac                        1302

<210> SEQ ID NO 28
<211> LENGTH: 1257
<212> TYPE: DNA
<213> ORGANISM: Artificial Sequence
<220> FEATURE:
<223> OTHER INFORMATION: Synthetic

<400> SEQUENCE: 28
ctgcagtgta tcaaggttaa caactgggat ttattcttca gcccgagtga agacaacttc      60
accaacgacc tgaacaaagg tgaagaaatc acctcagata ctaacatcga agcagccgaa     120
gaaaacatct cgctggacct gatccagcag tactacctga cctttaattt cgacaacgag     180
ccggaaaaca tttctatcga aacctgagc tctgatatca tcggccagct ggaactgatg     240
ccgaacatcg aacgtttccc aaacggtaaa agtacgagc tggacaaata taccatgttc     300
cactacctgc gcgcgcagga atttgaacac ggcaaatccc gtatcgcact gactaactcc     360
gttaacgaag ctctgctcaa cccgtcccgt gtatacacct tcttctctag cgactacgtg     420
aaaaaggtca acaagcgac tgaagctgca atgttcttgg gttgggttga acagcttgtt     480
tatgatttta ccgacgagac gtccgaagta tctactaccg acaaaattgc ggatatcact     540
```

```
atcatcatcc cgtacatcgg tccggctctg aacattggca acatgctgta caaagacgac    600
ttcgttggcg cactgatctt ctccggtgcg gtgatcctgc tggagttcat cccggaaatc    660
gccatcccgg tactgggcac ctttgctctg gtttcttaca ttgcaaacaa ggttctgact    720
gtacaaacca tcgacaacgc gctgagcaaa cgtaacgaaa atgggatga agtttacaaa    780
tatatcgtga ccaactggct ggctaaggtt aatactcaga tcgacctcat ccgcaaaaaa    840
atgaaagaag cactggaaaa ccaggcgaaa gctaccaagg caatcattaa ctaccagtac    900
aaccagtaca ccgaggaaga aaaaaacaac atcaacttca acatcgacga tctgtcctct    960
aaactgaacg aatccatcaa caaagctatg atcaacatca caagttcct gaaccagtgc   1020
tctgtaagct atctgatgaa ctccatgatc ccgtacggtg ttaaacgtct ggaggacttc   1080
gatgcgtctc tgaaagacgc cctgctgaaa tacatttacg acaaccgtgg cactctgatc   1140
ggtcaggttg atcgtctgaa ggacaaagtg aacaatacct tatcgaccga catcccttt    1200
cagctcagta aatatgtcga taaccaacgc ttttgtcca ctctagacta gaagctt      1257
```

<210> SEQ ID NO 29
<211> LENGTH: 1323
<212> TYPE: DNA
<213> ORGANISM: Artificial Sequence
<220> FEATURE:
<223> OTHER INFORMATION: Synthetic

<400> SEQUENCE: 29

```
ggatccatgc cggttaccat caacaacttc aactacaacg acccgatcga caacaacaac     60
atcattatga tggaaccgcc gttcgcacgt ggtaccggac gttactacaa ggcttttaag    120
atcaccgacc gtatctggat catcccggaa cgttacacct tcggttacaa acctgaggac    180
ttcaacaaga gtagcgggat tttcaatcgt gacgtctgcg agtactatga tccagattat    240
ctgaatacca acgataagaa gaacatattc cttcagacta tgattaaact cttcaaccgt    300
atcaaaagca aaccgctcgg tgaaaaactc ctcgaaatga ttatcaacgg tatcccgtac    360
ctcggtgacc gtcgtgtccc gcttgaagag ttcaacacca acatcgcaag cgtcaccgtc    420
aacaaactca tcagcaaccc aggtgaagtc gaacgtaaaa aaggtatctt cgcaaacctc    480
atcatcttcg gtccgggtcc ggtcctcaac gaaaacgaaa ccatcgacat cggtatccag    540
aaccacttcg caagccgtga aggtttcggt ggtatcatgc agatgaaatt ctgcccggaa    600
tacgtcagtg tcttcaacaa cgtccaggaa aacaaaggtg caagcatctt caaccgtcgt    660
ggttacttca gcgacccggc actcatcctc atgcatgaac tcatccacgt cctccacggt    720
ctctacggta tcaaagttga cgacctcccg atcgtcccga acgagaagaa attcttcatg    780
cagagcaccg acgcaatcca ggctgaggaa ctctacacct tcggtggcca agacccaagt    840
atcataaccc cgtccaccga caaaagcatc tacgacaaag tcctccagaa cttcagggt    900
atcgtggaca gactcaacaa agtcctcgtc tgcatcagcg cccgaacat caatatcaac    960
atatacaaga acaagttcaa agacaagtac aaattcgtcg aggacagcga aggcaaatac   1020
agcatcgacg tagaaagttt cgacaagctc tacaaaagcc tcatgttcgg tttcaccgaa   1080
accaacatcg ccgagaacta caagatcaag acaagggcaa gttacttcag cgacagcctc   1140
ccgcctgtca aaatcaagaa cctcttagac aacgagattt acacaattga gagggcttc    1200
aacatcagtg acaagacat ggagaaggaa tacagaggtc agaacaaggc tatcaacaaa   1260
caggcatacg aggagatcag caaagaacac ctcgcagtct acaagatcca gatgtgcgtc   1320
``` gac                                                           1323

<210> SEQ ID NO 30
<211> LENGTH: 1260
<212> TYPE: DNA
<213> ORGANISM: Artificial Sequence
<220> FEATURE:
<223> OTHER INFORMATION: Synthetic

<400> SEQUENCE: 30

| | | |
|---|---|---|
| ctgcagtgca tcgacgttga caacgaagac ctgttcttca tcgctgacaa aaacagcttc | 60 |
| agtgacgacc tgagcaaaaa cgaacgtatc gaatacaaca cccagagcaa ctacatcgaa | 120 |
| aacgacttcc cgatcaacga actgatcctg gacaccgacc tgataagtaa aatcgaactg | 180 |
| ccgagcgaaa acaccgaaag tctgaccgac ttcaacgttg acgttccggt ttacgaaaaa | 240 |
| cagccggcta tcaagaaaat cttcaccgac gaaaacacca tcttccagta cctgtacagc | 300 |
| cagaccttcc cgctggacat ccgtgacatc agtctgacca gcagtttcga cgacgctctg | 360 |
| ctgttcagca acaaagttta cagtttcttc agcatggact acatcaaaac cgctaacaaa | 420 |
| gttgttgaag cagggctgtt cgctggttgg gttaaacaga tcgttaacga cttcgttatc | 480 |
| gaagctaaca aaagcaacac tatggacaaa atcgctgaca tcagtctgat cgttccgtac | 540 |
| atcggtctgg ctctgaacgt tggtaacgaa accgctaaag gtaactttga aaacgctttc | 600 |
| gagatcgctg tgcaagcat cctgctggag ttcatcccgg aactgctgat cccggttgtt | 660 |
| ggtgctttcc tgctggaaag ttacatcgac aacaaaaaca agatcatcaa aaccatcgac | 720 |
| aacgctctga ccaaacgtaa cgaaaaatgg agtgatatgt acggtctgat cgttgctcag | 780 |
| tggctgagca ccgtcaacac ccagttctac accatcaaag aaggtatgta caaagctctg | 840 |
| aactaccagg ctcaggctct ggaagagatc atcaaatacc gttacaacat ctacagtgag | 900 |
| aaggaaaaga gtaacatcaa catcgacttc aacgacatca cagcaaaact gaacgaaggt | 960 |
| atcaaccagg ctatcgacaa catcaacaac ttcatcaacg gttgcagtgt tagctacctg | 1020 |
| atgaagaaga tgatcccgct ggctgttgaa aaactgctgg acttcgacaa caccctgaaa | 1080 |
| aagaacctgc tgaactacat cgacgaaaac aagctgtacc tgatcggtag tgctgaatac | 1140 |
| gaaaaaagta agtgaacaa atacctgaag accatcatgc cgttcgacct gagtatctac | 1200 |
| accaacgaca ccatcctgat cgaaatgttc aacaaataca actctctaga ctagaagctt | 1260 |

<210> SEQ ID NO 31
<211> LENGTH: 1329
<212> TYPE: DNA
<213> ORGANISM: Artificial Sequence
<220> FEATURE:
<223> OTHER INFORMATION: Synthetic

<400> SEQUENCE: 31

| | | |
|---|---|---|
| ggatccgaat tcatgccgat caccatcaac aacttcaact acagcgatcc ggtggataac | 60 |
| aaaaacatcc tgtacctgga tacccatctg aatccctggc gaacgaacc ggaaaaagcg | 120 |
| tttcgtatca ccggcaacat tgggttatt ccggatcgtt ttagccgtaa cagcaacccg | 180 |
| aatctgaata aaccgccgcg tgttaccagc ccgaaaagcg ttattacga tccgaactat | 240 |
| ctgagcaccg atagcgataa agataccttc ctgaaagaaa tcatcaaact gttcaaacgc | 300 |
| atcaacagcc gtgaaattgg cgaagaactg atctatcgcc tgagcaccga tattccgttt | 360 |
| ccgggcaaca caacaccccc gatcaacacc tttgatttcg atgtggattt caacagcgtt | 420 |
| gatgttaaaa cccgccaggg taacaattgg gtgaaaaccg gcagcattaa cccgagcgtg | 480 |

```
attattaccg gtccgcgcga aaacattatt gatccggaaa ccagcacctt taaactgacc    540
aacaacacct ttgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactgaaa tatgcgaaaa tctatgcgtt tggcggtccg    840
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt atacccccggt gaccgcgaat attctggatg ataacgtgta cgatatccag   1200
aacggcttta acatcccgaa aagcaacctg aacgttctgt ttatgggcca gaacctgagc   1260
cgtaatccgg cgctgcgtaa agtgaacccg gaaaacatgc tgtacctgtt caccaaattt   1320
tgcgtcgac                                                          1329
```

<210> SEQ ID NO 32
<211> LENGTH: 1263
<212> TYPE: DNA
<213> ORGANISM: Artificial Sequence
<220> FEATURE:
<223> OTHER INFORMATION: Synthetic

<400> SEQUENCE: 32

```
ctgcagtgtc gtgaactgct ggtgaaaaac accgatctgc cgtttattgg cgatatcagc     60
gatgtgaaaa ccgatatctt cctgcgcaaa gatatcaacg aagaaaccga agtgatctac    120
tacccggata acgtgagcgt tgatcaggtg atcctgagca aaaacaccag cgaacatggt    180
cagctggatc tgctgtatcc gagcattgat agcgaaagcg aaattctgcc gggcgaaaac    240
caggtgtttt acgataaccg tacccagaac gtggattacc tgaacagcta ttactacctg    300
gaaagccaga aactgagcga taacgtggaa gattttacct ttacccgcag cattgaagaa    360
gcgctggata cagcgcgaa agtttacacc tattttccga ccctggcgaa caaagttaat    420
gcgggtgttc agggcggtct gtttctgatg tgggcgaacg atgtggtgga agatttcacc    480
accaacatcc tgcgtaaaga tacccctggat aaaatcagcg atgttagcgc gattattccg    540
tatattggtc cggcgctgaa cattagcaat agcgtgcgtc gtggcaattt taccgaagcg    600
tttgcggtta ccggtgtgac cattctgctg aagcgtttc cggaatttac cattccggcg    660
ctgggtgcgt ttgtgatcta tagcaaagtg caggaacgca acgaaatcat caaaaccatc    720
gataactgcc tggaacagcg tattaaacgc tggaaagata gctatgaatg gatgatgggc    780
acctggctga gccgtattat cacccagttc aacaacatca gctaccagat gtacgatagc    840
ctgaactatc aggcgggtgc gattaaagcg aaaatcgatc tggaatacaa aaaatacagc    900
ggcagcgata agaaaaacat caaaagccag gttgaaaacc tgaaaacag cctgatgtgt    960 aaaattagcg aagcgatgaa taacatcaac aaattcatcc gcgaatgcag cgtgacctac   1020
ctgttcaaaa acatgctgcc gaaagtgatc gatgaactga cgaatttga tcgcaacacc   1080 aaagcgaaac tgatcaacct gatcgatagc cacaacatta ttctggtggg cgaagtggat   1140
```

| aaactgaaag cgaaagttaa caacagcttc cagaacacca tcccgtttaa catcttcagc | 1200 |
| tataccaaca acagcctgct gaaagatatc atcaacgaat acttcaatct agactagaag | 1260 |
| ctt | 1263 |

<210> SEQ ID NO 33
<211> LENGTH: 207
<212> TYPE: DNA
<213> ORGANISM: Artificial Sequence
<220> FEATURE:
<223> OTHER INFORMATION: Synthetic

<400> SEQUENCE: 33

| ggatccacgc acgtcgacgg catcattacc tccaaaacta atctctgat cgaaggtcgt | 60 |
| tttggcggtt tcacgggcgc acgcaaatca gcgcgtaaat tagctaacca ggcgctagcg | 120 |
| ggcggtggcg gtagcggcgg tggcggtagc ggcggtggcg gtagcgcact agtgctgcag | 180 |
| acgcacggtc tagaatgata aaagctt | 207 |

<210> SEQ ID NO 34
<211> LENGTH: 108
<212> TYPE: DNA
<213> ORGANISM: Artificial Sequence
<220> FEATURE:
<223> OTHER INFORMATION: Synthetic

<400> SEQUENCE: 34

| ggatccacgc acgtcgacgg catcattacc tccaaaacta atctctgat agaaggtaga | 60 |
| aacaaagcgc tgaacctgca gacgcacggt ctagaatgat aaaagctt | 108 |

<210> SEQ ID NO 35
<211> LENGTH: 186
<212> TYPE: DNA
<213> ORGANISM: Artificial Sequence
<220> FEATURE:
<223> OTHER INFORMATION: Synthetic

<400> SEQUENCE: 35

| catatgaata acctcgggat tgagggtcgt tttggcggtt tcacgggcgc acgcaaatca | 60 |
| gcgcgtaaat tagctaacca gactagtggc ggtgggggta gtggcggtgg cggttcgggc | 120 |
| gggggtggga gccctagggg atccgtcgac ctgcagggtc tagaagcgct agcgtgataa | 180 |
| aagctt | 186 |

<210> SEQ ID NO 36
<211> LENGTH: 180
<212> TYPE: DNA
<213> ORGANISM: Artificial Sequence
<220> FEATURE:
<223> OTHER INFORMATION: Synthetic

<400> SEQUENCE: 36

| ggatccacgc acgtcgacgc gattgatggt cgttttggcg gtttcacggg cgcacgcaaa | 60 |
| tcagcgcgta aattagctaa ccaggcgcta gcggcggtg gcggtagcgg cggtggcggt | 120 |
| agcggcggtg gcggtagcgc actagtgctg cagacgcacg gtctagaatg ataaaagctt | 180 |

<210> SEQ ID NO 37
<211> LENGTH: 249
<212> TYPE: DNA
<213> ORGANISM: Artificial Sequence
<220> FEATURE:
<223> OTHER INFORMATION: Synthetic

```
<400> SEQUENCE: 37
ggatccacgc acgtcgacgg catcattacc tccaaaacta atctctgat cgaaggtcgt    60 tacggtggtt tcatgacctc tgaaaaatct cagaccccgc tggttaccct gttcaaaaac   120
gctatcatca aaaacgctta caaaaaaggt gaagcgctag cgggtggtgg tggttctggt   180
ggtggtggtt ctggtggtgg tggttctgca ctagtgctgc agacgcacgg tctagaatga   240
taaaagctt                                                           249

<210> SEQ ID NO 38
<211> LENGTH: 207
<212> TYPE: DNA
<213> ORGANISM: Artificial Sequence
<220> FEATURE:
<223> OTHER INFORMATION: Synthetic

<400> SEQUENCE: 38
ggatccacgc acgtcgacgg catcattacc tccaaaacta atctctgat cgaaggtcgt    60 tttggcggtt tcacgggcgc acgcaaatca gcgcgtaaac gtaagaacca ggcgctagcg   120
ggcggtggcg gtagcggcgg tggcggtagc ggcggtggcg gtagcgcact agtgctgcag   180
acgcacggtc tagaatgata aaagctt                                       207

<210> SEQ ID NO 39
<211> LENGTH: 2709
<212> TYPE: DNA
<213> ORGANISM: Artificial Sequence
<220> FEATURE:
<223> OTHER INFORMATION: Synthetic

<400> SEQUENCE: 39
ggatccatgg agttcgttaa caacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gatacctta ctaacccgga agaaggtgac   180
ctgaacccgc caccggaagc gaaacaggtg ccggtatctt actatgactc cacctacctg   240
tctaccgata cgaaaagga caactacctg aaaggtgtta ctaaactgtt cgagcgtatt   300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
cagccggacg gttcctatcg ttccgaagaa ctgaacctgg tgatcatcgg cccgtctgct   480
gatatcatcc agtcgagtg taagagcttt ggtcacgaag ttctgaacct cacccgtaac   540
ggctacggtt ccactcagta catccgtttc tctccggact tcaccttcgg ttttgaagaa   600
tccctggaag tagacacgaa cccactgctg ggcgctggta attcgcaac tgatcctgcg   660 gttaccctgg ctcacgaact gattcatgca ggccaccgcc tgtacggtat cgccatcaat   720
ccgaaccgtg tcttcaaagt taacaccaac gcgtattacg agatgtccgg tctggaagtt   780
agcttcgaag aactgcgtac ttttggcggt cacgacgcta aattcatcga ctctctgcaa   840
gaaaacgagt tccgtctgta ctactataac aagttcaaag atatcgcatc caccctgaac   900
aaagcgaaat ccatcgtggg taccactgct tctctccagt acatgaagaa cgttttaaa   960 gaaaaatacc tgctcagcga agacacctcc ggcaaattct ctgtagacaa gttgaaattc  1020
gataaacttt acaaaatgct gactgaaatt tacaccgaag caacttcgt taagttcttt  1080 aaagttctga accgcaaaac ctatctgaac ttcgacaagg cagtattcaa aatcaacatc  1140
```

| | |
|---|---|
| gtgccgaaag ttaactacac tatctacgat ggtttcaacc tgcgtaacac caacctggct | 1200 |
| gctaatttta acggccagaa cacggaaatc aacaacatga acttcacaaa actgaaaaac | 1260 |
| ttcactggtc tgttcgagtt ttacaagctg ctgtgcgtcg acggcatcat acctccaaa | 1320 |
| actaaatctc tgatagaagg tagatttggc ggtttcacgg gcgcacgcaa atcagcgcgt | 1380 |
| aaattagcta accaggcgct agcgggcggt ggcggtagcg gcggtggcgg tagcggcggt | 1440 |
| ggcggtagcg cactagtgct gcagtgtatc aaggttaaca actgggattt attcttcagc | 1500 |
| ccgagtgaag acaacttcac caacgacctg aacaaaggtg aagaaatcac ctcagatact | 1560 |
| aacatcgaag cagccgaaga aaacatctcg ctggacctga tccagcagta ctacctgacc | 1620 |
| tttaatttcg acaacgagcc ggaaaacatt tctatcgaaa acctgagctc tgatatcatc | 1680 |
| ggccagctgg aactgatgcc gaacatcgaa cgtttcccaa acggtaaaaa gtacgagctg | 1740 |
| gacaaatata ccatgttcca ctacctgcgc gcgcaggaat ttgaacacgg caaatcccgt | 1800 |
| atcgcactga ctaactccgt taacgaagct ctgctcaacc cgtcccgtgt atacaccttc | 1860 |
| ttctctagcg actacgtgaa aaaggtcaac aaagcgactg aagctgcaat gttcttgggt | 1920 |
| tgggttgaac agcttgttta tgattttacc gacgagacgt ccgaagtatc tactaccgac | 1980 |
| aaaattgcgg atatcactat catcatcccg tacatcggtc cggctctgaa cattggcaac | 2040 |
| atgctgtaca agacgactt cgttggcgca ctgatcttct ccggtgcggt gatcctgctg | 2100 |
| gagttcatcc cggaaatcgc catcccggta ctgggcaccc ttgctctggt ttcttacatt | 2160 |
| gcaaacaagg ttctgactgt acaaaccatc gacaacgcgc tgagcaaacg taacgaaaaa | 2220 |
| tgggatgaag tttacaaata tatcgtgacc aactggctgg ctaaggttaa tactcagatc | 2280 |
| gacctcatcc gcaaaaaaat gaaagaagca ctggaaaacc aggcggaagc taccaaggca | 2340 |
| atcattaact accagtacaa ccagtacacc gaggaagaaa aaacaacat caacttcaac | 2400 |
| atcgacgatc tgtcctctaa actgaacgaa tccatcaaca agctatgat caacatcaac | 2460 |
| aagttcctga accagtgctc tgtaagctat ctgatgaact ccatgatccc gtacggtgtt | 2520 |
| aaacgtctgg aggacttcga tgcgtctctg aaagacgccc tgctgaaata catttacgac | 2580 |
| aaccgtggca ctctgatcgg tcaggttgat cgtctgaagg acaaagtgaa caatacctta | 2640 |
| tcgaccgaca tcccttttca gctcagtaaa tatgtcgata accaacgcct tttgtccact | 2700 |
| ctagactag | 2709 |

<210> SEQ ID NO 40
<211> LENGTH: 902
<212> TYPE: PRT
<213> ORGANISM: Artificial Sequence
<220> FEATURE:
<223> OTHER INFORMATION: Synthetic
<400> SEQUENCE: 40

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

```
Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Leu Ala Asn
    450                 455                 460

Gln Ala Leu Ala Gly Gly Gly Ser Gly Gly Gly Ser Gly Gly Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
```

```
                500             505             510
Gly Glu Glu Ile Thr Ser Asp Thr Asn Ile Glu Ala Ala Glu Glu Asn
            515                 520                 525

Ile Ser Leu Asp Leu Ile Gln Gln Tyr Tyr Leu Thr Phe Asn Phe Asp
        530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
        690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
        770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
        850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
                900

<210> SEQ ID NO 41
```

<211> LENGTH: 2736
<212> TYPE: DNA
<213> ORGANISM: Artificial Sequence
<220> FEATURE:
<223> OTHER INFORMATION: Synthetic

<400> SEQUENCE: 41

| | | | | | |
|---|---|---|---|---|---|
| ctcgggattg | agggtcgttt | tggcggtttc | acgggcgcac | gcaaatcagc | gcgtaaatta | 60 |
| gctaaccaga | ctagtggcgg | tggggtagt | ggcggtggcg | gttcgggcgg | gggtgggagc | 120 |
| cctagggat | ccatggagtt | cgttaacaaa | cagttcaact | ataaagaccc | agttaacggt | 180 |
| gttgacattg | cttacatcaa | aatcccgaac | gctggccaga | tgcagccggt | aaaggcattc | 240 |
| aaaatccaca | acaaaatctg | ggttatcccg | gaacgtgata | cctttactaa | cccggaagaa | 300 |
| ggtgacctga | acccgccacc | ggaagcgaaa | caggtgccgg | tatcttacta | tgactccacc | 360 |
| tacctgtcta | ccgataacga | aaaggacaac | tacctgaaag | gtgttactaa | actgttcgag | 420 |
| cgtatttact | ccaccgacct | gggccgtatg | ctgctgacta | gcatcgttcg | cggtatcccg | 480 |
| ttctggggcg | gttctaccat | cgataccgaa | ctgaaagtaa | tcgacactaa | ctgcatcaac | 540 |
| gttattcagc | cggacggttc | ctatcgttcc | gaagaactga | acctggtgat | catcggcccg | 600 |
| tctgctgata | tcatccagtt | cgagtgtaag | agctttggtc | acgaagttct | gaacctcacc | 660 |
| cgtaacggct | acggttccac | tcagtacatc | cgtttctctc | cggacttcac | cttcggtttt | 720 |
| gaagaatccc | tggaagtaga | cacgaaccca | ctgctgggcg | ctggtaaatt | cgcaactgat | 780 |
| cctgcggtta | ccctggctca | cgaactgatt | catgcaggcc | accgctgta | cggtatcgcc | 840 |
| atcaatccga | accgtgtctt | caaagttaac | accaacgcgt | attacgagat | gtccggtctg | 900 |
| gaagttagct | tcgaagaact | gcgtactttt | ggcggtcacg | acgctaaatt | catcgactct | 960 |
| ctgcaagaaa | acgagttccg | tctgtactac | tataacaagt | tcaaagatat | cgcatccacc | 1020 |
| ctgaacaaag | cgaaatccat | cgtgggtacc | actgcttctc | tccagtacat | gaagaacgtt | 1080 |
| tttaagaaa | aatacctgct | cagcgaagac | acctccggca | aattctctgt | agacaagttg | 1140 |
| aaattcgata | aactttacaa | aatgctgact | gaaatttaca | ccgaagacaa | cttcgttaag | 1200 |
| ttctttaaag | ttctgaaccg | caaaacctat | ctgaacttcg | acaaggcagt | attcaaaatc | 1260 |
| aacatcgtgc | cgaaagttaa | ctacactatc | tacgatggtt | tcaacctgcg | taacaccaac | 1320 |
| ctggctgcta | atttaacgg | ccagaacacg | gaaatcaaca | acatgaactt | cacaaaactg | 1380 |
| aaaaacttca | ctggtctgtt | cgagttttac | aagctgctgt | gcgtcgacgg | catcattacc | 1440 |
| tccaaaacta | aatctctgat | agaaggtaga | aacaaagcgc | tgaacgacct | ctgtatcaag | 1500 |
| gttaacaact | gggatttatt | cttcagcccg | agtgaagaca | acttcaccaa | cgacctgaac | 1560 |
| aaaggtgaag | aaatcaccctc | agatactaac | atcgaagcag | ccgaagaaaa | catctcgctg | 1620 |
| gacctgatcc | agcagtacta | cctgaccttt | aatttcgaca | acgagccgga | aaacatttct | 1680 |
| atcgaaaacc | tgagctctga | tatcatcggc | cagctggaac | tgatgccgaa | catcgaacgt | 1740 |
| ttcccaaacg | gtaaaaagta | cgagctggac | aaatatacca | tgttccacta | cctgcgcgcg | 1800 |
| caggaatttg | aacacggcaa | atcccgtatc | gcactgacta | actccgttaa | cgaagctctg | 1860 |
| ctcaacccgt | cccgtgtata | caccttcttc | tctagcgact | acgtgaaaaa | ggtcaacaaa | 1920 |
| gcgactgaag | ctgcaatgtt | cttgggttgg | gttgaacagc | ttgtttatga | ttttaccgac | 1980 |
| gagacgtccg | aagtatctac | taccgacaaa | attgcggata | tcactatcat | catcccgtac | 2040 |
| atcggtccgg | ctctgaacat | tggcaacatg | ctgtacaaag | acgacttcgt | tggcgcactg | 2100 |
| atcttctccg | gtgcggtgat | cctgctggag | ttcatcccgg | aaatcgccat | cccggtactg | 2160 |

```
ggcacctttg ctctggtttc ttacattgca aacaaggttc tgactgtaca aaccatcgac    2220
aacgcgctga gcaaacgtaa cgaaaaatgg gatgaagttt acaaatatat cgtgaccaac    2280
tggctggcta aggttaatac tcagatcgac ctcatccgca aaaaaatgaa agaagcactg    2340
gaaaaccagg cggaagctac caaggcaatc attaactacc agtacaacca gtacaccgag    2400
gaagaaaaaa acaacatcaa cttcaacatc gacgatctgt cctctaaact gaacgaatcc    2460
atcaacaaag ctatgatcaa catcaacaag ttcctgaacc agtgctctgt aagctatctg    2520
atgaactcca tgatcccgta cggtgttaaa cgtctggagg acttcgatgc gtctctgaaa    2580
gacgccctgc tgaaatacat ttacgacaac cgtggcactc tgatcggtca ggttgatcgt    2640
ctgaaggaca aagtgaacaa taccttatcg accgacatcc cttttcagct cagtaaatat    2700
gtcgataacc aacgccttt gtccactcta gactag                              2736
```

<210> SEQ ID NO 42
<211> LENGTH: 911
<212> TYPE: PRT
<213> ORGANISM: Artificial Sequence
<220> FEATURE:
<223> OTHER INFORMATION: Synthetic

<400> SEQUENCE: 42

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Ser Gly Gly
                20                  25                  30

Gly Gly Ser Gly Gly Gly Gly Ser Pro Arg Gly Ser Met Glu Phe Val
            35                  40                  45

Asn Lys Gln Phe Asn Tyr Lys Asp Pro Val Asn Gly Val Asp Ile Ala
        50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Glu Ala Lys Gln Val
            100                 105                 110

Pro Val Ser Tyr Tyr Asp Ser Thr Tyr Leu Ser Thr Asp Asn Glu Lys
        115                 120                 125

Asp Asn Tyr Leu Lys Gly Val Thr Lys Leu Phe Glu Arg Ile Tyr Ser
    130                 135                 140

Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu Glu
            180                 185                 190

Leu Asn Leu Val Ile Ile Gly Pro Ser Ala Asp Ile Gln Phe Glu
        195                 200                 205

Cys Lys Ser Phe Gly His Glu Val Leu Asn Leu Thr Arg Asn Gly Tyr
    210                 215                 220

Gly Ser Thr Gln Tyr Ile Arg Phe Ser Pro Asp Phe Thr Phe Gly Phe
225                 230                 235                 240

Glu Glu Ser Leu Glu Val Asp Thr Asn Pro Leu Leu Gly Ala Gly Lys
                245                 250                 255
```

```
Phe Ala Thr Asp Pro Ala Val Thr Leu Ala His Glu Leu Ile His Ala
            260                 265                 270

Gly His Arg Leu Tyr Gly Ile Ala Ile Asn Pro Asn Arg Val Phe Lys
        275                 280                 285

Val Asn Thr Asn Ala Tyr Tyr Glu Met Ser Gly Leu Glu Val Ser Phe
    290                 295                 300

Glu Glu Leu Arg Thr Phe Gly Gly His Asp Ala Lys Phe Ile Asp Ser
305                 310                 315                 320

Leu Gln Glu Asn Glu Phe Arg Leu Tyr Tyr Asn Lys Phe Lys Asp
                325                 330                 335

Ile Ala Ser Thr Leu Asn Lys Ala Lys Ser Ile Val Gly Thr Thr Ala
                340                 345                 350

Ser Leu Gln Tyr Met Lys Asn Val Phe Lys Glu Lys Tyr Leu Leu Ser
            355                 360                 365

Glu Asp Thr Ser Gly Lys Phe Ser Val Asp Lys Leu Lys Phe Asp Lys
    370                 375                 380

Leu Tyr Lys Met Leu Thr Glu Ile Tyr Thr Glu Asp Asn Phe Val Lys
385                 390                 395                 400

Phe Phe Lys Val Leu Asn Arg Lys Thr Tyr Leu Asn Phe Asp Lys Ala
                405                 410                 415

Val Phe Lys Ile Asn Ile Val Pro Lys Val Asn Tyr Thr Ile Tyr Asp
                420                 425                 430

Gly Phe Asn Leu Arg Asn Thr Asn Leu Ala Ala Asn Phe Asn Gly Gln
            435                 440                 445

Asn Thr Glu Ile Asn Asn Met Asn Phe Thr Lys Leu Lys Asn Phe Thr
    450                 455                 460

Gly Leu Phe Glu Phe Tyr Lys Leu Leu Cys Val Asp Gly Ile Ile Thr
465                 470                 475                 480

Ser Lys Thr Lys Ser Leu Ile Glu Gly Arg Asn Lys Ala Leu Asn Asp
                485                 490                 495

Leu Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
    515                 520                 525

Thr Asn Ile Glu Ala Ala Glu Glu Asn Ile Ser Leu Asp Leu Ile Gln
530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
        595                 600                 605

Arg Ile Ala Leu Thr Asn Ser Val Asn Glu Ala Leu Leu Asn Pro Ser
    610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
```

```
                675                 680                 685
Asn Met Leu Tyr Lys Asp Asp Phe Val Gly Ala Leu Ile Phe Ser Gly
    690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
        755                 760                 765

Ile Asp Leu Ile Arg Lys Lys Met Lys Glu Ala Leu Glu Asn Gln Ala
    770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
        835                 840                 845

Val Lys Arg Leu Glu Asp Phe Asp Ala Ser Leu Lys Asp Ala Leu Leu
850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
            900                 905                 910

<210> SEQ ID NO 43
<211> LENGTH: 2715
<212> TYPE: DNA
<213> ORGANISM: Artificial Sequence
<220> FEATURE:
<223> OTHER INFORMATION: Synthetic

<400> SEQUENCE: 43
ggatccgaat tcatgccgat caccatcaac aacttcaact acagcgatcc ggtggataac      60
aaaaacatcc tgtacctgga tacccatctg aatccctggc gaacgaaacc ggaaaaagcg     120
tttcgtatca ccggcaacat tgggttattc cggatcgtt ttagccgtaa cagcaacccg      180
aatctgaata aaccgccgcg tgttaccagc ccgaaaagcg gttattacga tccgaactat     240
ctgagcaccg atagcgataa agatacctcc tgaaagaaa tcatcaaact gttcaaacgc     300
atcaacagcc gtgaaattgg cgaagaactg atctatcgcc tgagcaccga tattccgttt     360
ccgggcaaca caacacccc gatcaacacc tttgatttcg atgtggattt caacagcgtt      420
gatgttaaaa cccgccaggg taacaattgg gtgaaaaccg gcagcattaa cccgagcgtg     480
attattaccg gtccgcgcga aaacattatt gatccggaaa ccagcacctt taaactgacc     540
aacaacacct tgcggcgca ggaaggtttt ggcgcgctga gcattattag cattagcccg      600
cgctttatgc tgacctatag caacgcgacc aacgatgttg gtgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
```

```
ttttacagcc agtacaacgt gaaactggaa tatgcggaaa tctatgcgtt tggcggtccg      840
accattgatc tgattccgaa aagcgcgcgc aaatacttcg aagaaaaagc gctggattac      900
tatcgcagca ttgcgaaacg tctgaacagc attaccaccg cgaatccgag cagcttcaac      960
aaatatatcg gcgaatataa acagaaactg atccgcaaat atcgctttgt ggtggaaagc     1020
agcggcgaag ttaccgttaa ccgcaataaa ttcgtggaac tgtacaacga actgacccag     1080
atcttcaccg aatttaacta tgcgaaaatc tataacgtgc agaaccgtaa aatctacctg     1140
agcaacgtgt atacccggt gaccgcgaat attctggatg ataacgtgta cgatatccag     1200
aacggcttta catcccgaa aagcaacctg aacgttctgt ttatgggcca gaacctgagc     1260
cgtaatccgg cgctgcgtaa agtgaacccg aaaacatgc tgtacctgtt caccaaattt     1320
tgcgtcgacg cgatagatgg tagatttggc ggtttcacgg cgcacgcaa atcagcgcgt     1380
aaattagcta accaggcgct agcgggcggt ggcggtagcg gcggtggcgg tagcggcggt     1440
ggcggtagcg cactagtgct gcagtgtcgt gaactgctgg tgaaaaacac cgatctgccg     1500
tttattggcg atatcagcga tgtgaaaacc gatatcttcc tgcgcaaaga tatcaacgaa     1560
gaaaccgaag tgatctacta cccggataac gtgagcgttg atcaggtgat cctgagcaaa     1620
aacaccagcg aacatggtca gctggatctg ctgtatccga gcattgatag cgaaagcgaa     1680
attctgccgg cgaaaaacca ggtgtttttac gataaccgta cccagaacgt ggattacctg     1740
aacagctatt actacctgga aagccagaaa ctgagcgata acgtggaaga ttttacccttt     1800
acccgcagca ttgaagaagc gctggataac agcgcgaaag tttacaccta ttttccgacc     1860
ctggcgaaca aagttaatgc gggtgttcag ggcggtctgt ttctgatgtg ggcgaacgat     1920
gtggtggaag atttcaccac caacatcctg cgtaaagata ccctggataa atcagcgat     1980
gttagcgcga ttattccgta tattggtccg gcgctgaaca ttagcaatag cgtgcgtcgt     2040
ggcaattta ccgaagcgtt tgcggttacc ggtgtgacca ttctgctgga agcgtttccg     2100
gaatttacca ttccggcgct gggtgcgttt gtgatctata gcaaagtgca ggaacgcaac     2160
gaaatcatca aaccatcga taactgcctg gaacagcgta ttaaacgctg gaaagatagc     2220
tatgaatgga tgatgggcac ctggctgagc cgtattatca cccagttcaa caacatcagc     2280
taccagatgt acgatagcct gaactatcag gcgggtgcga ttaaagcgaa aatcgatctg     2340
gaatacaaaa aatacagcgg cagcgataaa gaaaacatca aaagccaggt tgaaaacctg     2400
aaaaacagcc tggatgtgaa aattagcgaa gcgatgaata acatcaacaa attcatccgc     2460
gaatgcagcg tgacctacct gttcaaaaac atgctgccga aagtgatcga tgaactgaac     2520
gaatttgatc gcaacaccaa agcgaaactg atcaacctga tcgatagcca caacattatt     2580
ctggtgggcg aagtggataa actgaaagcg aaagttaaca acagcttcca gaacaccatc     2640
ccgtttaaca tcttcagcta taccaacaac agcctgctga agatatcat caacgaatac     2700
ttcaatctag actag                                                     2715
```

<210> SEQ ID NO 44
<211> LENGTH: 904
<212> TYPE: PRT
<213> ORGANISM: Artificial Sequence
<220> FEATURE:
<223> OTHER INFORMATION: Synthetic

<400> SEQUENCE: 44

Gly Ser Glu Phe Met Pro Ile Thr Ile Asn Asn Phe Asn Tyr Ser Asp
1               5                   10                  15

```
Pro Val Asp Asn Lys Asn Ile Leu Tyr Leu Asp Thr His Leu Asn Thr
             20                  25                  30

Leu Ala Asn Glu Pro Glu Lys Ala Phe Arg Ile Thr Gly Asn Ile Trp
         35                  40                  45

Val Ile Pro Asp Arg Phe Ser Arg Asn Ser Pro Asn Leu Asn Lys
 50                  55                  60

Pro Pro Arg Val Thr Ser Pro Lys Ser Gly Tyr Tyr Asp Pro Asn Tyr
 65                  70                  75                  80

Leu Ser Thr Asp Ser Asp Lys Asp Thr Phe Leu Lys Glu Ile Ile Lys
                 85                  90                  95

Leu Phe Lys Arg Ile Asn Ser Arg Glu Ile Gly Glu Leu Ile Tyr
             100                 105                 110

Arg Leu Ser Thr Asp Ile Pro Phe Pro Gly Asn Asn Asn Thr Pro Ile
             115                 120                 125

Asn Thr Phe Asp Phe Asp Val Asp Phe Asn Ser Val Asp Val Lys Thr
 130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                 165                 170                 175

Phe Lys Leu Thr Asn Asn Thr Phe Ala Ala Gln Glu Gly Phe Gly Ala
             180                 185                 190

Leu Ser Ile Ile Ser Ile Ser Pro Arg Phe Met Leu Thr Tyr Ser Asn
             195                 200                 205

Ala Thr Asn Asp Val Gly Glu Gly Arg Phe Ser Lys Ser Glu Phe Cys
             210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                 245                 250                 255

Thr Ser Asn Ile Phe Tyr Ser Gln Tyr Asn Val Lys Leu Glu Tyr Ala
             260                 265                 270

Glu Ile Tyr Ala Phe Gly Gly Pro Thr Ile Asp Leu Ile Pro Lys Ser
             275                 280                 285

Ala Arg Lys Tyr Phe Glu Glu Lys Ala Leu Asp Tyr Tyr Arg Ser Ile
             290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                 325                 330                 335

Val Val Glu Ser Ser Gly Glu Val Thr Val Asn Arg Asn Lys Phe Val
             340                 345                 350

Glu Leu Tyr Asn Glu Leu Thr Gln Ile Phe Thr Glu Phe Asn Tyr Ala
             355                 360                 365

Lys Ile Tyr Asn Val Gln Asn Arg Lys Ile Tyr Leu Ser Asn Val Tyr
             370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                 405                 410                 415

Gln Asn Leu Ser Arg Asn Pro Ala Leu Arg Lys Val Asn Pro Glu Asn
             420                 425                 430
```

```
Met Leu Tyr Leu Phe Thr Lys Phe Cys Val Asp Ala Ile Asp Gly Arg
            435                 440                 445

Phe Gly Gly Phe Thr Gly Ala Arg Lys Ser Ala Arg Lys Leu Ala Asn
450                 455                 460

Gln Ala Leu Ala Gly Gly Gly Ser Gly Gly Gly Ser Gly Gly
465                 470                 475                 480

Gly Gly Ser Ala Leu Val Leu Gln Cys Arg Glu Leu Leu Val Lys Asn
                485                 490                 495

Thr Asp Leu Pro Phe Ile Gly Asp Ile Ser Asp Val Lys Thr Asp Ile
                500                 505                 510

Phe Leu Arg Lys Asp Ile Asn Glu Glu Thr Glu Val Ile Tyr Tyr Pro
                515                 520                 525

Asp Asn Val Ser Val Asp Gln Val Ile Leu Ser Lys Asn Thr Ser Glu
530                 535                 540

His Gly Gln Leu Asp Leu Leu Tyr Pro Ser Ile Asp Ser Glu Ser Glu
545                 550                 555                 560

Ile Leu Pro Gly Glu Asn Gln Val Phe Tyr Asp Asn Arg Thr Gln Asn
                565                 570                 575

Val Asp Tyr Leu Asn Ser Tyr Tyr Leu Glu Ser Gln Lys Leu Ser
                580                 585                 590

Asp Asn Val Glu Asp Phe Thr Phe Thr Arg Ser Ile Glu Glu Ala Leu
                595                 600                 605

Asp Asn Ser Ala Lys Val Tyr Thr Tyr Phe Pro Thr Leu Ala Asn Lys
                610                 615                 620

Val Asn Ala Gly Val Gln Gly Gly Leu Phe Leu Met Trp Ala Asn Asp
625                 630                 635                 640

Val Val Glu Asp Phe Thr Thr Asn Ile Leu Arg Lys Asp Thr Leu Asp
                645                 650                 655

Lys Ile Ser Asp Val Ser Ala Ile Ile Pro Tyr Ile Gly Pro Ala Leu
                660                 665                 670

Asn Ile Ser Asn Ser Val Arg Arg Gly Asn Phe Thr Glu Ala Phe Ala
                675                 680                 685

Val Thr Gly Val Thr Ile Leu Leu Glu Ala Phe Pro Glu Phe Thr Ile
                690                 695                 700

Pro Ala Leu Gly Ala Phe Val Ile Tyr Ser Lys Val Gln Glu Arg Asn
705                 710                 715                 720

Glu Ile Ile Lys Thr Ile Asp Asn Cys Leu Glu Gln Arg Ile Lys Arg
                725                 730                 735

Trp Lys Asp Ser Tyr Glu Trp Met Met Gly Thr Trp Leu Ser Arg Ile
                740                 745                 750

Ile Thr Gln Phe Asn Asn Ile Ser Tyr Gln Met Tyr Asp Ser Leu Asn
                755                 760                 765

Tyr Gln Ala Gly Ala Ile Lys Ala Lys Ile Asp Leu Glu Tyr Lys Lys
                770                 775                 780

Tyr Ser Gly Ser Asp Lys Glu Asn Ile Lys Ser Gln Val Glu Asn Leu
785                 790                 795                 800

Lys Asn Ser Leu Asp Val Lys Ile Ser Glu Ala Met Asn Asn Ile Asn
                805                 810                 815

Lys Phe Ile Arg Glu Cys Ser Val Thr Tyr Leu Phe Lys Asn Met Leu
                820                 825                 830

Pro Lys Val Ile Asp Glu Leu Asn Glu Phe Asp Arg Asn Thr Lys Ala
                835                 840                 845

Lys Leu Ile Asn Leu Ile Asp Ser His Asn Ile Ile Leu Val Gly Glu
```

```
                850                 855                 860
Val Asp Lys Leu Lys Ala Lys Val Asn Asn Ser Phe Gln Asn Thr Ile
865                 870                 875                 880

Pro Phe Asn Ile Phe Ser Tyr Thr Asn Asn Ser Leu Leu Lys Asp Ile
                885                 890                 895

Ile Asn Glu Tyr Phe Asn Leu Asp
            900

<210> SEQ ID NO 45
<211> LENGTH: 2742
<212> TYPE: DNA
<213> ORGANISM: Artificial Sequence
<220> FEATURE:
<223> OTHER INFORMATION: Synthetic

<400> SEQUENCE: 45
ggatccgaat tcatgccgat caccatcaac aacttcaact acagcgatcc ggtggataac      60
aaaaacatcc tgtacctgga tacccatctg aatccctggc gaacgaacc ggaaaaagcg     120 tttcgtatca ccggcaacat ttgggttatt ccggatcgtt ttagccgtaa cagcaacccg     180
aatctgaata aaccgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca caacaccccc gatcaacacc tttgatttcg atgtggattt caacagcgtt     420
gatgttaaaa cccgccaggg taacaattgg gtgaaaaccg gcagcattaa cccgagcgtg     480
attattaccg gtccgcgcga aacattatt gatccggaaa ccagcacctt taaactgacc     540
aacaacacct ttgcggcgca ggaaggtttt ggcgcgctga gcattattag cattagcccg     600
cgctttatgc tgacctatag caacgcgacc aacgatgttg gtgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
ttttacagcc agtacaacgt gaaactggaa tatgcggaaa tctatgcgtt tggcggtccg     840
accattgatc tgattccgaa aagcgcgcgc aaatacttcg aagaaaaagc gctggattac     900
tatcgcagca ttgcgaaacg tctgaacagc attaccaccg cgaatccgag cagcttcaac     960
aaatatatcg cgaatataa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa atctacctg    1140 agcaacgtgt atacccggt gaccgcgaat attctggatg ataacgtgta cgatatccag    1200
aacggcttta acatcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg gcatcattac ctccaaaact aaatctctga tagaaggtag atttggcggt    1380
ttcacgggcg cacgcaaatc agcgcgtaaa ttagctaacc aggcgctagc gggcggtggc    1440
ggtagcggcg gtggcggtag cggcggtggc ggtagcgcac tagtgctgca gtgtcgtgaa    1500
ctgctggtga aaacaccga tctgccgttt attggcgata tcagcgatgt gaaaaccgat    1560
atcttcctgc gcaaagatat caacgaagaa accgaagtga tctactaccc ggataacgtg    1620
agcgttgatc aggtgatcct gagcaaaaac accagcgaac atggtcagct ggatctgctg    1680
tatccgagca ttgatagcga aagcgaaatt ctgccgggcg aaaaccaggt gttttacgat    1740
```

| | | |
|---|---|---|
| aaccgtaccc agaacgtgga ttacctgaac agctattact acctggaaag ccagaaactg | 1800 |
| agcgataacg tggaagattt tacctttacc cgcagcattg aagaagcgct ggataacagc | 1860 |
| gcgaaagttt acacctattt tccgaccctg gcgaacaaag ttaatgcggg tgttcagggc | 1920 |
| ggtctgtttc tgatgtgggc gaacgatgtg gtggaagatt tcaccaccaa catcctgcgt | 1980 |
| aaagataccc tggataaaat cagcgatgtt agcgcgatta ttccgtatat tggtccggcg | 2040 |
| ctgaacatta gcaatagcgt gcgtcgtggc aattttaccg aagcgtttgc ggttaccggt | 2100 |
| gtgaccattc tgctggaagc gtttccggaa tttaccattc cggcgctggg tgcgtttgtg | 2160 |
| atctatagca aagtgcagga acgcaacgaa atcatcaaaa ccatcgataa ctgcctggaa | 2220 |
| cagcgtatta aacgctggaa agatagctat gaatggatga tgggcacctg gctgagccgt | 2280 |
| attatcaccc agttcaacaa catcagctac cagatgtacg atagcctgaa ctatcaggcg | 2340 |
| ggtgcgatta aagcgaaaat cgatctggaa tacaaaaaat acagcggcag cgataaagaa | 2400 |
| aacatcaaaa gccaggttga aaacctgaaa aacagcctgg atgtgaaaat tagcgaagcg | 2460 |
| atgaataaca tcaacaaatt catccgcgaa tgcagcgtga cctacctgtt caaaaacatg | 2520 |
| ctgccgaaag tgatcgatga actgaacgaa tttgatcgca acaccaaagc gaaactgatc | 2580 |
| aacctgatcg atagccacaa cattattctg gtgggcgaag tggataaact gaaagcgaaa | 2640 |
| gttaacaaca gcttccagaa caccatcccg tttaacatct tcagctatac caacaacagc | 2700 |
| ctgctgaaag atatcatcaa cgaatacttc aatctagact ag | 2742 |

<210> SEQ ID NO 46
<211> LENGTH: 913
<212> TYPE: PRT
<213> ORGANISM: Artificial Sequence
<220> FEATURE:
<223> OTHER INFORMATION: Synthetic

<400> SEQUENCE: 46

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

```
Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Gly Ile Ile Thr Ser
        435                 440                 445

Lys Thr Lys Ser Leu Ile Glu Gly Arg Phe Gly Gly Phe Thr Gly Ala
450                 455                 460

Arg Lys Ser Ala Arg Lys Leu Ala Asn Gln Ala Leu Ala Gly Gly Gly
465                 470                 475                 480

Gly Ser Gly Gly Gly Ser Gly Gly Gly Ser Ala Leu Val Leu
                485                 490                 495

Gln Cys Arg Glu Leu Leu Val Lys Asn Thr Asp Leu Pro Phe Ile Gly
            500                 505                 510

Asp Ile Ser Asp Val Lys Thr Asp Ile Phe Leu Arg Lys Asp Ile Asn
        515                 520                 525

Glu Glu Thr Glu Val Ile Tyr Tyr Pro Asp Asn Val Ser Val Asp Gln
530                 535                 540

Val Ile Leu Ser Lys Asn Thr Ser Glu His Gly Gln Leu Asp Leu Leu
545                 550                 555                 560

Tyr Pro Ser Ile Asp Ser Glu Ser Glu Ile Leu Pro Gly Glu Asn Gln
                565                 570                 575

Val Phe Tyr Asp Asn Arg Thr Gln Asn Val Asp Tyr Leu Asn Ser Tyr
            580                 585                 590

Tyr Tyr Leu Glu Ser Gln Lys Leu Ser Asp Asn Val Glu Asp Phe Thr
        595                 600                 605
```

-continued

| | | | | | | | | | | | | |
|---|---|---|---|---|---|---|---|---|---|---|---|---|
|Phe|Thr|Arg|Ser|Ile|Glu|Glu|Ala|Leu|Asp|Asn|Ser|Ala|Lys|Val|Tyr|
| |610| | | |615| | | |620| | | | | | |
|Thr|Tyr|Phe|Pro|Thr|Leu|Ala|Asn|Lys|Val|Asn|Ala|Gly|Val|Gln|Gly|
|625| | | | |630| | | |635| | | | |640| |
|Gly|Leu|Phe|Leu|Met|Trp|Ala|Asn|Asp|Val|Val|Glu|Asp|Phe|Thr|Thr|
| | | | |645| | | | |650| | | |655| | |
|Asn|Ile|Leu|Arg|Lys|Asp|Thr|Leu|Asp|Lys|Ile|Ser|Asp|Val|Ser|Ala|
| | | |660| | | | |665| | | | |670| | |
|Ile|Ile|Pro|Tyr|Ile|Gly|Pro|Ala|Leu|Asn|Ile|Ser|Asn|Ser|Val|Arg|
| | |675| | | | |680| | | | |685| | | |
|Arg|Gly|Asn|Phe|Thr|Glu|Ala|Phe|Ala|Val|Thr|Gly|Val|Thr|Ile|Leu|
| |690| | | | |695| | | | |700| | | | |
|Leu|Glu|Ala|Phe|Pro|Glu|Phe|Thr|Ile|Pro|Ala|Leu|Gly|Ala|Phe|Val|
|705| | | | |710| | | | |715| | | | |720|
|Ile|Tyr|Ser|Lys|Val|Gln|Arg|Asn|Glu|Ile|Ile|Lys|Thr|Ile|Asp|
| | | | |725| | | | |730| | | | |735| |
|Asn|Cys|Leu|Glu|Gln|Arg|Ile|Lys|Arg|Trp|Lys|Asp|Ser|Tyr|Glu|Trp|
| | | |740| | | | |745| | | | |750| | |
|Met|Met|Gly|Thr|Trp|Leu|Ser|Arg|Ile|Ile|Thr|Gln|Phe|Asn|Asn|Ile|
| | |755| | | | |760| | | | |765| | | |
|Ser|Tyr|Gln|Met|Tyr|Asp|Ser|Leu|Asn|Tyr|Gln|Ala|Gly|Ala|Ile|Lys|
| |770| | | | |775| | | | |780| | | | |
|Ala|Lys|Ile|Asp|Leu|Glu|Tyr|Lys|Lys|Tyr|Ser|Gly|Ser|Asp|Lys|Glu|
|785| | | | |790| | | | |795| | | | |800|
|Asn|Ile|Lys|Ser|Gln|Val|Glu|Asn|Leu|Lys|Asn|Ser|Leu|Asp|Val|Lys|
| | | | |805| | | | |810| | | | |815| |
|Ile|Ser|Glu|Ala|Met|Asn|Asn|Ile|Asn|Lys|Phe|Ile|Arg|Glu|Cys|Ser|
| | | |820| | | | |825| | | | |830| | |
|Val|Thr|Tyr|Leu|Phe|Lys|Asn|Met|Leu|Pro|Lys|Val|Ile|Asp|Glu|Leu|
| | |835| | | | |840| | | | |845| | | |
|Asn|Glu|Phe|Asp|Arg|Asn|Thr|Lys|Ala|Lys|Leu|Ile|Asn|Leu|Ile|Asp|
| |850| | | | |855| | | | |860| | | | |
|Ser|His|Asn|Ile|Ile|Leu|Val|Gly|Glu|Val|Asp|Lys|Leu|Lys|Ala|Lys|
|865| | | | |870| | | | |875| | | | |880|
|Val|Asn|Asn|Ser|Phe|Gln|Asn|Thr|Ile|Pro|Phe|Asn|Ile|Phe|Ser|Tyr|
| | | | |885| | | | |890| | | | |895| |
|Thr|Asn|Asn|Ser|Leu|Leu|Lys|Asp|Ile|Ile|Asn|Glu|Tyr|Phe|Asn|Leu|
| | | |900| | | | |905| | | | |910| | |
|Asp| | | | | | | | | | | | | | | |

<210> SEQ ID NO 47
<211> LENGTH: 2673
<212> TYPE: DNA
<213> ORGANISM: Artificial Sequence
<220> FEATURE:
<223> OTHER INFORMATION: Synthetic

<400> SEQUENCE: 47

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc accggaagc gaaacaggtg ccggtatctt actatgactc cacctacctg     240
tctaccgata cgaaaagga caactacctg aaaggtgtta ctaaactgtt cgagcgtatt     300
```

```
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct ctctccagt acatgaagaa cgttttaaa     960
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc     1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatacggt ggtttcatgg cgctagcggg cggtggcggt    1380
agcggcggtg gcggtagcgg cggtggcggt agcgcactag tgctgcagtg tatcaaggtt    1440
aacaactggg atttattctt cagcccgagt gaagacaact tcaccaacga cctgaacaaa    1500
ggtgaagaaa tcacctcaga tactaacatc gaagcagccg aagaaaacat ctcgctggac    1560
ctgatccagc agtactacct gacctttaat ttcgacaacg agccggaaaa catttctatc    1620
gaaaacctga gctctgatat catcggccag ctggaactga tgccgaacat cgaacgtttc    1680
ccaaacggta aaaagtacga gctggacaaa tataccatgt tccactacct gcgcgcgcag    1740
gaatttgaac acggcaaatc ccgtatcgca ctgactaact ccgttaacga agctctgctc    1800
aacccgtccc gtgtatacac cttcttctct agcgactacg tgaaaaaggt caacaaagcg    1860
actgaagctg caatgttctt gggttgggtt gaacagcttg tttatgattt taccgacgag    1920
acgtccgaag tatctactac cgacaaaatt gcggatatca ctatcatcat cccgtacatc    1980
ggtccggctc tgaacattgg caacatgctg tacaaagacg acttcgttgg cgcactgatc    2040
ttctccggtg cggtgatcct gctggagttc atcccggaaa tcgccatccc ggtactgggc    2100
acctttgctc tggtttctta cattgcaaac aaggttctga ctgtacaaac catcgacaac    2160
gcgctgagca aacgtaacga aaatgggat gaagtttaca atatatcgt gaccaactgg     2220
ctggctaagg ttaatactca gatcgacctc atccgcaaaa aaatgaaaga agcactggaa    2280
aaccaggcgg aagctaccaa ggcaatcatt aactaccagt acaaccagta caccgaggaa    2340
gaaaaaaaca acatcaactt caacatcgac gatctgtcct ctaaactgaa cgaatccatc    2400
aacaaagcta tgatcaacat caacaagttc ctgaaccagt gctctgtaag ctatctgatg    2460
aactccatga tcccgtacgg tgttaaacgt ctggaggact cgatgcgtc tctgaaagac     2520
gccctgctga aatacattta cgacaaccgt ggcactctga tcggtcaggt tgatcgtctg    2580
aaggacaaag tgaacaatac cttatcgacc gacatccctt ttcagctcag taaatatgtc    2640
gataaccaac gccttttgtc cactctagac tag                                 2673
```

<210> SEQ ID NO 48
<211> LENGTH: 890
<212> TYPE: PRT
<213> ORGANISM: Artificial Sequence
<220> FEATURE:
<223> OTHER INFORMATION: Synthetic

<400> SEQUENCE: 48

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

```
Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Met Ala Leu Ala Gly Gly Gly Ser Gly Gly Gly
    450                 455                 460

Gly Ser Gly Gly Gly Ser Ala Leu Val Leu Gln Cys Ile Lys Val
465                 470                 475                 480

Asn Asn Trp Asp Leu Phe Phe Ser Pro Ser Glu Asp Asn Phe Thr Asn
            485                 490                 495

Asp Leu Asn Lys Gly Glu Ile Thr Ser Asp Thr Asn Ile Glu Ala
                500                 505                 510

Ala Glu Glu Asn Ile Ser Leu Asp Leu Ile Gln Tyr Tyr Leu Thr
    515                 520                 525

Phe Asn Phe Asp Asn Glu Pro Glu Asn Ile Ser Ile Glu Asn Leu Ser
    530                 535                 540

Ser Asp Ile Ile Gly Gln Leu Glu Leu Met Pro Asn Ile Glu Arg Phe
545                 550                 555                 560

Pro Asn Gly Lys Lys Tyr Glu Leu Asp Lys Tyr Thr Met Phe His Tyr
                565                 570                 575

Leu Arg Ala Gln Glu Phe Glu His Gly Lys Ser Arg Ile Ala Leu Thr
            580                 585                 590

Asn Ser Val Asn Glu Ala Leu Leu Asn Pro Ser Arg Val Tyr Thr Phe
        595                 600                 605

Phe Ser Ser Asp Tyr Val Lys Lys Val Asn Lys Ala Thr Glu Ala Ala
610                 615                 620

Met Phe Leu Gly Trp Val Glu Gln Leu Val Tyr Asp Phe Thr Asp Glu
625                 630                 635                 640

Thr Ser Glu Val Ser Thr Thr Asp Lys Ile Ala Asp Ile Thr Ile Ile
                645                 650                 655

Ile Pro Tyr Ile Gly Pro Ala Leu Asn Ile Gly Asn Met Leu Tyr Lys
            660                 665                 670

Asp Asp Phe Val Gly Ala Leu Ile Phe Ser Gly Ala Val Ile Leu Leu
        675                 680                 685

Glu Phe Ile Pro Glu Ile Ala Ile Pro Val Leu Gly Thr Phe Ala Leu
    690                 695                 700

Val Ser Tyr Ile Ala Asn Lys Val Leu Thr Val Gln Thr Ile Asp Asn
705                 710                 715                 720

Ala Leu Ser Lys Arg Asn Glu Lys Trp Asp Glu Val Tyr Lys Tyr Ile
                725                 730                 735

Val Thr Asn Trp Leu Ala Lys Val Asn Thr Gln Ile Asp Leu Ile Arg
            740                 745                 750

Lys Lys Met Lys Glu Ala Leu Glu Asn Gln Ala Glu Ala Thr Lys Ala
        755                 760                 765

Ile Ile Asn Tyr Gln Tyr Asn Gln Tyr Thr Glu Glu Lys Asn Asn
    770                 775                 780
```

| | | | | | | | | | | | | |
|---|---|---|---|---|---|---|---|---|---|---|---|---|
|Ile|Asn|Phe|Asn|Ile|Asp|Asp|Leu|Ser|Ser|Lys|Leu|Asn|Glu|Ser|Ile|
|785| | | |790| | | |795| | | |800| | | |

| | | | | | | | | | | | |
|---|---|---|---|---|---|---|---|---|---|---|---|
|Asn|Lys|Ala|Met|Ile|Asn|Ile|Asn|Lys|Phe|Leu|Asn|Gln|Cys|Ser|Val|
| | | | |805| | | |810| | | |815| | | |

Ser Tyr Leu Met Asn Ser Met Ile Pro Tyr Gly Val Lys Arg Leu Glu
            820                 825                 830

Asp Phe Asp Ala Ser Leu Lys Asp Ala Leu Leu Lys Tyr Ile Tyr Asp
        835                 840                 845

Asn Arg Gly Thr Leu Ile Gly Gln Val Asp Arg Leu Lys Asp Lys Val
        850                 855                 860

Asn Asn Thr Leu Ser Thr Asp Ile Pro Phe Gln Leu Ser Lys Tyr Val
865                 870                 875                 880

Asp Asn Gln Arg Leu Leu Ser Thr Leu Asp
            885                 890

<210> SEQ ID NO 49
<211> LENGTH: 2751
<212> TYPE: DNA
<213> ORGANISM: Artificial Sequence
<220> FEATURE:
<223> OTHER INFORMATION: Synthetic

<400> SEQUENCE: 49

```
ggatccatgg agttcgttaa caaacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gatacccttta ctaacccgga agaaggtgac   180
ctgaacccgc accggaagc gaaacaggtg ccggtatctt actatgactc cacctacctg    240
tctaccgata cgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt ccgtctgta ctactataac aagttcaaag atatcgcatc cacctgaac     900 aaagcgaaat ccatcgtggg taccactgct tctctccagt acatgaagaa cgttttaaa    960 gaaaaatacc tgctcagcga agacacctcc ggcaaattct ctgtagacaa gttgaaattc  1020
gataaacttt acaaaatgct gactgaaatt tacaccgaag acaacttcgt taagttcttt  1080
aaagttctga ccgcaaaac ctatctgaac ttcgacaagg cagtattcaa atcaacatc    1140 gtgccgaaag ttaactacac tatctacgat ggtttcaacc tgcgtaacac caacctggct  1200 gctaattttta acggccagaa cacggaaatc aacaacatga acttcacaaa actgaaaaac  1260
ttcactggtc tgttcgagtt ttacaagctg ctgtgcgtcg acggcatcat acctccaaa   1320 actaaatctc tgatcgaagg tcgttacggt ggtttcatga cctctgaaaa atctcagacc  1380
ccgctggtta ccctgttcaa aaacgctatc atcaaaaacg cttacaaaaa aggtgaagcg  1440
```

```
ctagcgggtg gtggtggttc tggtggtggt ggttctggtg gtggtggttc tgcactagtg    1500
ctgcagtgta tcaaggttaa caactgggat ttattcttca gcccgagtga agacaacttc    1560
accaacgacc tgaacaaagg tgaagaaatc acctcagata ctaacatcga agcagccgaa    1620
gaaaacatct cgctggacct gatccagcag tactacctga cctttaattt cgacaacgag    1680
ccggaaaaca tttctatcga aacctgagc tctgatatca tcggccagct ggaactgatg    1740
ccgaacatcg aacgtttccc aaacggtaaa agtacgagc tggacaaata ccatgttc      1800 cactacctgc gcgcgcagga atttgaacac ggcaaatccc gtatcgcact gactaactcc    1860
gttaacgaag ctctgctcaa cccgtcccgt gtatacacct tcttctctag cgactacgtg    1920
aaaaaggtca caaagcgac tgaagctgca atgttcttgg gttgggttga acagcttgtt    1980
tatgatttta ccgacgagac gtccgaagta tctactaccg acaaaattgc ggatatcact    2040
atcatcatcc cgtacatcgg tccggctctg aacattggca catgctgta caaagacgac    2100 ttcgttggcg cactgatctt ctccggtgcg gtgatcctgc tggagttcat cccggaaatc    2160
gccatcccgg tactgggcac ctttgctctg gtttcttaca ttgcaaacaa ggttctgact    2220
gtacaaacca tcgacaacgc gctgagcaaa cgtaacgaaa atgggatga gtttacaaa     2280 tatatcgtga ccaactggct ggctaaggtt aatactcaga tcgacctcat ccgcaaaaaa    2340
atgaaagaag cactggaaaa ccaggcggaa gctaccaagg caatcattaa ctaccagtac    2400
aaccagtaca ccgaggaaga aaaaacaac atcaacttca acatcgacga tctgtcctct    2460
aaactgaacg aatccatcaa caaagctatg atcaacatca caagttcct gaaccagtgc    2520 tctgtaagct atctgatgaa ctccatgatc ccgtacggtg ttaaacgtct ggaggacttc    2580
gatgcgtctc tgaaagacgc cctgctgaaa tacatttacg acaaccgtgg cactctgatc    2640
ggtcaggttg atcgtctgaa ggacaaagtg aacaatacct atcgaccga catccctttt    2700 cagctcagta aatatgtcga taaccaacgc cttttgtcca ctctagacta g             2751
```

<210> SEQ ID NO 50  
<211> LENGTH: 916  
<212> TYPE: PRT  
<213> ORGANISM: Artificial Sequence  
<220> FEATURE:  
<223> OTHER INFORMATION: Synthetic

<400> SEQUENCE: 50

```
Gly Ser Met Glu Phe Val Asn Lys Gln Phe Asn Tyr Lys Asp Pro Val
1               5                  10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
```

-continued

```
                130                 135                 140
Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Met Thr Ser Glu Lys Ser Gln Thr Pro Leu Val Thr
    450                 455                 460

Leu Phe Lys Asn Ala Ile Ile Lys Asn Ala Tyr Lys Lys Gly Glu Ala
465                 470                 475                 480

Leu Ala Gly Gly Gly Ser Gly Gly Gly Ser Gly Gly Gly
                485                 490                 495

Ser Ala Leu Val Leu Gln Cys Ile Lys Val Asn Asn Trp Asp Leu Phe
            500                 505                 510

Phe Ser Pro Ser Glu Asp Asn Phe Thr Asn Asp Leu Asn Lys Gly Glu
        515                 520                 525

Glu Ile Thr Ser Asp Thr Asn Ile Glu Ala Ala Glu Glu Asn Ile Ser
    530                 535                 540

Leu Asp Leu Ile Gln Gln Tyr Tyr Leu Thr Phe Asn Phe Asp Asn Glu
545                 550                 555                 560
```

Pro Glu Asn Ile Ser Ile Glu Asn Leu Ser Ser Asp Ile Ile Gly Gln
                565                 570                 575

Leu Glu Leu Met Pro Asn Ile Glu Arg Phe Pro Asn Gly Lys Lys Tyr
            580                 585                 590

Glu Leu Asp Lys Tyr Thr Met Phe His Tyr Leu Arg Ala Gln Glu Phe
        595                 600                 605

Glu His Gly Lys Ser Arg Ile Ala Leu Thr Asn Ser Val Asn Glu Ala
    610                 615                 620

Leu Leu Asn Pro Ser Arg Val Tyr Thr Phe Phe Ser Ser Asp Tyr Val
625                 630                 635                 640

Lys Lys Val Asn Lys Ala Thr Glu Ala Ala Met Phe Leu Gly Trp Val
                645                 650                 655

Glu Gln Leu Val Tyr Asp Phe Thr Asp Glu Thr Ser Glu Val Ser Thr
            660                 665                 670

Thr Asp Lys Ile Ala Asp Ile Thr Ile Ile Pro Tyr Ile Gly Pro
        675                 680                 685

Ala Leu Asn Ile Gly Asn Met Leu Tyr Lys Asp Asp Phe Val Gly Ala
    690                 695                 700

Leu Ile Phe Ser Gly Ala Val Ile Leu Leu Glu Phe Ile Pro Glu Ile
705                 710                 715                 720

Ala Ile Pro Val Leu Gly Thr Phe Ala Leu Val Ser Tyr Ile Ala Asn
                725                 730                 735

Lys Val Leu Thr Val Gln Thr Ile Asp Asn Ala Leu Ser Lys Arg Asn
            740                 745                 750

Glu Lys Trp Asp Glu Val Tyr Lys Tyr Ile Val Thr Asn Trp Leu Ala
        755                 760                 765

Lys Val Asn Thr Gln Ile Asp Leu Ile Arg Lys Lys Met Lys Glu Ala
    770                 775                 780

Leu Glu Asn Gln Ala Glu Ala Thr Lys Ala Ile Ile Asn Tyr Gln Tyr
785                 790                 795                 800

Asn Gln Tyr Thr Glu Glu Glu Lys Asn Asn Ile Asn Phe Asn Ile Asp
                805                 810                 815

Asp Leu Ser Ser Lys Leu Asn Glu Ser Ile Asn Lys Ala Met Ile Asn
            820                 825                 830

Ile Asn Lys Phe Leu Asn Gln Cys Ser Val Ser Tyr Leu Met Asn Ser
        835                 840                 845

Met Ile Pro Tyr Gly Val Lys Arg Leu Glu Asp Phe Asp Ala Ser Leu
    850                 855                 860

Lys Asp Ala Leu Leu Lys Tyr Ile Tyr Asp Asn Arg Gly Thr Leu Ile
865                 870                 875                 880

Gly Gln Val Asp Arg Leu Lys Asp Lys Val Asn Asn Thr Leu Ser Thr
                885                 890                 895

Asp Ile Pro Phe Gln Leu Ser Lys Tyr Val Asp Asn Gln Arg Leu Leu
            900                 905                 910

Ser Thr Leu Asp
        915

<210> SEQ ID NO 51
<211> LENGTH: 2709
<212> TYPE: DNA
<213> ORGANISM: Artificial Sequence
<220> FEATURE:
<223> OTHER INFORMATION: Synthetic

<400> SEQUENCE: 51

```
ggatccatgg agttcgttaa caaacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gataccttta ctaacccgga agaaggtgac   180
ctgaacccgc caccggaagc gaaacaggtg ccggtatctt actatgactc cacctacctg   240
tctaccgata acgaaaagga caactacctg aaaggtgtta ctaaactgtt cgagcgtatt   300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
cagccggacg gttcctatcg ttccgaagaa ctgaacctgg tgatcatcgg cccgtctgct   480
gatatcatcc agttcgagtg taagagcttt ggtcacgaag ttctgaacct cacccgtaac   540
ggctacggtt ccactcagta catccgtttc tctccggact tcaccttcgg ttttgaagaa   600
tccctggaag tagacacgaa cccactgctg ggcgctggta aattcgcaac tgatcctgcg   660
gttaccctgg ctcacgaact gattcatgca ggccaccgcc tgtacggtat cgccatcaat   720
ccgaaccgtg tcttcaaagt taacaccaac gcgtattacg agatgtccgg tctggaagtt   780
agcttcgaag aactgcgtac ttttggcggt cacgacgcta aattcatcga ctctctgcaa   840
gaaaacgagt tccgtctgta ctactataac aagttcaaag atatcgcatc caccctgaac   900
aaagcgaaat ccatcgtggg taccactgct tctctccagt acatgaagaa cgttttaaa    960
gaaaaatacc tgctcagcga agacacctcc ggcaaattct ctgtagacaa gttgaaattc  1020
gataaacttt acaaaatgct gactgaaatt tacaccgaag acaacttcgt taagttcttt  1080
aaagttctga accgcaaaac ctatctgaac ttcgacaagg cagtattcaa aatcaacatc  1140
gtgccgaaag ttaactacac tatctacgat ggtttcaacc tgcgtaacac caacctggct  1200
gctaattta acggccagaa cacggaaatc aacaacatga acttcacaaa actgaaaaac  1260
ttcactggtc tgttcgagtt ttacaagctg ctgtgcgtcg acggcatcat tacctccaaa  1320
actaaatctc tgatagaagg tagatttggc ggtttcacgg gcgcacgcaa atcagcgcgt  1380
aaacgtaaga accaggcgct agcgggcggt ggcggtagcg gcggtggcgg tagcggcggt  1440
ggcggtagcg cactagtgct gcagtgtatc aaggttaaca actgggattt attcttcagc  1500
ccgagtgaag acaacttcac caacgacctg aacaaaggtg aagaaatcac ctcagatact  1560
aacatcgaag cagccgaaga aaacatctcg ctggacctga tccagcagta ctacctgacc  1620
tttaatttcg acaacgagcc ggaaaacatt tctatcgaaa acctgagctc tgatatcatc  1680
ggccagctga aactgatgcc gaacatcgaa cgtttcccaa acggtaaaaa gtacgagctg  1740
gacaaatata ccatgttcca ctacctgcgc gcgcaggaat ttgaacacgg caaatcccgt  1800
atcgcactga ctaactccgt taacgaagct ctgctcaacc cgtcccgtgt ataccacttc  1860
ttctctagcg actacgtgaa aaaggtcaac aaagcgactg aagctgcaat gttcttgggt  1920
tgggttgaac agcttgttta tgattttacc gacgagacgt ccgaagtatc tactaccgac  1980
aaaattgcgg atatcactat catcatcccg tacatcggtc cggctctgaa cattggcaac  2040
atgctgtaca agacgacttt cgttggcgca ctgatcttct ccggtgcggt gatcctgctg  2100
gagttcatcc cggaaatcgc catcccggta ctgggcacct ttgctctggt ttcttacatt  2160
gcaaacaagg ttctgactgt acaaaccatc gacaacgcgc tgagcaaacg taacgaaaaa  2220
tgggatgaag tttacaaata tatcgtgacc aactggctgg ctaaggttaa tactcagatc  2280
gacctcatcc gcaaaaaaat gaaagaagca ctggaaaacc aggcggaagc taccaaggca  2340
```

-continued

```
atcattaact accagtacaa ccagtacacc gaggaagaaa aaaacaacat caacttcaac    2400
atcgacgatc tgtcctctaa actgaacgaa tccatcaaca agctatgat caacatcaac    2460 aagttcctga accagtgctc tgtaagctat ctgatgaact ccatgatccc gtacggtgtt   2520
aaacgtctgg aggacttcga tgcgtctctg aaagacgccc tgctgaaata catttacgac   2580
aaccgtggca ctctgatcgg tcaggttgat cgtctgaagg acaaagtgaa caataccta   2640 tcgaccgaca tcccttttca gctcagtaaa tatgtcgata ccaacgcct tttgtccact    2700 ctagactag                                                            2709
```

<210> SEQ ID NO 52
<211> LENGTH: 902
<212> TYPE: PRT
<213> ORGANISM: Artificial Sequence
<220> FEATURE:
<223> OTHER INFORMATION: Synthetic

<400> SEQUENCE: 52

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
```

```
                290                 295                 300
Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
                340                 345                 350

Glu Asp Asn Phe Val Lys Phe Phe Lys Val Leu Asn Arg Lys Thr Tyr
                355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Leu Ile Glu Gly Arg
                435                 440                 445

Phe Gly Gly Phe Thr Gly Ala Arg Lys Ser Ala Arg Lys Arg Lys Asn
450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
                500                 505                 510

Gly Glu Glu Ile Thr Ser Asp Thr Asn Ile Glu Ala Ala Glu Glu Asn
                515                 520                 525

Ile Ser Leu Asp Leu Ile Gln Gln Tyr Tyr Leu Thr Phe Asn Phe Asp
530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
                580                 585                 590

Glu Phe Glu His Gly Lys Ser Arg Ile Ala Leu Thr Asn Ser Val Asn
                595                 600                 605

Glu Ala Leu Leu Asn Pro Ser Arg Val Tyr Thr Phe Phe Ser Ser Asp
610                 615                 620

Tyr Val Lys Lys Val Asn Lys Ala Thr Glu Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
                660                 665                 670

Gly Pro Ala Leu Asn Ile Gly Asn Met Leu Tyr Lys Asp Asp Phe Val
                675                 680                 685

Gly Ala Leu Ile Phe Ser Gly Ala Val Ile Leu Leu Glu Phe Ile Pro
690                 695                 700

Glu Ile Ala Ile Pro Val Leu Gly Thr Phe Ala Leu Val Ser Tyr Ile
705                 710                 715                 720
```

Ala Asn Lys Val Leu Thr Val Gln Thr Ile Asp Asn Ala Leu Ser Lys
              725                 730                 735

Arg Asn Glu Lys Trp Asp Glu Val Tyr Lys Tyr Ile Val Thr Asn Trp
          740                 745                 750

Leu Ala Lys Val Asn Thr Gln Ile Asp Leu Ile Arg Lys Lys Met Lys
              755                 760                 765

Glu Ala Leu Glu Asn Gln Ala Glu Ala Thr Lys Ala Ile Ile Asn Tyr
      770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
              805                 810                 815

Ile Asn Ile Asn Lys Phe Leu Asn Gln Cys Ser Val Ser Tyr Leu Met
              820                 825                 830

Asn Ser Met Ile Pro Tyr Gly Val Lys Arg Leu Glu Asp Phe Asp Ala
              835                 840                 845

Ser Leu Lys Asp Ala Leu Leu Lys Tyr Ile Tyr Asp Asn Arg Gly Thr
      850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
              885                 890                 895

Leu Leu Ser Thr Leu Asp
              900

<210> SEQ ID NO 53
<211> LENGTH: 2691
<212> TYPE: DNA
<213> ORGANISM: Artificial Sequence
<220> FEATURE:
<223> OTHER INFORMATION: Synthetic

<400> SEQUENCE: 53
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc accggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg ttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc caccctgaac     900
aaagcgaaat ccatcgtggg taccactgct tctctccagt acatgaagaa cgttttaaa      960

```
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc     1140 gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat acctccaaa     1320 actaaatctc tgatagaagg tagatttggc ggtttcacgg gcgcacgcaa atcagcggcg    1380
ctagcgggcg gtggcggtag cggcggtggc ggtagcggcg gtggcggtag cgcactagtg    1440
ctgcagtgta tcaaggttaa caactgggat ttattcttca gcccgagtga agacaacttc    1500
accaacgacc tgaacaaagg tgaagaaatc acctcagata ctaacatcga agcagccgaa    1560 gaaacatct cgctggacct gatccagcag tactacctga cctttaattt cgacaacgag    1620
ccggaaaaca tttctatcga aaacctgagc tctgatatca tcggccagct ggaactgatg    1680
ccgaacatcg aacgtttccc aaacggtaaa agtacgagc tggacaaata ccatgttc      1740 cactacctgc gcgcgcagga atttgaacac ggcaaatccc gtatcgcact gactaactcc    1800
gttaacgaag ctctgctcaa cccgtcccgt gtatacacct tcttctctag cgactacgtg    1860
aaaaaggtca caaagcgac tgaagctgca atgttcttgg gttgggttga acagcttgtt     1920
tatgatttta ccgacgagac gtccgaagta tctactaccg acaaaattgc ggatatcact    1980
atcatcatcc cgtacatcgg tccggctctg aacattggca acatgctgta caaagacgac    2040
ttcgttggcg cactgatctt ctccggtgcg gtgatcctgc tggagttcat cccggaaatc    2100
gccatcccgg tactgggcac ctttgctctg gtttcttaca ttgcaaacaa ggttctgact    2160
gtacaaacca tcgacaacgc gctgagcaaa cgtaacgaaa atgggatga gtttacaaa     2220 tatatcgtga ccaactggct ggctaaggtt aatactcaga tcgacctcat ccgcaaaaaa    2280
atgaaagaag cactggaaaa ccaggcggaa gctaccaagg caatcattaa ctaccagtac    2340
aaccagtaca ccgaggaaga aaaaaacaac atcaacttca acatcgacga tctgtcctct    2400
aaactgaacg aatccatcaa caaagctatg atcaacatca caagttcct gaaccagtgc     2460 tctgtaagct atctgatgaa ctccatgatc ccgtacggtg ttaaacgtct ggaggacttc    2520
gatgcgtctc tgaaagacgc cctgctgaaa tacatttacg acaaccgtgg cactctgatc    2580
ggtcaggttg atcgtctgaa ggacaaagtg aacaatacct tatcgaccga catccctttt    2640
cagctcagta aatatgtcga taccaacgc cttttgtcca ctctagacta g              2691
```

<210> SEQ ID NO 54
<211> LENGTH: 896
<212> TYPE: PRT
<213> ORGANISM: Artificial Sequence
<220> FEATURE:
<223> OTHER INFORMATION: Synthetic

<400> SEQUENCE: 54

```
Gly Ser Met Glu Phe Val Asn Lys Gln Phe Asn Tyr Lys Asp Pro Val
1               5                  10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60
```

```
Pro Glu Ala Lys Gln Val Pro Val Ser Tyr Tyr Asp Ser Thr Tyr Leu
 65                  70                  75                  80

Ser Thr Asp Asn Glu Lys Asp Asn Tyr Leu Lys Gly Val Thr Lys Leu
                 85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Ala Leu Ala Gly Gly
450                 455                 460

Gly Gly Ser Gly Gly Gly Gly Ser Gly Gly Gly Gly Ser Ala Leu Val
465                 470                 475                 480
```

```
-continued

Leu Gln Cys Ile Lys Val Asn Asn Trp Asp Leu Phe Phe Ser Pro Ser
                485                 490                 495

Glu Asp Asn Phe Thr Asn Asp Leu Asn Lys Gly Glu Glu Ile Thr Ser
            500                 505                 510

Asp Thr Asn Ile Glu Ala Ala Glu Glu Asn Ile Ser Leu Asp Leu Ile
        515                 520                 525

Gln Gln Tyr Tyr Leu Thr Phe Asn Phe Asp Asn Glu Pro Glu Asn Ile
    530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                565                 570                 575

Tyr Thr Met Phe His Tyr Leu Arg Ala Gln Glu Phe Glu His Gly Lys
            580                 585                 590

Ser Arg Ile Ala Leu Thr Asn Ser Val Asn Glu Ala Leu Leu Asn Pro
        595                 600                 605

Ser Arg Val Tyr Thr Phe Phe Ser Ser Asp Tyr Val Lys Lys Val Asn
    610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
                645                 650                 655

Ala Asp Ile Thr Ile Ile Ile Pro Tyr Ile Gly Pro Ala Leu Asn Ile
            660                 665                 670

Gly Asn Met Leu Tyr Lys Asp Asp Phe Val Gly Ala Leu Ile Phe Ser
        675                 680                 685

Gly Ala Val Ile Leu Leu Glu Phe Ile Pro Glu Ile Ala Ile Pro Val
    690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
                725                 730                 735

Glu Val Tyr Lys Tyr Ile Val Thr Asn Trp Leu Ala Lys Val Asn Thr
            740                 745                 750

Gln Ile Asp Leu Ile Arg Lys Lys Met Lys Glu Ala Leu Glu Asn Gln
        755                 760                 765

Ala Glu Ala Thr Lys Ala Ile Ile Asn Tyr Gln Tyr Asn Gln Tyr Thr
    770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
                805                 810                 815

Leu Asn Gln Cys Ser Val Ser Tyr Leu Met Asn Ser Met Ile Pro Tyr
            820                 825                 830

Gly Val Lys Arg Leu Glu Asp Phe Asp Ala Ser Leu Lys Asp Ala Leu
        835                 840                 845

Leu Lys Tyr Ile Tyr Asp Asn Arg Gly Thr Leu Ile Gly Gln Val Asp
    850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Leu Asp
                885                 890                 895
```

<210> SEQ ID NO 55
<211> LENGTH: 2691
<212> TYPE: DNA
<213> ORGANISM: Artificial Sequence
<220> FEATURE:
<223> OTHER INFORMATION: Synthetic

<400> SEQUENCE: 55

```
ggatccatgg agttcgttaa caaacagttc aactataaag acccagttaa cggtgttgac     60
attgcttaca tcaaaatccc gaacgctggc cagatgcagc cggtaaaggc attcaaaatc    120
cacaacaaaa tctgggttat cccggaacgt gataccttta ctaacccgga agaaggtgac    180
ctgaacccgc caccggaagc gaaacaggtg ccggtatctt actatgactc cacctacctg    240
tctaccgata acgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg ttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc cacccctgaac    900
aaagcgaaat ccatcgtggg taccactgct tctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatttggc ggtttcacgg cgcacgcaa atatgcggcg   1380
ctagcgggcg gtggcggtag cggcggtggc ggtagcggcg gtggcggtag cgcactagtg   1440
ctgcagtgta tcaaggttaa caactgggat ttattcttca gcccgagtga agacaacttc   1500
accaacgacc tgaacaaagg tgaagaaatc acctcagata ctaacatcga agcagccgaa   1560
gaaacatctc gctggacct gatccagcag tactacctga ccttttaattt cgacaacgag   1620
ccggaaaaca tttctatcga aaacctgagc tctgatatca tcggccagct ggaactgatg   1680
ccgaacatcg aacgttttcc caaacggtaaa agtacgagc tggacaaata ccatgttc    1740
cactacctgc gcgcgcagga atttgaacac ggcaaatccc gtatcgcact gactaactcc   1800
gttaacgaag ctctgctcaa cccgtcccgt gtatacacct tcttctctag cgactacgtg   1860
aaaaaggtca caaagcgac tgaagctgca atgttcttgg gttgggttga acagcttgtt   1920
tatgatttta ccgacgagac gtccgaagta tctactaccg acaaaattgc ggatatcact   1980
atcatcatcc cgtacatcgg tccggctctg aacattggca acatgctgta caaagacgac   2040
ttcgttggcg cactgatctt ctccggtgcg gtgatcctgc tggagttcat cccggaaatc   2100
```

```
gccatcccgg tactgggcac ctttgctctg gtttcttaca ttgcaaacaa ggttctgact    2160
gtacaaacca tcgacaacgc gctgagcaaa cgtaacgaaa aatgggatga agtttacaaa    2220
tatatcgtga ccaactggct ggctaaggtt aatactcaga tcgacctcat ccgcaaaaaa    2280
atgaaagaag cactggaaaa ccaggcggaa gctaccaagg caatcattaa ctaccagtac    2340
aaccagtaca ccgaggaaga aaaaaacaac atcaacttca acatcgacga tctgtcctct    2400
aaactgaacg aatccatcaa caaagctatg atcaacatca caagttcct gaaccagtgc     2460 tctgtaagct atctgatgaa ctccatgatc ccgtacggtg ttaaacgtct ggaggacttc    2520
gatgcgtctc tgaaagacgc cctgctgaaa tacatttacg acaaccgtgg cactctgatc    2580
ggtcaggttg atcgtctgaa ggacaaagtg aacaatacct tatcgaccga catccctttt    2640
cagctcagta aatatgtcga taaccaacgc cttttgtcca ctctagacta g             2691
```

<210> SEQ ID NO 56
<211> LENGTH: 896
<212> TYPE: PRT
<213> ORGANISM: Artificial Sequence
<220> FEATURE:
<223> OTHER INFORMATION: Synthetic

<400> SEQUENCE: 56

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
```

```
                    260                 265                 270
Ala Lys Phe Ile Asp Ser Leu Gln Glu Asn Glu Phe Arg Leu Tyr Tyr
                275                 280                 285

Tyr Asn Lys Phe Lys Asp Ile Ala Ser Thr Leu Asn Lys Ala Lys Ser
            290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
            370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
            435                 440                 445

Phe Gly Gly Phe Thr Gly Ala Arg Lys Tyr Ala Ala Leu Ala Gly Gly
            450                 455                 460

Gly Gly Ser Gly Gly Gly Ser Gly Gly Gly Ser Ala Leu Val
465                 470                 475                 480

Leu Gln Cys Ile Lys Val Asn Asn Trp Asp Leu Phe Phe Ser Pro Ser
                485                 490                 495

Glu Asp Asn Phe Thr Asn Asp Leu Asn Lys Gly Glu Glu Ile Thr Ser
                500                 505                 510

Asp Thr Asn Ile Glu Ala Ala Glu Asn Ile Ser Leu Asp Leu Ile
            515                 520                 525

Gln Gln Tyr Tyr Leu Thr Phe Asn Phe Asp Asn Glu Pro Glu Asn Ile
            530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                565                 570                 575

Tyr Thr Met Phe His Tyr Leu Arg Ala Gln Glu Phe Glu His Gly Lys
            580                 585                 590

Ser Arg Ile Ala Leu Thr Asn Ser Val Asn Glu Ala Leu Leu Asn Pro
            595                 600                 605

Ser Arg Val Tyr Thr Phe Phe Ser Ser Asp Tyr Val Lys Lys Val Asn
            610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
                645                 650                 655

Ala Asp Ile Thr Ile Ile Ile Pro Tyr Ile Gly Pro Ala Leu Asn Ile
            660                 665                 670

Gly Asn Met Leu Tyr Lys Asp Asp Phe Val Gly Ala Leu Ile Phe Ser
            675                 680                 685
```

Gly Ala Val Ile Leu Leu Glu Phe Ile Pro Glu Ile Ala Ile Pro Val
            690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
                725                 730                 735

Glu Val Tyr Lys Tyr Ile Val Thr Asn Trp Leu Ala Lys Val Asn Thr
            740                 745                 750

Gln Ile Asp Leu Ile Arg Lys Lys Met Lys Glu Ala Leu Glu Asn Gln
                755                 760                 765

Ala Glu Ala Thr Lys Ala Ile Ile Asn Tyr Gln Tyr Asn Gln Tyr Thr
770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
                805                 810                 815

Leu Asn Gln Cys Ser Val Ser Tyr Leu Met Asn Ser Met Ile Pro Tyr
                820                 825                 830

Gly Val Lys Arg Leu Glu Asp Phe Asp Ala Ser Leu Lys Asp Ala Leu
            835                 840                 845

Leu Lys Tyr Ile Tyr Asp Asn Arg Gly Thr Leu Ile Gly Gln Val Asp
850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Leu Asp
                885                 890                 895

<210> SEQ ID NO 57
<211> LENGTH: 2691
<212> TYPE: DNA
<213> ORGANISM: Artificial Sequence
<220> FEATURE:
<223> OTHER INFORMATION: Synthetic

<400> SEQUENCE: 57
ggatccatgg agttcgttaa caaacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gatacctta ctaacccgga agaaggtgac   180
ctgaacccgc caccggaagc gaaacaggtg ccggtatctt actatgactc cacctacctg   240
tctaccgata cgaaaagga caactacctg aaaggtgtta ctaaactgtt cgagcgtatt   300
tactccaccg acctgggccg tatgctgcta ctagcatcg ttcgcggtat cccgttctgg   360
ggcggttcta ccatcgatac cgaactgaaa gtaatcgaca ctaactgcat caacgttatt   420
cagccggacg ttcctatcg ttccgaagaa ctgaacctgg tgatcatcgg cccgtctgct   480
gatatcatcc agttcgagtg taagagcttt ggtcacgaag ttctgaacct cacccgtaac   540
ggctacggtt ccactcagta catccgtttc tctccggact tcaccttcgg ttttgaagaa   600
tccctggaag tagacacgaa cccactgctg ggcgctggta aattcgcaac tgatcctgcg   660
gttaccctgg ctcacgaact gattcatgca ggccaccgcc tgtacggtat cgccatcaat   720
ccgaaccgtg tcttcaaagt taacaccaac gcgtattacg agatgtccgg tctggaagtt   780
agcttcgaag aactgcgtac ttttggcggt cacgacgcta aattcatcga ctctctgcaa   840
gaaaacgagt tccgtctgta ctactataac aagttcaaag atatcgcatc caccctgaac   900

```
aaagcgaaat ccatcgtggg taccactgct tctctccagt acatgaagaa cgttttaaa      960
gaaaatacc  tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc     1140
gtgccgaaag ttaactacac tatctacgat ggtttcaacc tgcgtaacac caacctggct    1200
gctaatttta acggccagaa cacgaaatc  aacaacatga acttcacaaa actgaaaaac    1260
ttcactggtc tgttcgagtt ttacaagctg ctgtgcgtcg acggcatcat tacctccaaa    1320
actaaatctc tgatagaagg tagatttggc ggtttcacgg gcgcacgcaa atcatatgcg    1380
ctagcgggcg gtggcggtag cggcggtggc ggtagcggcg gtggcggtag cgcactagtg    1440
ctgcagtgta tcaaggttaa caactgggat ttattcttca gcccgagtga agacaacttc    1500
accaacgacc tgaacaaagg tgaagaaatc acctcagata ctaacatcga agcagccgaa    1560
gaaacatct  cgctggacct gatccagcag tactacctga cctttaattt cgacaacgag    1620
ccggaaaaca tttctatcga aaacctgagc tctgatatca tcggccagct ggaactgatg    1680
ccgaacatcg aacgtttccc aaacggtaaa agtacgagc  tggacaaata ccatgttc     1740
cactacctgc gcgcgcagga atttgaacac ggcaaatccc gtatcgcact gactaactcc    1800
gttaacgaag ctctgctcaa cccgtcccgt gtatacacct tcttctctag cgactacgtg    1860
aaaaaggtca caaagcgac  tgaagctgca atgttcttgg gttgggttga acagcttgtt    1920
tatgatttta ccgacgagac gtccgaagta tctactaccg acaaaattgc ggatatcact    1980
atcatcatcc cgtacatcgg tccggctctg aacattggca acatgctgta caaagacgac    2040
ttcgttggcg cactgatctt ctccggtgcg gtgatcctgc tggagttcat cccggaaatc    2100
gccatcccgg tactgggcac ctttgctctg gtttcttaca ttgcaaacaa ggttctgact    2160
gtacaaacca tcgacaacgc gctgagcaaa cgtaacgaaa atgggatga  agtttacaaa    2220
tatatcgtga ccaactggct ggctaaggtt aatactcaga tcgacctcat ccgcaaaaaa    2280
atgaaagaag cactggaaaa ccaggcgaaa gctaccaagg caatcattaa ctaccagtac    2340
aaccagtaca ccgaggaaga aaaaaacaac atcaacttca acatcgacga tctgtcctct    2400
aaactgaacg aatccatcaa caaagctatg atcaacatca caagttcct  gaaccagtgc    2460
tctgtaagct atctgatgaa ctccatgatc ccgtacggtg ttaaacgtct ggaggacttc    2520
gatgcgtctc tgaaagacgc cctgctgaaa tacatttacg acaaccgtgg cactctgatc    2580
ggtcaggttg atcgtctgaa ggacaaagtg aacaatacct atcgaccga  catcccttt    2640
cagctcagta aatatgtcga taaccaacgc cttttgtcca ctctagacta g            2691
```

<210> SEQ ID NO 58
<211> LENGTH: 896
<212> TYPE: PRT
<213> ORGANISM: Artificial Sequence
<220> FEATURE:
<223> OTHER INFORMATION: Synthetic

<400> SEQUENCE: 58

```
Gly Ser Met Glu Phe Val Asn Lys Gln Phe Asn Tyr Lys Asp Pro Val
 1               5                  10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45
```

Glu Arg Asp Thr Phe Thr Asn Pro Glu Glu Gly Asp Leu Asn Pro Pro
    50                      55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Ser Thr Ile Asp Thr Glu
            115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
            195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
            245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
            325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
    355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
            435                 440                 445

Phe Gly Gly Phe Thr Gly Ala Arg Lys Ser Tyr Ala Leu Ala Gly Gly
    450                 455                 460

-continued

Gly Gly Ser Gly Gly Gly Ser Gly Gly Gly Ser Ala Leu Val
465             470             475             480

Leu Gln Cys Ile Lys Val Asn Asn Trp Asp Leu Phe Phe Ser Pro Ser
        485             490             495

Glu Asp Asn Phe Thr Asn Asp Leu Asn Lys Gly Glu Glu Ile Thr Ser
        500             505             510

Asp Thr Asn Ile Glu Ala Ala Glu Glu Asn Ile Ser Leu Asp Leu Ile
        515             520             525

Gln Gln Tyr Tyr Leu Thr Phe Asn Phe Asp Asn Glu Pro Glu Asn Ile
        530             535             540

Ser Ile Glu Asn Leu Ser Ser Asp Ile Ile Gly Gln Leu Glu Leu Met
545             550             555             560

Pro Asn Ile Glu Arg Phe Pro Asn Gly Lys Lys Tyr Glu Leu Asp Lys
                565             570             575

Tyr Thr Met Phe His Tyr Leu Arg Ala Gln Glu Phe Glu His Gly Lys
        580             585             590

Ser Arg Ile Ala Leu Thr Asn Ser Val Asn Glu Ala Leu Leu Asn Pro
        595             600             605

Ser Arg Val Tyr Thr Phe Phe Ser Ser Asp Tyr Val Lys Lys Val Asn
        610             615             620

Lys Ala Thr Glu Ala Ala Met Phe Leu Gly Trp Val Glu Gln Leu Val
625             630             635             640

Tyr Asp Phe Thr Asp Glu Thr Ser Glu Val Ser Thr Thr Asp Lys Ile
                645             650             655

Ala Asp Ile Thr Ile Ile Pro Tyr Ile Gly Pro Ala Leu Asn Ile
        660             665             670

Gly Asn Met Leu Tyr Lys Asp Asp Phe Val Gly Ala Leu Ile Phe Ser
        675             680             685

Gly Ala Val Ile Leu Leu Glu Phe Ile Pro Glu Ile Ala Ile Pro Val
        690             695             700

Leu Gly Thr Phe Ala Leu Val Ser Tyr Ile Ala Asn Lys Val Leu Thr
705             710             715             720

Val Gln Thr Ile Asp Asn Ala Leu Ser Lys Arg Asn Glu Lys Trp Asp
                725             730             735

Glu Val Tyr Lys Tyr Ile Val Thr Asn Trp Leu Ala Lys Val Asn Thr
        740             745             750

Gln Ile Asp Leu Ile Arg Lys Lys Met Lys Glu Ala Leu Glu Asn Gln
        755             760             765

Ala Glu Ala Thr Lys Ala Ile Ile Asn Tyr Gln Tyr Asn Gln Tyr Thr
        770             775             780

Glu Glu Glu Lys Asn Asn Ile Asn Phe Asn Ile Asp Asp Leu Ser Ser
785             790             795             800

Lys Leu Asn Glu Ser Ile Asn Lys Ala Met Ile Asn Ile Asn Lys Phe
                805             810             815

Leu Asn Gln Cys Ser Val Ser Tyr Leu Met Asn Ser Met Ile Pro Tyr
        820             825             830

Gly Val Lys Arg Leu Glu Asp Phe Asp Ala Ser Leu Lys Asp Ala Leu
        835             840             845

Leu Lys Tyr Ile Tyr Asp Asn Arg Gly Thr Leu Ile Gly Gln Val Asp
        850             855             860

Arg Leu Lys Asp Lys Val Asn Asn Thr Leu Ser Thr Asp Ile Pro Phe
865             870             875             880

Gln Leu Ser Lys Tyr Val Asp Asn Gln Arg Leu Leu Ser Thr Leu Asp

<210> SEQ ID NO 59
<211> LENGTH: 2709
<212> TYPE: DNA
<213> ORGANISM: Artificial Sequence
<220> FEATURE:
<223> OTHER INFORMATION: Synthetic

<400> SEQUENCE: 59

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg gcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc caccctgaac     900
aaagcgaaat ccatcgtggg taccactgct tctctccagt acatgaagaa cgttttaaa     960
gaaaatacc tgctcagcga agacacctcc ggcaaattct ctgtagacaa gttgaaattc    1020
gataaacttt acaaaatgct gactgaaatt tacaccgaag acaacttcgt taagttctt    1080
aaagttctga accgcaaaac ctatctgaac ttcgacaagg cagtattcaa atcaacatc    1140
gtgccgaaag ttaactacac tatctacgat ggtttcaacc tgcgtaacac caacctggct    1200
gctaatttta acgccagaa cacggaaatc aacaacatga acttcacaaa actgaaaaac    1260
ttcactggtc tgttcgagtt ttacaagctg ctgtgcgtcg acggcatcat acctccaaa    1320
actaaatctc tgatagaagg tagatttggc ggtttcacgg cgcacgcaa atcagcgcgt    1380
aaatatgcta accaggcgct agcgggcggt ggcggtagcg gcggtggcgg tagcggcggt    1440
ggcggtagcg cactagtgct gcagtgtatc aaggttaaca actgggattt attcttcagc    1500
ccgagtgaag acaacttcac caacgacctg aacaaaggtg aagaaatcac ctcagatact    1560
aacatcgaag cagccgaaga aaacatctcg ctggacctga tccagcagta ctacctgacc    1620
tttaatttcg acaacgagcc ggaaaacatt tctatcgaaa acctgagctc tgatatcatc    1680
ggccagctgg aactgatgcc gaacatcgaa cgtttcccaa acggtaaaaa gtacgagctg    1740
gacaaatata ccatgttcca ctacctgcgc gcgcaggaat ttgaacacgg caaatcccgt    1800
atcgcactga ctaactccgt taacgaagct ctgctcaacc cgtcccgtgt atacaccttc    1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
```

```
atgctgtaca aagacgactt cgttggcgca ctgatcttct ccggtgcggt gatcctgctg    2100
gagttcatcc cggaaatcgc catcccggta ctgggcacct ttgctctggt ttcttacatt    2160
gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaaat gaaagaagca ctggaaaacc aggcggaagc taccaaggca    2340
atcattaact accagtacaa ccagtacacc gaggaagaaa aaaacaacat caacttcaac    2400
atcgacgatc tgtcctctaa actgaacgaa tccatcaaca aagctatgat caacatcaac    2460
aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccttg    2640
tcgaccgaca tcccttttca gctcagtaaa tatgtcgata ccaacgcct tttgtccact    2700 ctagactag                                                           2709
```

<210> SEQ ID NO 60
<211> LENGTH: 902
<212> TYPE: PRT
<213> ORGANISM: Artificial Sequence
<220> FEATURE:
<223> OTHER INFORMATION: Synthetic

<400> SEQUENCE: 60

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240
```

```
Pro Asn Arg Val Phe Lys Val Asn Thr Asn Ala Tyr Glu Met Ser
            245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
        290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
        370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Tyr Ala Asn
450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
            485                 490                 495

Leu Phe Phe Ser Pro Ser Glu Asp Asn Phe Thr Asn Asp Leu Asn Lys
                500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
        530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
            595                 600                 605

Glu Ala Leu Leu Asn Pro Ser Arg Val Tyr Thr Phe Phe Ser Ser Asp
610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655
```

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
            725                 730                 735

Arg Asn Glu Lys Trp Asp Glu Val Tyr Lys Tyr Ile Val Thr Asn Trp
        740                 745                 750

Leu Ala Lys Val Asn Thr Gln Ile Asp Leu Ile Arg Lys Lys Met Lys
    755                 760                 765

Glu Ala Leu Glu Asn Gln Ala Glu Ala Thr Lys Ala Ile Ile Asn Tyr
770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
            805                 810                 815

Ile Asn Ile Asn Lys Phe Leu Asn Gln Cys Ser Val Ser Tyr Leu Met
        820                 825                 830

Asn Ser Met Ile Pro Tyr Gly Val Lys Arg Leu Glu Asp Phe Asp Ala
    835                 840                 845

Ser Leu Lys Asp Ala Leu Leu Lys Tyr Ile Tyr Asp Asn Arg Gly Thr
850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
            885                 890                 895

Leu Leu Ser Thr Leu Asp
            900

<210> SEQ ID NO 61
<211> LENGTH: 2697
<212> TYPE: DNA
<213> ORGANISM: Artificial Sequence
<220> FEATURE:
<223> OTHER INFORMATION: Synthetic

<400> SEQUENCE: 61
ggatccatgg agttcgttaa caaacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gataccttta ctaacccgga agaaggtgac   180
ctgaacccgc accggaagc gaaacaggtg ccggtatctt actatgactc cacctacctg   240
tctaccgata cgaaaagga caactacctg aaaggtgtta ctaaactgtt cgagcgtatt   300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
cagccggacg gttcctatcg ttccgaagaa ctgaacctgg tgatcatcgg cccgtctgct   480
gatatcatcc agttcgagtg taagagcttt ggtcacgaag ttctgaacct cacccgtaac   540
ggctacggtt ccactcagta catccgtttc tctccggact tcaccttcgg ttttgaagaa   600
tccctggaag tagacacgaa cccactgctg ggcgctggta aattcgcaac tgatcctgcg   660

```
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgtttttaaa    960
gaaaaatacc tgctcagcga agacacctcc ggcaaattct ctgtagacaa gttgaaattc    1020
gataaacttt acaaaatgct gactgaaatt taccgaag acaacttcgt taagttcttt    1080
aaagttctga accgcaaaac ctatctgaac ttcgacaagg cagtattcaa atcaacatc    1140 gtgccgaaag ttaactacac tatctacgat ggtttcaacc tgcgtaacac caacctggct    1200
gctaatttta acggcagaa cacgaaatc aacaacatga acttcacaaa actgaaaaac    1260
ttcactggtc tgttcgagtt ttacaagctg ctgtgcgtcg acggcatcat acctccaaa    1320 actaaatctc tgatagaagg tagatttggc ggtttcacgg gcgcacgcaa atcagcgcgt    1380
aaagcgctag cgggcggtgg cggtagcggc ggtggcggta gcggcggtgg cggtagcgca    1440
ctagtgctgc agtgtatcaa ggttaacaac tgggatttat tcttcagccc gagtgaagac    1500
aacttcacca acgacctgaa caaaggtgaa gaaatcaccct cagatactaa catcgaagca    1560
gccgaagaaa acatctcgct ggacctgatc cagcagtact acctgacctt taatttcgac    1620
aacgagccgg aaaacatttc tatcgaaaac ctgagctctg atatcatcgg ccagctggaa    1680
ctgatgccga catcgaacg tttcccaaac ggtaaaaagt acgagctgga caaatatacc    1740
atgttccact acctgcgcgc gcaggaattt gaacacggca atcccgtat cgcactgact    1800 aactccgtta acgaagctct gctcaacccg tcccgtgtat acaccttctt ctctagcgac    1860
tacgtgaaaa aggtcaacaa agcgactgaa gctgcaatgt tcttgggttg ggttgaacag    1920
cttgtttatg atttaccga cgagacgtcc gaagtatcta ctaccgacaa aattgcggat    1980
atcactatca tcatcccgta catcggtccg gctctgaaca ttggcaacat gctgtacaaa    2040
gacgacttcg ttggcgcact gatcttctcc ggtgcggtga tcctgctgga gttcatcccg    2100
gaaatcgcca tcccggtact gggcacctt gctctggttt cttacattgc aaacaaggtt    2160
ctgactgtac aaaccatcga caacgcgctg agcaacgta acgaaaaatg ggatgaagtt    2220
tacaaatata tcgtgaccaa ctggctggct aaggttaata ctcagatcga cctcatccgc    2280
aaaaaaatga agaagcact ggaaaaccag gcggaagcta ccaaggcaat cattaactac    2340
cagtacaacc agtacaccga ggaagaaaaa aacaacatca acttcaacat cgacgatctg    2400
tcctctaaac tgaacgaatc catcaacaaa gctatgatca acatcaacaa gttcctgaac    2460
cagtgctctg taagctatct gatgaactcc atgatcccgt acggtgttaa acgtctggag    2520
gacttcgatg cgtctctgaa agacgccctg ctgaaataca tttacgacaa ccgtggcact    2580
ctgatcggtc aggttgatcg tctgaaggac aaagtgaaca ataccttatc gaccgacatc    2640
ccttttcagc tcagtaaata tgtcgataac caacgccttt tgtccactct agactag       2697
```

<210> SEQ ID NO 62
<211> LENGTH: 898
<212> TYPE: PRT
<213> ORGANISM: Artificial Sequence
<220> FEATURE:
<223> OTHER INFORMATION: Synthetic

<400> SEQUENCE: 62

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
            35                  40                  45

Glu Arg Asp Thr Phe Thr Asn Pro Glu Glu Gly Asp Leu Asn Pro Pro
50              55                  60

Pro Glu Ala Lys Gln Val Pro Val Ser Tyr Tyr Asp Ser Thr Tyr Leu
65              70                  75                  80

Ser Thr Asp Asn Glu Lys Asp Asn Tyr Leu Lys Gly Val Thr Lys Leu
            85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
            115                 120                 125

Leu Lys Val Ile Asp Thr Asn Cys Ile Asn Val Ile Gln Pro Asp Gly
            130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
            165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
            195                 200                 205

Leu Leu Gly Ala Gly Lys Phe Ala Thr Asp Pro Ala Val Thr Leu Ala
            210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
            245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
            290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
            325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
            370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415

Lys Leu Lys Asn Phe Thr Gly Leu Phe Glu Phe Tyr Lys Leu Leu Cys
```

```
                420                 425                 430
Val Asp Gly Ile Ile Thr Ser Lys Thr Lys Ser Leu Ile Glu Gly Arg
                    435                 440                 445

Phe Gly Gly Phe Thr Gly Ala Arg Lys Ser Ala Arg Lys Ala Leu Ala
    450                 455                 460

Gly Gly Gly Gly Ser Gly Gly Gly Ser Gly Gly Gly Ser Ala
465                 470                 475                 480

Leu Val Leu Gln Cys Ile Lys Val Asn Asn Trp Asp Leu Phe Phe Ser
                    485                 490                 495

Pro Ser Glu Asp Asn Phe Thr Asn Asp Leu Asn Lys Gly Glu Glu Ile
                500                 505                 510

Thr Ser Asp Thr Asn Ile Glu Ala Ala Glu Asn Ile Ser Leu Asp
                515                 520                 525

Leu Ile Gln Gln Tyr Tyr Leu Thr Phe Asn Phe Asp Asn Glu Pro Glu
                530                 535                 540

Asn Ile Ser Ile Glu Asn Leu Ser Ser Asp Ile Ile Gly Gln Leu Glu
545                 550                 555                 560

Leu Met Pro Asn Ile Glu Arg Phe Pro Asn Gly Lys Lys Tyr Glu Leu
                565                 570                 575

Asp Lys Tyr Thr Met Phe His Tyr Leu Arg Ala Gln Glu Phe Glu His
                580                 585                 590

Gly Lys Ser Arg Ile Ala Leu Thr Asn Ser Val Asn Glu Ala Leu Leu
            595                 600                 605

Asn Pro Ser Arg Val Tyr Thr Phe Phe Ser Ser Asp Tyr Val Lys Lys
610                 615                 620

Val Asn Lys Ala Thr Glu Ala Ala Met Phe Leu Gly Trp Val Glu Gln
625                 630                 635                 640

Leu Val Tyr Asp Phe Thr Asp Glu Thr Ser Glu Val Ser Thr Thr Asp
                    645                 650                 655

Lys Ile Ala Asp Ile Thr Ile Ile Pro Tyr Ile Gly Pro Ala Leu
                660                 665                 670

Asn Ile Gly Asn Met Leu Tyr Lys Asp Asp Phe Val Gly Ala Leu Ile
                    675                 680                 685

Phe Ser Gly Ala Val Ile Leu Leu Glu Phe Ile Pro Glu Ile Ala Ile
                690                 695                 700

Pro Val Leu Gly Thr Phe Ala Leu Val Ser Tyr Ile Ala Asn Lys Val
705                 710                 715                 720

Leu Thr Val Gln Thr Ile Asp Asn Ala Leu Ser Lys Arg Asn Glu Lys
                    725                 730                 735

Trp Asp Glu Val Tyr Lys Tyr Ile Val Thr Asn Trp Leu Ala Lys Val
                740                 745                 750

Asn Thr Gln Ile Asp Leu Ile Arg Lys Lys Met Lys Glu Ala Leu Glu
                    755                 760                 765

Asn Gln Ala Glu Ala Thr Lys Ala Ile Ile Asn Tyr Gln Tyr Asn Gln
                770                 775                 780

Tyr Thr Glu Glu Glu Lys Asn Asn Ile Asn Phe Asn Ile Asp Asp Leu
785                 790                 795                 800

Ser Ser Lys Leu Asn Glu Ser Ile Asn Lys Ala Met Ile Asn Ile Asn
                    805                 810                 815

Lys Phe Leu Asn Gln Cys Ser Val Ser Tyr Leu Met Asn Ser Met Ile
                820                 825                 830

Pro Tyr Gly Val Lys Arg Leu Glu Asp Phe Asp Ala Ser Leu Lys Asp
                835                 840                 845
```

Ala Leu Leu Lys Tyr Ile Tyr Asp Asn Arg Gly Thr Leu Ile Gly Gln
        850                 855                 860

Val Asp Arg Leu Lys Asp Lys Val Asn Asn Thr Leu Ser Thr Asp Ile
865                 870                 875                 880

Pro Phe Gln Leu Ser Lys Tyr Val Asp Asn Gln Arg Leu Leu Ser Thr
                    885                 890                 895

Leu Asp

<210> SEQ ID NO 63
<211> LENGTH: 2736
<212> TYPE: DNA
<213> ORGANISM: Artificial Sequence
<220> FEATURE:
<223> OTHER INFORMATION: Synthetic

<400> SEQUENCE: 63

| | |
|---|---:|
| ctcgggattg agggtcgttt tggcggtttc acgggcgcac gcaaatcagc gcgtaaatta | 60 |
| gctaaccaga ctagtggcgg tggggtagt ggcggtggcg gttcgggcgg gggtgggagc | 120 |
| cctaggggat ccatggagtt cgttaacaaa cagttcaact ataaagaccc agttaacggt | 180 |
| gttgacattg cttacatcaa atcccgaac gctggccaga tgcagccggt aaaggcattc | 240 |
| aaaatccaca acaaaatctg gttatcccg aacgtgata cctttactaa cccggaagaa | 300 |
| ggtgacctga cccgccacc ggaagcgaaa caggtgccgg tatcttacta tgactccacc | 360 |
| tacctgtcta ccgataacga aaggacaac tacctgaaag gtgttactaa actgttcgag | 420 |
| cgtatttact ccaccgacct gggccgtatg ctgctgacta gcatcgttcg cggtatcccg | 480 |
| ttctggggcg gttctaccat cgataccgaa ctgaaagtaa tcgacactaa ctgcatcaac | 540 |
| gttattcagc cggacggttc ctatcgttcc gaagaactga acctggtgat catcggcccg | 600 |
| tctgctgata tcatccagtt cgagtgtaag agctttggtc acgaagttct gaacctcacc | 660 |
| cgtaacggct acgttccac tcagtacatc cgtttctctc cggacttcac cttcggtttt | 720 |
| gaagaatccc tggaagtaga cacgaaccca ctgctgggcg ctggtaaatt cgcaactgat | 780 |
| cctgcggtta ccctggctca cgaactgatt catgcaggcc accgcctgta cggtatcgcc | 840 |
| atcaatccga accgtgtctt caaagttaac accaacgcgt attacgagat gtccggtctg | 900 |
| gaagttagct tcgaagaact gcgtactttt ggcggtcacg acgctaaatt catcgactct | 960 |
| ctgcaagaaa acgagttccg tctgtactac tataacaagt caaagatat cgcatccacc | 1020 |
| ctgaacaaag cgaaatccat cgtgggtacc actgcttctc tccagtacat gaagaacgtt | 1080 |
| tttaaagaaa atacctgct cagcgaagac acctccggca attctctgt agacaagttg | 1140 |
| aaattcgata aactttacaa aatgctgact gaaatttaca ccgaagacaa cttcgttaag | 1200 |
| ttctttaaag ttctgaaccg caaaacctat ctgaacttcg acaaggcagt attcaaaatc | 1260 |
| aacatcgtgc cgaaagttaa ctacactatc tacgatggtt tcaacctgcg taacaccaac | 1320 |
| ctggctgcta tttttaacgg ccagaacacg gaaatcaaca acatgaactt cacaaaactg | 1380 |
| aaaaacttca ctggtctgtt cgagttttac aagctgctgt gcgtcgacgg catcattacc | 1440 |
| tccaaaacta aatctctgat agaaggtaga acaaagcgc tgaacctgca gtgtatcaag | 1500 |
| gttaacaact gggatttatt cttcagcccg agtgaagaca acttccacca cgacctgaac | 1560 |
| aaaggtgaag aaatcacctc agatactaac atcgaagcag ccgaagaaaa catctcgctg | 1620 |
| gacctgatcc agcagtacta cctgaccttt aatttcgaca acgagccgga aaacattctt | 1680 |
| atcgaaaacc tgagctctga tatcatcggc cagctggaac tgatgccgaa catcgaacgt | 1740 |

```
ttcccaaacg gtaaaaagta cgagctggac aaatatacca tgttccacta cctgcgcgcg    1800
caggaatttg aacacggcaa atcccgtatc gcactgacta actccgttaa cgaagctctg    1860
ctcaacccgt cccgtgtata caccttcttc tctagcgact acgtgaaaaa ggtcaacaaa    1920
gcgactgaag ctgcaatgtt cttgggttgg gttgaacagc ttgtttatga ttttaccgac    1980
gagacgtccg aagtatctac taccgacaaa attgcggata tcactatcat catcccgtac    2040
atcggtccgg ctctgaacat tggcaacatg ctgtacaaag acgacttcgt tggcgcactg    2100
atcttctccg gtgcggtgat cctgctggag ttcatcccgg aaatcgccat cccggtactg    2160
ggcacctttg ctctggtttc ttacattgca acaaggttc tgactgtaca aaccatcgac    2220
aacgcgctga gcaaacgtaa cgaaaaatgg gatgaagttt acaaatatat cgtgaccaac    2280
tggctggcta aggttaatac tcagatcgac ctcatccgca aaaaaatgaa agaagcactg    2340
gaaaaccagg cggaagctac caaggcaatc attaactacc agtacaacca gtacaccgag    2400
gaagaaaaaa acaacatcaa cttcaacatc gacgatctgt cctctaaact gaacgaatcc    2460
atcaacaaag ctatgatcaa catcaacaag ttcctgaacc agtgctctgt aagctatctg    2520
atgaactcca tgatcccgta cggtgttaaa cgtctggagg acttcgatgc gtctctgaaa    2580
gacgccctgc tgaaatacat ttacgacaac cgtggcactc tgatcggtca ggttgatcgt    2640
ctgaaggaca aagtgaacaa taccttatcg accgacatcc ttttcagct cagtaaatat    2700 gtcgataacc aacgcctttt gtccactcta gactag                              2736
```

<210> SEQ ID NO 64
<211> LENGTH: 911
<212> TYPE: PRT
<213> ORGANISM: Artificial Sequence
<220> FEATURE:
<223> OTHER INFORMATION: Synthetic

<400> SEQUENCE: 64

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Ser Gly Gly
            20                  25                  30

Gly Gly Ser Gly Gly Gly Gly Ser Pro Arg Gly Ser Met Glu Phe Val
        35                  40                  45

Asn Lys Gln Phe Asn Tyr Lys Asp Pro Val Asn Gly Val Asp Ile Ala
    50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Glu Ala Lys Gln Val
            100                 105                 110

Pro Val Ser Tyr Tyr Asp Ser Thr Tyr Leu Ser Thr Asp Asn Glu Lys
        115                 120                 125

Asp Asn Tyr Leu Lys Gly Val Thr Lys Leu Phe Glu Arg Ile Tyr Ser
    130                 135                 140

Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu Glu
```

```
                    180                 185                 190
Leu Asn Leu Val Ile Ile Gly Pro Ser Ala Asp Ile Ile Gln Phe Glu
                195                 200                 205
Cys Lys Ser Phe Gly His Glu Val Leu Asn Leu Thr Arg Asn Gly Tyr
            210                 215                 220
Gly Ser Thr Gln Tyr Ile Arg Phe Ser Pro Asp Phe Thr Phe Gly Phe
225                 230                 235                 240
Glu Glu Ser Leu Glu Val Asp Thr Asn Pro Leu Leu Gly Ala Gly Lys
                245                 250                 255
Phe Ala Thr Asp Pro Ala Val Thr Leu Ala His Glu Leu Ile His Ala
            260                 265                 270
Gly His Arg Leu Tyr Gly Ile Ala Ile Asn Pro Asn Arg Val Phe Lys
        275                 280                 285
Val Asn Thr Asn Ala Tyr Tyr Glu Met Ser Gly Leu Glu Val Ser Phe
        290                 295                 300
Glu Glu Leu Arg Thr Phe Gly Gly His Asp Ala Lys Phe Ile Asp Ser
305                 310                 315                 320
Leu Gln Glu Asn Glu Phe Arg Leu Tyr Tyr Tyr Asn Lys Phe Lys Asp
                325                 330                 335
Ile Ala Ser Thr Leu Asn Lys Ala Lys Ser Ile Val Gly Thr Thr Ala
            340                 345                 350
Ser Leu Gln Tyr Met Lys Asn Val Phe Lys Glu Lys Tyr Leu Leu Ser
        355                 360                 365
Glu Asp Thr Ser Gly Lys Phe Ser Val Asp Lys Leu Lys Phe Asp Lys
370                 375                 380
Leu Tyr Lys Met Leu Thr Glu Ile Tyr Thr Glu Asp Asn Phe Val Lys
385                 390                 395                 400
Phe Phe Lys Val Leu Asn Arg Lys Thr Tyr Leu Asn Phe Asp Lys Ala
                405                 410                 415
Val Phe Lys Ile Asn Ile Val Pro Lys Val Asn Tyr Thr Ile Tyr Asp
            420                 425                 430
Gly Phe Asn Leu Arg Asn Thr Asn Leu Ala Ala Asn Phe Asn Gly Gln
        435                 440                 445
Asn Thr Glu Ile Asn Asn Met Asn Phe Thr Lys Leu Lys Asn Phe Thr
        450                 455                 460
Gly Leu Phe Glu Phe Tyr Lys Leu Leu Cys Val Asp Gly Ile Ile Thr
465                 470                 475                 480
Ser Lys Thr Lys Ser Leu Ile Glu Gly Arg Asn Lys Ala Leu Asn Leu
                485                 490                 495
Gln Cys Ile Lys Val Asn Asn Trp Asp Leu Phe Phe Ser Pro Ser Glu
            500                 505                 510
Asp Asn Phe Thr Asn Asp Leu Asn Lys Gly Glu Glu Ile Thr Ser Asp
        515                 520                 525
Thr Asn Ile Glu Ala Ala Glu Glu Asn Ile Ser Leu Asp Leu Ile Gln
        530                 535                 540
Gln Tyr Tyr Leu Thr Phe Asn Phe Asp Asn Glu Pro Glu Asn Ile Ser
545                 550                 555                 560
Ile Glu Asn Leu Ser Ser Asp Ile Ile Gly Gln Leu Glu Leu Met Pro
                565                 570                 575
Asn Ile Glu Arg Phe Pro Asn Gly Lys Lys Tyr Glu Leu Asp Lys Tyr
            580                 585                 590
Thr Met Phe His Tyr Leu Arg Ala Gln Glu Phe Glu His Gly Lys Ser
        595                 600                 605
```

```
Arg Ile Ala Leu Thr Asn Ser Val Asn Glu Ala Leu Leu Asn Pro Ser
    610                 615                 620
Arg Val Tyr Thr Phe Phe Ser Ser Asp Tyr Val Lys Lys Val Asn Lys
625                 630                 635                 640
Ala Thr Glu Ala Ala Met Phe Leu Gly Trp Val Glu Gln Leu Val Tyr
                645                 650                 655
Asp Phe Thr Asp Glu Thr Ser Glu Val Ser Thr Thr Asp Lys Ile Ala
                660                 665                 670
Asp Ile Thr Ile Ile Ile Pro Tyr Ile Gly Pro Ala Leu Asn Ile Gly
            675                 680                 685
Asn Met Leu Tyr Lys Asp Asp Phe Val Gly Ala Leu Ile Phe Ser Gly
    690                 695                 700
Ala Val Ile Leu Leu Glu Phe Ile Pro Glu Ile Ala Ile Pro Val Leu
705                 710                 715                 720
Gly Thr Phe Ala Leu Val Ser Tyr Ile Ala Asn Lys Val Leu Thr Val
                725                 730                 735
Gln Thr Ile Asp Asn Ala Leu Ser Lys Arg Asn Glu Lys Trp Asp Glu
                740                 745                 750
Val Tyr Lys Tyr Ile Val Thr Asn Trp Leu Ala Lys Val Asn Thr Gln
            755                 760                 765
Ile Asp Leu Ile Arg Lys Lys Met Lys Glu Ala Leu Glu Asn Gln Ala
    770                 775                 780
Glu Ala Thr Lys Ala Ile Ile Asn Tyr Gln Tyr Asn Gln Tyr Thr Glu
785                 790                 795                 800
Glu Glu Lys Asn Asn Ile Asn Phe Asn Ile Asp Leu Ser Ser Lys
                805                 810                 815
Leu Asn Glu Ser Ile Asn Lys Ala Met Ile Asn Ile Asn Lys Phe Leu
                820                 825                 830
Asn Gln Cys Ser Val Ser Tyr Leu Met Asn Ser Met Ile Pro Tyr Gly
    835                 840                 845
Val Lys Arg Leu Glu Asp Phe Asp Ala Ser Leu Lys Asp Ala Leu Leu
850                 855                 860
Lys Tyr Ile Tyr Asp Asn Arg Gly Thr Leu Ile Gly Gln Val Asp Arg
865                 870                 875                 880
Leu Lys Asp Lys Val Asn Asn Thr Leu Ser Thr Asp Ile Pro Phe Gln
                885                 890                 895
Leu Ser Lys Tyr Val Asp Asn Gln Arg Leu Leu Ser Thr Leu Asp
            900                 905                 910

<210> SEQ ID NO 65
<211> LENGTH: 177
<212> TYPE: DNA
<213> ORGANISM: Artificial Sequence
<220> FEATURE:
<223> OTHER INFORMATION: Synthetic

<400> SEQUENCE: 65
ggatccacgc acgtcgacgg catcattacc tccaaaacta atctctgat agaaggtaga      60 tttggcggtt tcacgggcgc acgcaaatca gcgcgtaaat agctaacca ggcgctagcg     120 ggtggtggtg gttctgcact agtgctgcag acgcacggtc tagaatgata aaagctt      177

<210> SEQ ID NO 66
<211> LENGTH: 192
<212> TYPE: DNA
<213> ORGANISM: Artificial Sequence
```

```
<220> FEATURE:
<223> OTHER INFORMATION: Synthetic

<400> SEQUENCE: 66
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
ggtggtggtg gttctggtgg tggtggttct gcactagtgc tgcagacgca cggtctagaa     180
tgataaaagc tt                                                         192

<210> SEQ ID NO 67
<211> LENGTH: 222
<212> TYPE: DNA
<213> ORGANISM: Artificial Sequence
<220> FEATURE:
<223> OTHER INFORMATION: Synthetic

<400> SEQUENCE: 67
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
ggtggtggtg gttctggtgg tggtggttct ggtggtggtg gttctggtgg tggtggttct    180
gcactagtgc tgcagacgca cggtctagaa tgataaaagc tt                        222

<210> SEQ ID NO 68
<211> LENGTH: 237
<212> TYPE: DNA
<213> ORGANISM: Artificial Sequence
<220> FEATURE:
<223> OTHER INFORMATION: Synthetic

<400> SEQUENCE: 68
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
ggtggtggtg gttctggtgg tggtggttct ggtggtggtg gttctggtgg tggtggttct    180
ggtggtggtg gttctgcact agtgctgcag acgcacggtc tagaatgata aaagctt       237

<210> SEQ ID NO 69
<211> LENGTH: 228
<212> TYPE: DNA
<213> ORGANISM: Artificial Sequence
<220> FEATURE:
<223> OTHER INFORMATION: Synthetic

<400> SEQUENCE: 69
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
gctgaagctg ctgctaaaga agctgctgct aaagaagctg ctgctaaagc tggtggcggt    180
ggttccgcac tagtgctgca gacgcacggt ctagaatgat aaaagctt                  228

<210> SEQ ID NO 70
<211> LENGTH: 2694
<212> TYPE: DNA
<213> ORGANISM: Artificial Sequence
<220> FEATURE:
<223> OTHER INFORMATION: Synthetic

<400> SEQUENCE: 70
ggatccatgg agttcgttaa caacagttc aactataaag acccagttaa cggtgttgac     60
```

```
attgcttaca tcaaaatccc gaacgctggc cagatgcagc cggtaaaggc attcaaaatc    120
cacaacaaaa tctgggttat cccggaacgt gataccttta ctaacccgga agaaggtgac    180
ctgaacccgc caccggaagc gaaacaggtg ccggtatctt actatgactc cacctacctg    240
tctaccgata acgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt ccgtctgtaa ctactataac aagttcaaag atatcgcatc caccctgaac    900
aaagcgaaat ccatcgtggg taccactgct ctctccagt acatgaagaa cgtttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga ccgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat acctccaaa    1320 actaaatctc tgatagaagg tagatttggc ggtttcacgg gcgcacgcaa atcagcgcgt   1380
aaattagcta accaggcgct agcgggtggt ggtggttctg gtggtggtgg ttctgcacta   1440
gtgctgcagt gtatcaaggt taacaactgg gatttattct cagcccgag tgaagacaac   1500 ttcaccaacg acctgaacaa aggtgaagaa atcccctcag atactaacat cgaagcagcc   1560
gaagaaaaca tctcgctgga cctgatccag cagtactacc tgacctttaa tttcgacaac   1620
gagccggaaa catttctat cgaaaacctg agctctgata tcatcggcca gctgaactg    1680 atgccgaaca tcgaacgttt cccaaacggt aaaaagtacg agctggacaa atataccatg   1740
ttccactacc tgcgcgcgca ggaatttgaa cacggcaaat cccgtatcgc actgactaac   1800
tccgttaacg aagctctgct caacccgtcc cgtgtataca ccttcttctc tagcgactac   1860
gtgaaaaagg tcaacaaagc gactgaagct gcaatgttct tgggttgggt tgaacagctt   1920
gtttatgatt ttaccgacga gacgtccgaa gtatctacta ccgacaaaat tgcggatatc   1980
actatcatca tcccgtacat cggtccggct ctgaacattg caacatgct gtacaaagac    2040 gacttcgttg gcgcactgat cttctccggt gcggtgatcc tgctggagtt catcccggaa   2100
atcgccatcc cggtactggg caccttttgct ctggtttctt acattgcaaa caaggttctg   2160
actgtacaaa ccatcgacaa cgcgctgagc aaacgtaacg aaaaatggga tgaagtttac   2220
aaatatatcg tgaccaactg gctggctaag gttaatactc agatcgacct catccgcaaa   2280
aaaatgaaag aagcactgga aaaccaggcg gaagctacca aggcaatcat taactaccag   2340
tacaaccagt acaccgagga agaaaaaaac aacatcaact tcaacatcga cgatctgtcc   2400
tctaaactga acgaatccat caacaaagct atgatcaaca tcaacaagtt cctgaaccag   2460
```

```
tgctctgtaa gctatctgat gaactccatg atcccgtacg gtgttaaacg tctggaggac    2520
ttcgatgcgt ctctgaaaga cgccctgctg aaatacattt acgacaaccg tggcactctg    2580
atcggtcagg ttgatcgtct gaaggacaaa gtgaacaata ccttatcgac cgacatccct    2640
tttcagctca gtaaatatgt cgataaccaa cgccttttgt ccactctaga ctag          2694
```

<210> SEQ ID NO 71
<211> LENGTH: 897
<212> TYPE: PRT
<213> ORGANISM: Artificial Sequence
<220> FEATURE:
<223> OTHER INFORMATION: Synthetic

<400> SEQUENCE: 71

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320
```

```
Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415

Lys Leu Lys Asn Phe Thr Gly Leu Phe Glu Phe Tyr Lys Leu Leu Cys
        420                 425                 430

Val Asp Gly Ile Ile Thr Ser Lys Thr Lys Ser Leu Ile Glu Gly Arg
            435                 440                 445

Phe Gly Gly Phe Thr Gly Ala Arg Lys Ser Ala Arg Lys Leu Ala Asn
    450                 455                 460

Gln Ala Leu Ala Gly Gly Gly Ser Gly Gly Gly Ser Ala Leu
465                 470                 475                 480

Val Leu Gln Cys Ile Lys Val Asn Asn Trp Asp Leu Phe Phe Ser Pro
            485                 490                 495

Ser Glu Asp Asn Phe Thr Asn Asp Leu Asn Lys Gly Glu Glu Ile Thr
            500                 505                 510

Ser Asp Thr Asn Ile Glu Ala Ala Glu Glu Asn Ile Ser Leu Asp Leu
        515                 520                 525

Ile Gln Gln Tyr Tyr Leu Thr Phe Asn Phe Asp Asn Glu Pro Glu Asn
530                 535                 540

Ile Ser Ile Glu Asn Leu Ser Ser Asp Ile Ile Gly Gln Leu Glu Leu
545                 550                 555                 560

Met Pro Asn Ile Glu Arg Phe Pro Asn Gly Lys Lys Tyr Glu Leu Asp
            565                 570                 575

Lys Tyr Thr Met Phe His Tyr Leu Arg Ala Gln Glu Phe Glu His Gly
        580                 585                 590

Lys Ser Arg Ile Ala Leu Thr Asn Ser Val Asn Glu Ala Leu Leu Asn
        595                 600                 605

Pro Ser Arg Val Tyr Thr Phe Phe Ser Ser Asp Tyr Val Lys Lys Val
        610                 615                 620

Asn Lys Ala Thr Glu Ala Ala Met Phe Leu Gly Trp Val Glu Gln Leu
625                 630                 635                 640

Val Tyr Asp Phe Thr Asp Glu Thr Ser Glu Val Ser Thr Thr Asp Lys
            645                 650                 655

Ile Ala Asp Ile Thr Ile Ile Pro Tyr Ile Gly Pro Ala Leu Asn
            660                 665                 670

Ile Gly Asn Met Leu Tyr Lys Asp Asp Phe Val Gly Ala Leu Ile Phe
            675                 680                 685

Ser Gly Ala Val Ile Leu Leu Glu Phe Ile Pro Glu Ile Ala Ile Pro
    690                 695                 700

Val Leu Gly Thr Phe Ala Leu Val Ser Tyr Ile Ala Asn Lys Val Leu
705                 710                 715                 720

Thr Val Gln Thr Ile Asp Asn Ala Leu Ser Lys Arg Asn Glu Lys Trp
            725                 730                 735

Asp Glu Val Tyr Lys Tyr Ile Val Thr Asn Trp Leu Ala Lys Val Asn
```

```
                740                745                750
Thr Gln Ile Asp Leu Ile Arg Lys Lys Met Lys Glu Ala Leu Glu Asn
            755                760                765
Gln Ala Glu Ala Thr Lys Ala Ile Ile Asn Tyr Gln Tyr Asn Gln Tyr
        770                775                780
Thr Glu Glu Lys Asn Asn Ile Asn Phe Asn Ile Asp Asp Leu Ser
785                790                795                800
Ser Lys Leu Asn Glu Ser Ile Asn Lys Ala Met Ile Asn Ile Asn Lys
                805                810                815
Phe Leu Asn Gln Cys Ser Val Ser Tyr Leu Met Asn Ser Met Ile Pro
            820                825                830
Tyr Gly Val Lys Arg Leu Glu Asp Phe Asp Ala Ser Leu Lys Asp Ala
        835                840                845
Leu Leu Lys Tyr Ile Tyr Asp Asn Arg Gly Thr Leu Ile Gly Gln Val
    850                855                860
Asp Arg Leu Lys Asp Lys Val Asn Asn Thr Leu Ser Thr Asp Ile Pro
865                870                875                880
Phe Gln Leu Ser Lys Tyr Val Asp Asn Gln Arg Leu Leu Ser Thr Leu
                885                890                895
Asp
```

<210> SEQ ID NO 72
<211> LENGTH: 2724
<212> TYPE: DNA
<213> ORGANISM: Artificial Sequence
<220> FEATURE:
<223> OTHER INFORMATION: Synthetic

<400> SEQUENCE: 72

```
ggatccatgg agttcgttaa caaacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gatacctta  ctaacccgga agaaggtgac   180
ctgaacccgc accggaagc gaaacaggtg ccggtatctt actatgactc cacctacctg   240
tctaccgata cgaaaagga caactacctg aaaggtgtta ctaaactgtt cgagcgtatt   300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
cagccggacg ttcctatcg ttccgaagaa ctgaacctgg tgatcatcgg cccgtctgct   480
gatatcatcc agttcgagtg taagagcttt ggtcacgaag ttctgaacct cacccgtaac   540
ggctacggtt ccactcagta catccgtttc tctccggact tcaccttcgg ttttgaagaa   600
tccctggaag tagacacgaa cccactgctg ggcgctggta aattcgcaac tgatcctgcg   660
gttaccctgg ctcacgaact gattcatgca ggccaccgcc tgtacggtat cgccatcaat   720
ccgaaccgtg tcttcaaagt taacaccaac gcgtattacg agatgtccgg tctggaagtt   780
agcttcgaag aactgcgtac ttttggcggt cacgacgcta aattcatcga ctctctgcaa   840
gaaaacgagt tccgtctgta ctactataac aagttcaaag atatcgcatc caccctgaac   900
aaagcgaaat ccatcgtggg taccactgct tctctccagt acatgaagaa cgttttttaaa   960
gaaaaatacc tgctcagcga agacacctcc ggcaaattct ctgtagacaa gttgaaattc  1020
gataaacttt acaaaatgct gactgaaatt tacaccgaag acaacttcgt taagttcttt  1080
aaagttctga accgcaaaac ctatctgaac ttcgacaagg cagtattcaa atcaacatc  1140
```

-continued

```
gtgccgaaag ttaactacac tatctacgat ggtttcaacc tgcgtaacac caacctggct      1200
gctaatttta acggccagaa cacggaaatc aacaacatga acttcacaaa actgaaaaac      1260
ttcactggtc tgttcgagtt ttacaagctg ctgtgcgtcg acggcatcat acctccaaa       1320
actaaatctc tgatagaagg tagatttggc ggtttcacgg gcgcacgcaa atcagcgcgt      1380
aaattagcta accaggcgct agcgggtggt ggtggttctg gtggtggtgg ttctggtggt      1440
ggtggttctg gtggtggtgg ttctgcacta gtgctgcagt gtatcaaggt taacaactgg      1500
gatttattct tcagcccgag tgaagacaac ttcaccaacg acctgaacaa aggtgaagaa      1560
atcacctcag atactaacat cgaagcagcc gaagaaaaca tctcgctgga cctgatccag      1620
cagtactacc tgacctttaa tttcgacaac gagccggaaa catttctat cgaaaacctg       1680
agctctgata tcatcggcca gctggaactg atgccgaaca tcgaacgttt cccaaacggt      1740
aaaaagtacg agctggacaa atataccatg ttccactacc tgcgcgcgca ggaatttgaa      1800
cacggcaaat cccgtatcgc actgactaac tccgttaacg aagctctgct caacccgtcc      1860
cgtgtataca ccttcttctc tagcgactac gtgaaaaagg tcaacaaagc gactgaagct      1920
gcaatgttct gggttgggt tgaacagctt gtttatgatt ttaccgacga dacgtccgaa       1980
gtatctacta ccgacaaaat tgcggatatc actatcatca tcccgtacat cggtccggct      2040
ctgaacattg caacatgct gtacaaagac gacttcgttg gcgcactgat cttctccggt       2100
gcggtgatcc tgctggagtt catcccggaa atcgccatcc cggtactggg caccctttgct     2160
ctggtttctt acattgcaaa caaggttctg actgtacaaa ccatcgacaa cgcgctgagc      2220
aaacgtaacg aaaaatggga tgaagtttac aaatatatcg tgaccaactg gctggctaag      2280
gttaatactc agatcgacct catccgcaaa aaaatgaaag aagcactgga aaaccaggcg      2340
gaagctacca aggcaatcat taactaccag tacaaccagt acaccgagga agaaaaaaac      2400
aacatcaact tcaacatcga cgatctgtcc tctaaactga acgaatccat caacaaagct      2460
atgatcaaca tcaacaagtt cctgaaccag tgctctgtaa gctatctgat gaactccatg      2520
atcccgtacg gtgttaaacg tctggaggac ttcgatgcgt ctctgaaaga cgccctgctg      2580
aaatacattt acgacaaccg tggcactctg atcggtcagg ttgatcgtct gaaggacaaa      2640
gtgaacaata ccttatcgac cgacatccct tttcagctca gtaaatatgt cgataaccaa      2700
cgccttttgt ccactctaga ctag                                              2724
```

<210> SEQ ID NO 73
<211> LENGTH: 907
<212> TYPE: PRT
<213> ORGANISM: Artificial Sequence
<220> FEATURE:
<223> OTHER INFORMATION: Synthetic

<400> SEQUENCE: 73

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80
```

```
Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
    435                 440                 445

Phe Gly Gly Phe Thr Gly Ala Arg Lys Ser Ala Arg Lys Leu Ala Asn
    450                 455                 460

Gln Ala Leu Ala Gly Gly Gly Ser Gly Gly Gly Ser Gly Gly Gly Gly
465                 470                 475                 480

Gly Gly Ser Gly Gly Gly Gly Ser Ala Leu Val Leu Gln Cys Ile Lys
            485                 490                 495

Val Asn Asn Trp Asp Leu Phe Phe Ser Pro Ser Glu Asp Asn Phe Thr
```

Asn Asp Leu Asn Lys Gly Glu Glu Ile Thr Ser Asp Thr Asn Ile Glu
500                     505                     510

Ala Ala Glu Glu Asn Ile Ser Leu Asp Leu Ile Gln Gln Tyr Tyr Leu
        515                     520                     525

Thr Phe Asn Phe Asp Asn Glu Pro Glu Asn Ile Ser Ile Glu Asn Leu
            530                     535                     540

Ser Ser Asp Ile Ile Gly Gln Leu Glu Leu Met Pro Asn Ile Glu Arg
545                     550                     555                     560

Phe Pro Asn Gly Lys Lys Tyr Glu Leu Asp Lys Tyr Thr Met Phe His
            565                     570                     575

Tyr Leu Arg Ala Gln Glu Phe Glu His Gly Lys Ser Arg Ile Ala Leu
        580                     585                     590

Thr Asn Ser Val Asn Glu Ala Leu Leu Asn Pro Ser Arg Val Tyr Thr
    595                     600                     605

Phe Phe Ser Ser Asp Tyr Val Lys Lys Val Asn Lys Ala Thr Glu Ala
610                     615                     620

Ala Met Phe Leu Gly Trp Val Glu Gln Leu Val Tyr Asp Phe Thr Asp
625                     630                     635                     640

Glu Thr Ser Glu Val Ser Thr Thr Asp Lys Ile Ala Asp Ile Thr Ile
            645                     650                     655

Ile Ile Pro Tyr Ile Gly Pro Ala Leu Asn Ile Gly Asn Met Leu Tyr
        660                     665                     670

Lys Asp Asp Phe Val Gly Ala Leu Ile Phe Ser Gly Ala Val Ile Leu
    675                     680                     685

Leu Glu Phe Ile Pro Glu Ile Ala Ile Pro Val Leu Gly Thr Phe Ala
690                     695                     700

Leu Val Ser Tyr Ile Ala Asn Lys Val Leu Thr Val Gln Thr Ile Asp
705                     710                     715                     720

Asn Ala Leu Ser Lys Arg Asn Glu Lys Trp Asp Glu Val Tyr Lys Tyr
            725                     730                     735

Ile Val Thr Asn Trp Leu Ala Lys Val Asn Thr Gln Ile Asp Leu Ile
        740                     745                     750

Arg Lys Lys Met Lys Glu Ala Leu Glu Asn Gln Ala Glu Ala Thr Lys
    755                     760                     765

Ala Ile Ile Asn Tyr Gln Tyr Asn Gln Tyr Thr Glu Glu Glu Lys Asn
770                     775                     780

Asn Ile Asn Phe Asn Ile Asp Asp Leu Ser Ser Lys Leu Asn Glu Ser
785                     790                     795                     800

Ile Asn Lys Ala Met Ile Asn Ile Asn Lys Phe Leu Asn Gln Cys Ser
            805                     810                     815

Val Ser Tyr Leu Met Asn Ser Met Ile Pro Tyr Gly Val Lys Arg Leu
        820                     825                     830

Glu Asp Phe Asp Ala Ser Leu Lys Asp Ala Leu Leu Lys Tyr Ile Tyr
    835                     840                     845

Asp Asn Arg Gly Thr Leu Ile Gly Gln Val Asp Arg Leu Lys Asp Lys
850                     855                     860

Val Asn Asn Thr Leu Ser Thr Asp Ile Pro Phe Gln Leu Ser Lys Tyr
865                     870                     875                     880

Val Asp Asn Gln Arg Leu Leu Ser Thr Leu Asp
            885                     890                     895

<210> SEQ ID NO 74

```
<211> LENGTH: 207
<212> TYPE: DNA
<213> ORGANISM: Artificial Sequence
<220> FEATURE:
<223> OTHER INFORMATION: Synthetic

<400> SEQUENCE: 74
ggatccacgc acgtcgacgg catcattacc tccaaaacta aatctgacga tgacgataaa      60
tttggcggtt tcacgggcgc acgcaaatca gcgcgtaaac gtaagaacca ggcgctagcg     120
ggcggtggcg gtagcggcgg tggcggtagc ggcggtggcg gtagcgcact agtgctgcag     180
acgcacggtc tagaatgata aaagctt                                         207

<210> SEQ ID NO 75
<211> LENGTH: 2709
<212> TYPE: DNA
<213> ORGANISM: Artificial Sequence
<220> FEATURE:
<223> OTHER INFORMATION: Synthetic

<400> SEQUENCE: 75
ggatccatgg agttcgttaa caacagttc aactataaag acccagttaa cggtgttgac        60
attgcttaca tcaaaatccc gaacgctggc cagatgcagc cggtaaaggc attcaaaatc     120
cacaacaaaa tctgggttat cccggaacgt gataccttta ctaacccgga gaaggtgac     180 ctgaacccgc caccggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt ccgtctgta ctactataac aagttcaaag atatcgcatc cacctgaac      900 aaagcgaaat ccatcgtggg taccactgct ctctctccagt acatgaagaa cgttttaaa     960 gaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc    1140 gtgccgaaag ttaactacac tatctacgat ggtttcaacc tgcgtaacac caacctggct    1200 gctaattta acgccagaa cacggaaatc aacaacatga acttcacaaa actgaaaaac     1260
ttcactggtc tgttcgagtt ttacaagctg ctgtgcgtcg acggcatcat tacctccaaa    1320
actaaatctg acgatgacga taaatttggc ggtttcacgg gcgcacgcaa atcagcgcgt    1380
aaacgtaaga accaggcgct agcgggcggt ggcggtagcg gcggtggcgg tagcggcggt    1440
ggcggtagcg cactagtgct gcagtgtatc aaggttaaca actgggattt attcttcagc    1500
ccgagtgaag acaacttcac caacgacctg aacaaaggtg aagaaatcac ctcagatact    1560
aacatcgaag cagccgaaga aaacatctcg ctggacctga tccagcagta ctacctgacc    1620
```

```
tttaatttcg acaacgagcc ggaaaacatt tctatcgaaa acctgagctc tgatatcatc    1680
ggccagctgg aactgatgcc gaacatcgaa cgtttcccaa acggtaaaaa gtacgagctg    1740
gacaaatata ccatgttcca ctacctgcgc gcgcaggaat ttgaacacgg caaatcccgt    1800
atcgcactga ctaactccgt taacgaagct ctgctcaacc cgtcccgtgt atacaccttc    1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca agacgactt cgttggcgca ctgatcttct ccggtgcggt gatcctgctg    2100
gagttcatcc cggaaatcgc catcccggta ctgggcacct tgctctggt tcttacatt    2160 gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaaat gaagaagca ctggaaaacc aggcggaagc taccaaggca    2340
atcattaact accagtacaa ccagtacacc gaggaagaaa aaacaacat caacttcaac    2400 atcgacgatc tgtcctctaa actgaacgaa tccatcaaca aagctatgat caacatcaac    2460
aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caatacctta    2640
tcgaccgaca tcccttttca gctcagtaaa tatgtcgata ccaacgcct tttgtccact    2700 ctagactag                                                            2709

<210> SEQ ID NO 76
<211> LENGTH: 902
<212> TYPE: PRT
<213> ORGANISM: Artificial Sequence
<220> FEATURE:
<223> OTHER INFORMATION: Synthetic

<400> SEQUENCE: 76

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160
```

-continued

```
Asp Ile Ile Gln Phe Glu Cys Lys Ser Phe Gly His Glu Val Leu Asn
                165                 170                 175
Leu Thr Arg Asn Gly Tyr Gly Ser Thr Gln Tyr Ile Arg Phe Ser Pro
            180                 185                 190
Asp Phe Thr Phe Gly Phe Glu Glu Ser Leu Glu Val Asp Thr Asn Pro
        195                 200                 205
Leu Leu Gly Ala Gly Lys Phe Ala Thr Asp Pro Ala Val Thr Leu Ala
    210                 215                 220
His Glu Leu Ile His Ala Gly His Arg Leu Tyr Gly Ile Ala Ile Asn
225                 230                 235                 240
Pro Asn Arg Val Phe Lys Val Asn Thr Asn Ala Tyr Tyr Glu Met Ser
                245                 250                 255
Gly Leu Glu Val Ser Phe Glu Glu Leu Arg Thr Phe Gly Gly His Asp
            260                 265                 270
Ala Lys Phe Ile Asp Ser Leu Gln Glu Asn Glu Phe Arg Leu Tyr Tyr
        275                 280                 285
Tyr Asn Lys Phe Lys Asp Ile Ala Ser Thr Leu Asn Lys Ala Lys Ser
    290                 295                 300
Ile Val Gly Thr Thr Ala Ser Leu Gln Tyr Met Lys Asn Val Phe Lys
305                 310                 315                 320
Glu Lys Tyr Leu Leu Ser Glu Asp Thr Ser Gly Lys Phe Ser Val Asp
                325                 330                 335
Lys Leu Lys Phe Asp Lys Leu Tyr Lys Met Leu Thr Glu Ile Tyr Thr
            340                 345                 350
Glu Asp Asn Phe Val Lys Phe Phe Lys Val Leu Asn Arg Lys Thr Tyr
        355                 360                 365
Leu Asn Phe Asp Lys Ala Val Phe Lys Ile Asn Ile Val Pro Lys Val
    370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
            420                 425                 430
Val Asp Gly Ile Ile Thr Ser Lys Thr Lys Ser Asp Asp Asp Asp Lys
        435                 440                 445
Phe Gly Gly Phe Thr Gly Ala Arg Lys Ser Ala Arg Lys Arg Lys Asn
    450                 455                 460
Gln Ala Leu Ala Gly Gly Gly Ser Gly Gly Gly Gly Ser Gly Gly Gly
465                 470                 475                 480
Gly Gly Ser Ala Leu Val Leu Gln Cys Ile Lys Val Asn Asn Trp Asp
                485                 490                 495
Leu Phe Phe Ser Pro Ser Glu Asp Asn Phe Thr Asn Asp Leu Asn Lys
            500                 505                 510
Gly Glu Glu Ile Thr Ser Asp Thr Asn Ile Glu Ala Ala Glu Glu Asn
        515                 520                 525
Ile Ser Leu Asp Leu Ile Gln Gln Tyr Tyr Leu Thr Phe Asn Phe Asp
    530                 535                 540
Asn Glu Pro Glu Asn Ile Ser Ile Glu Asn Leu Ser Ser Asp Ile Ile
545                 550                 555                 560
Gly Gln Leu Glu Leu Met Pro Asn Ile Glu Arg Phe Pro Asn Gly Lys
                565                 570                 575
Lys Tyr Glu Leu Asp Lys Tyr Thr Met Phe His Tyr Leu Arg Ala Gln
```

580                 585                 590
Glu Phe Glu His Gly Lys Ser Arg Ile Ala Leu Thr Asn Ser Val Asn
            595                 600                 605

Glu Ala Leu Leu Asn Pro Ser Arg Val Tyr Thr Phe Phe Ser Ser Asp
        610                 615                 620

Tyr Val Lys Lys Val Asn Lys Ala Thr Glu Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Glu Phe Ile Pro
            690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
                740                 745                 750

Leu Ala Lys Val Asn Thr Gln Ile Asp Leu Ile Arg Lys Lys Met Lys
            755                 760                 765

Glu Ala Leu Glu Asn Gln Ala Glu Ala Thr Lys Ala Ile Ile Asn Tyr
        770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
                820                 825                 830

Asn Ser Met Ile Pro Tyr Gly Val Lys Arg Leu Glu Asp Phe Asp Ala
            835                 840                 845

Ser Leu Lys Asp Ala Leu Leu Lys Tyr Ile Tyr Asp Asn Arg Gly Thr
850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
            885                 890                 895

Leu Leu Ser Thr Leu Asp
            900

<210> SEQ ID NO 77
<211> LENGTH: 207
<212> TYPE: DNA
<213> ORGANISM: Artificial Sequence
<220> FEATURE:
<223> OTHER INFORMATION: Synthetic

<400> SEQUENCE: 77
ggatccacgc acgtcgacgg catcattacc tccaaaacta atctctgat agaaggtaga      60 tttggcggtt tcacgggcgc acgcaaatca gcgcgtaaac gtaagaacca ggcgctagcg    120
ggcggtggcg gtagcggcgg tggcggtagc ggcggtggcg gtagcgcact agtgctgcag    180
acgcacggtc tagaatgata aaagctt                                         207

<210> SEQ ID NO 78
<211> LENGTH: 2742
<212> TYPE: DNA
<213> ORGANISM: Artificial Sequence
<220> FEATURE:
<223> OTHER INFORMATION: Synthetic

<400> SEQUENCE: 78

```
ggatccgaat tcatgccgat caccatcaac aacttcaact acagcgatcc ggtggataac      60
aaaaacatcc tgtacctgga tacccatctg aataccctgg cgaacgaacc ggaaaaagcg     120
tttcgtatca ccggcaacat ttgggttatt ccggatcgtt ttagccgtaa cagcaacccg     180
aatctgaata accgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca caacaccccc gatcaacacc tttgatttcg atgtggattt caacagcgtt     420
gatgttaaaa cccgccaggg taacaattgg gtgaaaaccg gcagcattaa cccgagcgtg     480
attattaccg gtccgcgcga aaacattatt gatccggaaa ccagcacctt taaactgacc     540
aacaacacct ttgcggcgca ggaaggtttt ggcgcgctga gcattattag cattagcccg     600
cgctttatgc tgacctatag caacgcgacc aacgatgttg gtgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
ttttacagcc agtacaacgt gaaactggaa tatgcgaaaa tctatgcgtt tggcggtccg     840
accattgatc tgattccgaa aagcgcgcgc aaatacttcg aagaaaaagc gctggattac     900
tatcgcagca ttgcgaaacg tctgaacagc attaccaccg cgaatccgag cagcttcaac     960
aaatatatcg cgaatataaa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa aatctacctg    1140
agcaacgtgt atacccccggt gaccgcgaat attctggatg ataacgtgta cgatatccag    1200
aacggcttta acatcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg gcatcattac ctccaaaact aaatctctga tagaaggtag atttggcggt    1380
ttcacgggcg cacgcaaatc agcgcgtaaa cgtaagaacc aggcgctagc gggcggtggc    1440
ggtagcggcg gtggcggtag cggcggtggc ggtagcgcac tagtgctgca gtgtcgtgaa    1500
ctgctggtga aaaacaccga tctgccgttt attggcgata tcagcgatgt gaaaaccgat    1560
atcttcctgc gcaaagatat caacgaagaa accgaagtga tctactaccc ggataacgtg    1620
agcgttgatc aggtgatcct gagcaaaaac accagcgaac atggtcagct ggatctgctg    1680
tatccgagca ttgatagcga aagcgaaatt ctgccgggcg aaaaccaggt gttttacgat    1740
aaccgtaccc agaacgtgga ttacctgaac agctattact acctggaaag ccagaaactg    1800
agcgataacg tggaagattt taccttaccc cgcagcattg aagaagcgct ggataacagc    1860
gcgaaagttt acacctattt tccgaccctg gcgaacaaag ttaatgcggg tgttcagggc    1920
ggtctgtttc tgatgtgggc gaacgatgtg gtggaagatt tcaccaccaa catcctgcgt    1980
aaagataccc tggataaaat cagcgatgtt agcgcgatta ttccgtatat tggtccggcg    2040
```

```
ctgaacatta gcaatagcgt gcgtcgtggc aattttaccg aagcgtttgc ggttaccggt    2100
gtgaccattc tgctggaagc gtttccggaa tttaccattc cggcgctggg tgcgtttgtg    2160
atctatagca aagtgcagga acgcaacgaa atcatcaaaa ccatcgataa ctgcctggaa    2220
cagcgtatta acgctggaaa agatagctat gaatggatga tgggcacctg gctgagccgt    2280
attatcaccc agttcaacaa catcagctac agatgtacg atagcctgaa ctatcaggcg    2340
ggtgcgatta aagcgaaaat cgatctggaa tacaaaaaat acagcggcag cgataaagaa    2400
aacatcaaaa gccaggttga aaacctgaaa aacagcctgg atgtgaaaat tagcgaagcg    2460
atgaataaca tcaacaaatt catccgcgaa tgcagcgtga cctacctgtt caaaaacatg    2520
ctgccgaaag tgatcgatga actgaacgaa tttgatcgca acaccaaagc gaaactgatc    2580
aacctgatcg atagccacaa cattattctg gtgggcgaag tggataaact gaaagcgaaa    2640
gttaacaaca gcttccagaa caccatcccg tttaacatct tcagctatac caacaacagc    2700
ctgctgaaag atatcatcaa cgaatacttc aatctagact ag    2742
```

<210> SEQ ID NO 79
<211> LENGTH: 913
<212> TYPE: PRT
<213> ORGANISM: Artificial Sequence
<220> FEATURE:
<223> OTHER INFORMATION: Synthetic

<400> SEQUENCE: 79

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240
```

```
Asn Leu Tyr Gly Ile Ala Ile Pro Asn Asp Gln Thr Ile Ser Ser Val
            245                 250                 255

Thr Ser Asn Ile Phe Tyr Ser Gln Tyr Asn Val Lys Leu Glu Tyr Ala
        260                 265                 270

Glu Ile Tyr Ala Phe Gly Gly Pro Thr Ile Asp Leu Ile Pro Lys Ser
    275                 280                 285

Ala Arg Lys Tyr Phe Glu Glu Lys Ala Leu Asp Tyr Tyr Arg Ser Ile
290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Gly Ile Ile Thr Ser
        435                 440                 445

Lys Thr Lys Ser Leu Ile Glu Gly Arg Phe Gly Gly Phe Thr Gly Ala
    450                 455                 460

Arg Lys Ser Ala Arg Lys Arg Lys Asn Gln Ala Leu Ala Gly Gly Gly
465                 470                 475                 480

Gly Ser Gly Gly Gly Gly Ser Gly Gly Gly Gly Ser Ala Leu Val Leu
                485                 490                 495

Gln Cys Arg Glu Leu Leu Val Lys Asn Thr Asp Leu Pro Phe Ile Gly
            500                 505                 510

Asp Ile Ser Asp Val Lys Thr Asp Ile Phe Leu Arg Lys Asp Ile Asn
        515                 520                 525

Glu Glu Thr Glu Val Ile Tyr Tyr Pro Asp Asn Val Ser Val Asp Gln
    530                 535                 540

Val Ile Leu Ser Lys Asn Thr Ser Glu His Gly Gln Leu Asp Leu Leu
545                 550                 555                 560

Tyr Pro Ser Ile Asp Ser Glu Ser Glu Ile Leu Pro Gly Glu Asn Gln
                565                 570                 575

Val Phe Tyr Asp Asn Arg Thr Gln Asn Val Asp Tyr Leu Asn Ser Tyr
            580                 585                 590

Tyr Tyr Leu Glu Ser Gln Lys Leu Ser Asp Asn Val Glu Asp Phe Thr
        595                 600                 605

Phe Thr Arg Ser Ile Glu Glu Ala Leu Asp Asn Ser Ala Lys Val Tyr
    610                 615                 620

Thr Tyr Phe Pro Thr Leu Ala Asn Lys Val Asn Ala Gly Val Gln Gly
625                 630                 635                 640

Gly Leu Phe Leu Met Trp Ala Asn Asp Val Val Glu Asp Phe Thr Thr
                645                 650                 655

Asn Ile Leu Arg Lys Asp Thr Leu Asp Lys Ile Ser Asp Val Ser Ala
```

```
            660                 665                 670
Ile Ile Pro Tyr Ile Pro Ala Leu Asn Ile Ser Asn Ser Val Arg
        675                 680                 685

Arg Gly Asn Phe Thr Glu Ala Phe Ala Val Thr Gly Val Thr Ile Leu
    690                 695                 700

Leu Glu Ala Phe Pro Glu Phe Thr Ile Pro Ala Leu Gly Ala Phe Val
705                 710                 715                 720

Ile Tyr Ser Lys Val Gln Glu Arg Asn Glu Ile Ile Lys Thr Ile Asp
            725                 730                 735

Asn Cys Leu Glu Gln Arg Ile Lys Arg Trp Lys Asp Ser Tyr Glu Trp
            740                 745                 750

Met Met Gly Thr Trp Leu Ser Arg Ile Ile Thr Gln Phe Asn Asn Ile
        755                 760                 765

Ser Tyr Gln Met Tyr Asp Ser Leu Asn Tyr Gln Ala Gly Ala Ile Lys
    770                 775                 780

Ala Lys Ile Asp Leu Glu Tyr Lys Lys Tyr Ser Gly Ser Asp Lys Glu
785                 790                 795                 800

Asn Ile Lys Ser Gln Val Glu Asn Leu Lys Asn Ser Leu Asp Val Lys
            805                 810                 815

Ile Ser Glu Ala Met Asn Asn Ile Asn Lys Phe Ile Arg Glu Cys Ser
            820                 825                 830

Val Thr Tyr Leu Phe Lys Asn Met Leu Pro Lys Val Ile Asp Glu Leu
        835                 840                 845

Asn Glu Phe Asp Arg Asn Thr Lys Ala Lys Leu Ile Asn Leu Ile Asp
        850                 855                 860

Ser His Asn Ile Ile Leu Val Gly Glu Val Asp Lys Leu Lys Ala Lys
865                 870                 875                 880

Val Asn Asn Ser Phe Gln Asn Thr Ile Pro Phe Asn Ile Phe Ser Tyr
            885                 890                 895

Thr Asn Asn Ser Leu Leu Lys Asp Ile Ile Asn Glu Tyr Phe Asn Leu
            900                 905                 910

Asp
```

<210> SEQ ID NO 80
<211> LENGTH: 2673
<212> TYPE: DNA
<213> ORGANISM: Artificial Sequence
<220> FEATURE:
<223> OTHER INFORMATION: Synthetic

<400> SEQUENCE: 80

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga gaaggtgac     180 ctgaacccgc accggaagc gaaacaggtg ccggtatctt actatgactc cacctacctg     240
tctaccgata acgaaaagga caactacctg aaaggtgtta ctaaactgtt cgagcgtatt      300
tactccaccg acctgggccg tatgctgctg actagcatcg ttcgcggtat cccgttctgg      360
ggcggttcta ccatcgatac cgaactgaaa gtaatcgaca ctaactgcat caacgttatt      420
cagccggacg ttcctatcg ttccgaagaa ctgaacctgg tgatcatcgg cccgtctgct      480
gatatcatcc agttcgagtg taagagcttt ggtcacgaag ttctgaacct cacccgtaac      540
ggctacggtt ccactcagta catccgtttc tctccggact tcaccttcgg ttttgaagaa      600
```

-continued

```
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct ctctccagt acatgaagaa cgttttaaa     960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa atcaacatc    1140
gtgccgaaag ttaactacac tatctacgat ggtttcaacc tgcgtaacac caacctggct   1200
gctaatttta acggccagaa cacgaaatc aacaacatga acttcacaaa actgaaaaac    1260
ttcactggtc tgttcgagtt ttacaagctg ctgtgcgtcg acggcatcat acctccaaa    1320
actaaatctc tgatagaagg tagatacggt ggtttcctgg cgctagcggg cggtggcggt   1380
agcggcggtg gcgtagcgg cggtggcggt agcgcactag tgctgcagtg tatcaaggtt    1440
aacaactggg atttattctt cagcccgagt gaagacaact tcaccaacga cctgaacaaa   1500
ggtgaagaaa tcacctcaga tactaacatc gaagcagccg aagaaaacat ctcgctggac   1560
ctgatccagc agtactacct gacctttaat ttcgacaacg agccggaaaa catttctatc   1620
gaaaacctga gctctgatat catcggccag ctggaactga tgccgaacat cgaacgtttc   1680
ccaaacggta aaaagtacga gctggacaaa tataccatgt ccactacct gcgcgcgcag    1740
gaatttgaac acggcaaatc ccgtatcgca ctgactaact ccgttaacga agctctgctc   1800
aacccgtccc gtgtatacac cttcttctct agcgactacg tgaaaaaggt caacaaagcg   1860
actgaagctg caatgttctt gggttgggtt gaacagcttg tttatgattt taccgacgag   1920
acgtccgaag tatctactac cgacaaaatt gcggatatca ctatcatcat cccgtacatc   1980
ggtccggctc tgaacattgg caacatgctg tacaagacg acttcgttgg cgcactgatc   2040
ttctccggtg cggtgatcct gctggagttc atcccggaaa tcgccatccc ggtactgggc   2100
acctttgctc tggtttctta cattgcaaac aaggttctga ctgtacaaac catcgacaac   2160
gcgctgagca acgtaacga aaaatgggat gaagtttaca atatatcgt gaccaactgg    2220
ctggctaagg ttaatactca gatcgacctc atccgcaaaa aaatgaaaga agcactggaa   2280
aaccaggcgg aagctaccaa ggcaatcatt aactaccagt acaaccagta caccgaggaa   2340
gaaaaaaaca acatcaactt caacatcgac gatctgtcct ctaaactgaa cgaatccatc   2400
aacaaagcta tgatcaacat caacaagttc ctgaaccagt gctctgtaag ctatctgatg   2460
aactccatga tcccgtacgg tgttaaacgt ctggaggact cgatgcgtc tctgaaagac    2520
gccctgctga aatacatta cgacaaccgt ggcactctga tcggtcaggt tgatcgtctg   2580
aaggacaaag tgaacaatac cttatcgacc gacatcccct ttcagctcag taaatatgtc   2640
gataaccaac gccttttgtc cactctagac tag                                2673
```

<210> SEQ ID NO 81
<211> LENGTH: 890
<212> TYPE: PRT
<213> ORGANISM: Artificial Sequence
<220> FEATURE:
<223> OTHER INFORMATION: Synthetic

<400> SEQUENCE: 81

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
            35                  40                  45

Glu Arg Asp Thr Phe Thr Asn Pro Glu Glu Gly Asp Leu Asn Pro Pro
50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
            85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
            115                 120                 125

Leu Lys Val Ile Asp Thr Asn Cys Ile Asn Val Ile Gln Pro Asp Gly
            130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
            165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
            195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
            245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
            290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
            325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
            370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415
```

```
Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Leu Ala Leu Ala Gly Gly Gly Ser Gly Gly Gly
    450                 455                 460

Gly Ser Gly Gly Gly Ser Ala Leu Val Leu Gln Cys Ile Lys Val
465                 470                 475                 480

Asn Asn Trp Asp Leu Phe Phe Ser Pro Ser Asp Asn Phe Thr Asn
            485                 490                 495

Asp Leu Asn Lys Gly Glu Glu Ile Thr Ser Asp Thr Asn Ile Glu Ala
            500                 505                 510

Ala Glu Glu Asn Ile Ser Leu Asp Leu Ile Gln Gln Tyr Tyr Leu Thr
            515                 520                 525

Phe Asn Phe Asp Asn Glu Pro Glu Asn Ile Ser Ile Glu Asn Leu Ser
        530                 535                 540

Ser Asp Ile Ile Gly Gln Leu Glu Leu Met Pro Asn Ile Glu Arg Phe
545                 550                 555                 560

Pro Asn Gly Lys Lys Tyr Glu Leu Asp Lys Tyr Thr Met Phe His Tyr
            565                 570                 575

Leu Arg Ala Gln Glu Phe Glu His Gly Lys Ser Arg Ile Ala Leu Thr
        580                 585                 590

Asn Ser Val Asn Glu Ala Leu Leu Asn Pro Ser Arg Val Tyr Thr Phe
        595                 600                 605

Phe Ser Ser Asp Tyr Val Lys Lys Val Asn Lys Ala Thr Glu Ala Ala
610                 615                 620

Met Phe Leu Gly Trp Val Glu Gln Leu Val Tyr Asp Phe Thr Asp Glu
625                 630                 635                 640

Thr Ser Glu Val Ser Thr Thr Asp Lys Ile Ala Asp Ile Thr Ile Ile
                645                 650                 655

Ile Pro Tyr Ile Gly Pro Ala Leu Asn Ile Gly Asn Met Leu Tyr Lys
            660                 665                 670

Asp Asp Phe Val Gly Ala Leu Ile Phe Ser Gly Ala Val Ile Leu Leu
        675                 680                 685

Glu Phe Ile Pro Glu Ile Ala Ile Pro Val Leu Gly Thr Phe Ala Leu
    690                 695                 700

Val Ser Tyr Ile Ala Asn Lys Val Leu Thr Val Gln Thr Ile Asp Asn
705                 710                 715                 720

Ala Leu Ser Lys Arg Asn Glu Lys Trp Asp Glu Val Tyr Lys Tyr Ile
            725                 730                 735

Val Thr Asn Trp Leu Ala Lys Val Asn Thr Gln Ile Asp Leu Ile Arg
        740                 745                 750

Lys Lys Met Lys Glu Ala Leu Glu Asn Gln Ala Glu Ala Thr Lys Ala
        755                 760                 765

Ile Ile Asn Tyr Gln Tyr Asn Gln Tyr Thr Glu Glu Lys Asn Asn
770                 775                 780

Ile Asn Phe Asn Ile Asp Asp Leu Ser Ser Lys Leu Asn Glu Ser Ile
785                 790                 795                 800

Asn Lys Ala Met Ile Asn Ile Asn Lys Phe Leu Asn Gln Cys Ser Val
                805                 810                 815

Ser Tyr Leu Met Asn Ser Met Ile Pro Tyr Gly Val Lys Arg Leu Glu
        820                 825                 830

Asp Phe Asp Ala Ser Leu Lys Asp Ala Leu Leu Lys Tyr Ile Tyr Asp
```

Asn Arg Gly Thr Leu Ile Gly Gln Val Asp Arg Leu Lys Asp Lys Val
             850                 855                 860

Asn Asn Thr Leu Ser Thr Asp Ile Pro Phe Gln Leu Ser Lys Tyr Val
865                 870                 875                 880

Asp Asn Gln Arg Leu Leu Ser Thr Leu Asp
                885                 890

<210> SEQ ID NO 82
<211> LENGTH: 2709
<212> TYPE: DNA
<213> ORGANISM: Artificial Sequence
<220> FEATURE:
<223> OTHER INFORMATION: Synthetic

<400> SEQUENCE: 82

| | | | | | |
|---|---|---|---|---|---|
| ggatccatgg | agttcgttaa | caaacagttc | aactataaag | acccagttaa | cggtgttgac | 60 |
| attgcttaca | tcaaaatccc | gaacgctggc | cagatgcagc | cggtaaaggc | attcaaaatc | 120 |
| cacaacaaaa | tctgggttat | cccggaacgt | gataccttta | ctaacccgga | agaaggtgac | 180 |
| ctgaacccgc | caccggaagc | gaaacaggtg | ccggtatctt | actatgactc | cacctacctg | 240 |
| tctaccgata | acgaaaagga | caactacctg | aaaggtgtta | ctaaactgtt | cgagcgtatt | 300 |
| tactccaccg | acctgggccg | tatgctgctg | actagcatcg | ttcgcggtat | cccgttctgg | 360 |
| ggcggttcta | ccatcgatac | cgaactgaaa | gtaatcgaca | ctaactgcat | caacgttatt | 420 |
| cagccggacg | gttcctatcg | ttccgaagaa | ctgaacctgg | tgatcatcgg | cccgtctgct | 480 |
| gatatcatcc | agttcgagtg | taagagcttt | ggtcacgaag | ttctgaacct | cacccgtaac | 540 |
| ggctacggtt | ccactcagta | catccgtttc | tctccggact | tcaccttcgg | ttttgaagaa | 600 |
| tccctggaag | tagacacgaa | cccactgctg | ggcgctggta | aattcgcaac | tgatcctgcg | 660 |
| gttaccctgg | ctcacgaact | gattcatgca | ggccaccgcc | tgtacggtat | cgccatcaat | 720 |
| ccgaaccgtg | tcttcaaagt | taacaccaac | gcgtattacg | agatgtccgg | tctggaagtt | 780 |
| agcttcgaag | aactgcgtac | ttttggcggt | cacgacgcta | aattcatcga | ctctctgcaa | 840 |
| gaaaacgagt | tccgtctgta | ctactataac | aagttcaaag | atatcgcatc | caccctgaac | 900 |
| aaagcgaaat | ccatcgtggg | taccactgct | tctctccagt | acatgaagaa | cgttttttaaa | 960 |
| gaaaaatacc | tgctcagcga | agacacctcc | ggcaaattct | ctgtagacaa | gttgaaattc | 1020 |
| gataaacttt | acaaaatgct | gactgaaatt | tacaccgaag | acaacttcgt | taagttcttt | 1080 |
| aaagttctga | accgcaaaac | ctatctgaac | ttcgacaagg | cagtattcaa | atcaacatcg | 1140 |
| gtgccgaaag | ttaactacac | tatctacgat | ggtttcaacc | tgcgtaacac | caacctggct | 1200 |
| gctaatttta | acggcagaa | cacggaaatc | aacaacatga | acttcacaaa | actgaaaaac | 1260 |
| ttcactggtc | tgttcgagtt | ttacaagctg | ctgtgcgtcg | acggcatcat | tacctccaaa | 1320 |
| actaaatctc | tgatagaagg | tagatatggc | ggtttcacgg | cgcacgcaa | atcagcgcgt | 1380 |
| aaattagcta | accaggcgct | agcgggcggt | ggcggtagcg | gcggtggcgg | tagcggcggt | 1440 |
| ggcggtagcg | cactagtgct | gcagtgtatc | aaggttaaca | actgggattt | attcttcagc | 1500 |
| ccgagtgaag | acaacttcac | caacgacctg | aacaaaggtg | aagaaatcac | ctcagatact | 1560 |
| aacatcgaag | cagccgaaga | aaacatctcg | ctggacctga | tccagcagta | ctacctgacc | 1620 |
| tttaatttcg | acaacgagcc | ggaaaacatt | tctatcgaaa | acctgagctc | tgatatcatc | 1680 |
| ggccagctgg | aactgatgcc | gaacatcgaa | cgtttcccaa | acggtaaaaa | gtacgagctg | 1740 |

```
gacaaatata ccatgttcca ctacctgcgc gcgcaggaat ttgaacacgg caaatcccgt    1800
atcgcactga ctaactccgt taacgaagct ctgctcaacc cgtcccgtgt ataccacttc    1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca agacgactt cgttggcgca ctgatcttct ccggtgcggt gatcctgctg    2100
gagttcatcc cggaaatcgc catcccggta ctgggcacct ttgctctggt ttcttacatt    2160
gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaaat gaagaagca ctggaaaaacc aggcggaagc taccaaggca    2340
atcattaact accagtacaa ccagtacacc gaggaagaaa aaacaacat caacttcaac    2400
atcgacgatc tgtcctctaa actgaacgaa tccatcaaca agctatgat caacatcaac    2460
aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccta    2640
tcgaccgaca tccctttca gctcagtaaa tatgtcgata ccaacgcct tttgtccact     2700
ctagactag                                                           2709
```

<210> SEQ ID NO 83
<211> LENGTH: 902
<212> TYPE: PRT
<213> ORGANISM: Artificial Sequence
<220> FEATURE:
<223> OTHER INFORMATION: Synthetic

<400> SEQUENCE: 83

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190
```

```
Asp Phe Thr Phe Gly Phe Glu Glu Ser Leu Glu Val Asp Thr Asn Pro
    195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Thr Gly Ala Arg Lys Ser Ala Arg Lys Leu Ala Asn
    450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605
```

```
Glu Ala Leu Leu Asn Pro Ser Arg Val Tyr Thr Phe Phe Ser Ser Asp
        610             615                 620
Tyr Val Lys Lys Val Asn Lys Ala Thr Glu Ala Met Phe Leu Gly
625                 630                 635                 640
Trp Val Glu Gln Leu Val Tyr Asp Phe Thr Asp Glu Thr Ser Glu Val
            645                 650                 655
Ser Thr Thr Asp Lys Ile Ala Asp Ile Thr Ile Ile Pro Tyr Ile
        660                 665                 670
Gly Pro Ala Leu Asn Ile Gly Asn Met Leu Tyr Lys Asp Asp Phe Val
            675                 680                 685
Gly Ala Leu Ile Phe Ser Gly Ala Val Ile Leu Leu Glu Phe Ile Pro
        690                 695                 700
Glu Ile Ala Ile Pro Val Leu Gly Thr Phe Ala Leu Val Ser Tyr Ile
705                 710                 715                 720
Ala Asn Lys Val Leu Thr Val Gln Thr Ile Asp Asn Ala Leu Ser Lys
                725                 730                 735
Arg Asn Glu Lys Trp Asp Glu Val Tyr Lys Tyr Ile Val Thr Asn Trp
            740                 745                 750
Leu Ala Lys Val Asn Thr Gln Ile Asp Leu Ile Arg Lys Lys Met Lys
        755                 760                 765
Glu Ala Leu Glu Asn Gln Ala Glu Ala Thr Lys Ala Ile Ile Asn Tyr
770                 775                 780
Gln Tyr Asn Gln Tyr Thr Glu Glu Lys Asn Asn Ile Asn Phe Asn
785                 790                 795                 800
Ile Asp Asp Leu Ser Ser Lys Leu Asn Glu Ser Ile Asn Lys Ala Met
            805                 810                 815
Ile Asn Ile Asn Lys Phe Leu Asn Gln Cys Ser Val Ser Tyr Leu Met
        820                 825                 830
Asn Ser Met Ile Pro Tyr Gly Val Lys Arg Leu Glu Asp Phe Asp Ala
            835                 840                 845
Ser Leu Lys Asp Ala Leu Leu Lys Tyr Ile Tyr Asp Asn Arg Gly Thr
        850                 855                 860
Leu Ile Gly Gln Val Asp Arg Leu Lys Asp Lys Val Asn Asn Thr Leu
865                 870                 875                 880
Ser Thr Asp Ile Pro Phe Gln Leu Ser Lys Tyr Val Asp Asn Gln Arg
                885                 890                 895
Leu Leu Ser Thr Leu Asp
            900

<210> SEQ ID NO 84
<211> LENGTH: 2709
<212> TYPE: DNA
<213> ORGANISM: Artificial Sequence
<220> FEATURE:
<223> OTHER INFORMATION: Synthetic

<400> SEQUENCE: 84
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc acctacctg     240 tctaccgata cgaaaagga caactacctg aaaggtgtta ctaaactgtt cgagcgtatt     300
tactccaccg acctgggccg tatgctgctg actagcatcg ttcgcggtat cccgttctgg     360
```

```
ggcggttcta ccatcgatac cgaactgaaa gtaatcgaca ctaactgcat caacgttatt      420
cagccggacg gttcctatcg ttccgaagaa ctgaacctgg tgatcatcgg cccgtctgct      480
gatatcatcc agttcgagtg taagagcttt ggtcacgaag ttctgaacct cacccgtaac      540
ggctacggtt ccactcagta catccgtttc tctccggact tcaccttcgg ttttgaagaa      600
tccctggaag tagacacgaa cccactgctg ggcgctggta aattcgcaac tgatcctgcg      660
gttaccctgg ctcacgaact gattcatgca ggccaccgcc tgtacggtat cgccatcaat      720
ccgaaccgtg tcttcaaagt taacaccaac gcgtattacg agatgtccgg tctggaagtt      780
agcttcgaag aactgcgtac ttttggcggt cacgacgcta aattcatcga ctctctgcaa      840
gaaaacgagt tccgtctgta ctactataac aagttcaaag atatcgcatc caccctgaac      900
aaagcgaaat ccatcgtggg taccactgct ctctccagt acatgaagaa cgttttaaa       960
gaaaatacc tgctcagcga agacacctcc ggcaaattct ctgtagacaa gttgaaattc     1020
gataaacttt acaaaatgct gactgaaatt tacaccgaag caacttcgt taagttcttt     1080
aaagttctga accgcaaaac ctatctgaac ttcgacaagg cagtattcaa aatcaacatc     1140
gtgccgaaag ttaactacac tatctacgat ggtttcaacc tgcgtaacac caacctggct     1200
gctaatttta acgccagaa cacggaaatc aacaacatga acttcacaaa actgaaaaac     1260
ttcactggtc tgttcgagtt ttacaagctg ctgtgcgtcg acggcatcat tacctccaaa     1320
actaaatctc tgatagaagg tagatatggc ggtttcacgg gcgcacgcaa atcagcgcgt     1380
aaacgtaaga accaggcgct agcgggcggt ggcggtagcg gcggtggcgg tagcggcggt     1440
ggcggtagcg cactagtgct gcagtgtatc aaggttaaca actgggattt attcttcagc     1500
ccgagtgaag acaacttcac caacgacctg aacaaggtg aagaaatcac ctcagatact     1560
aacatcgaag cagccgaaga aaacatctcg ctggacctga tccagcagta ctacctgacc     1620
tttaatttcg acaacgagcc ggaaaacatt tctatcgaaa acctgagctc tgatatcatc     1680
ggccagctgg aactgatgcc gaacatcgaa cgtttcccaa acggtaaaaa gtacgagctg     1740
gacaaatata ccatgttcca ctacctgcgc gcgcaggaat ttgaacacgg caaatcccgt     1800
atcgcactga ctaactccgt taacgaagct ctgctcaacc cgtcccgtgt ataccacttc     1860
ttctctagcg actacgtgaa aaaggtcaac aaagcgactg aagctgcaat gttcttgggt     1920
tgggttgaac agcttgttta tgattttacc gacgagacgt ccgaagtatc tactaccgac     1980
aaaattgcgg atatcactat catcatcccg tacatcggtc cggctctgaa cattggcaac     2040
atgctgtaca agacgacttt cgttggcgca ctgatcttct ccggtgcggt gatcctgctg     2100
gagttcatcc cggaaatcgc catcccggta ctgggcacct ttgctctggt ttcttacatt     2160
gcaaacaagg ttctgactgt acaaaccatc gacaacgcgc tgagcaaacg taacgaaaaa     2220
tgggatgaag tttacaaata tatcgtgacc aactggctgg ctaaggttaa tactcagatc     2280
gacctcatcc gcaaaaaat gaagaagca ctggaaaacc aggcggaagc taccaaggca     2340
atcattaact accagtacaa ccagtacacc gaggaagaaa aaacaacat caacttcaac     2400
atcgacgatc tgtcctctaa actgaacgaa tccatcaaca agctatgat caacatcaac     2460
aagttcctga accagtgctc tgtaagctat ctgatgaact ccatgatccc gtacggtgtt     2520
aaacgtctgg aggacttcga tgcgtctctg aaagacgccc tgctgaaata catttacgac     2580
aaccgtggca ctctgatcgg tcaggttgat cgtctgaagg acaaagtgaa caataccta     2640
tcgaccgaca tcccttttca gctcagtaaa tatgtcgata ccaacgcct tttgtccact     2700
ctagactag                                                             2709
```

<210> SEQ ID NO 85
<211> LENGTH: 902
<212> TYPE: PRT
<213> ORGANISM: Artificial Sequence
<220> FEATURE:
<223> OTHER INFORMATION: Synthetic

<400> SEQUENCE: 85

| Gly | Ser | Met | Glu | Phe | Val | Asn | Lys | Gln | Phe | Asn | Tyr | Lys | Asp | Pro | Val |
|---|---|---|---|---|---|---|---|---|---|---|---|---|---|---|---|
| 1 | | | | 5 | | | | | 10 | | | | | 15 | |

| Asn | Gly | Val | Asp | Ile | Ala | Tyr | Ile | Lys | Ile | Pro | Asn | Ala | Gly | Gln | Met |
| | | | 20 | | | | | 25 | | | | | 30 | | |

| Gln | Pro | Val | Lys | Ala | Phe | Lys | Ile | His | Asn | Lys | Ile | Trp | Val | Ile | Pro |
| | | | 35 | | | | | 40 | | | | | 45 | | |

| Glu | Arg | Asp | Thr | Phe | Thr | Asn | Pro | Glu | Glu | Gly | Asp | Leu | Asn | Pro | Pro |
| | 50 | | | | | 55 | | | | | 60 | | | | |

| Pro | Glu | Ala | Lys | Gln | Val | Pro | Val | Ser | Tyr | Tyr | Asp | Ser | Thr | Tyr | Leu |
| 65 | | | | | 70 | | | | | 75 | | | | | 80 |

| Ser | Thr | Asp | Asn | Glu | Lys | Asp | Asn | Tyr | Leu | Lys | Gly | Val | Thr | Lys | Leu |
| | | | | 85 | | | | | 90 | | | | | 95 | |

| Phe | Glu | Arg | Ile | Tyr | Ser | Thr | Asp | Leu | Gly | Arg | Met | Leu | Leu | Thr | Ser |
| | | | 100 | | | | | 105 | | | | | 110 | | |

| Ile | Val | Arg | Gly | Ile | Pro | Phe | Trp | Gly | Gly | Ser | Thr | Ile | Asp | Thr | Glu |
| | | | | 115 | | | | | 120 | | | | | 125 | |

| Leu | Lys | Val | Ile | Asp | Thr | Asn | Cys | Ile | Asn | Val | Ile | Gln | Pro | Asp | Gly |
| | 130 | | | | | 135 | | | | | 140 | | | | |

| Ser | Tyr | Arg | Ser | Glu | Glu | Leu | Asn | Leu | Val | Ile | Ile | Gly | Pro | Ser | Ala |
| 145 | | | | | 150 | | | | | 155 | | | | | 160 |

| Asp | Ile | Ile | Gln | Phe | Glu | Cys | Lys | Ser | Phe | Gly | His | Glu | Val | Leu | Asn |
| | | | | 165 | | | | | 170 | | | | | 175 | |

| Leu | Thr | Arg | Asn | Gly | Tyr | Gly | Ser | Thr | Gln | Tyr | Ile | Arg | Phe | Ser | Pro |
| | | | 180 | | | | | 185 | | | | | 190 | | |

| Asp | Phe | Thr | Phe | Gly | Phe | Glu | Glu | Ser | Leu | Glu | Val | Asp | Thr | Asn | Pro |
| | | | | 195 | | | | | 200 | | | | | 205 | |

| Leu | Leu | Gly | Ala | Gly | Lys | Phe | Ala | Thr | Asp | Pro | Ala | Val | Thr | Leu | Ala |
| | 210 | | | | | 215 | | | | | 220 | | | | |

| His | Glu | Leu | Ile | His | Ala | Gly | His | Arg | Leu | Tyr | Gly | Ile | Ala | Ile | Asn |
| 225 | | | | | 230 | | | | | 235 | | | | | 240 |

| Pro | Asn | Arg | Val | Phe | Lys | Val | Asn | Thr | Asn | Ala | Tyr | Tyr | Glu | Met | Ser |
| | | | | 245 | | | | | 250 | | | | | 255 | |

| Gly | Leu | Glu | Val | Ser | Phe | Glu | Glu | Leu | Arg | Thr | Phe | Gly | Gly | His | Asp |
| | | | 260 | | | | | 265 | | | | | 270 | | |

| Ala | Lys | Phe | Ile | Asp | Ser | Leu | Gln | Glu | Asn | Glu | Phe | Arg | Leu | Tyr | Tyr |
| | | | | 275 | | | | | 280 | | | | | 285 | |

| Tyr | Asn | Lys | Phe | Lys | Asp | Ile | Ala | Ser | Thr | Leu | Asn | Lys | Ala | Lys | Ser |
| | 290 | | | | | 295 | | | | | 300 | | | | |

| Ile | Val | Gly | Thr | Thr | Ala | Ser | Leu | Gln | Tyr | Met | Lys | Asn | Val | Phe | Lys |
| 305 | | | | | 310 | | | | | 315 | | | | | 320 |

| Glu | Lys | Tyr | Leu | Leu | Ser | Glu | Asp | Thr | Ser | Gly | Lys | Phe | Ser | Val | Asp |
| | | | | 325 | | | | | 330 | | | | | 335 | |

| Lys | Leu | Lys | Phe | Asp | Lys | Leu | Tyr | Lys | Met | Leu | Thr | Glu | Ile | Tyr | Thr |
| | | | 340 | | | | | 345 | | | | | 350 | | |

| Glu | Asp | Asn | Phe | Val | Lys | Phe | Phe | Lys | Val | Leu | Asn | Arg | Lys | Thr | Tyr |
| | | | | 355 | | | | | 360 | | | | | 365 | |

```
Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Thr Gly Ala Arg Lys Ser Ala Arg Lys Arg Lys Asn
    450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780
```

```
Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
            805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
            835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
            885                 890                 895

Leu Leu Ser Thr Leu Asp
            900

<210> SEQ ID NO 86
<211> LENGTH: 2889
<212> TYPE: DNA
<213> ORGANISM: Artificial Sequence
<220> FEATURE:
<223> OTHER INFORMATION: Synthetic

<400> SEQUENCE: 86
ggatccttgg tacgagatga cgttgactat caaattttcc gcgactttgc ggaaaataaa      60
ggtaagtttt tcgtcggcgc cacagacctg tccgtcaaaa ataagagagg ccagaacatc     120
ggtaacgcac tgagcaacgt ccctatgatt gattttagtg tagcggacgt taataaacgg     180
attgcaaccg tcgttgatcc gcagtatgct gtcagcgtca acatgctaa agcggaagtt      240
catacgttct attacgggca atataacggc ataacgatg tggctgataa agaaaatgaa      300
tatcgcgtgg tcgagcagaa caattacgaa ccgcacaaag cgtggggcgc gagtaattta     360
ggccgcctgg aggactataa catggcccgt ttcaataaat tcgtgaccga ggtagcaccg     420
atcgccccca cagatgctgg tgggggcctg gataacctaca agataaaaa ccgcttctct     480
agcttcgtgc gcattggcgc cggtcgtcag ctcgtgtacg agaagggtgt ctatcaccag     540
gaaggtaatg aaaaggggta cgacctccgt gatttgtccc aggcgtatcg ctacgctatt     600
gccggaaccc cgtataaaga tattaatatc gatcaaacca tgaataccga aggcctaatt     660
ggtttcggga atcataataa gcaatatagc gcagaagagc taaagcaggc cctcagccaa     720
gatgcgttaa ccaattacgg agtgttaggc gatagcggca gtccgctgtt tgccttcgat     780
aaacagaaaa atcaatgggt gtttctgggc acttatgatt attgggccgg atatggtaaa     840
aagagctggc aggaatggaa tatttataaa aaggaattcg cagacaaaat caagcagcat     900
gacaacgcag gtacggtgaa ggggaacggc aacatcact ggaagacgac cggcacgaat      960
agtcatatcg gatcgacggc cgttcgcctg gcgaacaatg agggcgatgc aaacaatggg    1020
caaaacgtga cctttgagga caacggtacc ctggtcctta accagaacat aaatcagggc    1080
gcggagggct tgttctttaa aggcgactat actgttaagg gagcaaacaa tgacatcacc    1140
tggttagggg ccggtattga cgttgcggat ggaaaaaagg tggtttggca ggttaaaaac    1200
cctaacgggg accggctggc aaaaatcggc aaagggacat tggaaattaa tggtaccggt    1260
gtgaatcagg gtcagctgaa agtgggagat gggaccgtga ttctgaacca gaaagcagac    1320
gctgacaaaa aggtgcaagc ctttagccaa gtaggaattg ttagtggtcg tggcacactc    1380
```

```
gtcttgaact caagcaacca aataaatccg gataacctgt actttggatt tcgtggcgga   1440
cgcctggatg ctaacgggaa tgatctgacc tttgaacata tccgtaacgt tgacgagggt   1500
gcgcgcatag ttaatcataa tactgaccat gcatcaacta tcaccttgac cgggaaaagt   1560
ctgattacaa acccaaactc tctgtcagta cattccatcc agaatgatta tgatgaagac   1620
gattactcat actattaccg gccgcgtaga ccaattccac aaggtaaaga tctttattac   1680
aaaaattacc gttattacgc attaaaatcc ggagggcggc tgaatgcacc tatgccggaa   1740
aatggcgtgg ccgaaaacaa tgactggatt tttatgggtt atactcaaga gaggctcgc   1800 aaaaatgcaa tgaaccataa aaataaccga aggatcggtg atttcggcgg attttttcgat  1860 gaggaaaatg gtaaaggtca aatggtgcg ctgaatctaa attttaacgg caaaagtgcc   1920
cagaaacgtt tccttctgac tggtggcgct aatctgaatg gtaaaatcag tgtgacgcag   1980
ggtaacgtgc tgctttctgg ccggccaact ccgcatgcac gtgattttgt aaataaatcg   2040
agcgctcgta aagatgcgca tttttctaaa aataacgagg tcgtgtttga agatgactgg   2100
ataaatcgca cctttaaagc ggcagaaatc gcggttaatc agagtgcgag cttttcatcg   2160
ggtaggaatg tatctgatat tacagcaaac attacagcca ctgataatgc gaaggtcaac   2220
ctgggttata aaacggtga tgaagtttgt gttcgatcgg attacacggg ctatgttacc   2280
tgcaacactg gcaatctgtc tgataaagcg cttaactctt ttgacgccac gcgcattaac   2340
gggaatgtga acctgaacca aaacgctgcc ttggtacttg gtaaggccgc gttgtggggt   2400
aaaattcagg gccagggcaa ctcccgtgtg tctctgaacc agcactcgaa gtggcacctg   2460
acgggggact cgcaggtgca caacttgtcc ctggccgata gccatattca ccttaacaat   2520
gcgtccgatg cccagtcagc taataaatat catacgatca aaatcaatca cctctctggc   2580
aacggtcact ttcactactt aacggattta gcaaaaaact tagggggataa agtcctggta   2640 aaagaatcag cgagcggaca ttatcagtta catgtacaga acaaaacagg cgagccaaat   2700
caggaaggcc ttgacttatt tgatgcttca tcggtacaag atcgttccag actgttcgtt   2760
tcactcgcga atcactacgt tgatctgggt gcgctgcgct atactataaa gacggaaaat   2820
ggcataacac gcctctataa tccctatgcc ggtaacggcc gtccggtgaa acctgctccc   2880
tgcgtcgac                                                          2889
```

<210> SEQ ID NO 87
<211> LENGTH: 4296
<212> TYPE: DNA
<213> ORGANISM: Artificial Sequence
<220> FEATURE:
<223> OTHER INFORMATION: Synthetic

<400> SEQUENCE: 87

```
ggatccttgg tacgagatga cgttgactat caaattttcc gcgactttgc ggaaaataaa     60
ggtaagtttt tcgtcggcgc cacagacctg tccgtcaaaa ataagagagg ccagaacatc    120
ggtaacgcac tgagcaacgt ccctatgatt gattttagtg tagcggacgt taataaacgg    180
attgcaaccg tcgttgatcc gcagtatgct gtcagcgtca acatgctaa agcggaagtt    240 catacgttct attacgggca atataacggc cataacgatg tggctgataa agaaaatgaa    300
tatcgcgtgg tcgagcagaa caattacgaa ccgcacaaag cgtggggcgc gagtaattta    360
ggccgcctgg aggactataa catggcccgt ttcaataaat tcgtgaccga ggtagcaccg    420
atcgccccca cagatgctgg tgggggcctg gatacctaca aagataaaaa ccgcttctct    480
```

```
agcttcgtgc gcattggcgc cggtcgtcag ctcgtgtacg agaagggtgt ctatcaccag      540
gaaggtaatg aaaaggggta cgacctccgt gatttgtccc aggcgtatcg ctacgctatt      600
gccggaaccc cgtataaaga tattaatatc gatcaaacca tgaataccga aggcctaatt      660
ggtttcggga atcataataa gcaatatagc gcagaagagc taaagcaggc cctcagccaa      720
gatgcgttaa ccaattacgg agtgttaggc gatagcggca gtccgctgtt tgccttcgat      780
aaacagaaaa atcaatgggt gtttctgggc acttatgatt attgggccgg atatggtaaa      840
aagagctggc aggaatggaa tatttataaa aaggaattcg cagacaaaat caagcagcat      900
gacaacgcag gtacggtgaa ggggaacggc gaacatcact ggaagacgac cggcacgaat      960
agtcatatcg gatcgacggc cgttcgcctg gcgaacaatg agggcgatgc aaacaatggg     1020
caaaacgtga cctttgagga caacggtacc ctggtcctta accagaacat aaatcagggc     1080
gcgggaggct tgttctttaa aggcgactat actgttaagg gagcaaacaa tgacatcacc     1140
tggttagggg ccggtattga cgttgcggat ggaaaaaagg tggtttggca ggttaaaaac     1200
cctaacgggg accggctggc aaaaatcggc aaagggacat tggaaattaa tggtaccggt     1260
gtgaatcagg gtcagctgaa agtgggagat gggaccgtga ttctgaacca gaaagcagac     1320
gctgacaaaa aggtgcaagc ctttagccaa gtaggaattg ttagtggtcg tggcacactc     1380
gtcttgaact caagcaacca aataaatccg gataacctgt actttggatt tcgtggcgga     1440
cgcctggatg ctaacgggaa tgatctgacc tttgaacata tccgtaacgt tgacgagggt     1500
gcgcgcatag ttaatcataa tactgaccat gcatcaacta tcaccttgac cgggaaaagt     1560
ctgattacaa acccaaactc tctgtcagta cattccatcc agaatgatta tgatgaagac     1620
gattactcat actattaccg gccgcgtaga ccaattccac aaggtaaaga tctttattac     1680
aaaaattacc gttattacgc attaaaatcc ggagggcggc tgaatgcacc tatgccggaa     1740
aatggcgtgg ccgaaaacaa tgactggatt tttatgggtt atactcaaga agaggctcgc     1800
aaaaatgcaa tgaaccataa aaataaccga aggatcggtg atttcggcgg attttttcgat     1860 gaggaaaatg gtaaaggtca caatggtgcg ctgaatctaa attttaacgg caaaagtgcc     1920
cagaaacgtt tccttctgac tggtggcgct aatctgaatg gtaaaatcag tgtgacgcag     1980
ggtaacgtgc tgctttctgg ccggccaact ccgcatgcac gtgattttgt aaataaatcg     2040
agcgctcgta agatgcgca ttttcctaaa aataacgagg tcgtgtttga agatgactgg     2100
ataaatcgca cctttaaagc ggcagaaatc gcggttaatc agagtgcgag cttttcatcg     2160
ggtaggaatg tatctgatat tacagcaaac attacagcca ctgataatgc gaaggtcaac     2220
ctgggttata aaaacggtga tgaagtttgt gttcgatcgg attacacggg ctatgttacc     2280
tgcaacactg gcaatctgtc tgataaagcg cttaactctt ttgacgccac gcgcattaac     2340
gggaatgtga acctgaacca aaacgctgcc ttggtacttg gtaaggccgc gttgtggggt     2400
aaaattcagg gccagggcaa ctcccgtgtg tctctgaacc agcactcgaa gtggcacctg     2460 acggggggact cgcaggtgca caacttgtcc ctggccgata gccatattca ccttaacaat     2520
gcgtccgatg cccagtcagc taataaaatat catacgatca aaatcaatca cctctctggc     2580
aacggtcact ttcactactt aacgatttta gcaaaaaact tagggataa agtcctggta     2640 aaagaatcag cgagcggaca ttatcagtta catgtacaga acaaaacagg cgagccaaat     2700
caggaaggcc ttgacttatt tgatgcttca tcggtacaag atcgttccag actgttcgtt     2760
tcactcgcga atcactacgt tgatctgggt gcgctgcgct atactataaa gacgaaaaat     2820
ggcataacac gcctctataa tccctatgcc ggtaacggcc gtccggtgaa acctgctccc     2880
```

```
tgcgtcgacg gcatcattac ctccaaaact aaatctctga tagaaggtag atttggcggt    2940
ttcacgggcg cacgcaaatc agcgcgtaaa cgtaagaacc aggcgctagc gggcggtggc    3000
ggtagcggcg gtggcggtag cggcggtggc ggtagcgcac tagtgctgca gtgtatcaag    3060
gttaacaact gggatttatt cttcagcccg agtgaagaca acttcaccaa cgacctgaac    3120
aaaggtgaag aaatcacctc agatactaac atcgaagcag ccgaagaaaa catctcgctg    3180
gacctgatcc agcagtacta cctgaccttt aatttcgaca acgagccgga aaacatttct    3240
atcgaaaacc tgagctctga tatcatcggc cagctggaac tgatgccgaa catcgaacgt    3300
ttcccaaacg gtaaaaagta cgagctggac aaatatacca tgttccacta cctgcgcgcg    3360
caggaatttg aacacggcaa atcccgtatc gcactgacta actccgttaa cgaagctctg    3420 ctcaaccccgt cccgtgtata caccttcttc tctagcgact acgtgaaaaa ggtcaacaaa    3480
gcgactgaag ctgcaatgtt cttgggttgg gttgaacagc ttgtttatga ttttaccgac    3540
gagacgtccg aagtatctac taccgacaaa attgcggata tcactatcat catcccgtac    3600
atcggtccgg ctctgaacat tggcaacatg ctgtacaaag acgacttcgt tggcgcactg    3660
atcttctccg gtgcggtgat cctgctggag ttcatcccgg aaatcgccat cccggtactg    3720
ggcacctttg ctctggtttc ttacattgca aacaaggttc tgactgtaca aaccatcgac    3780
aacgcgctga gcaaacgtaa cgaaaaatgg gatgaagttt acaaatatat cgtgaccaac    3840
tggctggcta aggttaatac tcagatcgac ctcatccgca aaaaaatgaa agaagcactg    3900
gaaaaccagg cggaagctac caaggcaatc attaactacc agtacaacca gtacaccgag    3960
gaagaaaaaa acaacatcaa cttcaacatc gacgatctgt cctctaaact gaacgaatcc    4020
atcaacaaag ctatgatcaa catcaacaag ttcctgaacc agtgctctgt aagctatctg    4080
atgaactcca tgatcccgta cggtgttaaa cgtctggagg acttcgatgc gtctctgaaa    4140
gacgccctgc tgaaatacat ttacgacaac cgtggcactc tgatcggtca ggttgatcgt    4200
ctgaaggaca aagtgaacaa taccttatcg accgacatcc cttttcagct cagtaaatat    4260
gtcgataacc aacgcctttt gtccactcta gactag                              4296
```

<210> SEQ ID NO 88
<211> LENGTH: 1431
<212> TYPE: PRT
<213> ORGANISM: Artificial Sequence
<220> FEATURE:
<223> OTHER INFORMATION: Synthetic

<400> SEQUENCE: 88

```
Gly Ser Leu Val Arg Asp Asp Val Asp Tyr Gln Ile Phe Arg Asp Phe
1               5                   10                  15

Ala Glu Asn Lys Gly Lys Phe Phe Val Gly Ala Thr Asp Leu Ser Val
            20                  25                  30

Lys Asn Lys Arg Gly Gln Asn Ile Gly Asn Ala Leu Ser Asn Val Pro
        35                  40                  45

Met Ile Asp Phe Ser Val Ala Asp Val Asn Lys Arg Ile Ala Thr Val
    50                  55                  60

Val Asp Pro Gln Tyr Ala Val Ser Val Lys His Ala Lys Ala Glu Val
65                  70                  75                  80

His Thr Phe Tyr Tyr Gly Gln Tyr Asn Gly His Asn Asp Val Ala Asp
                85                  90                  95

Lys Glu Asn Glu Tyr Arg Val Val Glu Gln Asn Asn Tyr Glu Pro His
            100                 105                 110
```

```
Lys Ala Trp Gly Ala Ser Asn Leu Gly Arg Leu Glu Asp Tyr Asn Met
            115                 120                 125

Ala Arg Phe Asn Lys Phe Val Thr Glu Val Ala Pro Ile Ala Pro Thr
    130                 135                 140

Asp Ala Gly Gly Leu Asp Thr Tyr Lys Asp Lys Asn Arg Phe Ser
145                 150                 155                 160

Ser Phe Val Arg Ile Gly Ala Gly Arg Gln Leu Val Tyr Glu Lys Gly
                165                 170                 175

Val Tyr His Gln Glu Gly Asn Glu Lys Gly Tyr Asp Leu Arg Asp Leu
                180                 185                 190

Ser Gln Ala Tyr Arg Tyr Ala Ile Ala Gly Thr Pro Tyr Lys Asp Ile
            195                 200                 205

Asn Ile Asp Gln Thr Met Asn Thr Glu Gly Leu Ile Gly Phe Gly Asn
    210                 215                 220

His Asn Lys Gln Tyr Ser Ala Glu Glu Leu Lys Gln Ala Leu Ser Gln
225                 230                 235                 240

Asp Ala Leu Thr Asn Tyr Gly Val Leu Gly Asp Ser Gly Ser Pro Leu
                245                 250                 255

Phe Ala Phe Asp Lys Gln Lys Asn Gln Trp Val Phe Leu Gly Thr Tyr
                260                 265                 270

Asp Tyr Trp Ala Gly Tyr Gly Lys Lys Ser Trp Gln Glu Trp Asn Ile
            275                 280                 285

Tyr Lys Lys Glu Phe Ala Asp Lys Ile Lys Gln His Asp Asn Ala Gly
    290                 295                 300

Thr Val Lys Gly Asn Gly Glu His His Trp Lys Thr Thr Gly Thr Asn
305                 310                 315                 320

Ser His Ile Gly Ser Thr Ala Val Arg Leu Ala Asn Asn Glu Gly Asp
                325                 330                 335

Ala Asn Asn Gly Gln Asn Val Thr Phe Glu Asp Asn Gly Thr Leu Val
                340                 345                 350

Leu Asn Gln Asn Ile Asn Gln Gly Ala Gly Gly Leu Phe Phe Lys Gly
            355                 360                 365

Asp Tyr Thr Val Lys Gly Ala Asn Asn Asp Ile Thr Trp Leu Gly Ala
    370                 375                 380

Gly Ile Asp Val Ala Asp Gly Lys Lys Val Val Trp Gln Val Lys Asn
385                 390                 395                 400

Pro Asn Gly Asp Arg Leu Ala Lys Ile Gly Lys Gly Thr Leu Glu Ile
                405                 410                 415

Asn Gly Thr Gly Val Asn Gln Gly Gln Leu Lys Val Gly Asp Gly Thr
                420                 425                 430

Val Ile Leu Asn Gln Lys Ala Asp Ala Asp Lys Lys Val Gln Ala Phe
            435                 440                 445

Ser Gln Val Gly Ile Val Ser Gly Arg Gly Thr Leu Val Leu Asn Ser
    450                 455                 460

Ser Asn Gln Ile Asn Pro Asp Asn Leu Tyr Phe Gly Phe Arg Gly Gly
465                 470                 475                 480

Arg Leu Asp Ala Asn Gly Asn Asp Leu Thr Phe Glu His Ile Arg Asn
                485                 490                 495

Val Asp Glu Gly Ala Arg Ile Val Asn His Asn Thr Asp His Ala Ser
                500                 505                 510

Thr Ile Thr Leu Thr Gly Lys Ser Leu Ile Thr Asn Pro Asn Ser Leu
            515                 520                 525
```

-continued

```
Ser Val His Ser Ile Gln Asn Asp Tyr Asp Glu Asp Tyr Ser Tyr
    530                 535                 540

Tyr Tyr Arg Pro Arg Arg Pro Ile Pro Gln Gly Lys Asp Leu Tyr Tyr
545                 550                 555                 560

Lys Asn Tyr Arg Tyr Tyr Ala Leu Lys Ser Gly Gly Arg Leu Asn Ala
                565                 570                 575

Pro Met Pro Glu Asn Gly Val Ala Glu Asn Asn Asp Trp Ile Phe Met
            580                 585                 590

Gly Tyr Thr Gln Glu Glu Ala Arg Lys Asn Ala Met Asn His Lys Asn
        595                 600                 605

Asn Arg Arg Ile Gly Asp Phe Gly Gly Phe Asp Glu Glu Asn Gly
    610                 615                 620

Lys Gly His Asn Gly Ala Leu Asn Leu Asn Phe Asn Gly Lys Ser Ala
625                 630                 635                 640

Gln Lys Arg Phe Leu Leu Thr Gly Gly Ala Asn Leu Asn Gly Lys Ile
                645                 650                 655

Ser Val Thr Gln Gly Asn Val Leu Leu Ser Gly Arg Pro Thr Pro His
                660                 665                 670

Ala Arg Asp Phe Val Asn Lys Ser Ser Ala Arg Lys Asp Ala His Phe
            675                 680                 685

Ser Lys Asn Asn Glu Val Val Phe Glu Asp Asp Trp Ile Asn Arg Thr
690                 695                 700

Phe Lys Ala Ala Glu Ile Ala Val Asn Gln Ser Ala Ser Phe Ser Ser
705                 710                 715                 720

Gly Arg Asn Val Ser Asp Ile Thr Ala Asn Ile Thr Ala Thr Asp Asn
                725                 730                 735

Ala Lys Val Asn Leu Gly Tyr Lys Asn Gly Asp Glu Val Cys Val Arg
            740                 745                 750

Ser Asp Tyr Thr Gly Tyr Val Thr Cys Asn Thr Gly Asn Leu Ser Asp
        755                 760                 765

Lys Ala Leu Asn Ser Phe Asp Ala Thr Arg Ile Asn Gly Asn Val Asn
770                 775                 780

Leu Asn Gln Asn Ala Ala Leu Val Leu Gly Lys Ala Ala Leu Trp Gly
785                 790                 795                 800

Lys Ile Gln Gly Gln Gly Asn Ser Arg Val Ser Leu Asn Gln His Ser
                805                 810                 815

Lys Trp His Leu Thr Gly Asp Ser Gln Val His Asn Leu Ser Leu Ala
            820                 825                 830

Asp Ser His Ile His Leu Asn Asn Ala Ser Asp Ala Gln Ser Ala Asn
        835                 840                 845

Lys Tyr His Thr Ile Lys Ile Asn His Leu Ser Gly Asn Gly His Phe
850                 855                 860

His Tyr Leu Thr Asp Leu Ala Lys Asn Leu Gly Asp Lys Val Leu Val
865                 870                 875                 880

Lys Glu Ser Ala Ser Gly His Tyr Gln Leu His Val Gln Asn Lys Thr
                885                 890                 895

Gly Glu Pro Asn Gln Glu Gly Leu Asp Leu Phe Asp Ala Ser Ser Val
            900                 905                 910

Gln Asp Arg Ser Arg Leu Phe Val Ser Leu Ala Asn His Tyr Val Asp
        915                 920                 925

Leu Gly Ala Leu Arg Tyr Thr Ile Lys Thr Glu Asn Gly Ile Thr Arg
    930                 935                 940

Leu Tyr Asn Pro Tyr Ala Gly Asn Gly Arg Pro Val Lys Pro Ala Pro
```

```
                    945                 950                 955                 960
            Cys Val Asp Gly Ile Ile Thr Ser Lys Thr Lys Ser Leu Ile Glu Gly
                                965                 970                 975
            Arg Phe Gly Gly Phe Thr Gly Ala Arg Lys Ser Ala Arg Lys Arg Lys
                                980                 985                 990
            Asn Gln Ala Leu Ala Gly Gly Gly Ser Gly Gly Gly Ser Gly
                                995                1000                1005
            Gly Gly Gly Ser Ala Leu Val Leu Gln Cys Ile Lys Val Asn Asn
                1010                1015                1020
            Trp Asp Leu Phe Phe Ser Pro Ser Glu Asp Asn Phe Thr Asn Asp
                1025                1030                1035
            Leu Asn Lys Gly Glu Glu Ile Thr Ser Asp Thr Asn Ile Glu Ala
                1040                1045                1050
            Ala Glu Glu Asn Ile Ser Leu Asp Leu Ile Gln Gln Tyr Tyr Leu
                1055                1060                1065
            Thr Phe Asn Phe Asp Asn Glu Pro Glu Asn Ile Ser Ile Glu Asn
                1070                1075                1080
            Leu Ser Ser Asp Ile Ile Gly Gln Leu Glu Leu Met Pro Asn Ile
                1085                1090                1095
            Glu Arg Phe Pro Asn Gly Lys Lys Tyr Glu Leu Asp Lys Tyr Thr
                1100                1105                1110
            Met Phe His Tyr Leu Arg Ala Gln Glu Phe Glu His Gly Lys Ser
                1115                1120                1125
            Arg Ile Ala Leu Thr Asn Ser Val Asn Glu Ala Leu Leu Asn Pro
                1130                1135                1140
            Ser Arg Val Tyr Thr Phe Phe Ser Ser Asp Tyr Val Lys Lys Val
                1145                1150                1155
            Asn Lys Ala Thr Glu Ala Ala Met Phe Leu Gly Trp Val Glu Gln
                1160                1165                1170
            Leu Val Tyr Asp Phe Thr Asp Glu Thr Ser Glu Val Ser Thr Thr
                1175                1180                1185
            Asp Lys Ile Ala Asp Ile Thr Ile Ile Ile Pro Tyr Ile Gly Pro
                1190                1195                1200
            Ala Leu Asn Ile Gly Asn Met Leu Tyr Lys Asp Asp Phe Val Gly
                1205                1210                1215
            Ala Leu Ile Phe Ser Gly Ala Val Ile Leu Leu Glu Phe Ile Pro
                1220                1225                1230
            Glu Ile Ala Ile Pro Val Leu Gly Thr Phe Ala Leu Val Ser Tyr
                1235                1240                1245
            Ile Ala Asn Lys Val Leu Thr Val Gln Thr Ile Asp Asn Ala Leu
                1250                1255                1260
            Ser Lys Arg Asn Glu Lys Trp Asp Glu Val Tyr Lys Tyr Ile Val
                1265                1270                1275
            Thr Asn Trp Leu Ala Lys Val Asn Thr Gln Ile Asp Leu Ile Arg
                1280                1285                1290
            Lys Lys Met Lys Glu Ala Leu Glu Asn Gln Ala Glu Ala Thr Lys
                1295                1300                1305
            Ala Ile Ile Asn Tyr Gln Tyr Asn Gln Tyr Thr Glu Glu Glu Lys
                1310                1315                1320
            Asn Asn Ile Asn Phe Asn Ile Asp Asp Leu Ser Ser Lys Leu Asn
                1325                1330                1335
            Glu Ser Ile Asn Lys Ala Met Ile Asn Ile Asn Lys Phe Leu Asn
                1340                1345                1350
```

```
Gln Cys Ser Val Ser Tyr Leu Met Asn Ser Met Ile Pro Tyr Gly
    1355                1360                1365

Val Lys Arg Leu Glu Asp Phe Asp Ala Ser Leu Lys Asp Ala Leu
1370                1375                1380

Leu Lys Tyr Ile Tyr Asp Asn Arg Gly Thr Leu Ile Gly Gln Val
    1385                1390                1395

Asp Arg Leu Lys Asp Lys Val Asn Asn Thr Leu Ser Thr Asp Ile
1400                1405                1410

Pro Phe Gln Leu Ser Lys Tyr Val Asp Asn Gln Arg Leu Leu Ser
    1415                1420                1425

Thr Leu Asp
    1430

<210> SEQ ID NO 89
<211> LENGTH: 1357
<212> TYPE: DNA
<213> ORGANISM: Artificial Sequence
<220> FEATURE:
<223> OTHER INFORMATION: Synthetic

<400> SEQUENCE: 89
gctagcgggc ggtggcggta gcggcggtgg cggtagcggc ggtggcggta gcgcactagt    60
gctgcagtgt atcaaggtta caactgggga tttattcttc agcccgagtg aagacaactt   120
caccaacgac ctgaacaaag gtgaagaaat cacctcagat actaacatcg aagcagccga   180
agaaaacatc tcgctggacc tgatccagca gtactacctg acctttaatt tcgacaacga   240
gccggaaaac atttctatcg aaaacctgag ctctgatatc atcggccagc tggaactgat   300
gccgaacatc gaacgtttcc caaacggtaa aaagtacgag ctggacaaat ataccatgtt   360
ccactacctg cgcgcgcagg aatttgaaca cggcaaatcc cgtatcgcac tgactaactc   420
cgttaacgaa gctctgctca acccgtcccg tgtatacacc ttcttctcta gcgactacgt   480
gaaaaaggtc aacaaagcga ctgaagctgc aatgttcttg ggttgggttg aacagcttgt   540
ttatgatttt accgacgaga cgtccgaagt atctactacc gacaaaattg cggatatcac   600
tatcatcatc ccgtacatcg gtccggctct gaacattggc aacatgctgt acaaagacga   660
cttcgttggc gcactgatct ctctccggtgc ggtgatcctg ctggagttca tcccggaaat   720
cgccatcccg gtactgggca cctttgctct ggtttcttac attgcaaaca ggttctgac   780 tgtacaaacc atcgacaacg cgctgagcaa acgtaacgaa aaatgggatg aagtttacaa   840
atatatcgtg accaactggc tggctaaggt taatactcag atcgacctca tccgcaaaaa   900
aatgaaagaa gcactggaaa accaggcgga agctaccaag gcaatcatta ctaccagta   960 caaccagtac accgaggaag aaaaaaacaa catcaacttc aacatcgacg atctgtcctc  1020
taaactgaac gaatccatca acaaagctat gatcaacatc aacaagttcc tgaaccagtg  1080
ctctgtaagc tatctgatga ctccatgat cccgtacggt gttaaacgtc tggaggactt  1140
cgatgcgtct ctgaaagacg ccctgctgaa atacatttac gacaaccgtg gcactctgat  1200
cggtcaggtt gatcgtctga aggacaaagt gaacaatacc ttatcgaccg acatcccttt  1260
tcagctcagt aaatatgtcg ataaccaacg ccttttgtcc actctagaaa tagaaggtag  1320
aagtgggcac catcaccatc accattaatg aaagctt                          1357

<210> SEQ ID NO 90
<211> LENGTH: 2745
<212> TYPE: DNA
```

<213> ORGANISM: Artificial Sequence
<220> FEATURE:
<223> OTHER INFORMATION: Synthetic

<400> SEQUENCE: 90

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gatacctta ctaacccgga agaaggtgac      180
ctgaacccgc caccggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa    600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaaagcgaaat ccatcgtggg taccactgct tctctccagt acatgaagaa cgttttaaa    960
gaaaaatacc tgctcagcga agacacctcc ggcaaattct ctgtagacaa gttgaaattc   1020
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa    1320
actaaatctc tgatagaagg tagatttggc ggtttcacgg gcgcacgcaa atcagcgcgt    1380
aaacgtaaga accaggcgct agcgggcggt ggcggtagcg gcggtggcgg tagcggcggt   1440
ggcggtagcg cactagtgct gcagtgtatc aaggttaaca actgggattt attcttcagc    1500
ccgagtgaag acaacttcac caacgacctg aacaaaggtg aagaaatcac ctcagatact    1560
aacatcgaag cagccgaaga aaacatctcg ctggacctga tccagcagta ctacctgacc    1620
tttaatttcg acaacgagcc ggaaaacatt tctatcgaaa acctgagctc tgatatcatc    1680
ggccagctgg aactgatgcc gaacatcgaa cgtttcccaa acggtaaaaa gtacgagctg   1740
gacaaatata ccatgttcca ctacctgcgc gcgcaggaat ttgaacacgg caaatcccgt    1800
atcgcactga ctaactccgt taacgaagct ctgctcaacc cgtcccgtgt atacaccttc   1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca agacgacttc cgttggcgca ctgatcttct ccggtgcggt gatcctgctg    2100
gagttcatcc cggaaatcgc catcccggta ctgggcacct ttgctctggt tcttacatt    2160
gcaaacaagg ttctgactgt acaaaccatc gacaacgcgc tgagcaaacg taacgaaaaa    2220
```

```
tgggatgaag tttacaaata tatcgtgacc aactggctgg ctaaggttaa tactcagatc   2280
gacctcatcc gcaaaaaaat gaaagaagca ctggaaaacc aggcggaagc taccaaggca   2340
atcattaact accagtacaa ccagtacacc gaggaagaaa aaaacaacat caacttcaac   2400
atcgacgatc tgtcctctaa actgaacgaa tccatcaaca aagctatgat caacatcaac   2460
aagttcctga accagtgctc tgtaagctat ctgatgaact ccatgatccc gtacggtgtt   2520
aaacgtctgg aggacttcga tgcgtctctg aaagacgccc tgctgaaata catttacgac   2580
aaccgtggca ctctgatcgg tcaggttgat cgtctgaagg acaaagtgaa caataccta   2640 tcgaccgaca tccctttca gctcagtaaa tatgtcgata accaacgcct tttgtccact   2700
ctagaaatag aaggtagaag tgggcaccat caccatcacc attaa              2745
```

<210> SEQ ID NO 91
<211> LENGTH: 914
<212> TYPE: PRT
<213> ORGANISM: Artificial Sequence
<220> FEATURE:
<223> OTHER INFORMATION: Synthetic

<400> SEQUENCE: 91

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270
```

```
Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
                340                 345                 350

Glu Asp Asn Phe Val Lys Phe Lys Val Leu Asn Arg Lys Thr Tyr
                355                 360                 365

Leu Asn Phe Asp Lys Ala Val Phe Lys Ile Asn Ile Val Pro Lys Val
        370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Lys Asn
        450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
                500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
        530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
                580                 585                 590

Glu Phe Glu His Gly Lys Ser Arg Ile Ala Leu Thr Asn Ser Val Asn
                595                 600                 605

Glu Ala Leu Leu Asn Pro Ser Arg Val Tyr Thr Phe Phe Ser Ser Asp
        610                 615                 620

Tyr Val Lys Lys Val Asn Lys Ala Thr Glu Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
                660                 665                 670

Gly Pro Ala Leu Asn Ile Gly Asn Met Leu Tyr Lys Asp Asp Phe Val
        675                 680                 685
```

Gly Ala Leu Ile Phe Ser Gly Ala Val Ile Leu Glu Phe Ile Pro
    690             695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
            725                 730                 735

Arg Asn Glu Lys Trp Asp Glu Val Tyr Lys Tyr Ile Val Thr Asn Trp
        740                 745                 750

Leu Ala Lys Val Asn Thr Gln Ile Asp Leu Ile Arg Lys Lys Met Lys
            755                 760                 765

Glu Ala Leu Glu Asn Gln Ala Glu Ala Thr Lys Ala Ile Ile Asn Tyr
770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Glu Ile Glu Gly Arg Ser Gly His His His
            900                 905                 910

His His

<210> SEQ ID NO 92
<211> LENGTH: 619
<212> TYPE: DNA
<213> ORGANISM: Artificial Sequence
<220> FEATURE:
<223> OTHER INFORMATION: Synthetic

<400> SEQUENCE: 92
gctagcgggc ggtggcggta gcggcggtgg cggtagcggc ggtggcggta gcgcactagt      60
gctgcagtgt atcaatctgg attgggacgt aatccgtgat aagaccaaaa caaaaatcga    120
gtctttgaaa gaacacggcc cgatcaaaaa taagatgtct gaatcaccca ataaaactgt    180
ttcggaggaa aaagcgaaac agtatttgga agagtttcat caaaccgcgc ttgaacatcc    240
ggagctcagt gaactgaaaa cagtgacggg aacgaatcct gttttttgcag gcgcaaacta    300 tgcggcttgg gccgtgaatg ttgcccaagt aattgatagt gagaccgcag acaacctgga    360
aaagacgacc gcagcgttaa gcattttacc ggggattggt tccgtgatgg gtatagcgga    420
tggagcggtc caccataaca ctgaggaaat tgtcgcccag tcaatcgctc tgagttccct    480
gatggttgca caggctatcc cactcgtggg ggaactggtt gacataggtt tcgccgccta    540
caacttcgta gaaagcatta ttaatctttt tcaggtggtg cataacagct acaaccgccc    600
tctagaatga taaaagctt                                                  619

<210> SEQ ID NO 93
<211> LENGTH: 1971

<212> TYPE: DNA
<213> ORGANISM: Artificial Sequence
<220> FEATURE:
<223> OTHER INFORMATION: Synthetic

<400> SEQUENCE: 93

```
ggatccatgg agttcgttaa caaacagttc aactataaag acccagttaa cggtgttgac       60
attgcttaca tcaaaatccc gaacgctggc cagatgcagc cggtaaaggc attcaaaatc      120
cacaacaaaa tctgggttat cccggaacgt gataccttta ctaacccgga agaaggtgac      180
ctgaacccgc accggaagc gaaacaggtg ccggtatctt actatgactc cacctacctg       240
tctaccgata cgaaaagga caactacctg aaaggtgtta ctaaactgtt cgagcgtatt       300
tactccaccg acctgggccg tatgctgctg actagcatcg ttcgcggtat cccgttctgg      360
ggcggttcta ccatcgatac cgaactgaaa gtaatcgaca ctaactgcat caacgttatt      420
cagccggacg gttcctatcg ttccgaagaa ctgaacctgg tgatcatcgg cccgtctgct      480
gatatcatcc agttcgagtg taagagcttt ggtcacgaag ttctgaacct cacccgtaac      540
ggctacggtt ccactcagta catccgtttc tctccggact tcaccttcgg ttttgaagaa      600
tccctggaag tagacacgaa cccactgctg gcgctggta aattcgcaac tgatcctgcg       660
gttaccctgg ctcacgaact gattcatgca ggccaccgcc tgtacggtat cgccatcaat      720
ccgaaccgtg tcttcaaagt taacaccaac gcgtattacg agatgtccgg tctggaagtt      780
agcttcgaag aactgcgtac ttttggcggt cacgacgcta aattcatcga ctctctgcaa      840
gaaaacgagt tccgtctgta ctactataac aagttcaaag atatcgcatc caccctgaac      900
aaagcgaaat ccatcgtggg taccactgct tctctccagt acatgaagaa cgttttaaa      960
gaaaaatacc tgctcagcga agacacctcc ggcaaattct ctgtagacaa gttgaaattc     1020
gataaacttt acaaaatgct gactgaaatt tacaccgaag acaacttcgt taagttcttt     1080
aaagttctga accgcaaaac ctatctgaac ttcgacaagg cagtattcaa atcaacatc      1140
gtgccgaaag ttaactacac tatctacgat ggtttcaacc tgcgtaacac caacctggct     1200
gctaatttta cggccagaa cacgaaatc aacaacatga cttcacaaa actgaaaaac         1260
ttcactggtc tgttcgagtt ttacaagctg ctgtgcgtcg acggcatcat tacctccaaa     1320
actaaatctc tgatagaagg tagatacggt ggtttcctgg cgctagcggg cggtggcggt     1380
agcggcggtg gcggtagcgg cggtggcggt agcgcactag tgctgcagtg tatcaatctg     1440
gattgggacg taatccgtga taagaccaaa acaaaaatcg agtctttgaa agaacacggc     1500
ccgatcaaaa ataagatgtc tgaatcaccc aataaaactg tttcggagga aaaagcgaaa     1560
cagtatttgg aagagtttca tcaaaccgcg cttgaacatc cggagctcag tgaactgaaa     1620
acagtgacgg gaacgaatcc tgttttttgca ggcgcaaact atgcggcttg ggccgtgaat     1680
gttgcccaag taattgatag tgagaccgca gacaacctgg aaaagacgac cgcagcgtta     1740
agcattttac cggggattgg ttccgtgatg ggtatagcgg atggagcggt ccaccataac     1800
actgaggaaa ttgtcgccca gtcaatcgct ctgagttccc tgatggttgc acaggctatc     1860
ccactcgtgg gggaactggt tgacataggt ttcgccgcct acaacttcgt agaaagcatt     1920
attaatcttt tcaggtggt gcataacagc tacaaccgcc tctagaatg a                1971
```

<210> SEQ ID NO 94
<211> LENGTH: 656
<212> TYPE: PRT
<213> ORGANISM: Artificial Sequence
<220> FEATURE:

-continued

<223> OTHER INFORMATION: Synthetic

<400> SEQUENCE: 94

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400
```

| | | | | | | | | | | | | |
|---|---|---|---|---|---|---|---|---|---|---|---|---|
|Ala|Asn|Phe|Asn|Gly|Gln|Asn|Thr|Glu|Ile|Asn|Asn|Met|Asn|Phe|Thr|
| | | | |405| | | |410| | | |415| | | |

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
            435                 440                 445

Tyr Gly Gly Phe Leu Ala Leu Ala Gly Gly Gly Ser Gly Gly Gly
        450                 455                 460

Gly Ser Gly Gly Gly Ser Ala Leu Val Leu Gln Cys Ile Asn Leu
465                 470                 475                 480

Asp Trp Asp Val Ile Arg Asp Lys Thr Lys Thr Lys Ile Glu Ser Leu
                485                 490                 495

Lys Glu His Gly Pro Ile Lys Asn Lys Met Ser Glu Ser Pro Asn Lys
            500                 505                 510

Thr Val Ser Glu Glu Lys Ala Lys Gln Tyr Leu Glu Glu Phe His Gln
            515                 520                 525

Thr Ala Leu Glu His Pro Glu Leu Ser Glu Leu Lys Thr Val Thr Gly
            530                 535                 540

Thr Asn Pro Val Phe Ala Gly Ala Asn Tyr Ala Ala Trp Ala Val Asn
545                 550                 555                 560

Val Ala Gln Val Ile Asp Ser Glu Thr Ala Asp Asn Leu Glu Lys Thr
                565                 570                 575

Thr Ala Ala Leu Ser Ile Leu Pro Gly Ile Gly Ser Val Met Gly Ile
            580                 585                 590

Ala Asp Gly Ala Val His His Asn Thr Glu Glu Ile Val Ala Gln Ser
            595                 600                 605

Ile Ala Leu Ser Ser Leu Met Val Ala Gln Ala Ile Pro Leu Val Gly
            610                 615                 620

Glu Leu Val Asp Ile Gly Phe Ala Ala Tyr Asn Phe Val Glu Ser Ile
625                 630                 635                 640

Ile Asn Leu Phe Gln Val Val His Asn Ser Tyr Asn Arg Pro Leu Glu
                645                 650                 655

<210> SEQ ID NO 95
<211> LENGTH: 1329
<212> TYPE: DNA
<213> ORGANISM: Artificial Sequence
<220> FEATURE:
<223> OTHER INFORMATION: Synthetic

<400> SEQUENCE: 95

```
ggatccatgc ctattactat taacaatttt cgttatagcg atcccgtcaa caatgacacc      60
attatcatga tggaaccgcc atattgcaaa ggactggaca tttactataa agccttcaag     120
attactgacc gcatttggat tgttccagag cgttacgagt tcgggacgaa accagaagat     180
tttaaccccg cttcatcgct gatcgaagga gcatcagagt attacgatcc gaactatctg     240
cgtacggaca gcgataaaga ccgcttctta cagaccatgg tcaaactttt taaccgtatt     300
aagaacaatg tggccggaga agcactcttg ataagatta tcaacgcgat tccatacctg     360
ggcaattctt acagcctgct ggataaattt gacacaaata gtaattcagt cagctttaac     420
ctgttagaac aagatccgag tggcgcaacc acgaagtctg ccatgctgac aaatctgatc     480
atttttggtc aggtcctgt actgaataaa aatgaagtac gcggcatcgt tctccgcgtg     540
gacaataaga actacttccc atgccgtgac ggcttcggtt cgatcatgca gatggctttc     600
tgtccggagt acgttccgac gtttgataat gttattgaga atatcacgag tttaacaatc     660
```

```
ggtaagtcaa atatttttca agatccggcc cttctcctta tgcatgaact gattcacgtg    720
ctgcacggct tatatggtat gcaagtgtcc tcgcatgaaa tcattccgtc caaacaggaa    780
atttatatgc agcataccta cccgatttca gctgaagagt tgtttacgtt tggtggccag    840
gacgcgaatt tgatctccat cgacatcaaa acgatctgt atgagaaaac attaaatgac     900
tataaagcga ttgcgaacaa actgtctcag gtgactagct gcaacgatcc taacattgat    960
attgattcct acaaacaaat ttatcaacag aaataccagt tcgataaaga cagcaatggt   1020
cagtatatcg taaacgaaga taaatttcag atcctgtata acagcattat gtatggcttt   1080
accgaaattg agttggggaa gaaatttaac attaaaaccc gtctgtctta ttttagtatg   1140
aaccatgatc cggtgaaaat ccccaatctg cttgatgata ccatttataa tgataccgaa   1200
gggttcaaca ttgaatctaa ggatctgaaa tccgaataca aaggccaaaa tatgcgtgtt   1260
aatactaacg ctttccgtaa tgttgatggt agtggactcg tctcgaaact gattgggttg   1320
tgtgtcgac                                                           1329

<210> SEQ ID NO 96
<211> LENGTH: 2736
<212> TYPE: DNA
<213> ORGANISM: Artificial Sequence
<220> FEATURE:
<223> OTHER INFORMATION: Synthetic

<400> SEQUENCE: 96
ggatccatgc ctattactat taacaatttt cgttatagcg atcccgtcaa caatgacacc     60
attatcatga tggaaccgcc atattgcaaa ggactggaca tttactataa agccttcaag    120
attactgacc gcatttggat tgttccagag cgttacgagt tcgggacgaa accagaagat    180
tttaacccgc cttcatcgct gatcgaagga gcatcagagt attacgatcc gaactatctg    240
cgtacggaca gcgataaaga ccgcttctta cagaccatgg tcaaactttt taaccgtatt    300
aagaacaatg tggccggaga agcactcttg ataagatta tcaacgcgat tccatacctg    360
ggcaattctt acagcctgct ggataaattt gacacaaata gtaattcagt cagctttaac    420
ctgttagaac aagatccgag tggcgcaacc acgaagtctg ccatgctgac aaatctgatc    480 attttttggtc caggtcctgt actgaataaa aatgaagtac gcggcatcgt tctccgcgtg    540
gacaataaga actacttccc atgccgtgac ggcttcggtt cgatcatgca gatggctttc    600
tgtccggagt acgttccgac gtttgataat gttattgaga atatcacgag tttaacaatc    660
ggtaagtcaa atatttttca agatccggcc cttctcctta tgcatgaact gattcacgtg    720
ctgcacggct tatatggtat gcaagtgtcc tcgcatgaaa tcattccgtc caaacaggaa    780
atttatatgc agcataccta cccgatttca gctgaagagt tgtttacgtt tggtggccag    840
gacgcgaatt tgatctccat cgacatcaaa acgatctgt atgagaaaac attaaatgac     900
tataaagcga ttgcgaacaa actgtctcag gtgactagct gcaacgatcc taacattgat    960
attgattcct acaaacaaat ttatcaacag aaataccagt tcgataaaga cagcaatggt   1020
cagtatatcg taaacgaaga taaatttcag atcctgtata acagcattat gtatggcttt   1080
accgaaattg agttggggaa gaaatttaac attaaaaccc gtctgtctta ttttagtatg   1140
aaccatgatc cggtgaaaat ccccaatctg cttgatgata ccatttataa tgataccgaa   1200
gggttcaaca ttgaatctaa ggatctgaaa tccgaataca aaggccaaaa tatgcgtgtt   1260
aatactaacg ctttccgtaa tgttgatggt agtggactcg tctcgaaact gattgggttg   1320
```

```
tgtgtcgacg gcatcattac ctccaaaact aaatctctga tagaaggtag atttggcggt    1380
ttcacgggcg cacgcaaatc agcgcgtaaa cgtaagaacc aggcgctagc gggcggtggc    1440
ggtagcggcg gtggcggtag cggcggtggc ggtagcgcac tagtgctgca gtgtatcaag    1500
gttaacaact gggatttatt cttcagcccg agtgaagaca acttcaccaa cgacctgaac    1560
aaaggtgaag aaatcacctc agatactaac atcgaagcag ccgaagaaaa catctcgctg    1620
gacctgatcc agcagtacta cctgaccttt aatttcgaca acgagccgga aaacatttct    1680
atcgaaaacc tgagctctga tatcatcggc cagctggaac tgatgccgaa catcgaacgt    1740
ttcccaaacg gtaaaaagta cgagctggac aaatatacca tgttccacta cctgcgcgcg    1800
caggaatttg aacacggcaa atcccgtatc gcactgacta actccgttaa cgaagctctg    1860
ctcaacccgt cccgtgtata caccttcttc tctagcgact acgtgaaaaa ggtcaacaaa    1920
gcgactgaag ctgcaatgtt cttgggttgg gttgaacagc ttgtttatga ttttaccgac    1980
gagacgtccg aagtatctac taccgacaaa attgcggata tcactatcat catcccgtac    2040
atcggtccgg ctctgaacat tggcaacatg ctgtacaaag acgacttcgt tggcgcactg    2100
atcttctccg gtgcggtgat cctgctggag ttcatcccgg aaatcgccat cccggtactg    2160
ggcacctttg ctctggtttc ttacattgca aacaaggttc tgactgtaca aaccatcgac    2220
aacgcgctga gcaaacgtaa cgaaaaatgg gatgaagttt acaaatatat cgtgaccaac    2280
tggctggcta aggttaatac tcagatcgac ctcatccgca aaaaaatgaa agaagcactg    2340
gaaaaccagg cggaagctac caaggcaatc attaactacc agtacaacca gtacaccgag    2400
gaagaaaaaa acaacatcaa cttcaacatc gacgatctgt cctctaaact gaacgaatcc    2460
atcaacaaag ctatgatcaa catcaacaag ttcctgaacc agtgctctgt aagctatctg    2520
atgaactcca tgatcccgta cggtgttaaa cgtctggagg acttcgatgc gtctctgaaa    2580
gacgccctgc tgaaatacat ttacgacaac cgtggcactc tgatcggtca ggttgatcgt    2640
ctgaaggaca aagtgaacaa taccttatcg accgacatcc cttttcagct cagtaaatat    2700
gtcgataacc aacgcctttt gtccactcta gactag                              2736
```

<210> SEQ ID NO 97  
<211> LENGTH: 911  
<212> TYPE: PRT  
<213> ORGANISM: Artificial Sequence  
<220> FEATURE:  
<223> OTHER INFORMATION: Synthetic

<400> SEQUENCE: 97

```
Gly Ser Met Pro Ile Thr Ile Asn Asn Phe Arg Tyr Ser Asp Pro Val
1               5                   10                  15

Asn Asn Asp Thr Ile Ile Met Met Glu Pro Pro Tyr Cys Lys Gly Leu
            20                  25                  30

Asp Ile Tyr Tyr Lys Ala Phe Lys Ile Thr Asp Arg Ile Trp Ile Val
        35                  40                  45

Pro Glu Arg Tyr Glu Phe Gly Thr Lys Pro Glu Asp Phe Asn Pro Pro
    50                  55                  60

Ser Ser Leu Ile Glu Gly Ala Ser Glu Tyr Tyr Asp Pro Asn Tyr Leu
65                  70                  75                  80

Arg Thr Asp Ser Asp Lys Asp Arg Phe Leu Gln Thr Met Val Lys Leu
                85                  90                  95

Phe Asn Arg Ile Lys Asn Asn Val Ala Gly Glu Ala Leu Leu Asp Lys
            100                 105                 110
```

```
Ile Ile Asn Ala Ile Pro Tyr Leu Gly Asn Ser Tyr Ser Leu Leu Asp
            115                 120                 125

Lys Phe Asp Thr Asn Ser Asn Ser Val Ser Phe Asn Leu Leu Glu Gln
130                 135                 140

Asp Pro Ser Gly Ala Thr Thr Lys Ser Ala Met Leu Thr Asn Leu Ile
145                 150                 155                 160

Ile Phe Gly Pro Gly Pro Val Leu Asn Lys Asn Glu Val Arg Gly Ile
            165                 170                 175

Val Leu Arg Val Asp Asn Lys Asn Tyr Phe Pro Cys Arg Asp Gly Phe
            180                 185                 190

Gly Ser Ile Met Gln Met Ala Phe Cys Pro Glu Tyr Val Pro Thr Phe
            195                 200                 205

Asp Asn Val Ile Glu Asn Ile Thr Ser Leu Thr Ile Gly Lys Ser Lys
210                 215                 220

Tyr Phe Gln Asp Pro Ala Leu Leu Leu Met His Glu Leu Ile His Val
225                 230                 235                 240

Leu His Gly Leu Tyr Gly Met Gln Val Ser Ser His Glu Ile Ile Pro
            245                 250                 255

Ser Lys Gln Glu Ile Tyr Met Gln His Thr Tyr Pro Ile Ser Ala Glu
            260                 265                 270

Glu Leu Phe Thr Phe Gly Gly Gln Asp Ala Asn Leu Ile Ser Ile Asp
            275                 280                 285

Ile Lys Asn Asp Leu Tyr Glu Lys Thr Leu Asn Asp Tyr Lys Ala Ile
            290                 295                 300

Ala Asn Lys Leu Ser Gln Val Thr Ser Cys Asn Asp Pro Asn Ile Asp
305                 310                 315                 320

Ile Asp Ser Tyr Lys Gln Ile Tyr Gln Gln Lys Tyr Gln Phe Asp Lys
            325                 330                 335

Asp Ser Asn Gly Gln Tyr Ile Val Asn Glu Asp Lys Phe Gln Ile Leu
            340                 345                 350

Tyr Asn Ser Ile Met Tyr Gly Phe Thr Glu Ile Glu Leu Gly Lys Lys
            355                 360                 365

Phe Asn Ile Lys Thr Arg Leu Ser Tyr Phe Ser Met Asn His Asp Pro
370                 375                 380

Val Lys Ile Pro Asn Leu Leu Asp Asp Thr Ile Tyr Asn Asp Thr Glu
385                 390                 395                 400

Gly Phe Asn Ile Glu Ser Lys Asp Leu Lys Ser Glu Tyr Lys Gly Gln
            405                 410                 415

Asn Met Arg Val Asn Thr Asn Ala Phe Arg Asn Val Asp Gly Ser Gly
            420                 425                 430

Leu Val Ser Lys Leu Ile Gly Leu Cys Val Asp Gly Ile Ile Thr Ser
            435                 440                 445

Lys Thr Lys Ser Leu Ile Glu Gly Arg Phe Gly Phe Thr Gly Ala
450                 455                 460

Arg Lys Ser Ala Arg Lys Arg Asn Gln Ala Leu Ala Gly Gly Gly
465                 470                 475                 480

Gly Ser Gly Gly Gly Ser Gly Gly Gly Ser Ala Leu Val Leu
            485                 490                 495

Gln Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
            515                 520                 525

Thr Asn Ile Glu Ala Ala Glu Glu Asn Ile Ser Leu Asp Leu Ile Gln
```

```
                530                 535                 540
Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
        595                 600                 605

Arg Ile Ala Leu Thr Asn Ser Val Asn Glu Ala Leu Leu Asn Pro Ser
    610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
        675                 680                 685

Asn Met Leu Tyr Lys Asp Asp Phe Val Gly Ala Leu Ile Phe Ser Gly
    690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
        755                 760                 765

Ile Asp Leu Ile Arg Lys Lys Met Lys Glu Ala Leu Glu Asn Gln Ala
    770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
        835                 840                 845

Val Lys Arg Leu Glu Asp Phe Asp Ala Ser Leu Lys Asp Ala Leu Leu
    850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
            900                 905                 910

<210> SEQ ID NO 98
<211> LENGTH: 180
<212> TYPE: DNA
<213> ORGANISM: Artificial Sequence
<220> FEATURE:
<223> OTHER INFORMATION: Synthetic
```

<400> SEQUENCE: 98

```
ggatccacgc acgtcgacgc gattgatggt cgttttggcg gtttcacggg cgcacgcaaa      60
tcagcgcgta aacgtaagaa ccaggcgcta gcgggcggtg gcggtagcgg cggtggcggt     120
agcggcggtg gcggtagcgc actagtgctg cagacgcacg gtctagaatg ataaaagctt     180
```

<210> SEQ ID NO 99
<211> LENGTH: 2715
<212> TYPE: DNA
<213> ORGANISM: Artificial Sequence
<220> FEATURE:
<223> OTHER INFORMATION: Synthetic

<400> SEQUENCE: 99

```
ggatccgaat tcatgccgat caccatcaac aacttcaact acagcgatcc ggtggataac      60
aaaaacatcc tgtacctgga tacccatctg aatacccctgg cgaacgaacc ggaaaaagcg    120
tttcgtatca ccggcaacat ttgggttatt ccggatcgtt ttagccgtaa cagcaacccg    180
aatctgaata aaccgccgcg tgttaccagc ccgaaaagcg gttattacga tccgaactat    240
ctgagcaccg atagcgataa agataccttc ctgaaagaaa tcatcaaact gttcaaacgc    300
atcaacagcc gtgaaattgg cgaagaactg atctatcgcc tgagcaccga tattccgttt    360
ccgggcaaca caacaccccc gatcaacacc tttgatttcg atgtggattt caacagcgtt    420
gatgttaaaa cccgccaggg taacaattgg gtgaaaaccg gcagcattaa cccgagcgtg    480
attattaccg gtccgcgcga aacattatt gatccggaaa ccagcacctt taaactgacc    540
aacaacacct ttgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcggaaa tctatgcgtt tggcggtccg    840
accattgatc tgattccgaa aagcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa atctacctg   1140 agcaacgtgt atcccccggt gaccgcgaat attctggatg ataacgtgta cgatatccag   1200
aacggcttta acatcccgaa aagcaacctg aacgttctgt tatgggccca gaacctgagc   1260
cgtaatccgg cgctgcgtaa agtgaacccg gaaaacatgc tgtacctgtt caccaaattt   1320
tgcgtcgacg cgattgatgg tcgttttggc ggtttcacgg gcgcacgcaa atcagcgcgt   1380
aaacgtaaga accaggcgct agcgggcggt ggcggtagcg gcggtggcgg tagcggcggt   1440
ggcggtagcg cactagtgct gcagtgtcgt gaactgctgg tgaaaaacac cgatctgccg   1500
tttattggcg atatcagcga tgtgaaaacc gatatcttcc tgcgcaaaga tatcaacgaa   1560
gaaaccgaag tgatctacta cccggataac gtgagcgttg atcaggtgat cctgagcaaa   1620
aacaccagcg aacatggtca gctggatctg ctgtatccga gcattgatag cgaaagcgaa   1680
attctgccgg gcgaaaacca ggtgttttac gataaccgta cccagaacgt ggattacctg   1740
aacagctatt actacctgga aagccagaaa ctgagcgata acgtggaaga ttttaccttt   1800
acccgcagca ttgaagaagc gctggataac agcgcgaaag tttacaccta ttttccgacc   1860
```

```
ctggcgaaca aagttaatgc gggtgttcag ggcggtctgt ttctgatgtg ggcgaacgat   1920
gtggtggaag atttcaccac caacatcctg cgtaaagata ccctggataa atcagcgat    1980 gttagcgcga ttattccgta tattggtccg gcgctgaaca ttagcaatag cgtgcgtcgt   2040
ggcaatttta ccgaagcgtt tgcggttacc ggtgtgacca ttctgctgga agcgtttccg   2100
gaatttacca ttccggcgct gggtgcgttt gtgatctata gcaaagtgca ggaacgcaac   2160
gaaatcatca aaccatcga taactgcctg aacagcgta ttaaacgctg aaagatagc      2220 tatgaatgga tgatgggcac ctggctgagc cgtattatca cccagttcaa caacatcagc   2280
taccagatgt acgatagcct gaactatcag gcgggtgcga ttaaagcgaa aatcgatctg   2340
gaatacaaaa aatacagcgg cagcgataaa gaaaacatca aaagccaggt tgaaaacctg   2400
aaaaacagcc tggatgtgaa aattagcgaa gcgatgaata acatcaacaa attcatccgc   2460
gaatgcagcg tgacctacct gttcaaaaac atgctgccga agtgatcga tgaactgaac    2520 gaatttgatc gcaacaccaa agcgaaactg atcaacctga tcgatagcca caacattatt   2580
ctggtgggcg aagtggataa actgaaagcg aaagttaaca acagcttcca gaacaccatc   2640
ccgtttaaca tcttcagcta taccaacaac agcctgctga agatatcat caacgaatac    2700 ttcaatctag actag                                                   2715
```

<210> SEQ ID NO 100
<211> LENGTH: 904
<212> TYPE: PRT
<213> ORGANISM: Artificial Sequence
<220> FEATURE:
<223> OTHER INFORMATION: Synthetic

<400> SEQUENCE: 100

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

```
Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                    245                 250                 255

Thr Ser Asn Ile Phe Tyr Ser Gln Tyr Asn Val Lys Leu Glu Tyr Ala
                260                 265                 270

Glu Ile Tyr Ala Phe Gly Gly Pro Thr Ile Asp Leu Ile Pro Lys Ser
            275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                    325                 330                 335

Val Val Glu Ser Ser Gly Glu Val Thr Val Asn Arg Asn Lys Phe Val
                340                 345                 350

Glu Leu Tyr Asn Glu Leu Thr Gln Ile Phe Thr Glu Phe Asn Tyr Ala
            355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                    405                 410                 415

Gln Asn Leu Ser Arg Asn Pro Ala Leu Arg Lys Val Asn Pro Glu Asn
                420                 425                 430

Met Leu Tyr Leu Phe Thr Lys Phe Cys Val Asp Ala Ile Asp Gly Arg
            435                 440                 445

Phe Gly Gly Phe Thr Gly Ala Arg Lys Ser Ala Arg Lys Arg Lys Asn
    450                 455                 460

Gln Ala Leu Ala Gly Gly Gly Ser Gly Gly Gly Ser Gly
465                 470                 475                 480

Gly Gly Ser Ala Leu Val Leu Gln Cys Arg Glu Leu Leu Val Lys Asn
                485                 490                 495

Thr Asp Leu Pro Phe Ile Gly Asp Ile Ser Asp Val Lys Thr Asp Ile
                500                 505                 510

Phe Leu Arg Lys Asp Ile Asn Glu Glu Thr Glu Val Ile Tyr Tyr Pro
            515                 520                 525

Asp Asn Val Ser Val Asp Gln Val Ile Leu Ser Lys Asn Thr Ser Glu
    530                 535                 540

His Gly Gln Leu Asp Leu Leu Tyr Pro Ser Ile Asp Ser Glu Ser Glu
545                 550                 555                 560

Ile Leu Pro Gly Glu Asn Gln Val Phe Tyr Asp Asn Arg Thr Gln Asn
                    565                 570                 575

Val Asp Tyr Leu Asn Ser Tyr Tyr Leu Glu Ser Gln Lys Leu Ser
                580                 585                 590

Asp Asn Val Glu Asp Phe Thr Phe Thr Arg Ser Ile Glu Glu Ala Leu
            595                 600                 605

Asp Asn Ser Ala Lys Val Tyr Thr Tyr Phe Pro Thr Leu Ala Asn Lys
    610                 615                 620
```

Val Asn Ala Gly Val Gln Gly Gly Leu Phe Leu Met Trp Ala Asn Asp
625                 630                 635                 640

Val Val Glu Asp Phe Thr Thr Asn Ile Leu Arg Lys Asp Thr Leu Asp
            645                 650                 655

Lys Ile Ser Asp Val Ser Ala Ile Ile Pro Tyr Ile Gly Pro Ala Leu
            660                 665                 670

Asn Ile Ser Asn Ser Val Arg Arg Gly Asn Phe Thr Glu Ala Phe Ala
            675                 680                 685

Val Thr Gly Val Thr Ile Leu Leu Glu Ala Phe Pro Glu Phe Thr Ile
            690                 695                 700

Pro Ala Leu Gly Ala Phe Val Ile Tyr Ser Lys Val Gln Glu Arg Asn
705                 710                 715                 720

Glu Ile Ile Lys Thr Ile Asp Asn Cys Leu Glu Gln Arg Ile Lys Arg
            725                 730                 735

Trp Lys Asp Ser Tyr Glu Trp Met Met Gly Thr Trp Leu Ser Arg Ile
            740                 745                 750

Ile Thr Gln Phe Asn Asn Ile Ser Tyr Gln Met Tyr Asp Ser Leu Asn
            755                 760                 765

Tyr Gln Ala Gly Ala Ile Lys Ala Lys Ile Asp Leu Glu Tyr Lys Lys
770                 775                 780

Tyr Ser Gly Ser Asp Lys Glu Asn Ile Lys Ser Gln Val Glu Asn Leu
785                 790                 795                 800

Lys Asn Ser Leu Asp Val Lys Ile Ser Glu Ala Met Asn Asn Ile Asn
            805                 810                 815

Lys Phe Ile Arg Glu Cys Ser Val Thr Tyr Leu Phe Lys Asn Met Leu
            820                 825                 830

Pro Lys Val Ile Asp Glu Leu Asn Glu Phe Asp Arg Asn Thr Lys Ala
            835                 840                 845

Lys Leu Ile Asn Leu Ile Asp Ser His Asn Ile Ile Leu Val Gly Glu
850                 855                 860

Val Asp Lys Leu Lys Ala Lys Val Asn Asn Ser Phe Gln Asn Thr Ile
865                 870                 875                 880

Pro Phe Asn Ile Phe Ser Tyr Thr Asn Asn Ser Leu Leu Lys Asp Ile
            885                 890                 895

Ile Asn Glu Tyr Phe Asn Leu Asp
            900

<210> SEQ ID NO 101
<211> LENGTH: 17
<212> TYPE: PRT
<213> ORGANISM: Artificial Sequence
<220> FEATURE:
<223> OTHER INFORMATION: Synthetic

<400> SEQUENCE: 101

Tyr Gly Gly Phe Leu Arg Arg Ile Arg Pro Lys Leu Lys Trp Asp Asn
1               5                   10                  15

Gln

<210> SEQ ID NO 102
<211> LENGTH: 2709
<212> TYPE: DNA
<213> ORGANISM: Artificial Sequence
<220> FEATURE:
<223> OTHER INFORMATION: Synthetic

<400> SEQUENCE: 102

```
ggatccatgg agttcgttaa caaacagttc aactataaag acccagttaa cggtgttgac    60
attgcttaca tcaaaatccc gaacgctggc cagatgcagc cggtaaaggc attcaaaatc   120
cacaacaaaa tctgggttat cccggaacgt gataccttta ctaacccgga agaaggtgac   180
ctgaacccgc caccggaagc gaaacaggtg ccggtatctt actatgactc cacctacctg   240
tctaccgata acgaaaagga caactacctg aaaggtgtta ctaaactgtt cgagcgtatt   300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
cagccggacg gttcctatcg ttccgaagaa ctgaacctgg tgatcatcgg cccgtctgct   480
gatatcatcc agttcgagtg taagagcttt ggtcacgaag ttctgaacct cacccgtaac   540
ggctacggtt ccactcagta catccgtttc tctccggact tcaccttcgg ttttgaagaa   600
tccctggaag tagacacgaa cccactgctg ggcgctggta aattcgcaac tgatcctgcg   660
gttaccctgg ctcacgaact gattcatgca ggccaccgcc tgtacggtat cgccatcaat   720
ccgaaccgtg tcttcaaagt taacaccaac gcgtattacg agatgtccgg tctggaagtt   780
agcttcgaag aactgcgtac ttttggcggt cacgacgcta aattcatcga ctctctgcaa   840
gaaaacgagt tccgtctgta ctactataac aagttcaaag atatcgcatc caccctgaac   900
aaagcgaaat ccatcgtggg taccactgct tctctccagt acatgaagaa cgttttttaaa   960
gaaaaatacc tgctcagcga agacacctcc ggcaaattct ctgtagacaa gttgaaattc  1020
gataaacttt acaaaatgct gactgaaatt tacaccgaag acaacttcgt taagttcttt  1080
aaagttctga accgcaaaac ctatctgaac ttcgacaagg cagtattcaa aatcaacatc  1140
gtgccgaaag ttaactacac tatctacgat ggtttcaacc tgcgtaacac caacctggct  1200
gctaatttta acgccagaa cacggaaatc aacaacatga acttcacaaa actgaaaaac  1260
ttcactggtc tgttcgagtt ttacaagctg ctgtgcgtcg acggcatcat acctccaaa   1320
actaaatctg acgatgacga taaatatgga ggttttttga aaggatacg accaaaatta  1380
aagtgggata atcaagcgct agcgggcggt ggcggtagcg gcggtggcgg tagcggcggt  1440
ggcggtagcg cactagtgct gcagtgtatc aaggttaaca actgggattt attcttcagc  1500
ccgagtgaag acaacttcac caacgacctg aacaaaggtg aagaaatcac ctcagatact  1560
aacatcgaag cagccgaaga aaacatctcg ctggacctga tccagcagta ctacctgacc  1620
tttaatttcg acaacgagcc ggaaaacatt tctatcgaaa acctgagctc tgatatcatc  1680
ggccagctgg aactgatgcc gaacatcgaa cgtttcccaa acggtaaaaa gtacgagctg  1740
gacaaatata ccatgttcca ctacctgcgc gcgcaggaat ttgaacacgg caaatcccgt  1800
atcgcactga ctaactccgt taacgaagct ctgctcaacc cgtcccgtgt atacaccttc  1860
ttctctagcg actacgtgaa aaaggtcaac aaagcgactg aagctgcaat gttcttgggt  1920
tgggttgaac agcttgttta tgattttacc gacgagacgt ccgaagtatc tactaccgac  1980
aaaattgcgg atatcactat catcatcccg tacatcggtc cggctctgaa cattggcaac  2040
atgctgtaca agacgacttt cgttggcgca ctgatcttct ccggtgcggt gatcctgctg  2100
gagttcatcc cggaaatcgc catcccggta ctgggcacct ttgctctggt ttcttacatt  2160
gcaaacaagg ttctgactgt acaaaccatc gacaacgcgc tgagcaaacg taacgaaaaa  2220
tgggatgaag tttacaaata tatcgtgacc aactggctgg ctaaggttaa tactcagatc  2280
gacctcatcc gcaaaaaaat gaagaagca ctggaaaacc aggcggaagc taccaaggca  2340
atcattaact accagtacaa ccagtacacc gaggaagaaa aaacaacat caacttcaac  2400
```

```
atcgacgatc tgtcctctaa actgaacgaa tccatcaaca aagctatgat caacatcaac    2460
aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccttc    2640
tcgaccgaca tcccttttca gctcagtaaa tatgtcgata ccaacgcct tttgtccact    2700 ctagactag                                                            2709
```

<210> SEQ ID NO 103
<211> LENGTH: 902
<212> TYPE: PRT
<213> ORGANISM: Artificial Sequence
<220> FEATURE:
<223> OTHER INFORMATION: Synthetic

<400> SEQUENCE: 103

```
Gly Ser Met Glu Phe Val Asn Lys Gln Phe Asn Tyr Lys Asp Pro Val
  1               5                  10                  15

Asn Gly Val Asp Ile Ala Tyr Ile Lys Ile Pro Asn Ala Gly Gln Met
             20                  25                  30

Gln Pro Val Lys Ala Phe Lys Ile His Asn Lys Ile Trp Val Ile Pro
         35                  40                  45

Glu Arg Asp Thr Phe Thr Asn Pro Glu Gly Asp Leu Asn Pro Pro
     50                  55                  60

Pro Glu Ala Lys Gln Val Pro Val Ser Tyr Tyr Asp Ser Thr Tyr Leu
 65                  70                  75                  80

Ser Thr Asp Asn Glu Lys Asp Asn Tyr Leu Lys Gly Val Thr Lys Leu
                 85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300
```

```
Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Asp Asp Asp Asp Lys
        435                 440                 445

Tyr Gly Gly Phe Leu Arg Arg Ile Arg Pro Lys Leu Lys Trp Asp Asn
450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
                500                 505                 510

Gly Glu Glu Ile Thr Ser Asp Thr Asn Ile Glu Ala Ala Glu Glu Asn
            515                 520                 525

Ile Ser Leu Asp Leu Ile Gln Gln Tyr Tyr Leu Thr Phe Asn Phe Asp
530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
690                 695                 700

Glu Ile Ala Ile Pro Val Leu Gly Thr Phe Ala Leu Val Ser Tyr Ile
705                 710                 715                 720
```

```
Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
                820                 825                 830

Asn Ser Met Ile Pro Tyr Gly Val Lys Arg Leu Glu Asp Phe Asp Ala
            835                 840                 845

Ser Leu Lys Asp Ala Leu Leu Lys Tyr Ile Tyr Asp Asn Arg Gly Thr
        850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900

<210> SEQ ID NO 104
<211> LENGTH: 892
<212> TYPE: PRT
<213> ORGANISM: Artificial Sequence
<220> FEATURE:
<223> OTHER INFORMATION: Synthetic

<400> SEQUENCE: 104

Gly Ser Met Glu Phe Val Asn Lys Gln Phe Asn Tyr Lys Asp Pro Val
1               5                  10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Gly Pro Ser Ala
145                 150                 155                 160

Asp Ile Ile Gln Phe Glu Cys Lys Ser Phe Gly His Glu Val Leu Asn
                165                 170                 175
```

```
Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Asp Asp Asp Asp Lys
        435                 440                 445

Tyr Gly Gly Phe Leu Arg Arg Ile Arg Pro Lys Leu Lys Trp Asp Asn
    450                 455                 460

Gln Ala Leu Ala Gly Gly Gly Ser Ala Leu Val Leu Gln Cys Ile
465                 470                 475                 480

Lys Val Asn Asn Trp Asp Leu Phe Phe Ser Pro Ser Glu Asp Asn Phe
                485                 490                 495

Thr Asn Asp Leu Asn Lys Gly Glu Ile Thr Ser Asp Thr Asn Ile
            500                 505                 510

Glu Ala Ala Glu Glu Asn Ile Ser Leu Asp Leu Ile Gln Gln Tyr Tyr
        515                 520                 525

Leu Thr Phe Asn Phe Asp Asn Glu Pro Glu Asn Ile Ser Ile Glu Asn
    530                 535                 540

Leu Ser Ser Asp Ile Ile Gly Gln Leu Glu Leu Met Pro Asn Ile Glu
545                 550                 555                 560

Arg Phe Pro Asn Gly Lys Lys Tyr Glu Leu Asp Lys Tyr Thr Met Phe
                565                 570                 575

His Tyr Leu Arg Ala Gln Glu Phe Glu His Gly Lys Ser Arg Ile Ala
            580                 585                 590

Leu Thr Asn Ser Val Asn Glu Ala Leu Leu Asn Pro Ser Arg Val Tyr
```

595                 600                 605
Thr Phe Phe Ser Ser Asp Tyr Val Lys Lys Val Asn Lys Ala Thr Glu
        610                 615                 620
Ala Ala Met Phe Leu Gly Trp Val Glu Gln Leu Val Tyr Asp Phe Thr
625                 630                 635                 640
Asp Glu Thr Ser Glu Val Ser Thr Thr Asp Lys Ile Ala Asp Ile Thr
                645                 650                 655
Ile Ile Ile Pro Tyr Ile Gly Pro Ala Leu Asn Ile Gly Asn Met Leu
            660                 665                 670
Tyr Lys Asp Asp Phe Val Gly Ala Leu Ile Phe Ser Gly Ala Val Ile
        675                 680                 685
Leu Leu Glu Phe Ile Pro Glu Ile Ala Ile Pro Val Leu Gly Thr Phe
690                 695                 700
Ala Leu Val Ser Tyr Ile Ala Asn Lys Val Leu Thr Val Gln Thr Ile
705                 710                 715                 720
Asp Asn Ala Leu Ser Lys Arg Asn Glu Lys Trp Asp Glu Val Tyr Lys
                725                 730                 735
Tyr Ile Val Thr Asn Trp Leu Ala Lys Val Asn Thr Gln Ile Asp Leu
            740                 745                 750
Ile Arg Lys Lys Met Lys Glu Ala Leu Glu Asn Gln Ala Glu Ala Thr
        755                 760                 765
Lys Ala Ile Ile Asn Tyr Gln Tyr Asn Gln Tyr Thr Glu Glu Glu Lys
770                 775                 780
Asn Asn Ile Asn Phe Asn Ile Asp Asp Leu Ser Ser Lys Leu Asn Glu
785                 790                 795                 800
Ser Ile Asn Lys Ala Met Ile Asn Ile Asn Lys Phe Leu Asn Gln Cys
                805                 810                 815
Ser Val Ser Tyr Leu Met Asn Ser Met Ile Pro Tyr Gly Val Lys Arg
            820                 825                 830
Leu Glu Asp Phe Asp Ala Ser Leu Lys Asp Ala Leu Leu Lys Tyr Ile
        835                 840                 845
Tyr Asp Asn Arg Gly Thr Leu Ile Gly Gln Val Asp Arg Leu Lys Asp
850                 855                 860
Lys Val Asn Asn Thr Leu Ser Thr Asp Ile Pro Phe Gln Leu Ser Lys
865                 870                 875                 880
Tyr Val Asp Asn Gln Arg Leu Leu Ser Thr Leu Asp
                885                 890

<210> SEQ ID NO 105
<211> LENGTH: 897
<212> TYPE: PRT
<213> ORGANISM: Artificial Sequence
<220> FEATURE:
<223> OTHER INFORMATION: Synthetic

<400> SEQUENCE: 105

Gly Ser Met Glu Phe Val Asn Lys Gln Phe Asn Tyr Lys Asp Pro Val
1               5                   10                  15
Asn Gly Val Asp Ile Ala Tyr Ile Lys Ile Pro Asn Ala Gly Gln Met
            20                  25                  30
Gln Pro Val Lys Ala Phe Lys Ile His Asn Lys Ile Trp Val Ile Pro
        35                  40                  45
Glu Arg Asp Thr Phe Thr Asn Pro Glu Glu Gly Asp Leu Asn Pro Pro
    50                  55                  60
Pro Glu Ala Lys Gln Val Pro Val Ser Tyr Tyr Asp Ser Thr Tyr Leu

```
             65                  70                  75                  80
Ser Thr Asp Asn Glu Lys Asp Asn Tyr Leu Lys Gly Val Thr Lys Leu
                 85                  90                  95

Phe Glu Arg Ile Tyr Ser Thr Asp Leu Gly Arg Met Leu Leu Thr Ser
                100                 105                 110

Ile Val Arg Gly Ile Pro Phe Trp Gly Ser Thr Ile Asp Thr Glu
                115                 120                 125

Leu Lys Val Ile Asp Thr Asn Cys Ile Asn Val Ile Gln Pro Asp Gly
       130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
                180                 185                 190

Asp Phe Thr Phe Gly Phe Glu Glu Ser Leu Glu Val Asp Thr Asn Pro
                195                 200                 205

Leu Leu Gly Ala Gly Lys Phe Ala Thr Asp Pro Ala Val Thr Leu Ala
       210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
                260                 265                 270

Ala Lys Phe Ile Asp Ser Leu Gln Glu Asn Glu Phe Arg Leu Tyr Tyr
       275                 280                 285

Tyr Asn Lys Phe Lys Asp Ile Ala Ser Thr Leu Asn Lys Ala Lys Ser
       290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
                340                 345                 350

Glu Asp Asn Phe Val Lys Phe Phe Lys Val Leu Asn Arg Lys Thr Tyr
                355                 360                 365

Leu Asn Phe Asp Lys Ala Val Phe Lys Ile Asn Ile Val Pro Lys Val
       370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Asp Asp Asp Lys
       435                 440                 445

Tyr Gly Gly Phe Leu Arg Arg Ile Arg Pro Lys Leu Lys Trp Asp Asn
       450                 455                 460

Gln Ala Leu Ala Gly Gly Gly Ser Gly Gly Gly Ser Ala Leu
465                 470                 475                 480

Val Leu Gln Cys Ile Lys Val Asn Asn Trp Asp Leu Phe Phe Ser Pro
                485                 490                 495
```

```
Ser Glu Asp Asn Phe Thr Asn Asp Leu Asn Lys Gly Glu Glu Ile Thr
            500                 505                 510

Ser Asp Thr Asn Ile Glu Ala Ala Glu Glu Asn Ile Ser Leu Asp Leu
            515                 520                 525

Ile Gln Gln Tyr Tyr Leu Thr Phe Asn Phe Asp Asn Glu Pro Glu Asn
        530                 535                 540

Ile Ser Ile Glu Asn Leu Ser Ser Asp Ile Ile Gly Gln Leu Glu Leu
545                 550                 555                 560

Met Pro Asn Ile Glu Arg Phe Pro Asn Gly Lys Lys Tyr Glu Leu Asp
                565                 570                 575

Lys Tyr Thr Met Phe His Tyr Leu Arg Ala Gln Glu Phe Glu His Gly
            580                 585                 590

Lys Ser Arg Ile Ala Leu Thr Asn Ser Val Asn Glu Ala Leu Leu Asn
        595                 600                 605

Pro Ser Arg Val Tyr Thr Phe Phe Ser Ser Asp Tyr Val Lys Lys Val
        610                 615                 620

Asn Lys Ala Thr Glu Ala Ala Met Phe Leu Gly Trp Val Glu Gln Leu
625                 630                 635                 640

Val Tyr Asp Phe Thr Asp Glu Thr Ser Glu Val Ser Thr Thr Asp Lys
                645                 650                 655

Ile Ala Asp Ile Thr Ile Ile Ile Pro Tyr Ile Gly Pro Ala Leu Asn
            660                 665                 670

Ile Gly Asn Met Leu Tyr Lys Asp Asp Phe Val Gly Ala Leu Ile Phe
        675                 680                 685

Ser Gly Ala Val Ile Leu Leu Glu Phe Ile Pro Glu Ile Ala Ile Pro
        690                 695                 700

Val Leu Gly Thr Phe Ala Leu Val Ser Tyr Ile Ala Asn Lys Val Leu
705                 710                 715                 720

Thr Val Gln Thr Ile Asp Asn Ala Leu Ser Lys Arg Asn Glu Lys Trp
                725                 730                 735

Asp Glu Val Tyr Lys Tyr Ile Val Thr Asn Trp Leu Ala Lys Val Asn
            740                 745                 750

Thr Gln Ile Asp Leu Ile Arg Lys Lys Met Lys Glu Ala Leu Glu Asn
        755                 760                 765

Gln Ala Glu Ala Thr Lys Ala Ile Ile Asn Tyr Gln Tyr Asn Gln Tyr
        770                 775                 780

Thr Glu Glu Glu Lys Asn Asn Ile Asn Phe Asn Ile Asp Asp Leu Ser
785                 790                 795                 800

Ser Lys Leu Asn Glu Ser Ile Asn Lys Ala Met Ile Asn Ile Asn Lys
                805                 810                 815

Phe Leu Asn Gln Cys Ser Val Ser Tyr Leu Met Asn Ser Met Ile Pro
            820                 825                 830

Tyr Gly Val Lys Arg Leu Glu Asp Phe Asp Ala Ser Leu Lys Asp Ala
        835                 840                 845

Leu Leu Lys Tyr Ile Tyr Asp Asn Arg Gly Thr Leu Ile Gly Gln Val
        850                 855                 860

Asp Arg Leu Lys Asp Lys Val Asn Asn Thr Leu Ser Thr Asp Ile Pro
865                 870                 875                 880

Phe Gln Leu Ser Lys Tyr Val Asp Asn Gln Arg Leu Leu Ser Thr Leu
                885                 890                 895

Asp
```

-continued

```
<210> SEQ ID NO 106
<211> LENGTH: 907
<212> TYPE: PRT
<213> ORGANISM: Artificial Sequence
<220> FEATURE:
<223> OTHER INFORMATION: Synthetic

<400> SEQUENCE: 106
```

| | | | | | | | | | | | | | | | |
|---|---|---|---|---|---|---|---|---|---|---|---|---|---|---|---|
| Gly | Ser | Met | Glu | Phe | Val | Asn | Lys | Gln | Phe | Asn | Tyr | Lys | Asp | Pro | Val |
| 1 | | | | 5 | | | | | 10 | | | | | 15 | |
| Asn | Gly | Val | Asp | Ile | Ala | Tyr | Ile | Lys | Ile | Pro | Asn | Ala | Gly | Gln | Met |
| | | | 20 | | | | | 25 | | | | | 30 | | |
| Gln | Pro | Val | Lys | Ala | Phe | Lys | Ile | His | Asn | Lys | Ile | Trp | Val | Ile | Pro |
| | | 35 | | | | | 40 | | | | | 45 | | | |
| Glu | Arg | Asp | Thr | Phe | Thr | Asn | Pro | Glu | Glu | Gly | Asp | Leu | Asn | Pro | Pro |
| 50 | | | | | 55 | | | | | 60 | | | | | |
| Pro | Glu | Ala | Lys | Gln | Val | Pro | Val | Ser | Tyr | Tyr | Asp | Ser | Thr | Tyr | Leu |
| 65 | | | | 70 | | | | | 75 | | | | | 80 | |
| Ser | Thr | Asp | Asn | Glu | Lys | Asp | Asn | Tyr | Leu | Lys | Gly | Val | Thr | Lys | Leu |
| | | | | 85 | | | | | 90 | | | | | 95 | |
| Phe | Glu | Arg | Ile | Tyr | Ser | Thr | Asp | Leu | Gly | Arg | Met | Leu | Leu | Thr | Ser |
| | | | 100 | | | | | 105 | | | | | 110 | | |
| Ile | Val | Arg | Gly | Ile | Pro | Phe | Trp | Gly | Gly | Ser | Thr | Ile | Asp | Thr | Glu |
| | | 115 | | | | | 120 | | | | | 125 | | | |
| Leu | Lys | Val | Ile | Asp | Thr | Asn | Cys | Ile | Asn | Val | Ile | Gln | Pro | Asp | Gly |
| 130 | | | | | 135 | | | | | 140 | | | | | |
| Ser | Tyr | Arg | Ser | Glu | Glu | Leu | Asn | Leu | Val | Ile | Ile | Gly | Pro | Ser | Ala |
| 145 | | | | | 150 | | | | | 155 | | | | | 160 |
| Asp | Ile | Ile | Gln | Phe | Glu | Cys | Lys | Ser | Phe | Gly | His | Glu | Val | Leu | Asn |
| | | | | 165 | | | | | 170 | | | | | 175 | |
| Leu | Thr | Arg | Asn | Gly | Tyr | Gly | Ser | Thr | Gln | Tyr | Ile | Arg | Phe | Ser | Pro |
| | | | 180 | | | | | 185 | | | | | 190 | | |
| Asp | Phe | Thr | Phe | Gly | Phe | Glu | Glu | Ser | Leu | Glu | Val | Asp | Thr | Asn | Pro |
| | | 195 | | | | | 200 | | | | | 205 | | | |
| Leu | Leu | Gly | Ala | Gly | Lys | Phe | Ala | Thr | Asp | Pro | Ala | Val | Thr | Leu | Ala |
| 210 | | | | | 215 | | | | | 220 | | | | | |
| His | Glu | Leu | Ile | His | Ala | Gly | His | Arg | Leu | Tyr | Gly | Ile | Ala | Ile | Asn |
| 225 | | | | | 230 | | | | | 235 | | | | | 240 |
| Pro | Asn | Arg | Val | Phe | Lys | Val | Asn | Thr | Asn | Ala | Tyr | Tyr | Glu | Met | Ser |
| | | | | 245 | | | | | 250 | | | | | 255 | |
| Gly | Leu | Glu | Val | Ser | Phe | Glu | Glu | Leu | Arg | Thr | Phe | Gly | Gly | His | Asp |
| | | | 260 | | | | | 265 | | | | | 270 | | |
| Ala | Lys | Phe | Ile | Asp | Ser | Leu | Gln | Glu | Asn | Glu | Phe | Arg | Leu | Tyr | Tyr |
| | | 275 | | | | | 280 | | | | | 285 | | | |
| Tyr | Asn | Lys | Phe | Lys | Asp | Ile | Ala | Ser | Thr | Leu | Asn | Lys | Ala | Lys | Ser |
| | 290 | | | | | 295 | | | | | 300 | | | | |
| Ile | Val | Gly | Thr | Thr | Ala | Ser | Leu | Gln | Tyr | Met | Lys | Asn | Val | Phe | Lys |
| 305 | | | | | 310 | | | | | 315 | | | | | 320 |
| Glu | Lys | Tyr | Leu | Leu | Ser | Glu | Asp | Thr | Ser | Gly | Lys | Phe | Ser | Val | Asp |
| | | | | 325 | | | | | 330 | | | | | 335 | |
| Lys | Leu | Lys | Phe | Asp | Lys | Leu | Tyr | Lys | Met | Leu | Thr | Glu | Ile | Tyr | Thr |
| | | | 340 | | | | | 345 | | | | | 350 | | |
| Glu | Asp | Asn | Phe | Val | Lys | Phe | Phe | Lys | Val | Leu | Asn | Arg | Lys | Thr | Tyr |
| | | 355 | | | | | 360 | | | | | 365 | | | |
| Leu | Asn | Phe | Asp | Lys | Ala | Val | Phe | Lys | Ile | Asn | Ile | Val | Pro | Lys | Val |

```
               370                 375                 380
Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Asp Asp Asp Asp Lys
                435                 440                 445

Tyr Gly Gly Phe Leu Arg Arg Ile Arg Pro Lys Leu Lys Trp Asp Asn
                450                 455                 460

Gln Ala Leu Ala Gly Gly Gly Ser Gly Gly Gly Ser Gly Gly
465                 470                 475                 480

Gly Gly Ser Gly Gly Gly Ser Ala Leu Val Leu Gln Cys Ile Lys
                485                 490                 495

Val Asn Asn Trp Asp Leu Phe Phe Ser Pro Ser Glu Asp Asn Phe Thr
                500                 505                 510

Asn Asp Leu Asn Lys Gly Glu Ile Thr Ser Asp Thr Asn Ile Glu
                515                 520                 525

Ala Ala Glu Glu Asn Ile Ser Leu Asp Leu Ile Gln Gln Tyr Tyr Leu
                530                 535                 540

Thr Phe Asn Phe Asp Asn Glu Pro Glu Asn Ile Ser Ile Glu Asn Leu
545                 550                 555                 560

Ser Ser Asp Ile Ile Gly Gln Leu Glu Leu Met Pro Asn Ile Glu Arg
                565                 570                 575

Phe Pro Asn Gly Lys Lys Tyr Glu Leu Asp Lys Tyr Thr Met Phe His
                580                 585                 590

Tyr Leu Arg Ala Gln Glu Phe Glu His Gly Lys Ser Arg Ile Ala Leu
                595                 600                 605

Thr Asn Ser Val Asn Glu Ala Leu Leu Asn Pro Ser Arg Val Tyr Thr
                610                 615                 620

Phe Phe Ser Ser Asp Tyr Val Lys Lys Val Asn Lys Ala Thr Glu Ala
625                 630                 635                 640

Ala Met Phe Leu Gly Trp Val Glu Gln Leu Val Tyr Asp Phe Thr Asp
                645                 650                 655

Glu Thr Ser Glu Val Ser Thr Thr Asp Lys Ile Ala Asp Ile Thr Ile
                660                 665                 670

Ile Ile Pro Tyr Ile Gly Pro Ala Leu Asn Ile Gly Asn Met Leu Tyr
                675                 680                 685

Lys Asp Asp Phe Val Gly Ala Leu Ile Phe Ser Gly Ala Val Ile Leu
                690                 695                 700

Leu Glu Phe Ile Pro Glu Ile Ala Ile Pro Val Leu Gly Thr Phe Ala
705                 710                 715                 720

Leu Val Ser Tyr Ile Ala Asn Lys Val Leu Thr Val Gln Thr Ile Asp
                725                 730                 735

Asn Ala Leu Ser Lys Arg Asn Glu Lys Trp Asp Glu Val Tyr Lys Tyr
                740                 745                 750

Ile Val Thr Asn Trp Leu Ala Lys Val Asn Thr Gln Ile Asp Leu Ile
                755                 760                 765

Arg Lys Lys Met Lys Glu Ala Leu Glu Asn Gln Ala Glu Ala Thr Lys
                770                 775                 780

Ala Ile Ile Asn Tyr Gln Tyr Asn Gln Tyr Thr Glu Glu Glu Lys Asn
785                 790                 795                 800
```

```
Asn Ile Asn Phe Asn Ile Asp Asp Leu Ser Ser Lys Leu Asn Glu Ser
                805                 810                 815

Ile Asn Lys Ala Met Ile Asn Ile Asn Lys Phe Leu Asn Gln Cys Ser
            820                 825                 830

Val Ser Tyr Leu Met Asn Ser Met Ile Pro Tyr Gly Val Lys Arg Leu
        835                 840                 845

Glu Asp Phe Asp Ala Ser Leu Lys Asp Ala Leu Leu Lys Tyr Ile Tyr
850                 855                 860

Asp Asn Arg Gly Thr Leu Ile Gly Gln Val Asp Arg Leu Lys Asp Lys
865                 870                 875                 880

Val Asn Asn Thr Leu Ser Thr Asp Ile Pro Phe Gln Leu Ser Lys Tyr
                885                 890                 895

Val Asp Asn Gln Arg Leu Leu Ser Thr Leu Asp
                900                 905

<210> SEQ ID NO 107
<211> LENGTH: 913
<212> TYPE: PRT
<213> ORGANISM: Artificial Sequence
<220> FEATURE:
<223> OTHER INFORMATION: Synthetic

<400> SEQUENCE: 107

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255
```

-continued

```
Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
            420                 425                 430

Met Leu Tyr Leu Phe Thr Lys Phe Cys Val Asp Gly Ile Ile Thr Ser
        435                 440                 445

Lys Thr Lys Ser Asp Asp Asp Lys Tyr Gly Gly Phe Leu Arg Arg
    450                 455                 460

Ile Arg Pro Lys Leu Lys Trp Asp Asn Gln Ala Leu Ala Gly Gly Gly
465                 470                 475                 480

Gly Ser Gly Gly Gly Ser Gly Gly Gly Ser Ala Leu Val Leu
                485                 490                 495

Gln Cys Arg Glu Leu Leu Val Lys Asn Thr Asp Leu Pro Phe Ile Gly
            500                 505                 510

Asp Ile Ser Asp Val Lys Thr Asp Ile Phe Leu Arg Lys Asp Ile Asn
        515                 520                 525

Glu Glu Thr Glu Val Ile Tyr Tyr Pro Asp Asn Val Ser Val Asp Gln
    530                 535                 540

Val Ile Leu Ser Lys Asn Thr Ser Glu His Gly Gln Leu Asp Leu Leu
545                 550                 555                 560

Tyr Pro Ser Ile Asp Ser Glu Ser Glu Ile Leu Pro Gly Glu Asn Gln
                565                 570                 575

Val Phe Tyr Asp Asn Arg Thr Gln Asn Val Asp Tyr Leu Asn Ser Tyr
            580                 585                 590

Tyr Tyr Leu Glu Ser Gln Lys Leu Ser Asp Asn Val Glu Asp Phe Thr
        595                 600                 605

Phe Thr Arg Ser Ile Glu Glu Ala Leu Asp Asn Ser Ala Lys Val Tyr
    610                 615                 620

Thr Tyr Phe Pro Thr Leu Ala Asn Lys Val Asn Ala Gly Val Gln Gly
625                 630                 635                 640

Gly Leu Phe Leu Met Trp Ala Asn Asp Val Val Glu Asp Phe Thr Thr
                645                 650                 655

Asn Ile Leu Arg Lys Asp Thr Leu Asp Lys Ile Ser Asp Val Ser Ala
            660                 665                 670
```

```
Ile Ile Pro Tyr Ile Gly Pro Ala Leu Asn Ile Ser Asn Ser Val Arg
            675                 680                 685

Arg Gly Asn Phe Thr Glu Ala Phe Ala Val Thr Gly Val Thr Ile Leu
    690                 695                 700

Leu Glu Ala Phe Pro Glu Phe Thr Ile Pro Ala Leu Gly Ala Phe Val
705                 710                 715                 720

Ile Tyr Ser Lys Val Gln Glu Arg Asn Glu Ile Ile Lys Thr Ile Asp
            725                 730                 735

Asn Cys Leu Glu Gln Arg Ile Lys Arg Trp Lys Asp Ser Tyr Glu Trp
            740                 745                 750

Met Met Gly Thr Trp Leu Ser Arg Ile Ile Thr Gln Phe Asn Asn Ile
            755                 760                 765

Ser Tyr Gln Met Tyr Asp Ser Leu Asn Tyr Gln Ala Gly Ala Ile Lys
            770                 775                 780

Ala Lys Ile Asp Leu Glu Tyr Lys Lys Tyr Ser Gly Ser Asp Lys Glu
785                 790                 795                 800

Asn Ile Lys Ser Gln Val Glu Asn Leu Lys Asn Ser Leu Asp Val Lys
            805                 810                 815

Ile Ser Glu Ala Met Asn Asn Ile Asn Lys Phe Ile Arg Glu Cys Ser
            820                 825                 830

Val Thr Tyr Leu Phe Lys Asn Met Leu Pro Lys Val Ile Asp Glu Leu
            835                 840                 845

Asn Glu Phe Asp Arg Asn Thr Lys Ala Lys Leu Ile Asn Leu Ile Asp
850                 855                 860

Ser His Asn Ile Ile Leu Val Gly Glu Val Asp Lys Leu Lys Ala Lys
865                 870                 875                 880

Val Asn Asn Ser Phe Gln Asn Thr Ile Pro Phe Asn Ile Phe Ser Tyr
            885                 890                 895

Thr Asn Asn Ser Leu Leu Lys Asp Ile Ile Asn Glu Tyr Phe Asn Leu
            900                 905                 910

Asp

<210> SEQ ID NO 108
<211> LENGTH: 1432
<212> TYPE: PRT
<213> ORGANISM: Artificial Sequence
<220> FEATURE:
<223> OTHER INFORMATION: Synthetic

<400> SEQUENCE: 108

Gly Ser Leu Val Arg Asp Asp Val Asp Tyr Gln Ile Phe Arg Asp Phe
1               5                   10                  15

Ala Glu Asn Lys Gly Lys Phe Phe Val Gly Ala Thr Asp Leu Ser Val
            20                  25                  30

Lys Asn Lys Arg Gly Gln Asn Ile Gly Asn Ala Leu Ser Asn Val Pro
        35                  40                  45

Met Ile Asp Phe Ser Val Ala Asp Val Asn Lys Arg Ile Ala Thr Val
    50                  55                  60

Val Asp Pro Gln Tyr Ala Val Ser Val Lys His Ala Lys Ala Glu Val
65                  70                  75                  80

His Thr Phe Tyr Tyr Gly Gln Tyr Asn Gly His Asn Asp Val Ala Asp
            85                  90                  95

Lys Glu Asn Glu Tyr Arg Val Val Glu Gln Asn Asn Tyr Glu Pro His
            100                 105                 110

Lys Ala Trp Gly Ala Ser Asn Leu Gly Arg Leu Glu Asp Tyr Asn Met
```

```
                115                 120                 125
Ala Arg Phe Asn Lys Phe Val Thr Glu Val Ala Pro Ile Ala Pro Thr
            130                 135                 140
Asp Ala Gly Gly Gly Leu Asp Thr Tyr Lys Asp Lys Asn Arg Phe Ser
145                 150                 155                 160
Ser Phe Val Arg Ile Gly Ala Gly Arg Gln Leu Val Tyr Glu Lys Gly
                165                 170                 175
Val Tyr His Gln Glu Gly Asn Glu Lys Gly Tyr Asp Leu Arg Asp Leu
            180                 185                 190
Ser Gln Ala Tyr Arg Tyr Ala Ile Ala Gly Thr Pro Tyr Lys Asp Ile
            195                 200                 205
Asn Ile Asp Gln Thr Met Asn Thr Glu Gly Leu Ile Gly Phe Gly Asn
        210                 215                 220
His Asn Lys Gln Tyr Ser Ala Glu Glu Leu Lys Gln Ala Leu Ser Gln
225                 230                 235                 240
Asp Ala Leu Thr Asn Tyr Gly Val Leu Gly Asp Ser Gly Ser Pro Leu
                245                 250                 255
Phe Ala Phe Asp Lys Gln Lys Asn Gln Trp Val Phe Leu Gly Thr Tyr
            260                 265                 270
Asp Tyr Trp Ala Gly Tyr Gly Lys Lys Ser Trp Gln Glu Trp Asn Ile
            275                 280                 285
Tyr Lys Lys Glu Phe Ala Asp Lys Ile Lys Gln His Asp Asn Ala Gly
            290                 295                 300
Thr Val Lys Gly Asn Gly Glu His His Trp Lys Thr Thr Gly Thr Asn
305                 310                 315                 320
Ser His Ile Gly Ser Thr Ala Val Arg Leu Ala Asn Asn Glu Gly Asp
                325                 330                 335
Ala Asn Asn Gly Gln Asn Val Thr Phe Glu Asp Asn Gly Thr Leu Val
                340                 345                 350
Leu Asn Gln Asn Ile Asn Gln Gly Ala Gly Gly Leu Phe Phe Lys Gly
            355                 360                 365
Asp Tyr Thr Val Lys Gly Ala Asn Asn Asp Ile Thr Trp Leu Gly Ala
        370                 375                 380
Gly Ile Asp Val Ala Asp Gly Lys Lys Val Val Trp Gln Val Lys Asn
385                 390                 395                 400
Pro Asn Gly Asp Arg Leu Ala Lys Ile Gly Lys Gly Thr Leu Glu Ile
                405                 410                 415
Asn Gly Thr Gly Val Asn Gln Gly Gln Leu Lys Val Gly Asp Gly Thr
            420                 425                 430
Val Ile Leu Asn Gln Lys Ala Asp Ala Asp Lys Lys Val Gln Ala Phe
        435                 440                 445
Ser Gln Val Gly Ile Val Ser Gly Arg Gly Thr Leu Val Leu Asn Ser
            450                 455                 460
Ser Asn Gln Ile Asn Pro Asp Asn Leu Tyr Phe Gly Phe Arg Gly Gly
465                 470                 475                 480
Arg Leu Asp Ala Asn Gly Asn Asp Leu Thr Phe Glu His Ile Arg Asn
                485                 490                 495
Val Asp Glu Gly Ala Arg Ile Val Asn His Asn Thr Asp His Ala Ser
            500                 505                 510
Thr Ile Thr Leu Thr Gly Lys Ser Leu Ile Thr Asn Pro Asn Ser Leu
        515                 520                 525
Ser Val His Ser Ile Gln Asn Asp Tyr Asp Glu Asp Asp Tyr Ser Tyr
            530                 535                 540
```

-continued

```
Tyr Tyr Arg Pro Arg Arg Pro Ile Pro Gln Gly Lys Asp Leu Tyr Tyr
545                 550                 555                 560

Lys Asn Tyr Arg Tyr Tyr Ala Leu Lys Ser Gly Gly Arg Leu Asn Ala
            565                 570                 575

Pro Met Pro Glu Asn Gly Val Ala Glu Asn Asn Asp Trp Ile Phe Met
            580                 585                 590

Gly Tyr Thr Gln Glu Glu Ala Arg Lys Asn Ala Met Asn His Lys Asn
            595                 600                 605

Asn Arg Arg Ile Gly Asp Phe Gly Phe Phe Asp Glu Glu Asn Gly
610                 615                 620

Lys Gly His Asn Gly Ala Leu Asn Leu Asn Phe Asn Gly Lys Ser Ala
625                 630                 635                 640

Gln Lys Arg Phe Leu Leu Thr Gly Gly Ala Asn Leu Asn Gly Lys Ile
            645                 650                 655

Ser Val Thr Gln Gly Asn Val Leu Leu Ser Gly Arg Pro Thr Pro His
            660                 665                 670

Ala Arg Asp Phe Val Asn Lys Ser Ala Arg Lys Asp Ala His Phe
            675                 680                 685

Ser Lys Asn Asn Glu Val Val Phe Glu Asp Asp Trp Ile Asn Arg Thr
690                 695                 700

Phe Lys Ala Ala Glu Ile Ala Val Asn Gln Ser Ala Ser Phe Ser Ser
705                 710                 715                 720

Gly Arg Asn Val Ser Asp Ile Thr Ala Asn Ile Thr Ala Thr Asp Asn
            725                 730                 735

Ala Lys Val Asn Leu Gly Tyr Lys Asn Gly Asp Glu Val Cys Val Arg
            740                 745                 750

Ser Asp Tyr Thr Gly Tyr Val Thr Cys Asn Thr Gly Asn Leu Ser Asp
            755                 760                 765

Lys Ala Leu Asn Ser Phe Asp Ala Thr Arg Ile Asn Gly Asn Val Asn
770                 775                 780

Leu Asn Gln Asn Ala Ala Leu Val Leu Gly Lys Ala Ala Leu Trp Gly
785                 790                 795                 800

Lys Ile Gln Gly Gln Gly Asn Ser Arg Val Ser Leu Asn Gln His Ser
            805                 810                 815

Lys Trp His Leu Thr Gly Asp Ser Gln Val His Asn Leu Ser Leu Ala
            820                 825                 830

Asp Ser His Ile His Leu Asn Asn Ala Ser Asp Ala Gln Ser Ala Asn
            835                 840                 845

Lys Tyr His Thr Ile Lys Ile Asn His Leu Ser Gly Asn Gly His Phe
            850                 855                 860

His Tyr Leu Thr Asp Leu Ala Lys Asn Leu Gly Asp Lys Val Leu Val
865                 870                 875                 880

Lys Glu Ser Ala Ser Gly His Tyr Gln Leu His Val Gln Asn Lys Thr
            885                 890                 895

Gly Glu Pro Asn Gln Glu Gly Leu Asp Leu Phe Asp Ala Ser Ser Val
            900                 905                 910

Gln Asp Arg Ser Arg Leu Phe Val Ser Leu Ala Asn His Tyr Val Asp
            915                 920                 925

Leu Gly Ala Leu Arg Tyr Thr Ile Lys Thr Glu Asn Gly Ile Thr Arg
            930                 935                 940

Leu Tyr Asn Pro Tyr Ala Gly Asn Gly Arg Pro Val Lys Pro Ala Pro
945                 950                 955                 960
```

-continued

```
Cys Val Asp Gly Ile Ile Thr Ser Lys Thr Lys Ser Leu Asp Asp Asp
                965                 970                 975
Asp Lys Tyr Gly Gly Phe Leu Arg Arg Ile Arg Pro Lys Leu Lys Trp
        980                 985                 990
Asp Asn Gln Ala Leu Ala Gly Gly Gly Gly Ser Gly Gly Gly Gly Ser
        995                 1000                1005
Gly Gly Gly Gly Ser Ala Leu Val Leu Gln Cys Ile Lys Val Asn
    1010                1015                1020
Asn Trp Asp Leu Phe Phe Ser Pro Ser Glu Asp Asn Phe Thr Asn
    1025                1030                1035
Asp Leu Asn Lys Gly Glu Glu Ile Thr Ser Asp Thr Asn Ile Glu
    1040                1045                1050
Ala Ala Glu Glu Asn Ile Ser Leu Asp Leu Ile Gln Gln Tyr Tyr
    1055                1060                1065
Leu Thr Phe Asn Phe Asp Asn Glu Pro Glu Asn Ile Ser Ile Glu
    1070                1075                1080
Asn Leu Ser Ser Asp Ile Ile Gly Gln Leu Glu Leu Met Pro Asn
    1085                1090                1095
Ile Glu Arg Phe Pro Asn Gly Lys Lys Tyr Glu Leu Asp Lys Tyr
    1100                1105                1110
Thr Met Phe His Tyr Leu Arg Ala Gln Glu Phe Glu His Gly Lys
    1115                1120                1125
Ser Arg Ile Ala Leu Thr Asn Ser Val Asn Glu Ala Leu Leu Asn
    1130                1135                1140
Pro Ser Arg Val Tyr Thr Phe Phe Ser Ser Asp Tyr Val Lys Lys
    1145                1150                1155
Val Asn Lys Ala Thr Glu Ala Ala Met Phe Leu Gly Trp Val Glu
    1160                1165                1170
Gln Leu Val Tyr Asp Phe Thr Asp Glu Thr Ser Glu Val Ser Thr
    1175                1180                1185
Thr Asp Lys Ile Ala Asp Ile Thr Ile Ile Pro Tyr Ile Gly
    1190                1195                1200
Pro Ala Leu Asn Ile Gly Asn Met Leu Tyr Lys Asp Asp Phe Val
    1205                1210                1215
Gly Ala Leu Ile Phe Ser Gly Ala Val Ile Leu Leu Glu Phe Ile
    1220                1225                1230
Pro Glu Ile Ala Ile Pro Val Leu Gly Thr Phe Ala Leu Val Ser
    1235                1240                1245
Tyr Ile Ala Asn Lys Val Leu Thr Val Gln Thr Ile Asp Asn Ala
    1250                1255                1260
Leu Ser Lys Arg Asn Glu Lys Trp Asp Glu Val Tyr Lys Tyr Ile
    1265                1270                1275
Val Thr Asn Trp Leu Ala Lys Val Asn Thr Gln Ile Asp Leu Ile
    1280                1285                1290
Arg Lys Lys Met Lys Glu Ala Leu Glu Asn Gln Ala Glu Ala Thr
    1295                1300                1305
Lys Ala Ile Ile Asn Tyr Gln Tyr Asn Gln Tyr Thr Glu Glu Glu
    1310                1315                1320
Lys Asn Asn Ile Asn Phe Asn Ile Asp Asp Leu Ser Ser Lys Leu
    1325                1330                1335
Asn Glu Ser Ile Asn Lys Ala Met Ile Asn Ile Asn Lys Phe Leu
    1340                1345                1350
Asn Gln Cys Ser Val Ser Tyr Leu Met Asn Ser Met Ile Pro Tyr
```

```
                    1355                1360                1365

Gly Val Lys Arg Leu Glu Asp Phe Asp Ala Ser Leu Lys Asp Ala
        1370                1375                1380

Leu Leu Lys Tyr Ile Tyr Asp Asn Arg Gly Thr Leu Ile Gly Gln
    1385                1390                1395

Val Asp Arg Leu Lys Asp Lys Val Asn Asn Thr Leu Ser Thr Asp
    1400                1405                1410

Ile Pro Phe Gln Leu Ser Lys Tyr Val Asp Asn Gln Arg Leu Leu
    1415                1420                1425

Ser Thr Leu Asp
    1430

<210> SEQ ID NO 109
<211> LENGTH: 911
<212> TYPE: PRT
<213> ORGANISM: Artificial Sequence
<220> FEATURE:
<223> OTHER INFORMATION: Synthetic

<400> SEQUENCE: 109

Gly Ser Met Pro Ile Thr Ile Asn Asn Phe Arg Tyr Ser Asp Pro Val
1               5                   10                  15

Asn Asn Asp Thr Ile Ile Met Met Glu Pro Pro Tyr Cys Lys Gly Leu
                20                  25                  30

Asp Ile Tyr Tyr Lys Ala Phe Lys Ile Thr Asp Arg Ile Trp Ile Val
            35                  40                  45

Pro Glu Arg Tyr Glu Phe Gly Thr Lys Pro Glu Asp Phe Asn Pro Pro
        50                  55                  60

Ser Ser Leu Ile Glu Gly Ala Ser Glu Tyr Tyr Asp Pro Asn Tyr Leu
65                  70                  75                  80

Arg Thr Asp Ser Asp Lys Asp Arg Phe Leu Gln Thr Met Val Lys Leu
                85                  90                  95

Phe Asn Arg Ile Lys Asn Asn Val Ala Gly Glu Ala Leu Leu Asp Lys
            100                 105                 110

Ile Ile Asn Ala Ile Pro Tyr Leu Gly Asn Ser Tyr Ser Leu Leu Asp
        115                 120                 125

Lys Phe Asp Thr Asn Ser Asn Ser Val Ser Phe Asn Leu Leu Glu Gln
    130                 135                 140

Asp Pro Ser Gly Ala Thr Thr Lys Ser Ala Met Leu Thr Asn Leu Ile
145                 150                 155                 160

Ile Phe Gly Pro Gly Pro Val Leu Asn Lys Asn Glu Val Arg Gly Ile
                165                 170                 175

Val Leu Arg Val Asp Asn Lys Asn Tyr Phe Pro Cys Arg Asp Gly Phe
            180                 185                 190

Gly Ser Ile Met Gln Met Ala Phe Cys Pro Glu Tyr Val Pro Thr Phe
        195                 200                 205

Asp Asn Val Ile Glu Asn Ile Thr Ser Leu Thr Ile Gly Lys Ser Lys
    210                 215                 220

Tyr Phe Gln Asp Pro Ala Leu Leu Leu Met His Glu Leu Ile His Val
225                 230                 235                 240

Leu His Gly Leu Tyr Gly Met Gln Val Ser Ser His Glu Ile Ile Pro
                245                 250                 255

Ser Lys Gln Glu Ile Tyr Met Gln His Thr Tyr Pro Ile Ser Ala Glu
            260                 265                 270

Glu Leu Phe Thr Phe Gly Gly Gln Asp Ala Asn Leu Ile Ser Ile Asp
```

```
            275                 280                 285
Ile Lys Asn Asp Leu Tyr Glu Lys Thr Leu Asn Asp Tyr Lys Ala Ile
        290                 295                 300

Ala Asn Lys Leu Ser Gln Val Thr Ser Cys Asn Asp Pro Asn Ile Asp
305                 310                 315                 320

Ile Asp Ser Tyr Lys Gln Ile Tyr Gln Gln Lys Tyr Gln Phe Asp Lys
                325                 330                 335

Asp Ser Asn Gly Gln Tyr Ile Val Asn Glu Asp Lys Phe Gln Ile Leu
            340                 345                 350

Tyr Asn Ser Ile Met Tyr Gly Phe Thr Glu Ile Glu Leu Gly Lys Lys
        355                 360                 365

Phe Asn Ile Lys Thr Arg Leu Ser Tyr Phe Ser Met Asn His Asp Pro
370                 375                 380

Val Lys Ile Pro Asn Leu Leu Asp Asp Thr Ile Tyr Asn Asp Thr Glu
385                 390                 395                 400

Gly Phe Asn Ile Glu Ser Lys Asp Leu Lys Ser Glu Tyr Lys Gly Gln
                405                 410                 415

Asn Met Arg Val Asn Thr Asn Ala Phe Arg Asn Val Asp Gly Ser Gly
            420                 425                 430

Leu Val Ser Lys Leu Ile Gly Leu Cys Val Asp Gly Ile Ile Thr Ser
        435                 440                 445

Lys Thr Lys Ser Asp Asp Asp Lys Tyr Gly Gly Phe Leu Arg Arg
450                 455                 460

Ile Arg Pro Lys Leu Lys Trp Asp Asn Gln Ala Leu Ala Gly Gly Gly
465                 470                 475                 480

Gly Ser Gly Gly Gly Ser Gly Gly Gly Ser Ala Leu Val Leu
                485                 490                 495

Gln Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
            515                 520                 525

Thr Asn Ile Glu Ala Ala Glu Glu Asn Ile Ser Leu Asp Leu Ile Gln
        530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
        595                 600                 605

Arg Ile Ala Leu Thr Asn Ser Val Asn Glu Ala Leu Leu Asn Pro Ser
        610                 615                 620

Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Glu Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
        675                 680                 685

Asn Met Leu Tyr Lys Asp Asp Phe Val Gly Ala Leu Ile Phe Ser Gly
        690                 695                 700
```

```
Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
            725                 730                 735

Gln Thr Ile Asp Asn Ala Leu Ser Lys Arg Asn Glu Lys Trp Asp Glu
        740                 745                 750

Val Tyr Lys Tyr Ile Val Thr Asn Trp Leu Ala Lys Val Asn Thr Gln
    755                 760                 765

Ile Asp Leu Ile Arg Lys Lys Met Lys Glu Ala Leu Glu Asn Gln Ala
770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
            805                 810                 815

Leu Asn Glu Ser Ile Asn Lys Ala Met Ile Asn Ile Asn Lys Phe Leu
        820                 825                 830

Asn Gln Cys Ser Val Ser Tyr Leu Met Asn Ser Met Ile Pro Tyr Gly
    835                 840                 845

Val Lys Arg Leu Glu Asp Phe Asp Ala Ser Leu Lys Asp Ala Leu Leu
850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
            885                 890                 895

Leu Ser Lys Tyr Val Asp Asn Gln Arg Leu Leu Ser Thr Leu Asp
        900                 905                 910

<210> SEQ ID NO 110
<211> LENGTH: 23
<212> TYPE: PRT
<213> ORGANISM: Influenza virus

<400> SEQUENCE: 110

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 111
<211> LENGTH: 5
<212> TYPE: PRT
<213> ORGANISM: Artificial Sequence
<220> FEATURE:
<223> OTHER INFORMATION: chemically synthesized enterokinase cleavage
      site

<400> SEQUENCE: 111

Asp Asp Asp Asp Lys
1               5

<210> SEQ ID NO 112
<211> LENGTH: 8
<212> TYPE: PRT
<213> ORGANISM: Artificial Sequence
<220> FEATURE:
<223> OTHER INFORMATION: chemically synthesized Factor Xa cleavage site

<400> SEQUENCE: 112

Ile Glu Gly Arg Ile Asp Gly Arg
```

<210> SEQ ID NO 113
<211> LENGTH: 7
<212> TYPE: PRT
<213> ORGANISM: Artificial Sequence
<220> FEATURE:
<223> OTHER INFORMATION: chemically synthesized tobacco etch virus
      cleavage site

<400> SEQUENCE: 113

Glu Asn Leu Tyr Phe Gln Gly
1               5

<210> SEQ ID NO 114
<211> LENGTH: 6
<212> TYPE: PRT
<213> ORGANISM: Artificial Sequence
<220> FEATURE:
<223> OTHER INFORMATION: chemically synthesized thrombin cleavage site

<400> SEQUENCE: 114

Leu Val Pro Arg Gly Ser
1               5

<210> SEQ ID NO 115
<211> LENGTH: 8
<212> TYPE: PRT
<213> ORGANISM: Artificial Sequence
<220> FEATURE:
<223> OTHER INFORMATION: chemically synthesized PreScission cleavage
      site

<400> SEQUENCE: 115

Leu Glu Val Leu Phe Gln Gly Pro
1               5

<210> SEQ ID NO 116
<211> LENGTH: 48
<212> TYPE: DNA
<213> ORGANISM: Artificial Sequence
<220> FEATURE:
<223> OTHER INFORMATION: chemically synthesized PCR primer

<400> SEQUENCE: 116
tccaaaacta aatctctgat agaaggtaga aacaaagcgc tgaacgac            48

<210> SEQ ID NO 117
<211> LENGTH: 25
<212> TYPE: DNA
<213> ORGANISM: Artificial Sequence
<220> FEATURE:
<223> OTHER INFORMATION: chemically synthesized PCR primer

<400> SEQUENCE: 117
cttgatgtac tctgtgaacg tgctc                                     25

<210> SEQ ID NO 118
<211> LENGTH: 48
<212> TYPE: DNA
<213> ORGANISM: Artificial Sequence
<220> FEATURE:
<223> OTHER INFORMATION: chemically synthesized PCR primer

<400> SEQUENCE: 118
gtcgttcagc gctttgtttc taccttctat cagagattta gttttgga            48

<210> SEQ ID NO 119
<211> LENGTH: 24
<212> TYPE: DNA
<213> ORGANISM: Artificial Sequence
<220> FEATURE:
<223> OTHER INFORMATION: chemically synthesized PCR primer

<400> SEQUENCE: 119
atggagttcg ttaacaaaca gttc                                              24

<210> SEQ ID NO 120
<211> LENGTH: 25
<212> TYPE: PRT
<213> ORGANISM: Artificial Sequence
<220> FEATURE:
<223> OTHER INFORMATION: chemically synthesized activation loop

<400> SEQUENCE: 120

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 121
<211> LENGTH: 5
<212> TYPE: PRT
<213> ORGANISM: Artificial Sequence
<220> FEATURE:
<223> OTHER INFORMATION: chemically synthesized met-enkephalin peptide

<400> SEQUENCE: 121

Tyr Gly Gly Phe Met
1               5

<210> SEQ ID NO 122
<211> LENGTH: 13
<212> TYPE: PRT
<213> ORGANISM: Artificial Sequence
<220> FEATURE:
<223> OTHER INFORMATION: chemically synthesized peptide linker

<400> SEQUENCE: 122

Ala Leu Ala Gly Gly Gly Gly Ser Ala Leu Val Leu Gln
1               5                   10

<210> SEQ ID NO 123
<211> LENGTH: 18
<212> TYPE: PRT
<213> ORGANISM: Artificial Sequence
<220> FEATURE:
<223> OTHER INFORMATION: chemically synthesized peptide linker

<400> SEQUENCE: 123

Ala Leu Ala Gly Gly Gly Gly Ser Gly Gly Gly Gly Ser Ala Leu Val
1               5                   10                  15

Leu Gln

<210> SEQ ID NO 124
<211> LENGTH: 28
<212> TYPE: PRT
<213> ORGANISM: Artificial Sequence
<220> FEATURE:
<223> OTHER INFORMATION: chemically synthesized peptide linker

<400> SEQUENCE: 124

```
Ala Leu Ala Gly Gly Gly Ser Gly Gly Gly Ser Gly Gly Gly
1               5                   10                  15

Gly Ser Gly Gly Gly Gly Ser Ala Leu Val Leu Gln
            20                  25

<210> SEQ ID NO 125
<211> LENGTH: 33
<212> TYPE: PRT
<213> ORGANISM: Artificial Sequence
<220> FEATURE:
<223> OTHER INFORMATION: chemically synthesized peptide linker

<400> SEQUENCE: 125

Ala Leu Ala Gly Gly Gly Ser Gly Gly Gly Gly Ser Gly Gly Gly
1               5                   10                  15

Gly Ser Gly Gly Gly Gly Ser Gly Gly Gly Gly Ser Ala Leu Val Leu
            20                  25                  30

Gln

<210> SEQ ID NO 126
<211> LENGTH: 30
<212> TYPE: PRT
<213> ORGANISM: Artificial Sequence
<220> FEATURE:
<223> OTHER INFORMATION: chemically synthesized peptide linker

<400> SEQUENCE: 126

Ala Leu Ala Ala Glu Ala Ala Ala Lys Glu Ala Ala Ala Lys Glu Ala
1               5                   10                  15

Ala Ala Lys Ala Gly Gly Gly Gly Ser Ala Leu Val Leu Gln
            20                  25                  30
```